United States Patent [19]

Makabe et al.

[11] Patent Number: 4,945,091
[45] Date of Patent: Jul. 31, 1990

[54] 3(2H)-PYRIDAZINONE COMPOUNDS DERIVATIVES AND COMPOSITIONS FOR CONTROLLING AND/OR PREVENTING INSECT PESTS INTERMEDIATES FOR SUCH COMPOUNDS, AND A PROCESS FOR THEIR MANUFACTURE

[75] Inventors: Takahiro Makabe; Tomoyuki Ogura; Yasuo Kawamura; Tatsuo Numata, all of Funabashi; Kiminori Hirata, Minamisaitama; Masaki Kudo, Minamisaitama; Toshiro Miyake, Minamisaitama; Hiroshi Haruyama, Minamisaitama, all of Japan

[73] Assignee: Nissan Chemical Industries, Ltd., Tokyo, Japan

[21] Appl. No.: 217,664

[22] Filed: Jul. 12, 1988

[30] Foreign Application Priority Data

Jul. 30, 1987 [JP] Japan .................................. 62-191289
Dec. 17, 1987 [JP] Japan .................................. 62-319336

[51] Int. Cl.$^5$ .................... A01N 43/58; C07D 237/16
[52] U.S. Cl. ........................ 514/252; 514/247; 544/238; 544/240; 544/241
[58] Field of Search ............... 544/241, 239, 238, 240; 514/247, 252

[56] References Cited

U.S. PATENT DOCUMENTS

| | | | |
|---|---|---|---|
| 2,628,181 | 2/1953 | Mowry | 544/241 |
| 2,832,780 | 4/1958 | King | 544/239 |
| 3,108,103 | 10/1963 | Hensel et al. | 544/241 |
| 3,137,696 | 6/1964 | Reicheneder et al. | 544/239 |
| 3,657,243 | 4/1972 | Quintilla | 544/241 |
| 4,147,784 | 4/1979 | Wilson | 544/235 |
| 4,571,397 | 2/1986 | Taniguchi et al. | 544/241 |
| 4,663,324 | 5/1987 | Graf et al. | 544/240 |
| 4,783,462 | 11/1988 | Mutsukado | 514/249 |
| 4,820,704 | 4/1989 | Richarz et al. | 544/239 |
| 4,837,217 | 5/1989 | Ogura | 544/240 |
| 4,874,861 | 10/1989 | Ogura et al. | 544/238 |

OTHER PUBLICATIONS

Konecny I, abstracted in Chem. Abstr., vol. 104, 207222k (1986).
Konecny II, Chem. Abstr., vol. 78, 159646x (1973) abstracting Czech 146,712.
Mason et al, in Chem. Abstr., vol. 69, 77194y (1968).

Primary Examiner—Donald G. Daus
Attorney, Agent, or Firm—Oliff & Berridge

[57] ABSTRACT

A novel 3(2H)-pyridazinone derivative of the formula [I]:

$$\underset{R^1}{\underset{|}{R-N}}\overset{O}{\underset{N}{\|}}\diagdown\overset{A}{\diagup}\diagdown X-J$$

wherein,
R represents an alkenyl group having 2 to 16 carbon atoms, an alkynyl group having 2 to 16 carbon atoms, an alkyl group having 3 to 8 carbon atoms substituted by an alkoxy group having 1 to 6 carbon atoms or G-Ra-;
A represents hydrogen atom, halogen atom, an alkyl group having 1 to 4 carbon atoms, an alkoxy group having 1 to 4 carbon atoms, an alkylthio group having 1 to 4 carbon atoms, an alkylsulfinyl group having 1 to 4 carbon atoms or an alkylsulfonyl group having 1 to 4 carbon atoms;
$R^1$ represents hydrogen atom, halogen atom, an alkoxy group having 1 to 4 carbon atoms or hydroxyl group;
X represents oxygen or sulfur atom;
J represents $$-\underset{|}{\overset{R^2}{C}H}-Q, \quad -\underset{|}{\overset{Rc}{C}}\underset{|}{\overset{Rd}{H}}-Q, \quad -\underset{|}{\overset{Rc}{C}}\underset{|}{\overset{Rd}{H}}\underset{|}{\overset{Re}{C}H}-Q, \quad -\underset{|}{\overset{Rc}{C}}\underset{|}{\overset{Rd}{H}}=\underset{|}{\overset{Re}{C}}-Q,$$

$$-\underset{|}{\overset{Rc}{C}}\underset{Re}{\overset{Rd}{H}CX^1}-Q^1, \quad -\underset{|}{\overset{Rc}{C}}\underset{|}{\overset{Rd}{H}}\underset{|}{\overset{Re}{C}H}-CO_2Rf, \quad -\underset{|}{\overset{Rc}{C}}\underset{|}{\overset{Rd}{H}}=\underset{|}{\overset{Re}{C}}-CO_2Rf,$$

$$-\underset{|}{\overset{Rc}{C}}\underset{|}{\overset{Rd}{H}CX^1CRf}, \quad -\underset{|}{\overset{Rc}{C}}\underset{|}{\overset{Rd}{H}CX^1CO_2Rf}, \quad -\underset{|}{\overset{Rc}{C}}\underset{|}{\overset{Rd}{H}}\underset{|}{\overset{Re}{C}H}-C\!\!=\!\!C\text{-Hal},$$
$$\phantom{xxxxxxxxx}\overset{\|}{O}$$

$$-\underset{|}{\overset{Rc}{C}}\underset{|}{\overset{Rd}{H}C}=CCH_2ORf, \quad -\underset{|}{\overset{Rc}{C}}\underset{|}{\overset{Rd}{H}C}=NORf \text{ or}$$

$$-\underset{|}{\overset{Rc}{C}}\underset{|}{\overset{Rd}{H}CHO}-N\!\!=\!\!CHRf;$$

as well as insecticidal, acaricidal and nematicidal compositions and compositions for expelling ticks parasitic on animals, said compositions containing as an active ingredient at least one of the above derivatives.

12 Claims, No Drawings

3(2H)-PYRIDAZINONE COMPOUNDS DERIVATIVES AND COMPOSITIONS FOR CONTROLLING AND/OR PREVENTING INSECT PESTS INTERMEDIATES FOR SUCH COMPOUNDS, AND A PROCESS FOR THEIR MANUFACTURE

BACKGROUND OF THE INVENTION

The present invention relates to novel 3(2H)-pyridazinone derivatives and insecticidal, acaricidal and nematicidal compositions and compositions for expelling ticks parasitic on animals containing as an active ingredient said derivatives.

The present invention concerns EP-A-0088384 which corresponds to U.S. Pat. No. 4,571,397, EP-A-0134439 which corresponds to U.S. Pat. No. 4,877,787, EP-A-0183212 which corresponds to U.S. Pat. No. 4,874,861, EP-A-0199281 which corresponds to U.S. Pat. No. 4,837,217, EP-A-0210647, EP-A-0193853 which corresponds to U.S. Pat. No. 4,783,462 and EP-A-0232825. The known compounds contained in these patent publications are represented by the following general formula [II]:

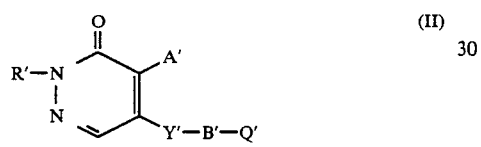

The characteristics of the compounds of these publications are, e.g., in the above formula [II]:

in case of EP-A-0088384, EP-A-0134439, EP-A-0183212, EP-A-0199281 and EP-A-0232825, Y' represents oxygen atom or sulfur atom, but R' represents an alkyl group;

in case of EP-A-0210647, R' represents an aryl group; and in case of EP-A-0193853, Y' represents nitrogen or oxygen atom, but R' represents hydrogen atom or an alkyl group.

However, the compounds of the present invention are novel compounds which are not covered by these European patent publications.

On the other hand, DT-OS-3328770 discloses the compounds of the following formula:

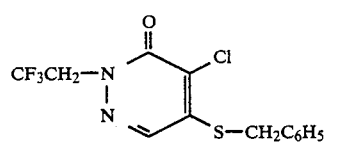

In the DT-OS-3328770, the above-described compound A is disclosed merely as an intermediate and the objective compounds derived from said compound A are described to have fungicidal activity for agriculture. However, said compound A is different from the present invention in chemical structure and use in comparison with the compound [I] of the present invention given below.

SUMMARY OF THE INVENTION

An object of the present invention is to provide novel 3(2H)-pyridazinone derivatives which have insecticidal, acaricidal and nematicidal activities.

Another object of the present invention is to provide a process for preparing such 3(2H)-pyridazinone derivatives.

Still another object of the present invention is to provide insecticidal, acaricidal and nematicidal compositions and compositions for expelling ticks parasitic on animals, said compositions containing at least one of such 3(2H)-pyridazinone derivatives as an active ingredient.

Still another object of the present invention is to provide a method for controlling and/or preventing insect pests by using the above-mentioned derivatives or compositions.

Other objects of the present invention will become apparent from the description given below.

DETAILED DESCRIPTION OF THE INVENTION

The present invention relates to novel 3(2H)-pyridazinone derivatives of the formula [I]:

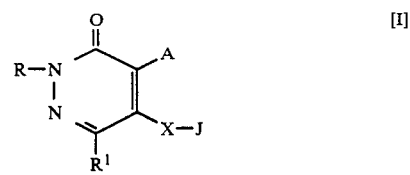

wherein,

R represents an alkenyl group having 2 to 16 carbon atoms, an alkynyl group having 2 to 16 carbon atoms, an alkyl group having 3 to 8 carbon atoms substituted by an alkoxy group having 1 to 6 carbon atoms or G-Ra in which G represents hydrogen atom, RbO-, RbS-,

$RbSO_2-$,

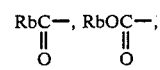

$RbCO_2-$,

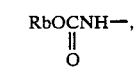

$RbNHCO_2-$, $RbNH-$, $(Rb)_2N-$ or a cyano group in which Rb represents an alkyl group having 1 to 4 carbon atoms, and Ra represents a halogenated alkylene group having 3 to 16 carbon atoms, a halogenated alkenylene group having 2 to 16 carbon atoms, a halogenated alkynylene group having 2 to 16 carbon atoms, a halogenated cycloalkylene group having 3 to 8 carbon atoms, a halogenated cycloalkylene having 5 to 8 carbon atoms, a halogenated oxacycloalkylene group having 5 to 8 carbon atoms, a halogenated thiacycloalkylene group having 5 to 8 carbon atoms, an alkylene group having 1 to 4 carbon atoms substituted by a cycloalkyl group having 3 to 8 carbon atoms and halogen atom, an alkylene group having 1 to 4 carbon atoms substituted by an oxirane group and halogen atom, an alkylene group having 1 to 4 carbon atoms substituted by a phenyl group which may be substituted and halogen atom or an alkylene group having 1 to 4 carbon atoms substituted by heterocyclic group which may be substituted and halogen atom;

A represents hydrogen atom, halogen atom, an alkyl group having 1 to 4 carbon atoms, an alkoxy group having 1 to 4 carbon atoms, an alkylthio group having 1 to 4 carbon atoms, an alkylsulfinyl group having 1 to 4 carbon atoms or an alkylsulfonyl group having 1 to 4 carbon atoms;

$R^1$ represents hydrogen atom, halogen atom, an alkoxy group having 1 to 4 carbon atoms or hydroxyl group;

X represents oxygen or sulfur atom;

J represents

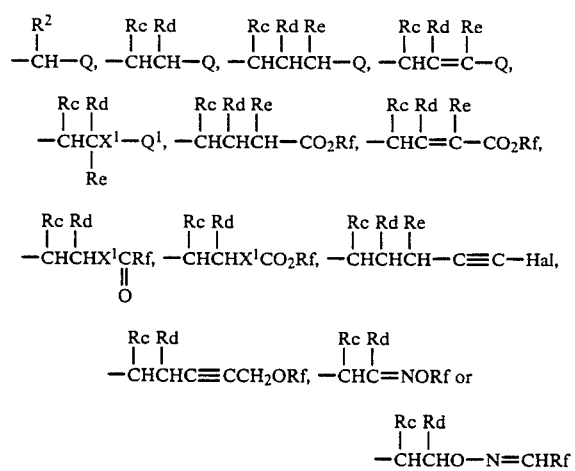

in which $R^2$, Rc, Rd, Re and Rf independently represent hydrogen atom or an alkyl group having 1 to 4 carbon atoms, $X^1$ represents $$-O-, -S-, -NH- \text{ or } -\overset{Rg}{\underset{|}{N}}-$$

(Rg represents an alkyl group having 1 to 4 carbon atoms) and Hal represents halogen atom, Q represents a substituted phenyl group, a naphthyl group which may be substituted or a heterocyclic group which may be substituted, and $Q^1$ represents a phenyl group which may be substituted, a naphthyl group which may be substituted or a heterocyclic group which may be substituted; a process for producing said derivatives and insecticidal, acaricidal or nematicidal compositions and compositions for expelling ticks parasitic on animals containing as an active ingredient at least one of said derivatives.

After the intensive researches, the present inventors have found that the compounds represented by the general formula [I] have excellent insecticidal, acari-. cidal and nematicidal activities.

For example, the known compounds of the formula [II] have strong insecticidal, acaricidal, nematicidal and fungicidal activities and have wide insecticidal spectrum and are excellent in prompt-effectiveness. On the other hand, the compounds of the present invention are slow in effectiveness because they have action to inhibit metamorphosis of insect pests. Moreover, the compounds of the present invention are effective, with very low drug-concentration, on various kinds of insect pests; e.g., agricultural insect pests such as green rice leafhopper (*Nephotettix cincticeps*), brown rice planthopper (*Nilaparvata lugens*), green peach aphid (*Myzus persicae*), diamondback moth (*Plutella xylostella*); sanitary insect pests such as house mosquito (*Culex pipiens palens*), house fly (*Musca domestica*), German cockroach (*Blattella germanica*), ant (Formicidae); stored product insect pests such as maize weevil (*Sitophilus oryzae*), red flour beetle (*Tribolium castaneum*), almond moth (*Cadra cautella*); house insect pests such as termites and veterinary insect pests such as ticks, mites, acarids, lice and the like. In other words, the compounds of the present invention can effectively control and prevent Dictyoptera, Isoptera, Hemiptera, Lepidoptera, Coleoptera, Hymenoptera, Diptera, ticks and lice.

The above-mentioned effects are described in detail in the biological examples later described.

In the substituent "J" in the above-mentioned formula [I], when Q represents an aryl group, J represents a substituted phenyl group or a substituted or unsubstituted napthyl group, and when $Q^1$ represents an aryl group, J represents a phenyl group which may be substituted or naphthyl group which may be substituted.

As the kinds of substituents are exemplified halogen atom, an alkyl group, an alkenyl group, an alkynyl group, a cycloalkyl group, an alkyloxy group, an alkenyloxy group, an alkynyloxy group, a methylenedioxy group, a halogenomethylenedioxy group, an alkylthio group, an alkenylthio group, an alkylsulfinyl group, an alkysulfonyl group, a cycloalkyloxy group, a haloalkyl group, a haloalkyloxy group, a haloalkylthio group, an alkylamino group, an alkylcarbonylamino group, nitro group, cyano group, hydroxyl group, an alkylcarbonyl group, an alkoxycarbonyl group, carboxyl group, aryl group, aryloxy group, an arylthio group, an arylamino group, an arylcarbonyl group, an arylmethyleneoxy group, an aryloxymethyl group, an arylmethylenecarbonyl group, substituted or unsubstituted pyridyloxy group, hydroxyalkyl group, an alkylcarbonyloxy alkyl group, an alkoxyalkyl group, an alkylthioalkyl group, an alkylcarbonylalkyl group, an alkoxycarbonylalkyl group, cyanoalkyl group, haloalkylcarbonyl group.

In the substituent "J" of the general formula (I), when Q or $Q^1$ is hetero ring group, the following are raised as hetero ring; e.g., thiophene, furan, pyrrole, imidazole, thiazole, oxazole, pyrazole, pyridine, pyridazine, pyrimidine, pyrazine, benzoxazole, benzothiazole, benzothiophene, dibenzothiophene, benzofuran, benzimidazole, indole, indazole, quinoline, isoquinoline, quinoxaline. In case that the hetero ring groups have substituents, the following is raised as the kinds of their substituent: e.g., halogen atom, an alkyl group, an alkoxy group, an alkylthio group, an alkylsulfonyl group, haloalkyl group, haloalkoxy group, nitro group, cyano group, an alkylcarbonyl group, phenyl group, substituted aryl group.

The compounds of the present invention may be produced by many producing methods. These methods are, for example, as follows:

Scheme (1)

(Process 1 - a)

-continued
Scheme (1)

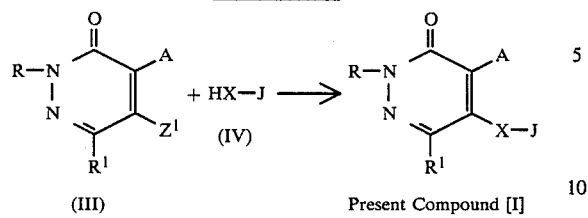

(III)   Present Compound [I]

(Process 1 - b)

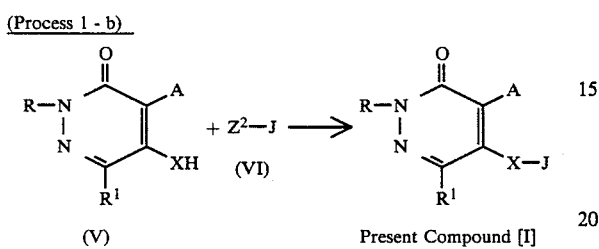

(V)   Present Compound [I]

Scheme (2)

(Process 2 - a)

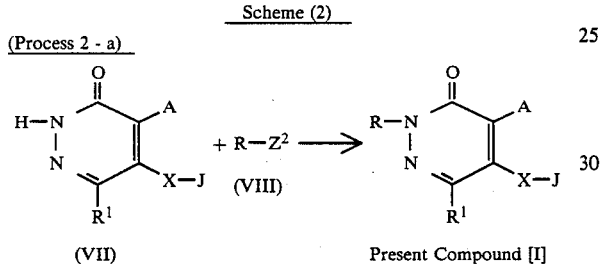

(VII)   Present Compound [I]

(Process 2 - b)

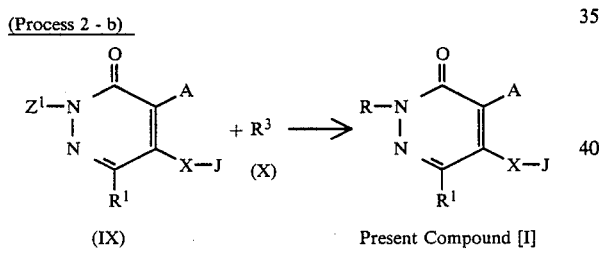

(IX)   Present Compound [I]

(Process 2 - c)

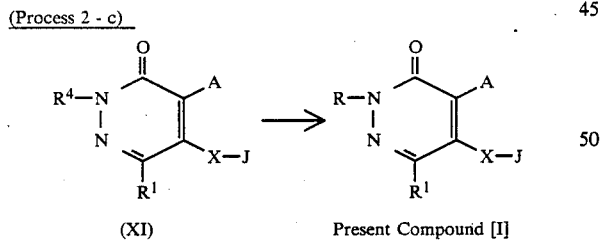

(XI)   Present Compound [I]

Scheme (3)

(Process 3 - a)

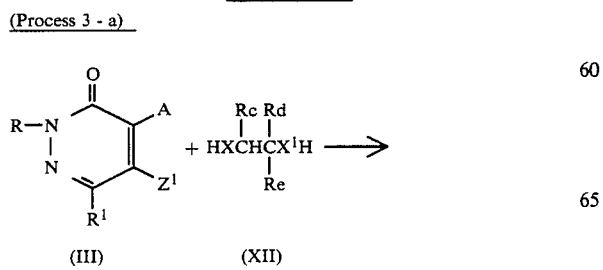

(III)   (XII)

-continued
Scheme (3)

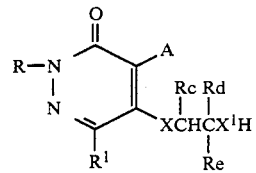

(XIII)

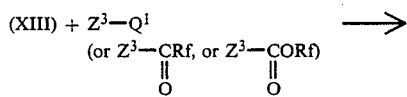

(XIV)

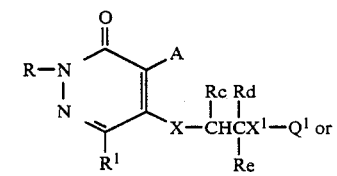

Present Compound

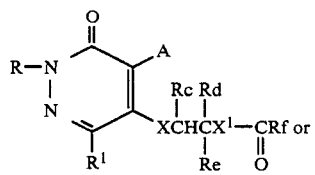

Present Compound

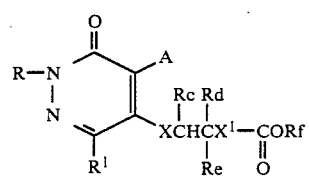

Present Compound

In the above schemes (1), (2) and (3), R, A, $R^1$, X, $X^1$, Rc, Rd, Re, Rf, $Q^1$ and J each have the same meanings as defined above and $Z^1$ represents halogen atom or azole group; $Z^2$ represents halogen atom, alkylsulfonate group and arylsulfonate group; $Z^3$ represents halogen atom, $R^3$ represents compounds having double bond and $R^4$ represents substituents having reactive functional group.

In the reaction shown in the schemes (1), (2) and (3), as the solvent may be used lower alcohols such as methanol and ethanol; ketones such as acetone and methylethylketone; hydrocarbons such as benzene and toluene; ethers such as isopropyl ether, tetrahydrofuran and 1,4-dioxane; amides such as N,N-dimethylformamides and hexamethyl phosphoric triamide; halogenated hydrocarbons such as dichloromethane and dichloroethane. If necessary, these solvents may be used as a mixture or mixture with water.

As the base may be used inorganic bases such as sodium hydride, sodium hydroxide, potassium hydroxide, sodium carbonate, potassium carbonate, sodium hydrogencarbonate and organic bases such as sodium methoxide, sodium ethoxide, triethylamine, pyridine, etc. If necessary, a tetraammonium salt such as triethylbenzylammonium chloride or the like can be added to reaction system as a catalyst. The reaction temperature ranges from −20° C. to the boiling point of the solvent used in the reaction system, and is preferably in the range of −5° C. to the boiling point of the solvent used therein. Molar ratio of the starting materials can be optionally selected for reaction. However, it is advantageous to use the materials in an equimolar ratio or near such ratio.

More specifically, in the Process 1-a of the scheme (1), the compound of the present invention of the formula [I] can be produced by reacting $Z^1$ of the compound of the formula [III] with alcohols or thiols of the formula [IV] in a suitable solvent in the presence of the base. $Z^1$ is preferable to be halogen atom, especially, chlorine or bromine atom, and azoles, especially, 1-imidazole. As the solvent, it is preferble to use N,N-dimethylformamide, methanol, ethanol, toluene and a mixture solvent of toluene-water. As the base, it is preferable to use inorganic base, especially, sodium carbonate, potassium carbonate, sodium hydroxide and potassium hydroxide. The reaction temperature is preferably in the range of from 20° C. to 50° C.

In this reaction, there may be a case that compounds are by-produced in which alcohols or thiols of the formula [IV] is substituted at the 4-position of pyridazinone ring. In that case, the by-products are required to be removed to purify the objective compounds of the present invention; thus the necessary separation and purification procedure being conducted by using conventional purification method such as re-crystallization, column chromatography and the like.

In the Process 1-b, the present compounds can be produced by reacting pyridazinone derivatives of the formula [V] with alkyl halides or alkylsulfonates of the formula [VI] in a suitable solvent in the presence of the base. $Z^2$ is preferable to be chlorine or bromine atom. As the solvent, it is preferable to use N,N-dimethylformamide, methanol, ethanol, acetonitrile, toluene and a mixture solvent of toluene-water. As the base, it is preferable to use inorganic base, especially, sodium carbonate, potassium carbonate, sodium hydroxide and potassium hydroxide. The reaction temperature is preferably in the range of from 20° C. to 120° C., with proviso that when XH of the pyridazinone derivatives of the formula [V] is OH, it is preferable in the range from 20° C. to 120° C. and that when XH is SH, it is preferable to be in the range from 20° C. to 50° C.

In the Process 2-a of the scheme (2), the present compounds can be produced by alkylating the 2-position of pyridazinone derivatives of the formula [VII] with $R-Z^2$ of the formula [VIII]. In the above procedure, the present compounds may be readily produced by adding inorganic or organic bases to the reaction system to raise the reactivity of the pyridazinone derivatives of the formula [VII].

In the Process 2-b of the scheme (2), the present compound of the formula [I] can be produced by adding N-halogenopyridazinones of the formula [IX] to olefin of the formula [X].

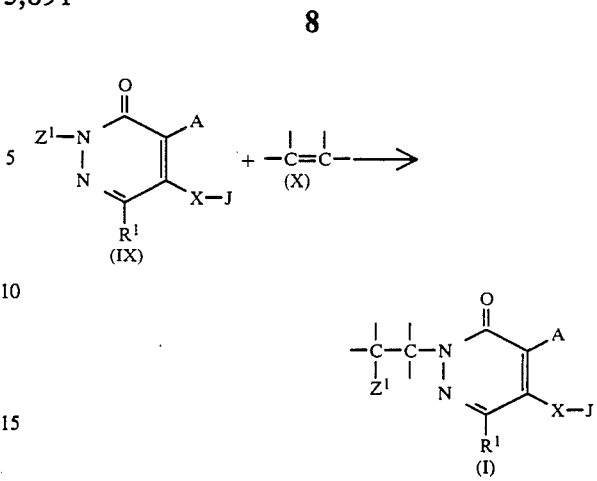

The Process 2-b is an appropriate process for producing the present compounds of the formula [I] by referring the related technology disclosed in G.B.P. 999,448.

$Z^1$ is preferable to be halogen atom, especially, chlorine, bromine or iodine atom. In this process, the present compounds of the formula [I] can be produced by reacting pyridazinone derivatives of the formula [IX] with equimolar or excess amount of (ten-time mols) of olefin of the formula [X] at the temperature of range from −5° C. to 120° C. The reaction may be well proceeded even by diluting the reaction system with a suitable solvent. As the solvent, it is preferable to use hydrocarbons, halogenated hydrocarbons, ketones, ethers, lower alcohols; more preferably, benzene, toluene, hexane, heptane, methylene chloride, chloroform, carbon tetrachloride, methyl ethyl ketone, methyl isobutyl ketone, isopropyl ether, 1,4-dioxane, methanol, ethanol. When olefin of the formula [X] having low boiling point is used, the good results can be obtained by using pressure reactor such as an autoclave.

N-Halogenopyridazinone derivative as a raw material can be synthesized according to the method disclosed by German Patent No. 1122069 or a somewhat improved method thereof. The Process 2-c of the scheme (2) is a method to produce the present compound of the formula [I] by chemically modifying the functional groups in the N-substituent ($R^4$) of the pyridazinone derivatives of the formula [XI] to be converted into an intended N-substituent (R).

More specifically, the following methods are exemplified: a method in which halogen atom contained in $R^4$ is substituted with neucleophic reagents ($R'O^-$, $R'S^-$, $CN^-$, $R'COO^-$, etc.); a method in which oxirane group contained in $R^4$ is ring-opened by the above-mentioned neucleophilic reagents or electrophillic reagents (alkyl halide Lewis acid reagent); a method in which double or triple bonds contained in $R^4$ are added with halogen molecules; a method in which the above-mentioned neucleophilic reagent is added in Michael type adding method to the double bond adjacent to the electron-withdrawing group contained in $R^4$; a method in which halogen atom contained in $R^4$ is converted into hydrogen halide in the presence of base and the hydrogen halide is splitted off from $R^4$ to form double bond; a method in which alcohol group contained in $R^4$ is oxidized into aldehyde group, ketone group or carboxyl group; a method in which the double bond contained in $R^4$ is converted into oxirane group by oxidizing agent; a method in which aldehyde group, ketone group, carboxyl group or carboxylate contained in $R^4$ is reduced into alcohol; a method in which halogen atom contained in $R^4$ is dehalogenated; a method in which alcohol group contained in $R^4$ is converted into the corresponding halide by using halogenating reagent; a method in which alcohol group and halogen atom contained in $R^4$ are intramolecularly cyclized in the presence of the base to convert into oxacycloalkyl group; and a method in which thiol group and halogen atom contained in $R^4$ are intramolecularly cyclized in the presence of the base to convert into thiacycloalkyl group.

The Process 3-a of the scheme (3) produces compounds of the formula [XIII] by reacting the compound of the formula [III] with compound of the formula [XII] in a suitable solvent in the presence of the base. Further, the produced compound in the above is reacted with heterocyclic halides or acid halides of the formula [XIV] in a suitable solvent in the presence of the base to produce the present compounds.

The compounds encompassed by the present invention are illustrated in detail by the compounds listed in Tables 1, 2 and 3. However, it should be understood that the compounds in Tables 1, 2 and 3 are merely illustrated and not to restrict the present invention.

In the Tables, Me represents methyl, Et represents ethyl, Pr represents propyl, Bu represents butyl, Pen represents pentyl, Hex represents hexyl, Ph represents unsubstituted phenyl, t represents tertiary, s represents secondary, i represents iso, and c represents cyclo.

Incidentally, a compound of the present invention which contains asymmetric carbon atom(s) includes optically active (+) compound and (−) compound.

Furthermore, compounds among the present invention in which geometric isomer exists therein include cis compound and trans compound.

TABLE 1

In Compounds of the formula:

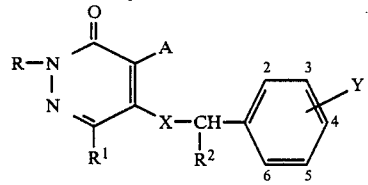

| R | A | X | $R^1$ | $R^2$ | Y |
|---|---|---|---|---|---|
| Cl$_2$CHC(Me)$_2$ | Cl | O | H | H | 4-Cl |
| Cl$_2$CHC(Me)$_2$ | Cl | O | H | H | 2,4-Cl$_2$ |
| Cl$_2$CHC(Me)$_2$ | Cl | O | H | H | 4-I |
| Cl$_2$CHC(Me)$_2$ | I | O | H | H | 4-Cl |
| Cl$_2$CHC(Me)$_2$ | I | O | H | H | 4-I |
| Cl$_2$CHC(Me)$_2$ | Cl | O | H | H | 4-Br |
| Cl$_2$CHC(Me)$_2$ | Cl | O | H | Me | 4-Cl |
| Cl$_2$CHC(Me)$_2$ | Cl | O | Cl | H | 4-Cl |
| Cl$_2$CHC(Me)$_2$ | Cl | O | H | H | 2,4,6-Cl$_3$ |
| Cl$_2$CHC(Me)$_2$ | Cl | S | H | H | 4-Cl |
| Cl$_2$CHC(Me)$_2$ | Cl | S | H | H | 4-Bu-t |
| Cl$_2$CHC(Me)$_2$ | Cl | S | H | H | 4-I |
| BrClCHC(Me)$_2$ | Cl | O | H | H | 4-Cl |
| BrClCHC(Me)$_2$ | Cl | O | H | H | 4-I |
| BrClCHC(Me)$_2$ | Br | O | H | H | 4-Cl |
| BrClCHC(Me)$_2$ | I | O | H | H | 4-Cl |
| BrClCHC(Me)$_2$ | Cl | O | H | H | 4-Br |
| BrClCHC(Me)$_2$ | Cl | O | H | H | 2,4-F$_2$ |
| BrClCHC(Me)$_2$ | Cl | S | H | H | 4-Cl |
| BrClCHC(Me)$_2$ | Cl | S | H | H | 4-Bu-t |
| Br$_2$CHC(Me)$_2$ | Cl | O | H | H | 4-Cl |
| Br$_2$CHC(Me)$_2$ | Cl | O | H | H | 4-I |
| Br$_2$CHC(Me)$_2$ | Br | O | H | H | 4-I |
| Br$_2$CHC(Me)$_2$ | I | O | H | H | 4-I |
| Br$_2$CHC(Me)$_2$ | Cl | O | H | H | 4-Br |
| Br$_2$CHC(Me)$_2$ | OMe | O | H | H | 4-Cl |
| Br$_2$CHC(Me)$_2$ | SMe | O | H | H | 4-Cl |
| Br$_2$CHC(Me)$_2$ | Cl | O | H | H | 3-CF$_3$ |
| Br$_2$CHC(Me)$_2$ | Cl | O | H | H | 4-Ph |
| Br$_2$CHC(Me)$_2$ | Cl | O | H | H | 4-OCH$_2$CF$_3$ |
| Br$_2$CHC(Me)$_2$ | Cl | S | H | H | 4-Cl |
| Br$_2$CHC(Me)$_2$ | Cl | S | H | H | 4-Bu-t |
| Br$_2$CHC(Me)$_2$ | Cl | S | H | H | 4-Et |
| BrClCHCH(Me) | Cl | O | H | H | 4-Cl |
| BrClCHCH(Me) | Cl | O | H | H | 4-I |
| Br$_2$CHCH(Me) | Cl | O | H | H | 4-Cl |
| Br$_2$CHCH(Me) | Cl | O | H | H | 4-I |
| Cl$_2$CHCH(CH$_2$Cl) | Cl | O | H | H | 4-Cl |
| Cl$_2$CHCH(CH$_2$Cl) | Cl | O | H | H | 4-I |
| Cl$_2$CHCH(CH$_2$Cl) | Br | O | H | H | 4-Cl |
| Cl$_2$CHCH(CH$_2$Cl) | I | O | H | H | 4-Cl |
| BrClCHCH(CH$_2$Cl) | Cl | O | H | H | 4-Cl |
| BrClCHCH(CH$_2$Cl) | Cl | O | H | H | 4-I |
| BrClCHCH(CH$_2$Br) | Cl | O | H | H | 4-Cl |
| Br$_2$CHCH(CH$_2$Br) | Cl | O | H | H | 4-Cl |
| Br$_2$CHCH(CH$_2$Br) | Cl | O | H | H | 4-I |
| Cl$_2$CHCCl(CH$_2$Cl) | Cl | O | H | H | 4-Cl |

TABLE 1-continued

In Compounds of the formula:

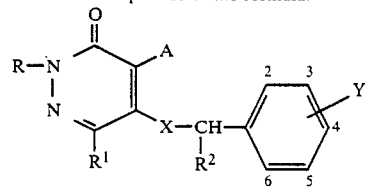

| R | A | X | R¹ | R² | Y |
|---|---|---|---|---|---|
| Cl₂CHCCl(CH₂Cl) | Cl | O | H | H | 4-I |
| Cl₂CHCCl(CH₂Cl) | I | O | H | H | 4-Cl |
| BrClCHCCl(CH₂Cl) | Cl | O | H | H | 4-Cl |
| BrClCHCCl(CH₂Cl) | Cl | O | H | H | 4-I |
| ClCH₂CCl(Me) | Cl | O | H | H | 4-Cl |
| ClCH₂CCl(Me) | Cl | O | H | H | 4-I |
| ClCH₂CCl(Me) | I | O | H | H | 4-Cl |
| BrCH₂CBr(Me) | Cl | O | H | H | 4-Cl |
| BrCH₂CBr(Me) | Cl | O | H | H | 4-I |
| BrCH₂CBr(Me) | Br | O | H | H | 4-Cl |
| BrCH₂CBr(Me) | I | O | H | H | 4-Cl |
| Cl₃CCH(Me) | Cl | O | H | H | 4-Cl |
| Cl₃CCH(Me) | Cl | O | H | H | 4-I |
| BrCl₂CCH(Me) | Cl | O | H | H | 4-Cl |
| MeCHClCHBr | Cl | O | H | H | 4-Cl |
| MeCHClCHBr | Cl | O | H | H | 4-I |
| MeCHBrCHBr | Cl | O | H | H | 4-Cl |
| MeCHBrCHBr | Cl | O | H | H | 4-I |
| MeCCl₂CH₂ | Cl | O | H | H | 4-Cl |
| MeCCl₂CH₂ | Cl | O | H | H | 4-I |
| MeCCl₂CH₂ | Br | O | H | H | 4-Cl |
| MeCCl₂CH₂ | I | O | H | H | 4-Cl |
| MeCCl₂CH₂ | Cl | O | H | H | 4-Br |
| MeCCl₂CH₂ | H | O | H | H | 4-Cl |
| MeCCl₂CH₂ | H | O | H | H | 4-I |
| MeCCl₂CH₂ | I | O | H | H | 4-I |
| MeCCl₂CH₂ | Cl | O | H | H | 2,4-Cl₂ |
| MeCCl₂CH₂ | F | O | H | H | 4-I |
| MeCCl₂CH₂ | SMe | O | H | H | 4-Cl |
| MeCCl₂CH₂ | I | O | H | Me | 4-Cl |
| MeCCl₂CH₂ | Cl | O | H | H | 4-OMe |
| MeCCl₂CH₂ | Cl | O | H | H | 4-C₆H₄Cl-4' |
| MeCCl₂CH₂ | Cl | O | H | H | 4-CN |
| MeCCl₂CH₂ | Cl | O | H | H | 3,5-Cl₂ |
| MeCCl₂CH₂ | Cl | S | H | H | 4-Cl |
| MeCCl₂CH₂ | Cl | S | H | H | 4-Bu-t |
| MeCCl₂CH₂ | Cl | S | H | H | 4-Hex |
| MeCCl₂CH₂ | Cl | S | H | H | 4-OC(Me)₂CH₂OPr |
| MeCCl₂CH₂ | Cl | S | H | H | 4-CH₂Ph |
| MeCCl₂CH₂ | Cl | S | H | H | 4-CH₂SMe |
| MeCBrClCH₂ | Cl | O | H | H | 4-Cl |
| MeCBrClCH₂ | Cl | O | H | H | 4-I |
| MeCBrClCH₂ | Br | O | H | H | 4-Cl |
| MeCBrClCH₂ | I | O | H | H | 4-Cl |
| MeCBrClCH₂ | Cl | O | H | H | 4-Br |
| MeCBrClCH₂ | Cl | O | H | H | 4-Pr |
| MeCBrClCH₂ | I | O | H | H | 4-I |
| MeCBrClCH₂ | Cl | O | H | H | 2,4-Cl₂ |
| MeCBrClCH₂ | Me | O | H | H | 4-Br |
| MeCBrClCH₂ | SMe | O | H | H | 2-F,4-Cl |
| MeCBrClCH₂ | Cl | O | OH | H | 4-Cl |
| MeCBrClCH₂ | Cl | O | H | H | 4-Pr |
| MeCBrClCH₂ | Cl | O | H | H | 2-Cl, 4-F |
| MeCBrClCH₂ | Cl | S | H | H | 4-Cl |
| MeCBrClCH₂ | Cl | S | H | H | 4-Bu-t |
| MeCBrClCH₂ | Cl | S | H | H | 4-(Q4) |
| MeCBrClCH₂ | Cl | S | H | H | 3,4-Cl₂ |
| MeCBr₂CH₂ | Cl | O | H | H | 4-Cl |
| MeCBr₂CH₂ | Cl | O | H | H | 4-I |
| MeCBr₂CH₂ | Br | O | H | H | 4-Cl |
| MeCBr₂CH₂ | I | O | H | H | 4-Cl |
| MeCBr₂CH₂ | Cl | O | H | H | 4-Br |
| MeCBr₂CH₂ | Cl | O | H | H | 2,4-Cl₂ |
| MeCBr₂CH₂ | Et | O | H | H | 4-Cl |
| MeCBr₂CH₂ | SEt | O | H | H | 4-Cl |
| MeCBr₂CH₂ | Cl | O | H | H | 4-Pen |
| MeCBr₂CH₂ | Cl | O | H | H | 4-OPr-i |
| MeCBr₂CH₂ | Cl | O | H | H | 2-Cl, 4-CF₃ |
| MeCBr₂CH₂ | Cl | S | H | H | 4-Bu-t |
| MeCBr₂CH₂ | Cl | S | H | H | 4-Cl |

TABLE 1-continued

In Compounds of the formula:

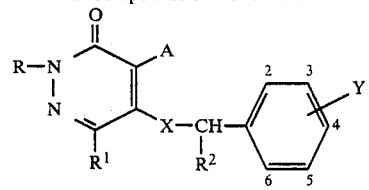

| R | A | X | R¹ | R² | Y |
|---|---|---|---|---|---|
| MeCBr₂CH₂ | Cl | S | H | H | 4-CH₂OPr |
| MeC(Br)₂CH₂ | Cl | S | H | H | 4-OPr |
| ClCH₂CHClCHCl | Cl | O | H | H | 4-Cl |
| ClCH₂CHClCHCl | Cl | O | H | H | 4-I |
| ClCH₂CHClCHCl | Br | O | H | H | 4-Cl |
| ClCH₂CHClCHCl | I | O | H | H | 4-Cl |
| BrCH₂CHClCHBr | Cl | O | H | H | 4-Cl |
| BrCH₂CHClCHBr | Cl | O | H | H | 4-I |
| BrCH₂CHClCHBr | I | O | H | H | 4-Cl |
| ClCH₂CHBrCHCl | Cl | O | H | H | 4-Cl |
| ClCH₂CHBrCHCl | Cl | O | H | H | 4-I |
| BrCH₂CHBrCHBr | Cl | O | H | H | 4-Cl |
| BrCH₂CHBrCHBr | Cl | O | H | H | 4-I |
| BrCH₂CHBrCHBr | Br | O | H | H | 4-Cl |
| BrCH₂CHBrCHBr | I | O | H | H | 4-Cl |
| ClCH₂CCl₂CH₂ | Cl | O | H | H | 4-Cl |
| ClCH₂CCl₂CH₂ | Cl | O | H | H | 4-I |
| ClCH₂CCl₂CH₂ | Br | O | H | H | 4-Cl |
| ClCH₂CCl₂CH₂ | I | O | H | H | 4-Cl |
| ClCH₂CCl₂CH₂ | Cl | O | H | H | 4-Br |
| ClCH₂CCl₂CH₂ | H | O | H | H | 4-Cl |
| ClCH₂CCl₂CH₂ | H | O | H | H | 4-I |
| ClCH₂CCl₂CH₂ | I | O | H | H | 4-I |
| ClCH₂CCl₂CH₂ | Cl | O | H | H | 2,4-Cl₂ |
| ClCH₂CCl₂CH₂ | Pr | O | H | H | 4-Cl |
| ClCH₂CCl₂CH₂ | SEt | O | H | H | 4-I |
| ClCH₂CCl₂CH₂ | Br | O | Cl | H | 4-Cl |
| ClCH₂CCl₂CH₂ | Cl | O | H | H | 2,3,4,5,6-F₅ |
| ClCH₂CCl₂CH₂ | Cl | O | H | H | 2,6-Cl₂, 4-F |
| ClCH₂CCl₂CH₂ | Cl | S | H | H | 4-Cl |
| ClCH₂CCl₂CH₂ | Cl | S | H | H | 4-Bu-t |
| ClCH₂CCl₂CH₂ | Cl | S | H | H | 4-O(CH₂)₃OMe |
| ClCH₂CCl₂CH₂ | Cl | S | H | H | 4-Et |
| ClCH₂CCl₂CH₂ | Cl | S | H | H | 4-CH₂OEt |
| ClCH₂CBrClCH₂ | Cl | O | H | H | 4-Cl |
| ClCH₂CBrClCH₂ | Cl | O | H | H | 4-I |
| ClCH₂CBrClCH₂ | Br | O | H | H | 4-Cl |
| ClCH₂CBrClCH₂ | I | O | H | H | 4-Cl |
| ClCH₂CBrClCH₂ | Cl | O | H | H | 4-Br |
| ClCH₂CBrClCH₂ | Cl | O | H | H | 2,4-Cl₂ |
| ClCH₂CBrClCH₂ | Pr-i | O | H | H | 4-Cl |
| ClCH₂CBrClCH₂ | SPr | O | H | H | 4-Cl |
| ClCH₂CBrClCH₂ | Br | O | OMe | H | 4-Cl |
| ClCH₂CBrClCH₂ | Cl | O | H | H | 4-Bu-t |
| ClCH₂CBrClCH₂ | Cl | O | H | H | 2-OMe, 4-Cl |
| ClCH₂CBrClCH₂ | Cl | S | H | H | 4-Cl |
| ClCH₂CBrClCH₂ | Cl | S | H | H | 4-Bu-t |
| ClCH₂CBrClCH₂ | Cl | S | H | H | 4-C₈H₁₇ |
| ClCH₂CBrClCH₂ | Cl | S | H | H | 4-OCH₂C₆H₄Cl-4' |
| ClCH₂CBrClCH₂ | Cl | S | H | H | 4-OCH₂CH=CHMe |
| BrCH₂CBrClCH₂ | Cl | O | H | H | 4-Cl |
| BrCH₂CBrClCH₂ | Cl | O | H | H | 4-I |
| BrCH₂CBrClCH₂ | Br | O | H | H | 4-Cl |
| BrCH₂CBrClCH₂ | I | O | H | H | 4-Cl |
| BrCH₂CBrClCH₂ | Cl | O | H | H | 4-Br |
| BrCH₂CBrClCH₂ | Bu | O | H | H | 4-Cl |
| BrCH₂CBrClCH₂ | SOMe | O | H | H | 4-Cl |
| BrCH₂CBrClCH₂ | Cl | O | H | H | 4-OBu-s |
| BrCH₂CBrClCH₂ | Cl | S | H | H | 4-Cl |
| BrCH₂CBrClCH₂ | Cl | S | H | H | 4-CH₂OMe |
| BrCH₂CBrClCH₂ | Cl | S | H | H | 4-CH₂-Q1 |
| BrCH₂CBrClCH₂ | Cl | S | H | H | 4-OPh |
| BrCH₂CBr₂CH₂ | Cl | O | H | H | 4-Cl |
| BrCH₂CBr₂CH₂ | Cl | O | H | H | 4-I |
| BrCH₂CBr₂CH₂ | Br | O | H | H | 4-Cl |
| BrCH₂CBr₂CH₂ | I | O | H | H | 4-Cl |
| BrCH₂CBr₂CH₂ | Cl | O | H | H | 4-Br |
| BrCH₂CBr₂CH₂ | OMe | O | H | H | 4-Br |
| BrCH₂CBr₂CH₂ | SO₂Et | O | H | H | 4-Cl |
| BrCH₂CBr₂CH₂ | Cl | O | H | H | 2,4,5-Cl₃ |

TABLE 1-continued

In Compounds of the formula:

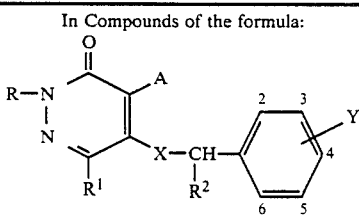

| R | A | X | R¹ | R² | Y |
|---|---|---|----|----|---|
| BrCH$_2$CBr$_2$CH$_2$ | Cl | S | H | H | 4-Cl |
| BrCH$_2$CBr$_2$CH$_2$ | Cl | S | H | H | 4-Bu-t |
| BrCH$_2$CBr$_2$CH$_2$ | Cl | S | H | H | 4-C$_6$H$_4$Cl—4' |
| BrCH$_2$CBr$_2$CH$_2$ | Cl | S | H | H | 4-CH—(C$_6$H$_3$F$_2$-2,4) |
| BrCH$_2$CBr$_2$CH$_2$ | Cl | S | H | H | 4-NMe$_2$ |
| MeCHBrCCl$_2$ | Cl | O | H | H | 4-Cl |
| MeCHBrCCl$_2$ | Cl | O | H | H | 4-I |
| MeCHBrCCl$_2$ | Cl | O | H | H | 4-Cl |
| MeCHBrCCl$_2$ | Cl | O | H | H | 4-I |
| ClCH$_2$CHClCH$_2$ | Cl | O | H | H | 4-Cl |
| ClCH$_2$CHClCH$_2$ | Cl | O | H | H | 2,4-Cl$_2$ |
| ClCH$_2$CHClCH$_2$ | Cl | O | H | H | 4-I |
| ClCH$_2$CHClCH$_2$ | Br | O | H | H | 4-Cl |
| ClCH$_2$CHClCH$_2$ | Br | O | H | H | 4-I |
| ClCH$_2$CHClCH$_2$ | I | O | H | H | 4-Cl |
| ClCH$_2$CHClCH$_2$ | I | O | H | H | 4-I |
| ClCH$_2$CHClCH$_2$ | Cl | S | H | H | 4-Cl |
| ClCH$_2$CHClCH$_2$ | Cl | S | H | H | 4-Bu-t |
| ClCH$_2$CHClCH$_2$ | Cl | S | H | H | 4-CO-Q1 |
| ClCH$_2$CHClCH$_2$ | Cl | S | H | H | 4-CH$_2$—(C$_6$H$_3$Cl$_2$-2,4) |
| ClCH$_2$CHClCH$_2$ | Cl | S | H | H | 4-OCH$_2$CH$_2$NMe$_2$ |
| ClCH$_2$CHClCH$_2$ | Cl | S | H | H | 4-O(CH$_2$)$_3$OMe |
| ClCH$_2$CHClCH$_2$ | Cl | S | H | H | 4-I |
| ClCH$_2$CHClCH$_2$ | Cl | O | H | H | 4-Cl |
| ClCH$_2$CHClCH$_2$ | Cl | O | H | H | 4-I |
| ClCH$_2$CHClCH$_2$ | Br | O | H | H | 4-Cl |
| ClCH$_2$CHClCH$_2$ | I | O | H | H | 4-Cl |
| ClCH$_2$CHClCH$_2$ | Cl | S | H | H | 4-Cl |
| ClCH$_2$CHClCH$_2$ | Cl | S | H | H | 4-Bu-t |
| ClCH$_2$CHClCH$_2$ | Cl | S | H | H | 4-CH$_2$CH=CH$_2$ |
| ClCH$_2$CHClCH$_2$ | Cl | S | H | H | 4-SPh |
| BrCH$_2$CHClCH$_2$ | Cl | O | H | H | 4-Cl |
| BrCH$_2$CHClCH$_2$ | Cl | O | H | H | 2,4-Cl$_2$ |
| BrCH$_2$CHClCH$_2$ | Cl | O | H | H | 4-I |
| BrCH$_2$CHClCH$_2$ | Br | O | H | H | 4-Cl |
| BrCH$_2$CHClCH$_2$ | I | O | H | H | 4-Cl |
| BrCH$_2$CHClCH$_2$ | Cl | S | H | H | 4-Cl |
| BrCH$_2$CHClCH$_2$ | Cl | S | H | H | 4-Bu-t |
| BrCH$_2$CHClCH$_2$ | Cl | S | H | H | 4-OCH$_2$CH$_2$SEt |
| BrCH$_2$CHClCH$_2$ | Cl | S | H | H | 4-SO$_2$Pr |
| BrCH$_2$CHClCH$_2$ | Cl | S | H | H | 4-C$_6$H$_4$F-4' |
| BrCH$_2$CHClCH$_2$ | Cl | O | H | H | 4-Cl |
| BrCH$_2$CHClCH$_2$ | Cl | O | H | H | 2,4-Cl$_2$ |
| BrCH$_2$CHClCH$_2$ | Cl | O | H | H | 4-I |
| BrCH$_2$CHClCH$_2$ | Br | O | H | H | 4-Cl |
| BrCH$_2$CHClCH$_2$ | I | O | H | H | 4-Cl |
| BrCH$_2$CHClCH$_2$ | H | O | H | H | 4-Cl |
| BrCH$_2$CHClCH$_2$ | H | O | H | H | 4-I |
| BrCH$_2$CHClCH$_2$ | Cl | S | H | H | 4-Cl |
| BrCH$_2$CHClCH$_2$ | Cl | S | H | H | 4-Bu-t |
| BrCH$_2$CHClCH$_2$ | Cl | S | H | H | 4-CH$_2$Ph |
| ICH$_2$CHClCH$_2$ | Cl | O | H | H | 4-Cl |
| ICH$_2$CHClCH$_2$ | Cl | O | H | H | 4-I |
| ICH$_2$CHClCH$_2$ | Br | O | H | H | 4-Cl |
| ICH$_2$CHClCH$_2$ | I | O | H | H | 4-Cl |
| ICH$_2$CHClCH$_2$ | I | O | H | H | 4-I |
| ICH$_2$CHClCH$_2$ | Cl | S | H | H | 4-Cl |
| ICH$_2$CHClCH$_2$ | Cl | S | H | H | 4-Bu-t |
| ICH$_2$CHClCH$_2$ | Cl | S | H | H | 4-OEt |
| ICH$_2$CHClCH$_2$ | Cl | S | H | H | 3,4-Cl$_2$ |
| ICH$_2$CHClCH$_2$ | Cl | O | H | H | 4-Cl |
| ICH$_2$CHClCH$_2$ | Cl | O | H | H | 2,4-Cl$_2$ |
| ICH$_2$CHClCH$_2$ | Cl | O | H | H | 4-I |
| ICH$_2$CHClCH$_2$ | Br | O | H | H | 4-Cl |
| ICH$_2$CHClCH$_2$ | I | O | H | H | 4-Cl |
| ICH$_2$CHClCH$_2$ | Cl | S | H | H | 4-Cl |
| ICH$_2$CHClCH$_2$ | Cl | S | H | H | 4-Bu-t |
| MeCHClCCl(Me) | Cl | O | H | H | 4-Cl |
| MeCHClCCl(Me) | Cl | O | H | H | 4-I |
| MeCHClCCl(Me) | Cl | O | H | H | 4-Cl |

TABLE 1-continued

In Compounds of the formula:

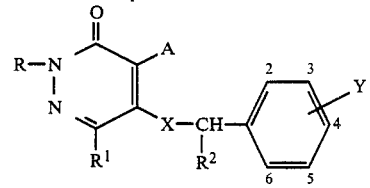

| R | A | X | R¹ | R² | Y |
|---|---|---|----|----|---|
| MeCHClCCl(Me) | Cl | O | H | H | 4-I |
| MeCHClCCl(Me) | Cl | O | H | H | 4-Cl |
| MeCHClCCl(Me) | Cl | O | H | H | 4-I |
| MeCHClCCl(Me) | Cl | O | H | H | 4-Cl |
| MeCHClCCl(Me) | Cl | O | H | H | 4-I |
| MeCCl₂CH(Me) | Cl | O | H | H | 4-Cl |
| MeCCl₂CH(Me) | Cl | O | H | H | 4-I |
| MeCBrClCH(Me) | Cl | O | H | H | 4-Cl |
| MeCBrClCH(Me) | Cl | O | H | H | 4-I |
| MeCBr₂CH(Me) | Cl | O | H | H | 4-Cl |
| MeCBr₂CH(Me) | Cl | O | H | H | 4-I |
| Me₂CClCHCl | Cl | O | H | H | 4-Cl |
| Me₂CClCHCl | Cl | O | H | H | 2,4-Cl₂ |
| Me₂CClCHCl | Cl | O | H | H | 4-I |
| Me₂CClCHCl | Br | O | H | H | 4-Cl |
| Me₂CClCHCl | Br | O | H | H | 4-I |
| Me₂CClCHCl | I | O | H | H | 4-Cl |
| Me₂CClCHCl | I | O | H | H | 4-I |
| Me₂CClCHCl | Cl | S | H | H | 4-Cl |
| Me₂CClCHCl | Cl | S | H | H | 4-Bu-t |
| Me₂CClCHCl | Cl | S | H | H | 4-O(CH₂)₃OMe |
| Me₂CClCHCl | Cl | S | H | H | 4-Et |
| Me₂CClCHCl | Cl | S | H | H | 4-OCF₃ |
| Me₂CClCHCl | Cl | O | H | H | 4-Cl |
| Me₂CClCHCl | Cl | O | H | H | 4-I |
| Me₂CClCHCl | Br | O | H | H | 4-Cl |
| Me₂CClCHCl | I | O | H | H | 4-Cl |
| Me₂CClCHCl | Cl | S | H | H | 4-Cl |
| Me₂CClCHCl | Cl | S | H | H | 4-Bu-t |
| Me₂CClCHCl | Cl | S | H | H | 4-OCH₂C₆H₄Cl-4′ |
| Me₂CClCHCl | Cl | S | H | H | 4-SOEt |
| Me₂CClCHCl | Cl | S | H | H | 4-OCH₂CH=CHMe |
| Me₂CBrCHCl | Cl | O | H | H | 4-Cl |
| Me₂CBrCHCl | Cl | O | ·H | H | 2,4-Cl₂ |
| Me₂CBrCHCl | Cl | O | H | H | 4-I |
| Me₂CBrCHCl | Br | O | H | H | 4-Cl |
| Me₂CBrCHCl | I | O | H | H | 4-Cl |
| Me₂CBrCHCl | Cl | S | H | H | 4-Cl |
| Me₂CBrCHCl | Cl | S | H | H | 4-Bu-t |
| Me₂CBrCHCl | Cl | S | H | H | 4-OPh |
| Me₂CBrCHCl | Cl | S | H | H | 4-(Q1) |
| Me₂CBrCHCl | Cl | S | H | H | 4-SBu |
| Me₂CBrCHBr | Cl | O | H | H | 4-Cl |
| Me₂CBrCHBr | Cl | O | H | H | 2,4-Cl₂ |
| Me₂CBrCHBr | Br | O | H | H | 4-Cl |
| Me₂CBrCHBr | I | O | H | H | 4-Cl |
| Me₂CBrCHBr | H | O | H | H | 4-Cl |
| Me₂CBrCHBr | H | O | H | H | 4-I |
| Me₂CBrCHBr | Cl | S | H | H | 4-Cl |
| Me₂CBrCHBr | Cl | S | H | H | 4-Bu-t |
| (ClCH₂)₂CClCH₂ | Cl | O | H | H | 4-Cl |
| (ClCH₂)₂CClCH₂ | Cl | O | H | H | 4-I |
| (ClCH₂)₂CClCH₂ | Br | O | H | H | 4-Cl |
| (ClCH₂)₂CClCH₂ | I | O | H | H | 4-Cl |
| (ClCH₂)₂CClCH₂ | Cl | O | H | H | 4-Br |
| (ClCH₂)₂CClCH₂ | Cl | O | H | H | 2-F, 4-Cl |
| (ClCH₂)₂CClCH₂ | OBu | O | H | H | 4-Cl |
| (ClCH₂)₂CClCH₂ | Cl | O | H | Me | 4-I |
| (ClCH₂)₂CClCH₂ | Cl | O | H | H | 2,5-Me₂ |
| (ClCH₂)₂CClCH₂ | Cl | O | H | H | 4-OCHF₂ |
| (ClCH₂)₂CClCH₂ | Cl | O | H | H | 2,4,6-Cl₃ |
| (ClCH₂)₂CClCH₂ | Cl | S | H | H | 4-Cl |
| (ClCH₂)₂CClCH₂ | Cl | S | H | H | 4-Bu-t |
| (ClCH₂)₂CClCH₂ | Cl | S | H | H | 4-SO₂Et |
| (ClCH₂)₂CClCH₂ | Cl | S | H | H | 4-SMe |
| (ClCH₂)₂CClCH₂ | Cl | S | H | H | 4-I |
| (ClCH₂)₂CClCH₂ | Cl | S | H | H | 4-O(CH₂)₃OMe |
| (ClCH₂)₂CBrCH₂ | Cl | O | H | H | 4-Cl |
| (ClCH₂)₂CBrCH₂ | Cl | O | H | H | 4-I |
| (ClCH₂)₂CBrCH₂ | Br | O | H | H | 4-Cl |

TABLE 1-continued

In Compounds of the formula:

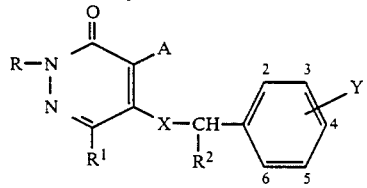

| R | A | X | R¹ | R² | Y |
|---|---|---|----|----|---|
| (ClCH₂)₂CBrCH₂ | I | O | H | H | 4-Cl |
| (ClCH₂)₂CBrCH₂ | Cl | O | H | H | 4-Br |
| (ClCH₂)₂CBrCH₂ | Cl | O | H | Et | 4-Cl |
| (ClCH₂)₂CBrCH₂ | Cl | O | H | H | 4-Bu-s |
| (ClCH₂)₂CBrCH₂ | Cl | O | H | H | 2,4-F₂ |
| (ClCH₂)₂CBrCH₂ | Cl | S | H | H | 4-Cl |
| (ClCH₂)₂CBrCH₂ | Cl | S | H | H | 4-Bu-t |
| (ClCH₂)₂CBrCH₂ | Cl | S | H | H | 4-SPh |
| ClCH₂CBr(CH₂Br)CH₂ | Cl | O | H | H | 4-Cl |
| ClCH₂CBr(CH₂Br)CH₂ | Cl | O | H | H | 4-I |
| ClCH₂CBr(CH₂Br)CH₂ | Br | O | H | Me | 4-Cl |
| ClCH₂CBr(CH₂Br)CH₂ | Cl | O | H | H | 3-CF₃ |
| ClCH₂CBr(CH₂Br)CH₂ | Cl | O | H | H | 4-OCH₂CF₃ |
| ClCH₂CBr(CH₂Br)CH₂ | Cl | S | H | H | 4-Cl |
| ClCH₂CBr(CH₂Br)CH₂ | Cl | S | H | H | 4-Bu-t |
| ClCH₂CBr(CH₂Br)CH₂ | Cl | S | H | H | 4-CH₂C₆H₄Cl-4' |
| ClCH₂CCl(Me)CH₂ | Cl | O | H | H | 4-Cl |
| ClCH₂CCl(Me)CH₂ | Cl | O | H | H | 4-Br |
| ClCH₂CCl(Me)CH₂ | Cl | O | H | H | 2,4-Cl₂ |
| ClCH₂CCl(Me)CH₂ | Cl | O | H | H | 4-I |
| ClCH₂CCl(Me)CH₂ | Br | O | H | H | 4-Cl |
| ClCH₂CCl(Me)CH₂ | Br | O | H | H | 2,4-Cl₂ |
| ClCH₂CCl(Me)CH₂ | I | O | H | H | 4-Cl |
| ClCH₂CCl(Me)CH₂ | I | O | H | H | 4-I |
| ClCH₂CCl(Me)CH₂ | F | O | H | H | 4-Cl |
| ClCH₂CCl(Me)CH₂ | Me | O | H | H | 4-Cl |
| ClCH₂CCl(Me)CH₂ | OMe | O | H | H | 4-Cl |
| ClCH₂CCl(Me)CH₂ | OMe | O | H | H | 4-I |
| ClCH₂CCl(Me)CH₂ | SMe | O | H | H | 4-Cl |
| ClCH₂CCl(Me)CH₂ | SO₂Me | O | H | H | 4-Cl |
| ClCH₂CCl(Me)CH₂ | Cl | O | H | Me | 4-Cl |
| ClCH₂CCl(Me)CH₂ | Cl | O | Cl | H | 4-Cl |
| ClCH₂CCl(Me)CH₂ | F | O | H | H | 4-I |
| ClCH₂CCl(Me)CH₂ | SMe | O | H | H | 2,4-Cl₂ |
| ClCH₂CCl(Me)CH₂ | I | O | H | Me | 4-Cl |
| ClCH₂CCl(Me)CH₂ | Cl | O | H | H | 4-OMe |
| ClCH₂CCl(Me)CH₂ | Cl | O | H | H | 4-C₆H₄Cl-4' |
| ClCH₂CCl(Me)CH₂ | Cl | O | H | H | 4-CN |
| ClCH₂CCl(Me)CH₂ | Cl | O | H | H | 3,5-Cl₂ |
| ClCH₂CCl(Me)CH₂ | Cl | S | H | H | 4-Cl |
| ClCH₂CCl(Me)CH₂ | Cl | S | H | H | 4-Bu-t |
| ClCH₂CCl(Me)CH₂ | Cl | S | H | H | 4-Hex |
| ClCH₂CCl(Me)CH₂ | Cl | S | H | H | 4-O-(Q4) |
| ClCH₂CCl(Me)CH₂ | Cl | S | H | H | 4-OC(Me)₂CH₂OPr |
| ClCH₂CCl(Me)CH₂ | Cl | S | H | H | 4-COC₆H₄CF₃-4' |
| ClCH₂CCl(Me)CH₂ | Cl | S | H | H | 4-COEt |
| ClCH₂CCl(Me)CH₂ | Cl | O | H | H | 4-Cl |
| ClCH₂CCl(Me)CH₂ | Cl | O | H | H | 4-Br |
| ClCH₂CCl(Me)CH₂ | Cl | O | H | H | 2,4-Cl₂ |
| ClCH₂CCl(Me)CH₂ | Cl | O | H | H | 4-I |
| ClCH₂CBr(Me)CH₂ | Br | O | H | H | 4-Cl |
| ClCH₂CCl(Me)CH₂ | Br | O | H | H | 4-I |
| ClCH₂CCl(Me)CH₂ | I | O | H | H | 4-Cl |
| ClCH₂CCl(Me)CH₂ | I | O | H | H | 4-I |
| ClCH₂CCl(Me)CH₂ | F | O | H | H | 4-Cl |
| ClCH₂CCl(Me)CH₂ | Me | O | H | H | 4-Cl |
| ClCH₂CCl(Me)CH₂ | OMe | O | H | H | 4-Cl |
| ClCH₂CCl(Me)CH₂ | OMe | O | H | H | 4-I |
| ClCH₂CCl(Me)CH₂ | SMe | O | H | H | 4-Cl |
| ClCH₂CCl(Me)CH₂ | SO₂Me | O | H | H | 4-Cl |
| ClCH₂CBr(Me)CH₂ | Cl | O | H | Me | 4-Cl |
| ClCH₂CCl(Me)CH₂ | Cl | O | Cl | H | 4-Cl |
| ClCH₂CCl(Me)CH₂ | Pr | O | H | H | 4-Cl |
| ClCH₂CCl(Me)CH₂ | SBu | O | H | H | 2-F, 4-Cl |
| ClCH₂CCl(Me)CH₂ | Cl | O | OH | H | 4-Cl |
| ClCH₂CCl(Me)CH₂ | Cl | O | H | H | 2-Cl, 4-F |
| ClCH₂CCl(Me)CH₂ | Cl | S | H | H | 4-Cl |
| ClCH₂CCl(Me)CH₂ | Cl | S | H | H | 4-Bu-t |
| ClCH₂CCl(Me)CH₂ | Cl | S | H | H | 4-COC₆H₄F-4' |
| ClCH₂CCl(Me)CH₂ | Cl | S | H | H | 3,4-Cl₂ |

TABLE 1-continued

In Compounds of the formula:

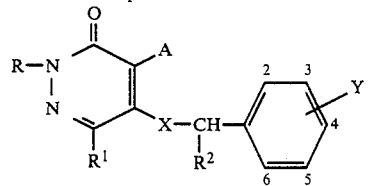

| R | A | X | $R^1$ | $R^2$ | Y |
|---|---|---|---|---|---|
| ClCH$_2$CHClCH(CH$_2$Cl) | Cl | O | H | H | 4-Cl |
| ClCH$_2$CHClCH(CH$_2$Cl) | Cl | O | H | H | 4-I |
| ClCH$_2$CHClCH(CH$_2$Cl) | Br | O | H | H | 4-Cl |
| ClCH$_2$CHClCH(CH$_2$Cl) | I | O | H | H | 4-Cl |
| ClCH$_2$CHClCH(CH$_2$Cl) | Cl | O | H | H | 4-Cl |
| ClCH$_2$CHClCH(CH$_2$Cl) | Cl | O | H | H | 4-I |
| BrCH$_2$CHClCH(CH$_2$Br) | Cl | O | H | H | 4-Cl |
| BrCH$_2$CHClCH(CH$_2$Br) | Cl | O | H | H | 4-I |
| BrCH$_2$CHClCH(CH$_2$Br) | Cl | O | H | H | 4-Cl |
| BrCH$_2$CHClCH(CH$_2$Br) | Cl | O | H | H | 4-I |
| BrCH$_2$CHClCH(CH$_2$Br) | Br | O | H | H | 4-Cl |
| BrCH$_2$CHClCH(CH$_2$Br) | I | O | H | H | 4-Cl |
| MeCCl$_2$CH(CH$_2$Cl) | Cl | O | H | H | 4-Cl |
| MeCCl$_2$CH(CH$_2$Cl) | Cl | O | H | H | 4-I |
| MeCCl$_2$CH(CH$_2$Cl) | Br | O | H | H | 4-Cl |
| MeCCl$_2$CH(CH$_2$Cl) | I | O | H | H | 4-Cl |
| MeCCl$_2$CH(CH$_2$Cl) | Cl | O | H | H | 4-Cl |
| MeCCl$_2$CH(CH$_2$Cl) | Cl | O | H | H | 4-I |
| MeCCl$_2$CH(CH$_2$Cl) | I | O | H | H | 4-Cl |
| ClCH$_2$CHClCHCl | Cl | O | H | H | 4-Cl |
| ClCH$_2$CHClCHCl | Cl | O | H | H | 4-I |
| ClCH$_2$CHBrCHCl | Cl | O | H | H | 4-Cl |
| ClCH$_2$CHBrCHCl | Cl | O | H | H | 4-I |
| (Me)$_2$CClCH(CH$_2$Br) | Cl | O | H | H | 4-Cl |
| (Me)$_2$CClCH(CH$_2$Br) | Cl | O | H | H | 4-I |
| (Me)$_2$CClCH(CH$_2$Br) | Br | O | H | H | 4-Cl |
| (Me)$_2$CClCH(CH$_2$Br) | I | O | H | H | 4-Cl |
| (Me)$_2$CBrCH(CH$_2$Br) | Cl | O | H | H | 4-Cl |
| (Me)$_2$CBrCH(CH$_2$Br) | Cl | O | H | H | 4-I |
| (Me)$_2$CBrCH(CH$_2$Br) | Br | O | H | H | 4-Cl |
| (Me)$_2$CBrCH(CH$_2$Br) | I | O | H | H | 4-Cl |
| (Me)$_2$CClCH(C$_2$H$_4$Br) | Cl | O | H | H | 4-Cl |
| (Me)$_2$CClCH(C$_2$H$_4$Br) | Cl | O | H | H | 4-I |
| (Me)$_2$CBrCH(C$_2$H$_4$Br) | Cl | O | H | H | 4-Cl |
| (Me)$_2$CBrCH(C$_2$H$_5$Br) | Cl | O | H | H | 4-I |
| ClCH$_2$CHClC(Me)$_2$ | Cl | O | H | H | 4-Cl |
| ClCH$_2$CHClC(Me)$_2$ | Cl | O | H | H | 4-I |
| ClCH$_2$CHClC(Me)$_2$ | Br | O | H | H | 4-Cl |
| ClCH$_2$CHClC(Me)$_2$ | I | O | H | H | 4-Cl |
| ClCH$_2$CHBrC(Me)$_2$ | Cl | O | H | H | 4-Cl |
| ClCH$_2$CHBrC(Me)$_2$ | Cl | O | H | H | 4-I |
| BrCH$_2$CHClC(Me)$_2$ | Cl | O | H | H | 4-Cl |
| BrCH$_2$CHClC(Me)$_2$ | Cl | O | H | H | 4-I |
| BrCH$_2$CHClC(Me)$_2$ | I | O | H | H | 4-Cl |
| BrCH$_2$CHClC(Me)$_2$ | Cl | O | H | H | 4-Cl |
| BrCH$_2$CHClC(Me)$_2$ | Cl | O | H | H | 4-I |
| BrCH$_2$CHClC(Me)$_2$ | I | O | H | H | 4-Cl |
| ClCH$_2$CHClCH(Me) | Cl | O | H | H | 4-Cl |
| ClCH$_2$CHClCH(Me) | Cl | O | H | H | 4-I |
| ClCH$_2$CHClCH(Me) | Br | O | H | H | 4-Cl |
| ClCH$_2$CHClCH(Me) | I | O | H | H | 4-Cl |
| ClCH$_2$CHBrCH(Me) | Cl | O | H | H | 4-Cl |
| ClCH$_2$CHBrCH(Me) | Cl | O | H | H | 4-I |
| MeCHClCH(CH$_2$Cl) | Cl | O | H | H | 4-Cl |
| MeCHClCH(CH$_2$Cl) | Cl | O | H | H | 4-I |
| MeCHClCH(CH$_2$Cl) | Br | O | H | H | 4-Cl |
| MeCHClCH(CH$_2$Cl) | I | O | H | H | 4-Cl |
| MeCHBrCH(CH$_2$Cl) | Cl | O | H | H | 4-Cl |
| MeCHBrCH(CH$_2$Cl) | Cl | O | H | H | 4-I |
| ClCH$_2$CCl$_2$CHCl | Cl | O | H | H | 4-Cl |
| ClCH$_2$CCl$_2$CHCl | Cl | O | H | H | 4-I |
| ClCH$_2$CCl$_2$CHCl | Br | O | H | H | 4-Cl |
| ClCH$_2$CCl$_2$CHCl | I | O | H | H | 4-Cl |
| ClCH$_2$CBrClCHCl | Cl | O | H | H | 4-Cl |
| ClCH$_2$CBrClCHCl | Cl | O | H | H | 4-I |
| ClCH$_2$CHClCCl(Me) | Cl | O | H | H | 4-Cl |
| ClCH$_2$CHClCCl(Me) | Cl | O | H | H | 4-I |
| ClCH$_2$CHClCCl(Me) | Br | O | H | H | 4-Cl |
| ClCH$_2$CHClCCl(Me) | I | O | H | H | 4-Cl |
| ClCH$_2$CHBrCCl(Me) | Cl | O | H | H | 4-Cl |

TABLE 1-continued

In Compounds of the formula:

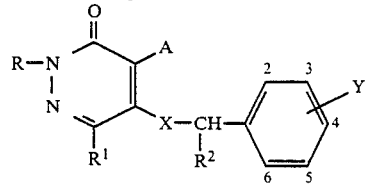

| R | A | X | R¹ | R² | Y |
|---|---|---|----|----|---|
| ClCH₂CHBrCCl(Me) | Cl | O | H | H | 4-I |
| Cl₂CHCHClCH₂ | Cl | O | H | H | 4-Cl |
| Cl₂CHCHClCH₂ | Cl | O | H | H | 4-I |
| Cl₂CHCHClCH₂ | Br | O | H | H | 4-Cl |
| Cl₂CHCHClCH₂ | I | O | H | H | 4-Cl |
| BrClCHCHBrCH₂ | Cl | O | H | H | 4-Cl |
| BrClCHCHBrCH₂ | Cl | O | H | H | 4-I |
| BrClCHCHBrCH₂ | Br | O | H | H | 4-Cl |
| BrClCHCHBrCH₂ | I | O | H | H | 4-Cl |
| Cl₂CHCCl₂CH₂ | Cl | O | H | H | 4-Cl |
| Cl₂CHCCl₂CH₂ | Cl | O | H | H | 4-Br |
| Cl₂CHCCl₂CH₂ | Cl | O | H | H | 4-I |
| Cl₂CHCCl₂CH₂ | Br | O | H | H | 4-Cl |
| Cl₂CHCCl₂CH₂ | Br | O | H | H | 4-I |
| Cl₂CHCCl₂CH₂ | I | O | H | H | 4-Cl |
| Cl₂CHCCl₂CH₂ | I | O | H | H | 4-I |
| Cl₂CHCCl₂CH₂ | Et | O | H | H | 4-Cl |
| Cl₂CHCCl₂CH₂ | SEt | O | H | H | 4-Cl |
| Cl₂CHCCl₂CH₂ | Cl | O | OMe | H | 4-Cl |
| Cl₂CHCCl₂CH₂ | Cl | O | H | H | 4-Pen |
| Cl₂CHCCl₂CH₂ | Cl | O | H | H | 4-Bu-i |
| Cl₂CHCCl₂CH₂ | Cl | O | H | H | 4-OPr-i |
| Cl₂CHCCl₂CH₂ | Cl | O | H | H | 2-Cl, 4-CF₃ |
| Cl₂CHCCl₂CH₂ | Cl | S | H | H | 4-Bu-t |
| Cl₂CHCCl₂CH₂ | Cl | S | H | H | 4-Cl |
| Cl₂CHCCl₂CH₂ | Cl | S | H | H | 4-OCH₂C(Me)=CH₂ |
| Cl₂CHCCl₂CH₂ | Cl | S | H | H | 4-OPr |
| ClBrCHCClBrCH₂ | Cl | O | H | H | 4-Cl |
| ClBrCHCClBrCH₂ | Cl | O | H | H | 4-I |
| ClBrCHCClBrCH₂ | Br | O | H | H | 4-Cl |
| ClBrCHCClBrCH₂ | H | O | H | H | 4-Cl |
| ClBrCHCClBrCH₂ | H | O | H | H | 4-I |
| ClBrCHCClBrCH₂ | Bu | O | H | H | 4-Cl |
| ClBrCHCClBrCH₂ | SEt | O | H | H | 4-I |
| ClBrCHCClBrCH₂ | Cl | O | H | H | 3-Cl |
| ClBrCHCClBrCH₂ | Cl | S | H | H | 4-Cl |
| ClBrCHCClBrCH₂ | Cl | S | H | H | 4-Bu-t |
| ClCH₂CH₂CHClCH₂ | Cl | O | H | H | 4-Cl |
| ClCH₂CH₂CHClCH₂ | Cl | O | H | H | 4-I |
| ClCH₂CH₂CHClCH₂ | Br | O | H | H | 4-Cl |
| ClCH₂CH₂CHClCH₂ | I | O | H | H | 4-Cl |
| ClCH₂CH₂CHClCH₂ | Cl | O | H | H | 4-Cl |
| ClCH₂CH₂CHClCH₂ | Cl | O | H | H | 4-I |
| BrCH₂CH₂CHClCH₂ | Cl | O | H | H | 4-Cl |
| BrCH₂CH₂CHClCH₂ | Cl | O | H | H | 4-I |
| BrCH₂CH₂CHClCH₂ | Cl | O | H | H | 4-Cl |
| BrCH₂CH₂CHClCH₂ | Cl | O | H | H | 4-I |
| BrCH₂CH₂CHClCH₂ | Br | O | H | H | 4-Cl |
| BrCH₂CH₂CHClCH₂ | I | O | H | H | 4-Cl |
| MeCHClCHClCH₂ | Cl | O | H | H | 4-Cl |
| MeCHClCHClCH₂ | Cl | O | H | H | 2,4-Cl₂ |
| MeCHClCHClCH₂ | Cl | O | H | H | 4-I |
| MeCHClCHClCH₂ | Br | O | H | H | 4-Cl |
| MeCHClCHClCH₂ | Br | O | H | H | 4-I |
| MeCHClCHClCH₂ | I | O | H | H | 4-Cl |
| MeCHClCHClCH₂ | I | O | H | H | 4-I |
| MeCHClCHBrCH₂ | Cl | O | H | H | 4-Cl |
| MeCHClCHBrCH₂ | Cl | O | H | H | 2,4-Cl₂ |
| MeCHClCHBrCH₂ | Cl | O | H | H | 4-I |
| MeCHClCHBrCH₂ | Br | O | H | H | 4-Cl |
| MeCHClCHBrCH₂ | Br | O | H | H | 4-I |
| MeCHClCHBrCH₂ | I | O | H | H | 4-Cl |
| MeCHClCHBrCH₂ | I | O | H | H | 4-I |
| MeCHBrCHClCH₂ | Cl | O | H | H | 4-Cl |
| MeCHBrCHClCH₂ | Cl | O | H | H | 2,4-Cl₂ |
| MeCHBrCHClCH₂ | Cl | O | H | H | 4-I |
| MeCHBrCHClCH₂ | Br | O | H | H | 4-Cl |
| MeCHBrCHClCH₂ | I | O | H | H | 4-Cl |
| MeCHBrCHBrCH₂ | Cl | O | H | H | 4-Cl |
| MeCHBrCHBrCH₂ | Cl | O | H | H | 4-I |

TABLE 1-continued

In Compounds of the formula:

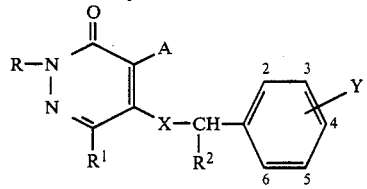

| R | A | X | R$^1$ | R$^2$ | Y |
|---|---|---|---|---|---|
| MeCHBrCHBrCH$_2$ | Br | O | H | H | 4-Cl |
| MeCHBrCHBrCH$_2$ | I | O | H | H | 4-Cl |
| ClCH$_2$CHClCHClCH$_2$ | Cl | O | H | H | 4-Cl |
| ClCH$_2$CHClCHClCH$_2$ | Cl | O | H | H | 4-I |
| ClCH$_2$CHClCHClCH$_2$ | Br | O | H | H | 4-Cl |
| ClCH$_2$CHClCHClCH$_2$ | I | O | H | H | 4-Cl |
| ClCH$_2$CHClCHBrCH$_2$ | Cl | O | H | H | 4-Cl |
| ClCH$_2$CHClCHBrCH$_2$ | Cl | O | H | H | 4-I |
| ClCH$_2$CHBrCHBrCH$_2$ | Cl | O | H | H | 4-Cl |
| ClCH$_2$CHBrCHBrCH$_2$ | Cl | O | H | H | 4-I |
| BrCH$_2$CH$_2$CHClC(Me)$_2$ | Cl | O | H | H | 4-Cl |
| BrCH$_2$CH$_2$CHClC(Me)$_2$ | Cl | O | H | H | 4-I |
| BrCH$_2$CH$_2$CHClC(Me)$_2$ | Cl | O | H | H | 4-Cl |
| BrCH$_2$CH$_2$CHClC(Me)$_2$ | Cl | O | H | H | 4-I |
| Me$_2$CClCHClCH$_2$ | Cl | O | H | H | 4-Cl |
| Me$_2$CClCHClCH$_2$ | Cl | O | H | H | 4-I |
| Me$_2$CClCHClCH$_2$ | Br | O | H | H | 4-Cl |
| Me$_2$CClCHClCH$_2$ | I | O | H | H | 4-Cl |
| Me$_2$CClCHBrCH$_2$ | Cl | O | H | H | 4-Cl |
| Me$_2$CClCHBrCH$_2$ | Cl | O | H | H | 4-I |
| Me$_2$CBrCHClCH$_2$ | Cl | O | H | H | 4-Cl |
| Me$_2$CBrCHClCH$_2$ | Cl | O | H | H | 4-I |
| Me$_2$CBrCHClCH$_2$ | I | O | H | H | 4-Cl |
| Me$_2$CBrCHBrCH$_2$ | Cl | O | H | H | 4-Cl |
| Me$_2$CBrCHBrCH$_2$ | Cl | O | H | H | 4-I |
| Me$_2$CBrCHBrCH$_2$ | Br | O | H | H | 4-Cl |
| Me$_2$CBrCHBrCH$_2$ | I | O | H | H | 4-Cl |
| ClCH$_2$CHClCH$_2$CH$_2$ | Cl | O | H | H | 4-Cl |
| ClCH$_2$CHClCH$_2$CH$_2$ | Cl | O | H | H | 4-I |
| ClCH$_2$CHClCH$_2$CH$_2$ | Br | O | H | H | 4-Cl |
| ClCH$_2$CHClCH$_2$CH$_2$ | I | O | H | H | 4-Cl |
| BrCH$_2$CHBrCH$_2$CH$_2$ | Cl | O | H | H | 4-Cl |
| BrCH$_2$CHBrCH$_2$CH$_2$ | Cl | O | H | H | 4-I |
| BrCH$_2$CHBrCH$_2$CH$_2$ | Br | O | H | H | 4-Cl |
| BrCH$_2$CHBrCH$_2$CH$_2$ | I | O | H | H | 4-Cl |
| MeCCl$_2$CHClCH$_2$ | Cl | O | H | H | 4-Cl |
| MeCCl$_2$CHClCH$_2$ | Cl | O | H | H | 4-I |
| MeCCl$_2$CHClCH$_2$ | Br | O | H | H | 4-Cl |
| MeCCl$_2$CHClCH$_2$ | I | O | H | H | 4-Cl |
| MeCClBrCHBrCH$_2$ | Cl | O | H | H | 4-Cl |
| MeCClBrCHBrCH$_2$ | Cl | O | H | H | 4-I |
| Br(CH$_2$)$_3$CHClCH$_2$ | Cl | O | H | H | 4-Cl |
| Br(CH$_2$)$_3$CHClCH$_2$ | Cl | O | H | H | 4-I |
| Br(CH$_2$)$_3$CHBrCH$_2$ | Cl | O | H | H | 4-Cl |
| Br(CH$_2$)$_3$CHBrCH$_2$ | Cl | O | H | H | 4-I |
| PrCCl(CH$_2$Cl)CH$_2$ | Cl | O | H | H | 4-Cl |
| PrCCl(CH$_2$Cl)CH$_2$ | Cl | O | H | H | 4-I |
| PrCCl(CH$_2$Cl)CH$_2$ | I | O | H | H | 4-I |
| PrCCl(CH$_2$Cl)CH$_2$ | Cl | O | H | H | 4-Cl |
| PrCCl(CH$_2$Cl)CH$_2$ | Cl | O | H | H | 4-I |
| Br(CH$_2$)$_4$CHClCH$_2$ | Cl | O | H | H | 4-Cl |
| Br(CH$_2$)$_4$CHClCH$_2$ | Cl | O | H | H | 4-I |
| Br(CH$_2$)$_4$CHBrCH$_2$ | Cl | O | H | H | 4-Cl |
| Br(CH$_2$)$_4$CHBrCH$_2$ | Cl | O | H | H | 4-I |
| Br(CH$_2$)$_6$CHClCH$_2$ | Cl | O | H | H | 4-Cl |
| Br(CH$_2$)$_6$CHClCH$_2$ | Cl | O | H | H | 4-I |
| Br(CH$_2$)$_6$CHBrCH$_2$ | Cl | O | H | H | 4-Cl |
| Br(CH$_2$)$_6$CHBrCH$_2$ | Cl | O | H | H | 4-I |
| ClCH$_2$CH(Me) | Cl | O | H | H | 4-Cl |
| ClCH$_2$CH(Me) | Cl | O | H | H | 4-I |
| ClCH$_2$C(Me)$_2$ | Cl | O | H | H | 4-Cl |
| ClCH$_2$C(Me) | Cl | O | H | H | 4-I |
| Cl(CH$_2$)$_3$ | Cl | O | H | H | 4-Cl |
| Cl(CH$_2$)$_3$ | Cl | O | H | H | 4-I |
| Cl(CH$_2$)$_3$ | Cl | O | H | H | 2,4-Cl$_2$ |
| Cl(CH$_2$)$_3$ | Br | O | H | H | 4-Cl |
| Cl(CH$_2$)$_3$ | I | O | H | H | 4-Cl |
| Cl(CH$_2$)$_3$ | Cl | S | H | H | 4-Cl |
| Cl(CH$_2$)$_3$ | Cl | S | H | H | 4-Bu-t |
| Br(CH$_2$)$_3$ | Cl | O | H | H | 4-Cl |

TABLE 1-continued

In Compounds of the formula:

| R | A | X | R¹ | R² | Y |
|---|---|---|----|----|---|
| Br(CH₂)₃ | Cl | O | H | H | 4-I |
| Br(CH₂)₃ | Cl | O | H | H | 2,4-Cl₂ |
| Br(CH₂)₃ | Br | O | H | H | 4-Cl |
| Br(CH₂)₃ | I | O | H | H | 4-Cl |
| Br(CH₂)₃ | Cl | S | H | H | 4-Cl |
| Br(CH₂)₃ | Cl | S | H | H | 4-Bu-t |
| I(CH₂)₃ | Cl | O | H | H | 4-Cl |
| I(CH₂)₃ | Cl | O | H | H | 4-I |
| I(CH₂)₃ | Cl | O | H | H | 2,4-Cl₂ |
| I(CH₂)₃ | Br | O | H | H | 4-Cl |
| I(CH₂)₃ | I | O | H | H | 4-Cl |
| I(CH₂)₃ | Cl | S | H | H | 4-Cl |
| I(CH₂)₃ | Cl | S | H | H | 4-Bu-t |
| MeCHClCH₂ | Cl | O | H | H | 4-Cl |
| MeCHClCH₂ | Cl | O | H | H | 4-I |
| MeCHBrCH₂ | Cl | O | H | H | 4-Cl |
| MeCHBrCH₂ | Cl | O | H | H | 4-I |
| Me₂CClC(Me)₂ | Cl | O | H | H | 4-Cl |
| Me₂CClC(Me)₂ | Cl | O | H | H | 4-I |
| Me₂CBrC(Me)₂ | Cl | O | H | H | 4-Cl |
| Me₂CBrC(Me)₂ | Cl | O | H | H | 4-I |
| MeCHClCH(Et) | Cl | O | H | H | 4-Cl |
| MeCHClCH(Et) | Cl | O | H | H | 4-I |
| MeCHBrCH(Et) | Cl | O | H | H | 4-Cl |
| MeCHBrCH(Et) | Cl | O | H | H | 4-I |
| MeCHClCH(Pr) | Cl | O | H | H | 4-Cl |
| MeCHClCH(Pr) | Cl | O | H | H | 4-I |
| MeCHBrCH(Pr) | Cl | O | H | H | 4-Cl |
| MeCHBrCH(Pr) | Cl | O | H | H | 4-I |
| MeCHClCH(Pr-i) | Cl | O | H | H | 4-Cl |
| MeCHClCH(Pr-i) | Cl | O | H | H | 4-I |
| MeCHBrCH(Pr-i) | Cl | O | H | H | 4-Cl |
| MeCHBrCH(Pr-i) | Cl | O | H | H | 4-I |
| MeCHClCH(Bu) | Cl | O | H | H | 4-Cl |
| MeCHClCH(Bu) | Cl | O | H | H | 4-I |
| MeCHBrCH(Bu) | Cl | O | H | H | 4-Cl |
| MeCHBrCH(Bu) | Cl | O | H | H | 4-I |
| MeCHClCH(Pen) | Cl | O | H | H | 4-Cl |
| MeCHClCH(Pen) | Cl | O | H | H | 4-I |
| MeCHBrCH(Pen) | Cl | O | H | H | 4-Cl |
| MeCHBrCH(Pen) | Cl | O | H | H | 4-I |
| Me₂CClCH₂ | Cl | O | H | H | 4-Cl |
| Me₂CClCH₂ | Cl | O | H | H | 4-Br |
| Me₂CClCH₂ | Br | O | H | H | 4-Cl |
| Me₂CClCH₂ | Br | O | H | H | 4-I |
| Me₂CClCH₂ | I | O | H | H | 4-Cl |
| Me₂CClCH₂ | I | O | H | H | 4-I |
| Me₂CClCH₂ | Cl | O | H | H | 2,4-Cl₂ |
| Me₂CClCH₂ | Pr-i | O | H | H | 4-Cl |
| Me₂CClCH₂ | SPr | O | H | H | 4-Cl |
| Me₂CClCH₂ | Br | O | OMe | H | 4-Cl |
| Me₂CClCH₂ | Cl | O | H | H | 4-Bu-t |
| Me₂CClCH₂ | Cl | O | H | H | 3-OBu |
| Me₂CClCH₂ | Cl | O | H | H | 4-F |
| Me₂CClCH₂ | Cl | S | H | H | 4-Cl |
| Me₂CClCH₂ | Cl | S | H | H | 4-Bu-t |
| Me₂CClCH₂ | Cl | S | H | H | 4-CF₃ |
| Me₂CClCH₂ | Cl | S | H | H | 4-CH(OH)Et |
| Me₂CClCH₂ | Cl | S | H | H | 4-OCH₂CH=CHMe |
| Me₂CBrCH₂ | Cl | O | H | H | 4-Cl |
| Me₂CBrCH₂ | Cl | O | H | H | 4-Br |
| Me₂CBrCH₂ | Br | O | H | H | 4-Cl |
| Me₂CBrCH₂ | I | O | H | H | 4-Cl |
| Me₂CBrCH₂ | H | O | H | H | 4-Cl |
| Me₂CBrCH₂ | H | O | H | H | 4-I |
| Me₂CBrCH₂ | Cl | O | H | H | 2,4-Cl₂ |
| Me₂CBrCH₂ | Bu | O | H | H | 4-Cl |
| Me₂CBrCH₂ | SOEt | O | H | H | 4-Cl |
| Me₂CBrCH₂ | I | O | Cl | H | 4-Cl |
| Me₂CBrCH₂ | Cl | O | H | H | 4-OBu-s |

TABLE 1-continued

In Compounds of the formula:

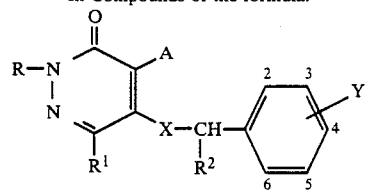

| R | A | X | R$^1$ | R$^2$ | Y |
|---|---|---|---|---|---|
| Me$_2$CBrCH$_2$ | Cl | S | H | H | 4-Cl |
| Me$_2$CBrCH$_2$ | Cl | S | H | H | 4-Bu-t |
| Me$_2$CBrCH$_2$ | Cl | S | H | H | 4-Ph |
| Me$_2$CBrCH$_2$ | Cl | S | H | H | 4-OPh |
| Me$_2$CBrCH$_2$ | Cl | S | H | H | 4-CH(OMe)Et |
| MeCHClCH(Me) | Cl | O | H | H | 4-Cl |
| MeCHClCH(Me) | Cl | O | H | H | 4-I |
| MeCHBrCH(Me) | Cl | O | H | h | 4-Cl |
| MeCHBrCH(Me) | Cl | O | H | h | 4-I |
| MeCHClC(Me)$_2$ | Cl | O | H | H | 4-Cl |
| MeCHClC(Me)$_2$ | Cl | O | H | H | 4-I |
| MeCHBrC(Me)$_2$ | Cl | O | H | H | 4-Cl |
| MeCHBrC(Me)$_2$ | Cl | O | H | H | 4-I |
| Me$_2$CClCH(Me) | Cl | O | H | H | 4-Cl |
| Me$_2$CClCH(Me) | Cl | O | H | H | 4-I |
| Me$_2$CBrCH(Me) | Cl | O | H | H | 4-Cl |
| Me$_2$CBrCH(Me) | Cl | O | H | H | 4-I |
| Me$_2$CClCH(Bu-t) | Cl | O | H | H | 4-Cl |
| Me$_2$CClCH(Bu-t) | Cl | O | H | H | 4-I |
| Me$_2$CBrCH(Bu-t) | Cl | O | H | H | 4-Cl |
| Me$_2$CBrCH(Bu-t) | Cl | O | H | H | 4-I |
| MeCHClC(Me)(Et) | Cl | O | H | H | 4-Cl |
| MeCHClC(Me)(Et) | Cl | O | H | H | 4-I |
| MeCHBrC(Me)(Et) | Cl | O | H | H | 4-Cl |
| MeCHBrC(Me)(Et) | Cl | O | H | H | 4-I |
| Cl(CH$_2$)$_4$ | Cl | O | H | H | 4-Cl |
| Cl(CH$_2$)$_4$ | Cl | O | H | H | 2,4-Cl$_2$ |
| Cl(CH$_2$)$_4$ | Cl | O | H | H | 4-I |
| Cl(CH$_2$)$_4$ | Br | O | H | H | 4-Cl |
| Cl(CH$_2$)$_4$ | I | O | H | H | 4-Cl |
| Cl(CH$_2$)$_4$ | Cl | S | H | H | 4-Cl |
| Cl(CH$_2$)$_4$ | Cl | S | H | H | 4-Bu-t |
| Br(CH$_2$)$_4$ | Cl | O | H | H | 4-Cl |
| Br(CH$_2$)$_4$ | Cl | O | H | H | 2,4-Cl$_2$ |
| Br(CH$_2$)$_4$ | Cl | O | H | H | 4-I |
| Br(CH$_2$)$_4$ | Br | O | H | H | 4-Cl |
| Br(CH$_2$)$_4$ | I | O | H | H | 4-Cl |
| Br(CH$_2$)$_4$ | Cl | S | H | H | 4-Cl |
| Br(CH$_2$)$_4$ | Cl | S | H | H | 4-Bu-t |
| I(CH$_2$)$_4$ | Cl | O | H | H | 4-Cl |
| I(CH$_2$)$_4$ | Cl | O | H | H | 2,4-Cl$_2$ |
| I(CH$_2$)$_4$ | Cl | O | H | H | 4-I |
| I(CH$_2$)$_4$ | Br | O | H | H | 4-Cl |
| I(CH$_2$)$_4$ | I | O | H | H | 4-Cl |
| I(CH$_2$)$_4$ | Cl | S | H | H | 4-Cl |
| I(CH$_2$)$_4$ | Cl | S | H | H | 4-Bu-t |
| MeCHClCH$_2$CH$_2$ | Cl | O | H | H | 4-Cl |
| MeCHClCH$_2$CH$_2$ | Cl | O | H | H | 4-I |
| Cl(CH$_2$)$_5$ | Cl | O | H | H | 4-Cl |
| Cl(CH$_2$)$_5$ | Cl | O | H | H | 4-I |
| Br(CH$_2$)$_5$ | Cl | O | H | H | 4-Cl |
| Br(CH$_2$)$_5$ | Cl | O | H | H | 4-I |
| I(CH$_2$)$_5$ | Cl | O | H | H | 4-Cl |
| I(CH$_2$)$_5$ | Cl | O | H | H | 4-I |
| MeCHBrCH$_2$CH$_2$CH$_2$ | Cl | O | H | H | 4-Cl |
| MeCHBrCH$_2$CH$_2$CH$_2$ | Cl | O | H | H | 4-I |
| Cl(CH$_2$)$_6$ | Cl | O | H | H | 4-Cl |
| Cl(CH$_2$)$_6$ | Cl | O | H | H | 4-I |
| I(CH$_2$)$_6$ | Cl | O | H | H | 4-Cl |
| I(CH$_2$)$_6$ | Cl | O | H | H | 4-I |
| Br(CH$_2$)$_8$ | Cl | O | H | H | 4-Cl |
| Br(CH$_2$)$_8$ | Cl | O | H | H | 4-I |
| I(CH$_2$)$_8$ | Cl | O | H | H | 4-Cl |
| I(CH$_2$)$_8$ | Cl | O | H | H | 4-I |
| EtCHClCH$_2$ | Cl | O | H | H | 4-Cl |
| EtCHClCH$_2$ | Cl | O | H | H | 4-I |
| EtCHBrCH$_2$ | Cl | O | H | H | 4-Cl |
| EtCHBrCH$_2$ | Cl | O | H | H | 4-I |
| i-PrCCl(Et)CH$_2$ | Cl | O | H | H | 4-Cl |
| i-PrCCl(Et)CH$_2$ | Cl | O | H | H | 4-Br |

TABLE 1-continued

In Compounds of the formula:

| R | A | X | R$^1$ | R$^2$ | Y |
|---|---|---|---|---|---|
| i-PrCCl(Et)CH$_2$ | Cl | O | H | H | 4-I |
| i-PrCCl(Et)CH$_2$ | Br | O | H | H | 4-Cl |
| i-PrCCl(Et)CH$_2$ | Br | O | H | H | 4-I |
| i-PrCCl(Et)CH$_2$ | I | O | H | H | 4-Cl |
| i-PrCCl(Et)CH$_2$ | I | O | H | H | 4-I |
| i-PrCCl(Et)CH$_2$ | Cl | O | H | H | 2,4-Cl$_2$ |
| i-PrCCl(Et)CH$_2$ | OMe | O | H | H | 4-Br |
| i-PrCCl(Et)CH$_2$ | SO$_2$Pr | O | H | H | 4-Cl |
| i-PrCCl(Et)CH$_2$ | Cl | O | H | H | 4-OPr |
| i-PrCCl(Et)CH$_2$ | Cl | O | H | H | 4-CF$_3$ |
| i-PrCCl(Et)CH$_2$ | Cl | O | H | H | 2,4,5-Cl$_3$ |
| i-PrCCl(Et)CH$_2$ | Cl | S | H | H | 4-Cl |
| i-PrCCl(Et)CH$_2$ | Cl | S | H | H | 4-Bu-t |
| i-PrCCl(Et)CH$_2$ | Cl | S | H | H | 4-C$_6$H$_4$Cl-' |
| i-PrCCl(Et)CH$_2$ | Cl | S | H | H | 4-OC$_6$H$_4$F-4' |
| i-PrCCl(Et)CH$_2$ | Cl | S | H | H | 4-SiMe$_3$ |
| i-PrCBr(Et)CH$_2$ | Cl | O | H | H | 4-Cl |
| i-PrCBr(Et)CH$_2$ | Cl | O | H | H | 4-Br |
| i-PrCBr(Et)CH$_2$ | Cl | O | H | H | 4-I |
| i-PrCBr(Et)CH$_2$ | Br | O | H | H | 4-Cl |
| i-PrCBr(Et)CH$_2$ | I | O | H | H | 4-Cl |
| i-PrCBr(Et)CH$_2$ | H | O | H | H | 4-Cl |
| i-PrCBr(Et)CH$_2$ | H | O | H | H | 4-I |
| i-PrCBr(Et)CH$_2$ | Cl | O | H | H | 2,4-Cl$_2$ |
| i-PrCBr(Et)CH$_2$ | Cl | O | H | H | 2-F, 4-Cl |
| i-PrCBr(Et)CH$_2$ | OEt | O | H | H | 4-Cl |
| i-PrCBr(Et)CH$_2$ | Cl | O | H | Me | 4-I |
| i-PrCBr(Et)CH$_2$ | Cl | O | H | H | 4-Me |
| i-PrCBr(Et)CH$_2$ | Cl | O | H | H | 2,5-Me$_2$ |
| i-PrCBr(Et)CH$_2$ | Cl | O | H | H | 4-OCHF$_2$ |
| i-PrCBr(Et)CH$_2$ | Cl | O | H | H | 2,4,5-Cl$_3$ |
| i-PrCBr(Et)CH$_2$ | Cl | S | H | H | 4-Cl |
| i-PrCBr(Et)CH$_2$ | Cl | S | H | H | 4-Bu-t |
| i-PrCBr(Et)CH$_2$ | Cl | S | H | H | 3-Me |
| i-PrCBr(Et)CH$_2$ | Cl | S | H | H | 4-CH=CHMe |
| i-PrCBr(Et)CH$_2$ | Cl | S | H | H | 4-C(Me)$_2$CH$_2$CN |
| i-PrCBr(Et)CH$_2$ | Cl | S | H | H | 4-O(CH$_2$)$_3$OMe |
| EtCCl(Me)CH$_2$ | Cl | O | H | H | 4-Cl |
| EtCCl(Me)CH$_2$ | Cl | O | H | H | 4-Br |
| EtCCl(Me)CH$_2$ | Cl | O | H | H | 4-I |
| EtCCl(Me)CH$_2$ | Cl | O | H | H | 2,4-Cl$_2$ |
| EtCCl(Me)CH$_2$ | Br | O | H | H | 4-Cl |
| EtCCl(Me)CH$_2$ | Br | O | H | H | 4-I |
| EtCCl(Me)CH$_2$ | I | O | H | H | 4-Cl |
| EtCCl(Me)CH$_2$ | I | O | H | H | 4-I |
| EtCCl(Me)CH$_2$ | F | O | H | H | 4-Cl |
| EtCCl(Me)CH$_2$ | Me | O | H | H | 4-Cl |
| EtCCl(Me)CH$_2$ | OMe | O | H | H | 4-Cl |
| EtCCl(Me)CH$_2$ | OMe | O | H | H | 4-I |
| EtCCl(Me)CH$_2$ | SMe | O | H | H | 4-Cl |
| EtCCl(Me)CH$_2$ | SMe | O | H | H | 4-I |
| EtCCl(Me)CH$_2$ | SO$_2$Me | O | H | H | 4-Cl |
| EtCCl(Me)CH$_2$ | Cl | O | H | Me | 4-Cl |
| EtCCl(Me)CH$_2$ | Cl | O | Cl | H | 4-Cl |
| EtCCl(Me)CH$_2$ | Cl | O | H | H | 2,Cl, 4-Br |
| EtCCl(Me)CH$_2$ | OBu | O | H | H | 4-Cl |
| EtCCl(Me)CH$_2$ | Cl | O | H | Et | 4-Cl |
| EtCCl(Me)CH$_2$ | Cl | O | H | H | 4-Bu-s |
| EtCCl(Me)CH$_2$ | Cl | O | H | H | 3,4-Cl$_2$ |
| EtCCl(Me)CH$_2$ | Cl | O | H | H | 4-OCF$_3$ |
| EtCCl(Me)CH$_2$ | Cl | O | H | H | 2,4-F$_2$ |
| EtCCl(Me)CH$_2$ | Cl | S | H | H | 4-Cl |
| EtCCl(Me)CH$_2$ | Cl | S | H | H | 4-Bu-t |
| EtCCl(Me)CH$_2$ | Cl | S | H | H | 4-Me |
| EtCCl(Me)CH$_2$ | Cl | S | H | H | 4-OPr |
| EtCCl(Me)CH$_2$ | Cl | S | H | H | 4-CH$_2$—(C$_6$H$_3$Cl$_2$-2,4) |
| EtCCl(Me)CH$_2$ | Cl | S | H | H | 4-COC$_6$H$_4$Cl-4' |
| EtCCl(Me)CH$_2$ | Cl | S | H | H | 4-OCH(Me)CH$_2$OEt |
| EtCBr(Me)CH$_2$ | Cl | O | H | H | 4-Cl |
| EtCBr(Me)CH$_2$ | Cl | O | H | H | 4-Br |

TABLE 1-continued

In Compounds of the formula:

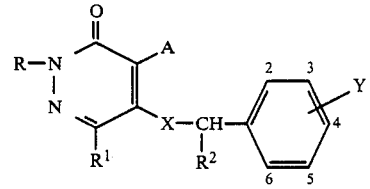

| R | A | X | R¹ | R² | Y |
|---|---|---|----|----|---|
| EtCBr(Me)CH₂ | Cl | O | H | H | 4-I |
| EtCBr(Me)CH₂ | Cl | O | H | H | 2,4-Cl₂ |
| EtCBr(Me)CH₂ | Br | O | H | H | 4-Cl |
| EtCBr(Me)CH₂ | Br | O | H | H | 4-I |
| EtCBr(Me)CH₂ | I | O | H | H | 4-Cl |
| EtCBr(Me)CH₂ | I | O | H | H | 4-I |
| EtCBr(Me)CH₂ | F | O | H | H | 4-Cl |
| EtCBr(Me)CH₂ | Me | O | H | H | 4-Cl |
| EtCBr(Me)CH₂ | OMe | O | H | H | 4-Cl |
| EtCBr(Me)CH₂ | SMe | O | H | H | 4-Cl |
| EtCBr(Me)CH₂ | Cl | O | H | Me | 4-Cl |
| EtCBr(Me)CH₂ | Br | O | H | Me | 4-Cl |
| EtCBr(Me)CH₂ | Cl | O | H | H | 3-CF₃ |
| EtCBr(Me)CH₂ | Cl | O | H | H | 4-Ph |
| EtCBr(Me)CH₂ | Cl | O | H | H | 4-OCH₂CF₃ |
| EtCBr(Me)CH₂ | Cl | O | H | H | 2,6-Cl₂ |
| EtCBr(Me)CH₂ | Cl | S | H | H | 4-Cl |
| EtCBr(Me)CH₂ | Cl | S | H | H | 4-Bu-t |
| EtCBr(Me)CH₂ | Cl | S | H | H | 4-OC₁₀H₂₁ |
| EtCBr(Me)CH₂ | Cl | S | H | H | 4-C₆H₄F-4' |
| EtCBr(Me)CH₂ | Cl | S | H | H | 4-CH₂—(C₆H₃Cl₂-3,5) |
| Et₂CClCH₂ | Cl | O | H | H | 4-Cl |
| Et₂CClCH₂ | Cl | O | H | H | 4-Br |
| Et₂CClCH₂ | Cl | O | H | H | 4-I |
| Et₂CClCH₂ | Cl | O | H | H | 2,4-Cl₂ |
| Et₂CClCH₂ | Br | O | H | H | 4-Cl |
| Et₂CClCH₂ | Br | O | H | H | 4-I |
| Et₂CClCH₂ | I | O | H | H | 4-Cl |
| Et₂CClCH₂ | I | O | H | H | 4-I |
| Et₂CClCH₂ | F | O | H | H | 4-Cl |
| Et₂CClCH₂ | Me | O | H | H | 4-Cl |
| Et₂CClCH₂ | OMe | O | H | H | 4-Cl |
| Et₂CClCH₂ | OMe | O | H | H | 4-I |
| Et₂CClCH₂ | SMe | O | H | H | 4-Cl |
| Et₂CClCH₂ | Cl | O | H | H | 4-OC₁₀H₂₁ |
| Et₂CClCH₂ | SO₂Me | O | H | H | 4-Cl |
| Et₂CClCH₂ | Cl | O | H | Me | 4-Cl |
| Et₂CClCH₂ | Cl | O | Cl | H | 4-Cl |
| Et₂CClCH₂ | F | O | H | H | 4-I |
| Et₂CClCH₂ | SMe | O | H | H | 2,4-Cl₂ |
| Et₂CClCH₂ | I | O | H | Me | 4-Cl |
| Et₂CClCH₂ | Cl | O | H | H | 4-C₆H₄Cl-4' |
| Et₂CClCH₂ | Cl | O | H | H | 4-CN |
| Et₂CClCH₂ | Cl | O | H | H | 4-OCH₂CH₂—NHCOOEt |
| Et₂CClCH₂ | Cl | S | H | H | 4-Cl |
| Et₂CClCH₂ | Cl | S | H | H | 4-Bu-t |
| Et₂CClCH₂ | Cl | S | H | H | 4-Hex |
| Et₂CClCH₂ | Cl | S | H | H | 4-OC(Me)₂CH₂OPr |
| Et₂CClCH₂ | Cl | S | H | H | 4-OCH₂CH=CH₂ |
| Et₂CClCH₂ | Cl | S | H | H | 4-CH₂CH₂Ph |
| Et₂CBrCH₂ | Cl | O | H | H | 4-Cl |
| Et₂CBrCH₂ | Cl | O | H | H | 4-Br |
| Et₂CBrCH₂ | Cl | O | H | H | 4-I |
| Et₂CBrCH₂ | Cl | O | H | H | 2,4-Cl₂ |
| Et₂CBrCH₂ | Br | O | H | H | 4-Cl |
| Et₂CBrCH₂ | I | O | H | H | 4-Cl |
| Et₂CBrCH₂ | H | O | H | H | 4-Cl |
| Et₂CBrCH₂ | H | O | H | H | 4-I |
| Et₂CBrCH₂ | F | O | H | H | 4-Cl |
| Et₂CBrCH₂ | Me | O | H | H | 4-Cl |
| Et₂CBrCH₂ | OMe | O | H | H | 4-Cl |
| Et₂CBrCH₂ | SMe | O | H | H | 4-Cl |
| Et₂CBrCH₂ | Me | O | H | H | 4-Br |
| Et₂CBrCH₂ | Cl | O | OH | H | 4-Cl |
| Et₂CBrCH₂ | Cl | O | H | H | 4-Pr |
| Et₂CBrCH₂ | Cl | O | H | H | 2-Cl, 4-F |
| Et₂CBrCH₂ | Cl | S | H | H | 4-Cl |
| Et₂CBrCH₂ | Cl | S | H | H | 4-Bu-t |
| Et₂CBrCH₂ | Cl | S | H | H | 4-(Q4) |
| Et₂CBrCH₂ | Cl | S | H | H | 4-OCH₂CH₂—NHCOOEt |

TABLE 1-continued

In Compounds of the formula:

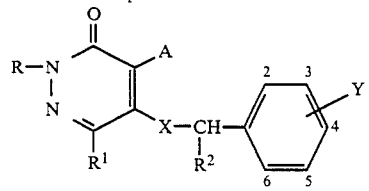

| R | A | X | R¹ | R² | Y |
|---|---|---|----|----|---|
| t-BuCHBrCH₂ | Cl | O | H | H | 4-Cl |
| t-BuCHBrCH₂ | Cl | O | H | H | 4-I |
| t-BuCHBrCH₂ | Br | O | H | H | 4-Cl |
| t-BuCHBrCH₂ | I | O | H | H | 4-Cl |
| t-BuCHBrCH₂ | Cl | O | H | H | 4-Cl |
| t-BuCHBrCH₂ | Cl | O | H | H | 4-I |
| EtCHClCH(Me) | Cl | O | H | H | 4-Cl |
| EtCHClCH(Me) | Cl | O | H | H | 4-I |
| EtCHBrCH(Me) | Cl | O | H | H | 4-Cl |
| EtCHBrCH(Me) | Cl | O | H | H | 4-I |
| EtCHClCH(Et) | Cl | O | H | H | 4-Cl |
| EtCHClCH(Et) | Cl | O | H | H | 4-I |
| EtCHBrCH(Me) | Cl | O | H | H | 4-Cl |
| EtCHBrCH(Et) | Cl | O | H | H | 4-I |
| EtCHClCH(Pr) | Cl | O | H | H | 4-Cl |
| EtCHClCH(Pr) | Cl | O | H | H | 4-I |
| EtCHBrCH(Pr) | Cl | O | H | H | 4-Cl |
| EtCHBrCH(Pr) | Cl | O | H | H | 4-I |
| i-PrCHClCH₂ | Cl | O | H | H | 4-Cl |
| i-PrCHClCH₂ | Cl | O | H | H | 4-I |
| i-PrCHBrCH₂ | Cl | O | H | H | 4-Cl |
| i-PrCHBrCH₂ | Cl | O | H | H | 4-I |
| EtCHClC(Me)₂ | Cl | O | H | H | 4-Cl |
| EtCHClC(Me)₂ | Cl | O | H | H | 4-I |
| EtCHBrC(Me)₂ | Cl | O | H | H | 4-Cl |
| EtCHBrC(Me)₂ | Cl | O | H | H | 4-I |
| EtCCl(Me)CH(Me) | Cl | O | H | H | 4-Cl |
| EtCCl(Me)CH(Me) | Cl | O | H | H | 4-I |
| EtCBr(Me)CH(Me) | Cl | O | H | H | 4-Cl |
| EtCBr(Me)CH(Me) | Cl | O | H | H | 4-I |
| i-PrCHClCH(Me) | Cl | O | H | H | 4-Cl |
| i-PrCHClCH(Me) | Cl | O | H | H | 4-I |
| i-PrCHBrCH(Me) | Cl | O | H | H | 4-Cl |
| i-PrCHBrCH(Me) | Cl | O | H | H | 4-I |
| t-BuCCl(Me)CH₂ | Cl | O | H | H | 4-Cl |
| t-BuCCl(Me)CH₂ | Cl | O | H | H | 4-Br |
| t-BuCCl(Me)CH₂ | Cl | O | H | H | 4-I |
| t-BuCCl(Me)CH₂ | Br | O | H | H | 4-Cl |
| t-BuCCl(Me)CH₂ | Br | O | H | H | 4-I |
| t-BuCCl(Me)CH₂ | I | O | H | H | 4-Cl |
| t-BuCCl(Me)CH₂ | I | O | H | H | 4-I |
| t-BuCCl(Me)CH₂ | Cl | O | H | H | 2,4-Cl₂ |
| t-BuCCl(Me)CH₂ | F | O | H | H | 4-Cl |
| t-BuCCl(Me)CH₂ | Me | O | H | H | 4-Cl |
| t-BuCCl(Me)CH₂ | OMe | O | H | H | 4-Cl |
| t-BuCCl(Me)CH₂ | OMe | O | H | H | 4-I |
| t-BuCCl(Me)CH₂ | SMe | O | H | H | 4-Cl |
| t-BuCCl(Me)CH₂ | Me | O | H | H | 4-I |
| t-BuCCl(Me)CH₂ | Cl | O | H | H | 2-F, 4-Cl |
| t-BuCCl(Me)CH₂ | OEt | O | H | H | 4-Cl |
| t-BuCCl(Me)CH₂ | Cl | O | H | Me | 4-I |
| t-BuCCl(Me)CH₂ | Cl | O | H | H | 4-Me |
| t-BuCCl(Me)CH₂ | Cl | O | H | H | 2,5-Me₂ |
| t-BuCCl(Me)CH₂ | Cl | O | H | H | 4-OCHF₂ |
| t-BuCCl(Me)CH₂ | Cl | S | H | H | 4-Cl |
| t-BuCCl(Me)CH₂ | Cl | S | H | H | 4-Bu-t |
| t-BuCCl(Me)CH₂ | Cl | S | H | H | 3-Me |
| t-BuCCl(Me)CH₂ | Cl | S | H | H | 4-SMe |
| t-BuCCl(Me)CH₂ | Cl | S | H | H | 4-I |
| t-BuCCl(Me)CH₂ | Cl | S | H | H | 4-SPr |
| t-BuCBr(Me)CH₂ | Cl | O | H | H | 4-Cl |
| t-BuCBr(Me)CH₂ | Cl | O | H | H | 4-Br |
| t-BuCBr(Me)CH₂ | Cl | O | H | H | 4-I |
| t-BuCBr(Me)CH₂ | Br | O | H | H | 4-Cl |
| t-BuCBr(Me)CH₂ | Br | O | H | H | 4-I |
| t-BuCBr(Me)CH₂ | I | O | H | H | 4-Cl |
| t-BuCBr(Me)CH₂ | I | O | H | H | 4-I |
| Br(CH₂)₆CHClCH₂ | Cl | O | H | H | 4-Cl |
| Br(CH₂)₆CHClCH₂ | Cl | O | H | H | 4-I |
| Br(CH₂)₆CHBrCH₂ | Cl | O | H | H | 4-Cl |

TABLE 1-continued

In Compounds of the formula:

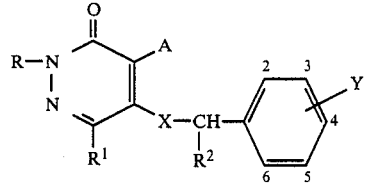

| R | A | X | R¹ | R² | Y |
|---|---|---|---|---|---|
| Br(CH₂)₆CHBrCH₂ | Cl | O | H | H | 4-I |
| ClCH₂CH(Me) | Cl | O | H | H | 4-Cl |
| ClCH₂CH(Me) | Cl | O | H | H | 4-I |
| ClCH₂C(Me)₂ | Cl | O | H | H | 4-Cl |
| ClCH₂C(Me) | Cl | O | H | H | 4-I |
| Cl(CH₂)₃ | Cl | O | H | H | 4-Cl |
| Cl(CH₂)₃ | Cl | O | H | H | 4-I |
| Cl(CH₂)₃ | Cl | O | H | H | 2,4-Cl₂ |
| Cl(CH₂)₃ | Br | O | H | H | 4-Cl |
| Cl(CH₂)₃ | I | O | H | H | 4-Cl |
| Cl(CH₂)₃ | Cl | S | H | H | 4-Cl |
| Cl(CH₂)₃ | Cl | S | H | H | 4-Bu-t |
| Br(CH₂)₃ | Cl | O | H | H | 4-Cl |
| Br(CH₂)₃ | Cl | O | H | H | 4-I |
| Br(CH₂)₃ | Cl | O | H | H | 2,4-Cl₂ |
| Br(CH₂)₃ | Br | O | H | H | 4-Cl |
| Br(CH₂)₃ | I | O | H | H | 4-Cl |
| Br(CH₂)₃ | Cl | S | H | H | 4-Cl |
| Br(CH₂)₃ | Cl | S | H | H | 4-Bu-t |
| I(CH₂)₃ | Cl | O | H | H | 4-Cl |
| I(CH₂)₃ | Cl | O | H | H | 4-I |
| I(CH₂)₃ | Cl | O | H | H | 2,4-Cl₂ |
| I(CH₂)₃ | Br | O | H | H | 4-Cl |
| I(CH₂)₃ | I | O | H | H | 4-Cl |
| I(CH₂)₃ | Cl | S | H | H | 4-Cl |
| I(CH₂)₃ | Cl | S | H | H | 4-Bu-t |
| MeCHClCH₂ | Cl | O | H | H | 4-Cl |
| MeCHClCH₂ | Cl | O | H | H | 4-I |
| MeCHBrCH₂ | Cl | O | H | H | 4-Cl |
| MeCHBrCH₂ | Cl | O | H | H | 4-I |
| Me₂CClC(Me)₂ | Cl | O | H | H | 4-Cl |
| Me₂CClC(Me)₂ | Cl | O | H | H | 4-I |
| Me₂CBrC(Me)₂ | Cl | O | H | H | 4-Cl |
| Me₂CBrC(Me)₂ | Cl | O | H | H | 4-I |
| MeCHClCH(Et) | Cl | O | H | H | 4-Cl |
| MeCHClCH(Et) | Cl | O | H | H | 4-I |
| MeCHBrCH(Et) | Cl | O | H | H | 4-Cl |
| MeCHBrCH(Et) | Cl | O | H | H | 4-I |
| MeCHClCH(Pr) | Cl | O | H | H | 4-Cl |
| MeCHClCH(Pr) | Cl | O | H | H | 4-I |
| MeCHBrCH(Pr) | Cl | O | H | H | 4-Cl |
| MeCHBrCH(Pr) | Cl | O | H | H | 4-I |
| MeCHClCH(Pr-i) | Cl | O | H | H | 4-Cl |
| MeCHClCH(Pr-i) | Cl | O | H | H | 4-I |
| MeCHBrCH(Pr-i) | Cl | O | H | H | 4-Cl |
| MeCHBrCH(Pr-i) | Cl | O | H | H | 4-I |
| MeCHClCH(Bu) | Cl | O | H | H | 4-Cl |
| MeCHClCH(Bu) | Cl | O | H | H | 4-I |
| MeCHBrCH(Bu) | Cl | O | H | H | 4-Cl |
| MeCHBrCH(Bu) | Cl | O | H | H | 4-I |
| MeCHClCH(Pen) | Cl | O | H | H | 4-Cl |
| MeCHClCH(Pen) | Cl | O | H | H | 4-I |
| MeCHBrCH(Pen) | Cl | O | H | H | 4-Cl |
| MeCHBrCH(Pen) | Cl | O | H | H | 4-I |
| Me₂CClCH₂ | Cl | O | H | H | 4-Cl |
| Me₂CClCH₂ | Cl | O | H | H | 4-Br |
| Me₂CClCH₂ | Br | O | H | H | 4-Cl |
| Me₂CClCH₂ | Br | O | H | H | 4-I |
| Me₂CClCH₂ | I | O | H | H | 4-Cl |
| Me₂CClCH₂ | I | O | H | H | 4-I |
| Me₂CClCH₂ | Cl | O | H | H | 2,4-Cl₂ |
| Me₂CClCH₂ | Pr-i | O | H | H | 4-Cl |
| Me₂CClCH₂ | SPr | O | H | H | 4-Cl |
| Me₂CClCH₂ | Br | O | OMe | H | 4-Cl |
| Me₂CClCH₂ | Cl | O | H | H | 4-Bu-t |
| Me₂CClCH₂ | Cl | O | H | H | 3-OBu |
| Me₂CClCH₂ | Cl | O | H | H | 4-F |
| Me₂CClCH₂ | Cl | S | H | H | 4-Cl |
| Me₂CClCH₂ | Cl | S | H | H | 4-Bu-t |
| Me₂CClCH₂ | Cl | S | H | H | 4-CF₃ |

TABLE 1-continued

In Compounds of the formula:

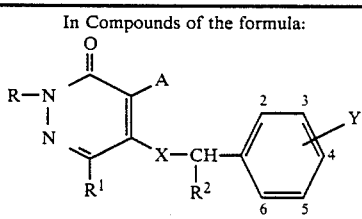

| R | A | X | R¹ | R² | Y |
|---|---|---|----|----|---|
| Me₂CClCH₂ | Cl | S | H | H | 4-CH(OH)Et |
| Me₂CClCH₂ | Cl | S | H | H | 4-OCH₂CH=CHMe |
| Me₂CBrCH₂ | Cl | O | H | H | 4-Cl |
| Me₂CBrCH₂ | Cl | O | H | H | 4-Br |
| Me₂CBrCH₂ | Br | O | H | H | 4-Cl |
| Me₂CBrCH₂ | I | O | H | H | 4-Cl |
| Me₂CBrCH₂ | H | O | H | H | 4-Cl |
| Me₂CBrCH₂ | H | O | H | H | 4-I |
| Me₂CBrCH₂ | Cl | O | H | H | 2,4-Cl₂ |
| Me₂CBrCH₂ | Bu | O | H | H | 4-Cl |
| Me₂CBrCH₂ | SOEt | O | H | H | 4-Cl |
| Me₂CBrCH₂ | I | O | Cl | H | 4-Cl |
| Me₂CBrCH₂ | Cl | O | H | H | 4-OBu-s |
| Me₂CBrCH₂ | Cl | S | H | H | 4-Cl |
| Me₂CBrCH₂ | Cl | S | H | H | 4-Bu-t |
| Me₂CBrCH₂ | Cl | S | H | H | 4-Ph |
| Me₂CBrCH₂ | Cl | S | H | H | 4-OPh |
| Me₂CBrCH₂ | Cl | S | H | H | 4-CH(OMe)Et |
| MeCHClCH(Me) | Cl | O | H | H | 4-Cl |
| MeCHClCH(Me) | Cl | O | H | H | 4-I |
| MeCHBrCH(Me) | Cl | O | H | h | 4-Cl |
| MeCHBrCH(Me) | Cl | O | H | h | 4-I |
| MeCHClC(Me)₂ | Cl | O | H | H | 4-Cl |
| MeCHClC(Me)₂ | Cl | O | H | H | 4-I |
| MeCHBrC(Me)₂ | Cl | O | H | H | 4-Cl |
| MeCHBrC(Me)₂ | Cl | O | H | H | 4-I |
| Me₂CClCH(Me) | Cl | O | H | H | 4-Cl |
| Me₂CClCH(Me) | Cl | O | H | H | 4-I |
| Me₂CBrCH(Me) | Cl | O | H | H | 4-Cl |
| Me₂CBrCH(Me) | Cl | O | H | H | 4-I |
| Me₂CClCH(Bu-t) | Cl | O | H | H | 4-Cl |
| Me₂CClCH(Bu-t) | Cl | O | H | H | 4-I |
| Me₂CBrCH(Bu-t) | Cl | O | H | H | 4-Cl |
| Me₂CBrCH(Bu-t) | Cl | O | H | H | 4-I |
| MeCHClC(Me)(Et) | Cl | O | H | H | 4-Cl |
| MeCHClC(Me)(Et) | Cl | O | H | H | 4-I |
| MeCHBrC(Me)(Et) | Cl | O | H | H | 4-Cl |
| MeCHBrC(Me)(Et) | Cl | O | H | H | 4-I |
| Cl(CH₂)₄ | Cl | O | H | H | 4-Cl |
| Cl(CH₂)₄ | Cl | O | H | H | 2,4-Cl₂ |
| Cl(CH₂)₄ | Cl | O | H | H | 4-I |
| Cl(CH₂)₄ | Br | O | H | H | 4-Cl |
| Cl(CH₂)₄ | I | O | H | H | 4-Cl |
| Cl(CH₂)₄ | Cl | S | H | H | 4-Cl |
| Cl(CH₂)₄ | Cl | S | H | H | 4-Bu-t |
| Br(CH₂)₄ | Cl | O | H | H | 4-Cl |
| Br(CH₂)₄ | Cl | O | H | H | 2,4-Cl₂ |
| Br(CH₂)₄ | Cl | O | H | H | 4-I |
| Br(CH₂)₄ | Br | O | H | H | 4-Cl |
| Br(CH₂)₄ | I | O | H | H | 4-Cl |
| Br(CH₂)₄ | Cl | S | H | H | 4-Cl |
| Br(CH₂)₄ | Cl | S | H | H | 4-Bu-t |
| I(CH₂)₄ | Cl | O | H | H | 4-Cl |
| I(CH₂)₄ | Cl | O | H | H | 2,4-Cl₂ |
| I(CH₂)₄ | Cl | O | H | H | 4-I |
| I(CH₂)₄ | Br | O | H | H | 4-Cl |
| I(CH₂)₄ | I | O | H | H | 4-Cl |
| I(CH₂)₄ | Cl | S | H | H | 4-Cl |
| I(CH₂)₄ | Cl | S | H | H | 4-Bu-t |
| MeCHClCH₂CH₂ | Cl | O | H | H | 4-Cl |
| MeCHClCH₂CH₂ | Cl | O | H | H | 4-I |
| Cl(CH₂)₅ | Cl | O | H | H | 4-Cl |
| Cl(CH₂)₅ | Cl | O | H | H | 4-I |
| Br(CH₂)₅ | Cl | O | H | H | 4-Cl |
| Br(CH₂)₅ | Cl | O | H | H | 4-I |
| I(CH₂)₅ | Cl | O | H | H | 4-Cl |
| I(CH₂)₅ | Cl | O | H | H | 4-I |
| MeCHBrCH₂CH₂CH₂ | Cl | O | H | H | 4-Cl |
| MeCHBrCH₂CH₂CH₂ | Cl | O | H | H | 4-I |
| Cl(CH₂)₆ | Cl | O | H | H | 4-Cl |

TABLE 1-continued

In Compounds of the formula:

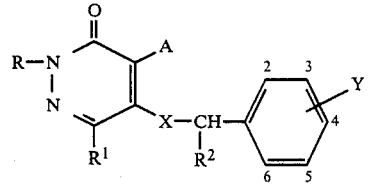

| R | A | X | R¹ | R² | Y |
|---|---|---|---|---|---|
| Cl(CH₂)₆ | Cl | O | H | H | 4-I |
| I(CH₂)₆ | Cl | O | H | H | 4-Cl |
| I(CH₂)₆ | Cl | O | H | H | 4-I |
| Br(CH₂)₈ | Cl | O | H | H | 4-Cl |
| Br(CH₂)₈ | Cl | O | H | H | 4-I |
| I(CH₂)₈ | Cl | O | H | H | 4-Cl |
| I(CH₂)₈ | Cl | O | H | H | 4-I |
| EtCHClCH₂ | Cl | O | H | H | 4-Cl |
| EtCHClCH₂ | Cl | O | H | H | 4-I |
| EtCHBrCH₂ | Cl | O | H | H | 4-Cl |
| EtCHBrCH₂ | Cl | O | H | H | 4-I |
| i-PrCCl(Et)CH₂ | Cl | O | H | H | 4-Cl |
| i-PrCCl(Et)CH₂ | Cl | O | H | H | 4-Br |
| i-PrCCl(Et)CH₂ | Cl | O | H | H | 4-I |
| i-PrCCl(Et)CH₂ | Br | O | H | H | 4-Cl |
| i-PrCCl(Et)CH₂ | Br | O | H | H | 4-I |
| i-PrCCl(Et)CH₂ | I | O | H | H | 4-Cl |
| i-PrCCl(Et)CH₂ | I | O | H | H | 4-I |
| i-PrCCl(Et)CH₂ | Cl | O | H | H | 2,4-Cl₂ |
| i-PrCCl(Et)CH₂ | OMe | O | H | H | 4-Br |
| i-PrCCl(Et)CH₂ | SO₂Pr | O | H | H | 4-Cl |
| i-PrCCl(Et)CH₂ | Cl | O | H | H | 4-OPr |
| i-PrCCl(Et)CH₂ | Cl | O | H | H | 4-CF₃ |
| i-PrCCl(Et)CH₂ | Cl | O | H | H | 2,4,5-Cl₃ |
| i-PrCCl(Et)CH₂ | Cl | S | H | H | 4-Cl |
| i-PrCCl(Et)CH₂ | Cl | S | H | H | 4-Bu-t |
| i-PrCCl(Et)CH₂ | Cl | S | H | H | 4-C₆H₄Cl-' |
| i-PrCCl(Et)CH₂ | Cl | S | H | H | 4-OC₆H₄F-4' |
| i-PrCCl(Et)CH₂ | Cl | S | H | H | 4-SiMe₃ |
| i-PrCBr(Et)CH₂ | Cl | O | H | H | 4-Cl |
| i-PrCBr(Et)CH₂ | Cl | O | H | H | 4-Br |
| i-PrCBr(Et)CH₂ | Cl | O | H | H | 4-I |
| i-PrCBr(Et)CH₂ | Br | O | H | H | 4-Cl |
| i-PrCBr(Et)CH₂ | I | O | H | H | 4-Cl |
| i-PrCBr(Et)CH₂ | H | O | H | H | 4-Cl |
| i-PrCBr(Et)CH₂ | H | O | H | H | 4-I |
| i-PrCBr(Et)CH₂ | Cl | O | H | H | 2,4-Cl₂ |
| i-PrCBr(Et)CH₂ | Cl | O | H | H | 2-F, 4-Cl |
| i-PrCBr(Et)CH₂ | OEt | O | H | H | 4-Cl |
| i-PrCBr(Et)CH₂ | Cl | O | H | Me | 4-I |
| i-PrCBr(Et)CH₂ | Cl | O | H | H | 4-Me |
| i-PrCBr(Et)CH₂ | Cl | O | H | H | 2,5-Me₂ |
| i-PrCBr(Et)CH₂ | Cl | O | H | H | 4-OCHF₂ |
| i-PrCBr(Et)CH₂ | Cl | O | H | H | 2,4,5-Cl₃ |
| i-PrCBr(Et)CH₂ | Cl | S | H | H | 4-Cl |
| i-PrCBr(Et)CH₂ | Cl | S | H | H | 4-Bu-t |
| i-PrCBr(Et)CH₂ | Cl | S | H | H | 3-Me |
| i-PrCBr(Et)CH₂ | Cl | S | H | H | 4-CH=CHMe |
| i-PrCBr(Et)CH₂ | Cl | S | H | H | 4-C(Me)₂CH₂CN |
| i-PrCBr(Et)CH₂ | Cl | S | H | H | 4-O(CH₂)₃OMe |
| EtCCl(Me)CH₂ | Cl | O | H | H | 4-Cl |
| EtCCl(Me)CH₂ | Cl | O | H | H | 4-Br |
| EtCCl(Me)CH₂ | Cl | O | H | H | 4-I |
| EtCCl(Me)CH₂ | Cl | O | H | H | 2,4-Cl₂ |
| EtCCl(Me)CH₂ | Br | O | H | H | 4-Cl |
| EtCCl(Me)CH₂ | Br | O | H | H | 4-I |
| EtCCl(Me)CH₂ | I | O | H | H | 4-Cl |
| EtCCl(Me)CH₂ | I | O | H | H | 4-I |
| EtCCl(Me)CH₂ | F | O | H | H | 4-Cl |
| EtCCl(Me)CH₂ | Me | O | H | H | 4-Cl |
| EtCCl(Me)CH₂ | OMe | O | H | H | 4-Cl |
| EtCCl(Me)CH₂ | OMe | O | H | H | 4-I |
| EtCCl(Me)CH₂ | SMe | O | H | H | 4-Cl |
| EtCCl(Me)CH₂ | SMe | O | H | H | 4-I |
| EtCCl(Me)CH₂ | SO₂Me | O | H | H | 4-Cl |
| EtCCl(Me)CH₂ | Cl | O | H | Me | 4-Cl |
| EtCCl(Me)CH₂ | Cl | O | Cl | H | 4-Cl |
| EtCCl(Me)CH₂ | Cl | O | H | H | 2,Cl, 4-Br |
| EtCCl(Me)CH₂ | OBu | O | H | H | 4-Cl |
| EtCCl(Me)CH₂ | Cl | O | H | Et | 4-Cl |

TABLE 1-continued

In Compounds of the formula:

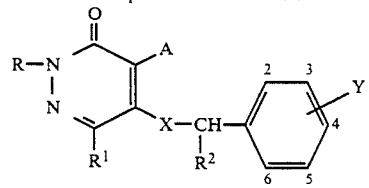

| R | A | X | R¹ | R² | Y |
|---|---|---|----|----|---|
| EtCCl(Me)CH₂ | Cl | O | H | H | 4-Bu-s |
| EtCCl(Me)CH₂ | Cl | O | H | H | 3,4-Cl₂ |
| EtCCl(Me)CH₂ | Cl | O | H | H | 4-OCF₃ |
| EtCCl(Me)CH₂ | Cl | O | H | H | 2,4-F₂ |
| EtCCl(Me)CH₂ | Cl | S | H | H | 4-Cl |
| EtCCl(Me)CH₂ | Cl | S | H | H | 4-Bu-t |
| EtCCl(Me)CH₂ | Cl | S | H | H | 4-Me |
| EtCCl(Me)CH₂ | Cl | S | H | H | 4-OPr |
| EtCCl(Me)CH₂ | Cl | S | H | H | 4-CH₂—(C₆H₃Cl₂-2,4) |
| EtCCl(Me)CH₂ | Cl | S | H | H | 4-COC₆H₄Cl-4' |
| EtCCl(Me)CH₂ | Cl | S | H | H | 4-OCH(Me)CH₂OEt |
| EtCBr(Me)CH₂ | Cl | O | H | H | 4-Cl |
| EtCBr(Me)CH₂ | Cl | O | H | H | 4-Br |
| EtCBr(Me)CH₂ | Cl | O | H | H | 4-I |
| EtCBr(Me)CH₂ | Cl | O | H | H | 2,4-Cl₂ |
| EtCBr(Me)CH₂ | Br | O | H | H | 4-Cl |
| EtCBr(Me)CH₂ | Br | O | H | H | 4-I |
| EtCBr(Me)CH₂ | I | O | H | H | 4-Cl |
| EtCBr(Me)CH₂ | I | O | H | H | 4-I |
| EtCBr(Me)CH₂ | F | O | H | H | 4-Cl |
| EtCBr(Me)CH₂ | Me | O | H | H | 4-Cl |
| EtCBr(Me)CH₂ | OMe | O | H | H | 4-Cl |
| EtCBr(Me)CH₂ | SMe | O | H | H | 4-Cl |
| EtCBr(Me)CH₂ | Cl | O | H | Me | 4-Cl |
| EtCBr(Me)CH₂ | Br | O | H | Me | 4-Cl |
| EtCBr(Me)CH₂ | Cl | O | H | H | 3-CF₃ |
| EtCBr(Me)CH₂ | Cl | O | H | H | 4-Ph |
| EtCBr(Me)CH₂ | Cl | O | H | H | 4-OCH₂CF₃ |
| EtCBr(Me)CH₂ | Cl | O | H | H | 2,6-Cl₂ |
| EtCBr(Me)CH₂ | Cl | S | H | H | 4-Cl |
| EtCBr(Me)CH₂ | Cl | S | H | H | 4-Bu-t |
| EtCBr(Me)CH₂ | Cl | S | H | H | 4-OC₁₀H₂₁ |
| EtCBr(Me)CH₂ | Cl | S | H | H | 4-C₆H₄F-4' |
| EtCBr(Me)CH₂ | Cl | S | H | H | 4-CH₂—(C₆H₃Cl₂-3,5) |
| Et₂CClCH₂ | Cl | O | H | H | 4-Cl |
| Et₂CClCH₂ | Cl | O | H | H | 4-Br |
| Et₂CClCH₂ | Cl | O | H | H | 4-I |
| Et₂CClCH₂ | Cl | O | H | H | 2,4-Cl₂ |
| Et₂CClCH₂ | Br | O | H | H | 4-Cl |
| Et₂CClCH₂ | Br | O | H | H | 4-I |
| Et₂CClCH₂ | I | O | H | H | 4-Cl |
| Et₂CClCH₂ | I | O | H | H | 4-I |
| Et₂CClCH₂ | F | O | H | H | 4-Cl |
| Et₂CClCH₂ | Me | O | H | H | 4-Cl |
| Et₂CClCH₂ | OMe | O | H | H | 4-Cl |
| Et₂CClCH₂ | OMe | O | H | H | 4-I |
| Et₂CClCH₂ | SMe | O | H | H | 4-Cl |
| Et₂CClCH₂ | Cl | O | H | H | 4-OC₁₀H₂₁ |
| Et₂CClCH₂ | SO₂Me | O | H | H | 4-Cl |
| Et₂CClCH₂ | Cl | O | H | Me | 4-Cl |
| Et₂CClCH₂ | Cl | O | Cl | H | 4-Cl |
| Et₂CClCH₂ | F | O | H | H | 4-I |
| Et₂CClCH₂ | SMe | O | H | H | 2,4-Cl₂ |
| Et₂CClCH₂ | I | O | H | Me | 4-Cl |
| Et₂CClCH₂ | Cl | O | H | H | 4-C₆H₄Cl-4' |
| Et₂CClCH₂ | Cl | O | H | H | 4-CN |
| Et₂CClCH₂ | Cl | O | H | H | 4-OCH₂CH₂—NHCOOEt |
| Et₂CClCH₂ | Cl | S | H | H | 4-Cl |
| Et₂CClCH₂ | Cl | S | H | H | 4-Bu-t |
| Et₂CClCH₂ | Cl | S | H | H | 4-Hex |
| Et₂CClCH₂ | Cl | S | H | H | 4-OC(Me)₂CH₂OPr |
| Et₂CClCH₂ | Cl | S | H | H | 4-OCH₂CH=CH₂ |
| Et₂CClCH₂ | Cl | S | H | H | 4-CH₂CH₂Ph |
| Et₂CBrCH₂ | Cl | O | H | H | 4-Cl |
| Et₂CBrCH₂ | Cl | O | H | H | 4-Br |
| Et₂CBrCH₂ | Cl | O | H | H | 4-I |
| Et₂CBrCH₂ | Cl | O | H | H | 2,4-Cl₂ |
| Et₂CBrCH₂ | Br | O | H | H | 4-Cl |
| Et₂CBrCH₂ | I | O | H | H | 4-Cl |
| Et₂CBrCH₂ | H | O | H | H | 4-Cl |

TABLE 1-continued

In Compounds of the formula:

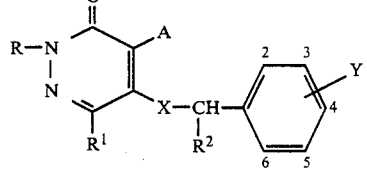

| R | A | X | R¹ | R² | Y |
|---|---|---|---|---|---|
| Et₂CBrCH₂ | H | O | H | H | 4-I |
| Et₂CBrCH₂ | F | O | H | H | 4-Cl |
| Et₂CBrCH₂ | Me | O | H | H | 4-Cl |
| Et₂CBrCH₂ | OMe | O | H | H | 4-Cl |
| Et₂CBrCH₂ | SMe | O | H | H | 4-Cl |
| Et₂CBrCH₂ | Me | O | H | H | 4-Br |
| Et₂CBrCH₂ | Cl | O | OH | H | 4-Cl |
| Et₂CBrCH₂ | Cl | O | H | H | 4-Pr |
| Et₂CBrCH₂ | Cl | O | H | H | 2-Cl, 4-F |
| Et₂CBrCH₂ | Cl | S | H | H | 4-Cl |
| Et₂CBrCH₂ | Cl | S | H | H | 4-Bu-t |
| Et₂CBrCH₂ | Cl | S | H | H | 4-(Q4) |
| Et₂CBrCH₂ | Cl | S | H | H | 4-OCH₂CH₂—NHCOOEt |
| t-BuCHBrCH₂ | Cl | O | H | H | 4-Cl |
| t-BuCHBrCH₂ | Cl | O | H | H | 4-I |
| t-BuCHBrCH₂ | Br | O | H | H | 4-Cl |
| t-BuCHBrCH₂ | I | O | H | H | 4-Cl |
| t-BuCHBrCH₂ | Cl | O | H | H | 4-Cl |
| t-BuCHBrCH₂ | Cl | O | H | H | 4-I |
| EtCHClCH(Me) | Cl | O | H | H | 4-Cl |
| EtCHClCH(Me) | Cl | O | H | H | 4-I |
| EtCHBrCH(Me) | Cl | O | H | H | 4-Cl |
| EtCHBrCH(Me) | Cl | O | H | H | 4-I |
| EtCHClCH(Et) | Cl | O | H | H | 4-Cl |
| EtCHClCH(Et) | Cl | O | H | H | 4-I |
| EtCHBrCH(Me) | Cl | O | H | H | 4-Cl |
| EtCHBrCH(Et) | Cl | O | H | H | 4-I |
| EtCHClCH(Pr) | Cl | O | H | H | 4-Cl |
| EtCHClCH(Pr) | Cl | O | H | H | 4-I |
| EtCHBrCH(Pr) | Cl | O | H | H | 4-Cl |
| EtCHBrCH(Pr) | Cl | O | H | H | 4-I |
| i-PrCHClCH₂ | Cl | O | H | H | 4-Cl |
| i-PrCHClCH₂ | Cl | O | H | H | 4-I |
| i-PrCHBrCH₂ | Cl | O | H | H | 4-Cl |
| i-PrCHBrCH₂ | Cl | O | H | H | 4-I |
| EtCHClC(Me)₂ | Cl | O | H | H | 4-Cl |
| EtCHClC(Me)₂ | Cl | O | H | H | 4-I |
| EtCHBrC(Me)₂ | Cl | O | H | H | 4-Cl |
| EtCHBrC(Me)₂ | Cl | O | H | H | 4-I |
| EtCCl(Me)CH(Me) | Cl | O | H | H | 4-Cl |
| EtCCl(Me)CH(Me) | Cl | O | H | H | 4-I |
| EtCBr(Me)CH(Me) | Cl | O | H | H | 4-Cl |
| EtCBr(Me)CH(Me) | Cl | O | H | H | 4-I |
| i-PrCHClCH(Me) | Cl | O | H | H | 4-Cl |
| i-PrCHClCH(Me) | Cl | O | H | H | 4-I |
| i-PrCHBrCH(Me) | Cl | O | H | H | 4-Cl |
| i-PrCHBrCH(Me) | Cl | O | H | H | 4-I |
| t-BuCCl(Me)CH₂ | Cl | O | H | H | 4-Cl |
| t-BuCCl(Me)CH₂ | Cl | O | H | H | 4-Br |
| t-BuCCl(Me)CH₂ | Cl | O | H | H | 4-I |
| t-BuCCl(Me)CH₂ | Br | O | H | H | 4-Cl |
| t-BuCCl(Me)CH₂ | Br | O | H | H | 4-I |
| t-BuCCl(Me)CH₂ | I | O | H | H | 4-Cl |
| t-BuCCl(Me)CH₂ | I | O | H | H | 4-I |
| t-BuCCl(Me)CH₂ | Cl | O | H | H | 2,4-Cl₂ |
| t-BuCCl(Me)CH₂ | F | O | H | H | 4-Cl |
| t-BuCCl(Me)CH₂ | Me | O | H | H | 4-Cl |
| t-BuCCl(Me)CH₂ | OMe | O | H | H | 4-Cl |
| t-BuCCl(Me)CH₂ | OMe | O | H | H | 4-I |
| t-BuCCl(Me)CH₂ | SMe | O | H | H | 4-Cl |
| t-BuCCl(Me)CH₂ | Me | O | H | H | 4-I |
| t-BuCCl(Me)CH₂ | Cl | O | H | H | 2-F, 4-Cl |
| t-BuCCl(Me)CH₂ | OEt | O | H | H | 4-Cl |
| t-BuCCl(Me)CH₂ | Cl | O | H | Me | 4-I |
| t-BuCCl(Me)CH₂ | Cl | O | H | H | 4-Me |
| t-BuCCl(Me)CH₂ | Cl | O | H | H | 2,5-Me₂ |
| t-BuCCl(Me)CH₂ | Cl | O | H | H | 4-OCHF₂ |
| t-BuCCl(Me)CH₂ | Cl | S | H | H | 4-Cl |
| t-BuCCl(Me)CH₂ | Cl | S | H | H | 4-Bu-t |
| t-BuCCl(Me)CH₂ | Cl | S | H | H | 3-Me |

TABLE 1-continued

In Compounds of the formula:

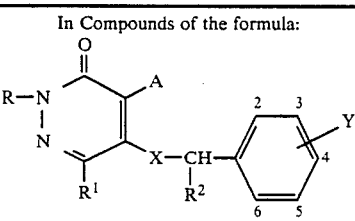

| R | A | X | R¹ | R² | Y |
|---|---|---|----|----|---|
| t-BuCCl(Me)CH₂ | Cl | S | H | H | 4-SMe |
| t-BuCCl(Me)CH₂ | Cl | S | H | H | 4-I |
| t-BuCCl(Me)CH₂ | Cl | S | H | H | 4-SPr |
| t-BuCBr(Me)CH₂ | Cl | O | H | H | 4-Cl |
| t-BuCBr(Me)CH₂ | Cl | O | H | H | 4-Br |
| t-BuCBr(Me)CH₂ | Cl | O | H | H | 4-I |
| t-BuCBr(Me)CH₂ | Br | O | H | H | 4-Cl |
| t-BuCBr(Me)CH₂ | Br | O | H | H | 4-I |
| t-BuCBr(Me)CH₂ | I | O | H | H | 4-Cl |
| t-BuCBr(Me)CH₂ | I | O | H | H | 4-I |
| Br(CH₂)₆CHClCH₂ | Cl | O | H | H | 4-Cl |
| Br(CH₂)₆CHClCH₂ | Cl | O | H | H | 4-I |
| Br(CH₂)₆CHBrCH₂ | Cl | O | H | H | 4-Cl |
| Br(CH₂)₆CHBrCH₂ | Cl | O | H | H | 4-I |
| ClCH₂CH(Me) | Cl | O | H | H | 4-Cl |
| ClCH₂CH(Me) | Cl | O | H | H | 4-I |
| ClCH₂C(Me)₂ | Cl | O | H | H | 4-Cl |
| ClCH₂C(Me) | Cl | O | H | H | 4-I |
| Cl(CH₂)₃ | Cl | O | H | H | 4-Cl |
| Cl(CH₂)₃ | Cl | O | H | H | 4-I |
| Cl(CH₂)₃ | Cl | O | H | H | 2,4-Cl₂ |
| Cl(CH₂)₃ | Br | O | H | H | 4-Cl |
| Cl(CH₂)₃ | I | O | H | H | 4-Cl |
| Cl(CH₂)₃ | Cl | S | H | H | 4-Cl |
| Cl(CH₂)₃ | Cl | S | H | H | 4-Bu-t |
| Br(CH₂)₃ | Cl | O | H | H | 4-Cl |
| Br(CH₂)₃ | Cl | O | H | H | 4-I |
| Br(CH₂)₃ | Cl | O | H | H | 2,4-Cl₂ |
| Br(CH₂)₃ | Br | O | H | H | 4-Cl |
| Br(CH₂)₃ | I | O | H | H | 4-Cl |
| Br(CH₂)₃ | Cl | S | H | H | 4-Cl |
| Br(CH₂)₃ | Cl | S | H | H | 4-Bu-t |
| I(CH₂)₃ | Cl | O | H | H | 4-Cl |
| I(CH₂)₃ | Cl | O | H | H | 4-I |
| I(CH₂)₃ | Cl | O | H | H | 2,4-Cl₂ |
| I(CH₂)₃ | Br | O | H | H | 4-Cl |
| I(CH₂)₃ | I | O | H | H | 4-Cl |
| I(CH₂)₃ | Cl | S | H | H | 4-Cl |
| I(CH₂)₃ | Cl | S | H | H | 4-Bu-t |
| MeCHClCH₂ | Cl | O | H | H | 4-Cl |
| MeCHClCH₂ | Cl | O | H | H | 4-I |
| MeCHBrCH₂ | Cl | O | H | H | 4-Cl |
| MeCHBrCH₂ | Cl | O | H | H | 4-I |
| Me₂CClC(Me)₂ | Cl | O | H | H | 4-Cl |
| Me₂CClC(Me)₂ | Cl | O | H | H | 4-I |
| Me₂CBrC(Me)₂ | Cl | O | H | H | 4-Cl |
| Me₂CBrC(Me)₂ | Cl | O | H | H | 4-I |
| MeCHClCH(Et) | Cl | O | H | H | 4-Cl |
| MeCHClCH(Et) | Cl | O | H | H | 4-I |
| MeCHBrCH(Et) | Cl | O | H | H | 4-Cl |
| MeCHBrCH(Et) | Cl | O | H | H | 4-I |
| MeCHClCH(Pr) | Cl | O | H | H | 4-Cl |
| MeCHClCH(Pr) | Cl | O | H | H | 4-I |
| MeCHBrCH(Pr) | Cl | O | H | H | 4-Cl |
| MeCHBrCH(Pr) | Cl | O | H | H | 4-I |
| MeCHClCH(Pr-i) | Cl | O | H | H | 4-Cl |
| MeCHClCH(Pr-i) | Cl | O | H | H | 4-I |
| MeCHBrCH(Pr-i) | Cl | O | H | H | 4-Cl |
| MeCHBrCH(Pr-i) | Cl | O | H | H | 4-I |
| MeCHClCH(Bu) | Cl | O | H | H | 4-Cl |
| MeCHClCH(Bu) | Cl | O | H | H | 4-I |
| MeCHBrCH(Bu) | Cl | O | H | H | 4-Cl |
| MeCHBrCH(Bu) | Cl | O | H | H | 4-I |
| MeCHClCH(Pen) | Cl | O | H | H | 4-Cl |
| MeCHClCH(Pen) | Cl | O | H | H | 4-I |
| MeCHBrCH(Pen) | Cl | O | H | H | 4-Cl |
| MeCHBrCH(Pen) | Cl | O | H | H | 4-I |
| Me₂CClCH₂ | Cl | O | H | H | 4-Cl |
| Me₂CClCH₂ | Cl | O | H | H | 4-Br |
| Me₂CClCH₂ | Br | O | H | H | 4-Cl |

TABLE 1-continued

In Compounds of the formula:

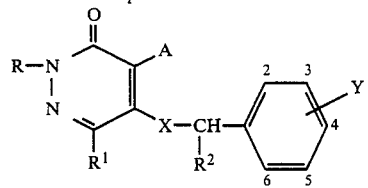

| R | A | X | R¹ | R² | Y |
|---|---|---|---|---|---|
| Me₂CClCH₂ | Br | O | H | H | 4-I |
| Me₂CClCH₂ | I | O | H | H | 4-Cl |
| Me₂CClCH₂ | I | O | H | H | 4-I |
| Me₂CClCH₂ | Cl | O | H | H | 2,4-Cl₂ |
| Me₂CClCH₂ | Pr-i | O | H | H | 4-Cl |
| Me₂CClCH₂ | SPr | O | H | H | 4-Cl |
| Me₂CClCH₂ | Br | O | OMe | H | 4-Cl |
| Me₂CClCH₂ | Cl | O | H | H | 4-Bu-t |
| Me₂CClCH₂ | Cl | O | H | H | 3-OBu |
| Me₂CClCH₂ | Cl | O | H | H | 4-F |
| Me₂CClCH₂ | Cl | S | H | H | 4-Cl |
| Me₂CClCH₂ | Cl | S | H | H | 4-Bu-t |
| Me₂CClCH₂ | Cl | S | H | H | 4-CF₃ |
| Me₂CClCH₂ | Cl | S | H | H | 4-CH(OH)Et |
| Me₂CClCH₂ | Cl | S | H | H | 4-OCH₂CH=CHMe |
| Me₂CBrCH₂ | Cl | O | H | H | 4-Cl |
| Me₂CBrCH₂ | Cl | O | H | H | 4-Br |
| Me₂CBrCH₂ | Br | O | H | H | 4-Cl |
| Me₂CBrCH₂ | I | O | H | H | 4-Cl |
| Me₂CBrCH₂ | H | O | H | H | 4-Cl |
| Me₂CBrCH₂ | H | O | H | H | 4-I |
| Me₂CBrCH₂ | Cl | O | H | H | 2,4-Cl₂ |
| Me₂CBrCH₂ | Bu | O | H | H | 4-Cl |
| Me₂CBrCH₂ | SOEt | O | H | H | 4-Cl |
| Me₂CBrCH₂ | I | O | Cl | H | 4-Cl |
| Me₂CBrCH₂ | Cl | O | H | H | 4-OBu-s |
| Me₂CBrCH₂ | Cl | S | H | H | 4-Cl |
| Me₂CBrCH₂ | Cl | S | H | H | 4-Bu-t |
| Me₂CBrCH₂ | Cl | S | H | H | 4-Ph |
| Me₂CBrCH₂ | Cl | S | H | H | 4-OPh |
| Me₂CBrCH₂ | Cl | S | H | H | 4-CH(OMe)Et |
| MeCHClCH(Me) | Cl | O | H | H | 4-Cl |
| MeCHClCH(Me) | Cl | O | H | H | 4-I |
| MeCHBrCH(Me) | Cl | O | H | h | 4-Cl |
| MeCHBrCH(Me) | Cl | O | H | h | 4-I |
| MeCHClC(Me)₂ | Cl | O | H | H | 4-Cl |
| MeCHClC(Me)₂ | Cl | O | H | H | 4-I |
| MeCHBrC(Me)₂ | Cl | O | H | H | 4-Cl |
| MeCHBrC(Me)₂ | Cl | O | H | H | 4-I |
| Me₂CClCH(Me) | Cl | O | H | H | 4-Cl |
| Me₂CClCH(Me) | Cl | O | H | H | 4-I |
| Me₂CBrCH(Me) | Cl | O | H | H | 4-Cl |
| Me₂CBrCH(Me) | Cl | O | H | H | 4-I |
| Me₂CClCH(Bu-t) | Cl | O | H | H | 4-Cl |
| Me₂CClCH(Bu-t) | Cl | O | H | H | 4-I |
| Me₂CBrCH(Bu-t) | Cl | O | H | H | 4-Cl |
| Me₂CBrCH(Bu-t) | Cl | O | H | H | 4-I |
| MeCHClC(Me)(Et) | Cl | O | H | H | 4-Cl |
| MeCHClC(Me)(Et) | Cl | O | H | H | 4-I |
| MeCHBrC(Me)(Et) | Cl | O | H | H | 4-Cl |
| MeCHBrC(Me)(Et) | Cl | O | H | H | 4-I |
| Cl(CH₂)₄ | Cl | O | H | H | 4-Cl |
| Cl(CH₂)₄ | Cl | O | H | H | 2,4-Cl₂ |
| Cl(CH₂)₄ | Cl | O | H | H | 4-I |
| Cl(CH₂)₄ | Br | O | H | H | 4-Cl |
| Cl(CH₂)₄ | I | O | H | H | 4-Cl |
| Cl(CH₂)₄ | Cl | S | H | H | 4-Cl |
| Cl(CH₂)₄ | Cl | S | H | H | 4-Bu-t |
| Br(CH₂)₄ | Cl | O | H | H | 4-Cl |
| Br(CH₂)₄ | Cl | O | H | H | 2,4-Cl₂ |
| Br(CH₂)₄ | Cl | O | H | H | 4-I |
| Br(CH₂)₄ | Br | O | H | H | 4-Cl |
| Br(CH₂)₄ | I | O | H | H | 4-Cl |
| Br(CH₂)₄ | Cl | S | H | H | 4-Cl |
| Br(CH₂)₄ | Cl | S | H | H | 4-Bu-t |
| I(CH₂)₄ | Cl | O | H | H | 4-Cl |
| I(CH₂)₄ | Cl | O | H | H | 2,4-Cl₂ |
| I(CH₂)₄ | Cl | O | H | H | 4-I |
| I(CH₂)₄ | Br | O | H | H | 4-Cl |
| I(CH₂)₄ | I | O | H | H | 4-Cl |

TABLE 1-continued

In Compounds of the formula:

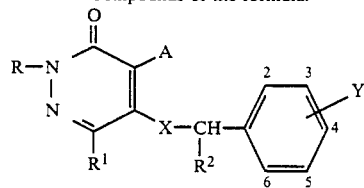

| R | A | X | R¹ | R² | Y |
|---|---|---|----|----|---|
| I(CH$_2$)$_4$ | Cl | S | H | H | 4-Cl |
| I(CH$_2$)$_4$ | Cl | S | H | H | 4-Bu-t |
| MeCHClCH$_2$CH$_2$ | Cl | O | H | H | 4-Cl |
| MeCHClCH$_2$CH$_2$ | Cl | O | H | H | 4-I |
| Cl(CH$_2$)$_5$ | Cl | O | H | H | 4-Cl |
| Cl(CH$_2$)$_5$ | Cl | O | H | H | 4-I |
| Br(CH$_2$)$_5$ | Cl | O | H | H | 4-Cl |
| Br(CH$_2$)$_5$ | Cl | O | H | H | 4-I |
| I(CH$_2$)$_5$ | Cl | O | H | H | 4-Cl |
| I(CH$_2$)$_5$ | Cl | O | H | H | 4-I |
| MeCHBrCH$_2$CH$_2$CH$_2$ | Cl | O | H | H | 4-Cl |
| MeCHBrCH$_2$CH$_2$CH$_2$ | Cl | O | H | H | 4-I |
| Cl(CH$_2$)$_6$ | Cl | O | H | H | 4-Cl |
| Cl(CH$_2$)$_6$ | Cl | O | H | H | 4-I |
| I(CH$_2$)$_6$ | Cl | O | H | H | 4-Cl |
| I(CH$_2$)$_6$ | Cl | O | H | H | 4-I |
| Br(CH$_2$)$_8$ | Cl | O | H | H | 4-Cl |
| Br(CH$_2$)$_8$ | Cl | O | H | H | 4-I |
| I(CH$_2$)$_8$ | Cl | O | H | H | 4-Cl |
| I(CH$_2$)$_8$ | Cl | O | H | H | 4-I |
| EtCHClCH$_2$ | Cl | O | H | H | 4-Cl |
| EtCHClCH$_2$ | Cl | O | H | H | 4-I |
| EtCHBrCH$_2$ | Cl | O | H | H | 4-Cl |
| EtCHBrCH$_2$ | Cl | O | H | H | 4-I |
| i-PrCCl(Et)CH$_2$ | Cl | O | H | H | 4-Cl |
| i-PrCCl(Et)CH$_2$ | Cl | O | H | H | 4-Br |
| i-PrCCl(Et)CH$_2$ | Cl | O | H | H | 4-I |
| i-PrCCl(Et)CH$_2$ | Br | O | H | H | 4-Cl |
| i-PrCCl(Et)CH$_2$ | Br | O | H | H | 4-I |
| i-PrCCl(Et)CH$_2$ | I | O | H | H | 4-Cl |
| i-PrCCl(Et)CH$_2$ | I | O | H | H | 4-I |
| i-PrCCl(Et)CH$_2$ | Cl | O | H | H | 2,4-Cl$_2$ |
| i-PrCCl(Et)CH$_2$ | OMe | O | H | H | 4-Br |
| i-PrCCl(Et)CH$_2$ | SO$_2$Pr | O | H | H | 4-Cl |
| i-PrCCl(Et)CH$_2$ | Cl | O | H | H | 4-OPr |
| i-PrCCl(Et)CH$_2$ | Cl | O | H | H | 4-CF$_3$ |
| i-PrCCl(Et)CH$_2$ | Cl | O | H | H | 2,4,5-Cl$_3$ |
| i-PrCCl(Et)CH$_2$ | Cl | S | H | H | 4-Cl |
| i-PrCCl(Et)CH$_2$ | Cl | S | H | H | 4-Bu-t |
| i-PrCCl(Et)CH$_2$ | Cl | S | H | H | 4-C$_6$H$_4$Cl-' |
| i-PrCCl(Et)CH$_2$ | Cl | S | H | H | 4-OC$_6$H$_4$F-4' |
| i-PrCCl(Et)CH$_2$ | Cl | S | H | H | 4-SiMe$_3$ |
| i-PrCBr(Et)CH$_2$ | Cl | O | H | H | 4-Cl |
| i-PrCBr(Et)CH$_2$ | Cl | O | H | H | 4-Br |
| i-PrCBr(Et)CH$_2$ | Cl | O | H | H | 4-I |
| i-PrCBr(Et)CH$_2$ | Br | O | H | H | 4-Cl |
| i-PrCBr(Et)CH$_2$ | I | O | H | H | 4-Cl |
| i-PrCBr(Et)CH$_2$ | H | O | H | H | 4-Cl |
| i-PrCBr(Et)CH$_2$ | H | O | H | H | 4-I |
| i-PrCBr(Et)CH$_2$ | Cl | O | H | H | 2,4-Cl$_2$ |
| i-PrCBr(Et)CH$_2$ | Cl | O | H | H | 2-F, 4-Cl |
| i-PrCBr(Et)CH$_2$ | OEt | O | H | H | 4-Cl |
| i-PrCBr(Et)CH$_2$ | Cl | O | H | Me | 4-I |
| i-PrCBr(Et)CH$_2$ | Cl | O | H | H | 4-Me |
| i-PrCBr(Et)CH$_2$ | Cl | O | H | H | 2,5-Me$_2$ |
| i-PrCBr(Et)CH$_2$ | Cl | O | H | H | 4-OCHF$_2$ |
| i-PrCBr(Et)CH$_2$ | Cl | O | H | H | 2,4,5-Cl$_3$ |
| i-PrCBr(Et)CH$_2$ | Cl | S | H | H | 4-Cl |
| i-PrCBr(Et)CH$_2$ | Cl | S | H | H | 4-Bu-t |
| i-PrCBr(Et)CH$_2$ | Cl | S | H | H | 3-Me |
| i-PrCBr(Et)CH$_2$ | Cl | S | H | H | 4-CH=CHMe |
| i-PrCBr(Et)CH$_2$ | Cl | S | H | H | 4-C(Me)$_2$CH$_2$CN |
| i-PrCBr(Et)CH$_2$ | Cl | S | H | H | 4-O(CH$_2$)$_3$OMe |
| EtCCl(Me)CH$_2$ | Cl | O | H | H | 4-Cl |
| EtCCl(Me)CH$_2$ | Cl | O | H | H | 4-Br |
| EtCCl(Me)CH$_2$ | Cl | O | H | H | 4-I |
| EtCCl(Me)CH$_2$ | Cl | O | H | H | 2,4-Cl$_2$ |
| EtCCl(Me)CH$_2$ | Br | O | H | H | 4-Cl |
| EtCCl(Me)CH$_2$ | Br | O | H | H | 4-I |
| EtCCl(Me)CH$_2$ | I | O | H | H | 4-Cl |

TABLE 1-continued

In Compounds of the formula:

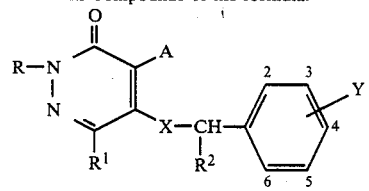

| R | A | X | $R^1$ | $R^2$ | Y |
|---|---|---|---|---|---|
| EtCCl(Me)CH$_2$ | I | O | H | H | 4-I |
| EtCCl(Me)CH$_2$ | F | O | H | H | 4-Cl |
| EtCCl(Me)CH$_2$ | Me | O | H | H | 4-Cl |
| EtCCl(Me)CH$_2$ | OMe | O | H | H | 4-Cl |
| EtCCl(Me)CH$_2$ | OMe | O | H | H | 4-I |
| EtCCl(Me)CH$_2$ | SMe | O | H | H | 4-Cl |
| EtCCl(Me)CH$_2$ | SMe | O | H | H | 4-I |
| EtCCl(Me)CH$_2$ | SO$_2$Me | O | H | H | 4-Cl |
| EtCCl(Me)CH$_2$ | Cl | O | H | Me | 4-Cl |
| EtCCl(Me)CH$_2$ | Cl | O | Cl | H | 4-Cl |
| EtCCl(Me)CH$_2$ | Cl | O | H | H | 2,Cl, 4-Br |
| EtCCl(Me)CH$_2$ | OBu | O | H | H | 4-Cl |
| EtCCl(Me)CH$_2$ | Cl | O | H | Et | 4-Cl |
| EtCCl(Me)CH$_2$ | Cl | O | H | H | 4-Bu-s |
| EtCCl(Me)CH$_2$ | Cl | O | H | H | 3,4-Cl$_2$ |
| EtCCl(Me)CH$_2$ | Cl | O | H | H | 4-OCF$_3$ |
| EtCCl(Me)CH$_2$ | Cl | O | H | H | 2,4-F$_2$ |
| EtCCl(Me)CH$_2$ | Cl | S | H | H | 4-Cl |
| EtCCl(Me)CH$_2$ | Cl | S | H | H | 4-Bu-t |
| EtCCl(Me)CH$_2$ | Cl | S | H | H | 4-Me |
| EtCCl(Me)CH$_2$ | Cl | S | H | H | 4-OPr |
| EtCCl(Me)CH$_2$ | Cl | S | H | H | 4-CH$_2$—(C$_6$H$_3$Cl$_2$-2,4) |
| EtCCl(Me)CH$_2$ | Cl | S | H | H | 4-COC$_6$H$_4$Cl-4' |
| EtCCl(Me)CH$_2$ | Cl | S | H | H | 4-OCH(Me)CH$_2$OEt |
| EtCBr(Me)CH$_2$ | Cl | O | H | H | 4-Cl |
| EtCBr(Me)CH$_2$ | Cl | O | H | H | 4-Br |
| EtCBr(Me)CH$_2$ | Cl | O | H | H | 4-I |
| EtCBr(Me)CH$_2$ | Cl | O | H | H | 2,4-Cl$_2$ |
| EtCBr(Me)CH$_2$ | Br | O | H | H | 4-Cl |
| EtCBr(Me)CH$_2$ | Br | O | H | H | 4-I |
| EtCBr(Me)CH$_2$ | I | O | H | H | 4-Cl |
| EtCBr(Me)CH$_2$ | I | O | H | H | 4-I |
| EtCBr(Me)CH$_2$ | F | O | H | H | 4-Cl |
| EtCBr(Me)CH$_2$ | Me | O | H | H | 4-Cl |
| EtCBr(Me)CH$_2$ | OMe | O | H | H | 4-Cl |
| EtCBr(Me)CH$_2$ | SMe | O | H | H | 4-Cl |
| EtCBr(Me)CH$_2$ | Cl | O | H | Me | 4-Cl |
| EtCBr(Me)CH$_2$ | Br | O | H | Me | 4-Cl |
| EtCBr(Me)CH$_2$ | Cl | O | H | H | 3-CF$_3$ |
| EtCBr(Me)CH$_2$ | Cl | O | H | H | 4-Ph |
| EtCBr(Me)CH$_2$ | Cl | O | H | H | 4-OCH$_2$CF$_3$ |
| EtCBr(Me)CH$_2$ | Cl | O | H | H | 2,6-Cl$_2$ |
| EtCBr(Me)CH$_2$ | Cl | S | H | H | 4-Cl |
| EtCBr(Me)CH$_2$ | Cl | S | H | H | 4-Bu-t |
| EtCBr(Me)CH$_2$ | Cl | S | H | H | 4-OC$_{10}$H$_{21}$ |
| EtCBr(Me)CH$_2$ | Cl | S | H | H | 4-C$_6$H$_4$F-4' |
| EtCBr(Me)CH$_2$ | Cl | S | H | H | 4-CH$_2$—(C$_6$H$_3$Cl$_2$-3,5) |
| Et$_2$CClCH$_2$ | Cl | O | H | H | 4-Cl |
| Et$_2$CClCH$_2$ | Cl | O | H | H | 4-Br |
| Et$_2$CClCH$_2$ | Cl | O | H | H | 4-I |
| Et$_2$CClCH$_2$ | Cl | O | H | H | 2,4-Cl$_2$ |
| Et$_2$CClCH$_2$ | Br | O | H | H | 4-Cl |
| Et$_2$CClCH$_2$ | Br | O | H | H | 4-I |
| Et$_2$CClCH$_2$ | I | O | H | H | 4-Cl |
| Et$_2$CClCH$_2$ | I | O | H | H | 4-I |
| Et$_2$CClCH$_2$ | F | O | H | H | 4-Cl |
| Et$_2$CClCH$_2$ | Me | O | H | H | 4-Cl |
| Et$_2$CClCH$_2$ | OMe | O | H | H | 4-Cl |
| Et$_2$CClCH$_2$ | OMe | O | H | H | 4-I |
| Et$_2$CClCH$_2$ | SMe | O | H | H | 4-Cl |
| Et$_2$CClCH$_2$ | Cl | O | H | H | 4-OC$_{10}$H$_{21}$ |
| Et$_2$CClCH$_2$ | SO$_2$Me | O | H | H | 4-Cl |
| Et$_2$CClCH$_2$ | Cl | O | H | Me | 4-Cl |
| Et$_2$CClCH$_2$ | Cl | O | Cl | H | 4-Cl |
| Et$_2$CClCH$_2$ | F | O | H | H | 4-I |
| Et$_2$CClCH$_2$ | SMe | O | H | H | 2,4-Cl$_2$ |
| Et$_2$CClCH$_2$ | I | O | H | Me | 4-Cl |
| Et$_2$CClCH$_2$ | Cl | O | H | H | 4-C$_6$H$_4$Cl-4' |
| Et$_2$CClCH$_2$ | Cl | O | H | H | 4-CN |
| Et$_2$CClCH$_2$ | Cl | O | H | H | 4-OCH$_2$CH$_2$—NHCOOEt |

TABLE 1-continued

In Compounds of the formula:

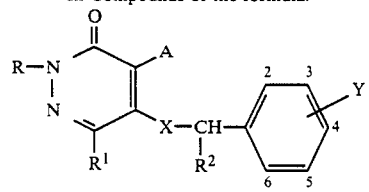

| R | A | X | R¹ | R² | Y |
|---|---|---|---|---|---|
| Et₂CClCH₂ | Cl | S | H | H | 4-Cl |
| Et₂CClCH₂ | Cl | S | H | H | 4-Bu-t |
| Et₂CClCH₂ | Cl | S | H | H | 4-Hex |
| Et₂CClCH₂ | Cl | S | H | H | 4-OC(Me)₂CH₂OPr |
| Et₂CClCH₂ | Cl | S | H | H | 4-OCH₂CH=CH₂ |
| Et₂CClCH₂ | Cl | S | H | H | 4-CH₂CH₂Ph |
| Et₂CBrCH₂ | Cl | O | H | H | 4-Cl |
| Et₂CBrCH₂ | Cl | O | H | H | 4-Br |
| Et₂CBrCH₂ | Cl | O | H | H | 4-I |
| Et₂CBrCH₂ | Cl | O | H | H | 2,4-Cl₂ |
| Et₂CBrCH₂ | Br | O | H | H | 4-Cl |
| Et₂CBrCH₂ | I | O | H | H | 4-Cl |
| Et₂CBrCH₂ | H | O | H | H | 4-Cl |
| Et₂CBrCH₂ | H | O | H | H | 4-I |
| Et₂CBrCH₂ | F | O | H | H | 4-Cl |
| Et₂CBrCH₂ | Me | O | H | H | 4-Cl |
| Et₂CBrCH₂ | OMe | O | H | H | 4-Cl |
| Et₂CBrCH₂ | SMe | O | H | H | 4-Cl |
| Et₂CBrCH₂ | Me | O | H | H | 4-Br |
| Et₂CBrCH₂ | Cl | O | OH | H | 4-Cl |
| Et₂CBrCH₂ | Cl | O | H | H | 4-Pr |
| Et₂CBrCH₂ | Cl | O | H | H | 2-Cl, 4-F |
| Et₂CBrCH₂ | Cl | S | H | H | 4-Cl |
| Et₂CBrCH₂ | Cl | S | H | H | 4-Bu-t |
| Et₂CBrCH₂ | Cl | S | H | H | 4-(Q4) |
| Et₂CBrCH₂ | Cl | S | H | H | 4-OCH₂CH₂—NHCOOEt |
| t-BuCHBrCH₂ | Cl | O | H | H | 4-Cl |
| t-BuCHBrCH₂ | Cl | O | H | H | 4-I |
| t-BuCHBrCH₂ | Br | O | H | H | 4-Cl |
| t-BuCHBrCH₂ | I | O | H | H | 4-Cl |
| t-BuCHBrCH₂ | Cl | O | H | H | 4-Cl |
| t-BuCHBrCH₂ | Cl | O | H | H | 4-I |
| EtCHClCH(Me) | Cl | O | H | H | 4-Cl |
| EtCHClCH(Me) | Cl | O | H | H | 4-I |
| EtCHBrCH(Me) | Cl | O | H | H | 4-Cl |
| EtCHBrCH(Me) | Cl | O | H | H | 4-I |
| EtCHClCH(Et) | Cl | O | H | H | 4-Cl |
| EtCHClCH(Et) | Cl | O | H | H | 4-I |
| EtCHBrCH(Me) | Cl | O | H | H | 4-Cl |
| EtCHBrCH(Et) | Cl | O | H | H | 4-I |
| EtCHClCH(Pr) | Cl | O | H | H | 4-Cl |
| EtCHClCH(Pr) | Cl | O | H | H | 4-I |
| EtCHBrCH(Pr) | Cl | O | H | H | 4-Cl |
| EtCHBrCH(Pr) | Cl | O | H | H | 4-I |
| i-PrCHClCH₂ | Cl | O | H | H | 4-Cl |
| i-PrCHClCH₂ | Cl | O | H | H | 4-I |
| i-PrCHBrCH₂ | Cl | O | H | H | 4-Cl |
| i-PrCHBrCH₂ | Cl | O | H | H | 4-I |
| EtCHClC(Me)₂ | Cl | O | H | H | 4-Cl |
| EtCHClC(Me)₂ | Cl | O | H | H | 4-I |
| EtCHBrC(Me)₂ | Cl | O | H | H | 4-Cl |
| EtCHBrC(Me)₂ | Cl | O | H | H | 4-I |
| EtCCl(Me)CH(Me) | Cl | O | H | H | 4-Cl |
| EtCCl(Me)CH(Me) | Cl | O | H | H | 4-I |
| EtCBr(Me)CH(Me) | Cl | O | H | H | 4-Cl |
| EtCBr(Me)CH(Me) | Cl | O | H | H | 4-I |
| i-PrCHClCH(Me) | Cl | O | H | H | 4-Cl |
| i-PrCHClCH(Me) | Cl | O | H | H | 4-I |
| i-PrCHBrCH(Me) | Cl | O | H | H | 4-Cl |
| i-PrCHBrCH(Me) | Cl | O | H | H | 4-I |
| t-BuCCl(Me)CH₂ | Cl | O | H | H | 4-Cl |
| t-BuCCl(Me)CH₂ | Cl | O | H | H | 4-Br |
| t-BuCCl(Me)CH₂ | Cl | O | H | H | 4-I |
| t-BuCCl(Me)CH₂ | Br | O | H | H | 4-Cl |
| t-BuCCl(Me)CH₂ | Br | O | H | H | 4-I |
| t-BuCCl(Me)CH₂ | I | O | H | H | 4-Cl |
| t-BuCCl(Me)CH₂ | I | O | H | H | 4-I |
| t-BuCCl(Me)CH₂ | Cl | O | H | H | 2,4-Cl₂ |
| t-BuCCl(Me)CH₂ | F | O | H | H | 4-Cl |
| t-BuCCl(Me)CH₂ | Me | O | H | H | 4-Cl |

TABLE 1-continued

In Compounds of the formula:

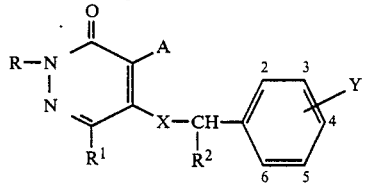

| R | A | X | R¹ | R² | Y |
|---|---|---|----|----|---|
| t-BuCCl(Me)CH$_2$ | OMe | O | H | H | 4-Cl |
| t-BuCCl(Me)CH$_2$ | OMe | O | H | H | 4-I |
| t-BuCCl(Me)CH$_2$ | SMe | O | H | H | 4-Cl |
| t-BuCCl(Me)CH$_2$ | Me | O | H | H | 4-I |
| t-BuCCl(Me)CH$_2$ | Cl | O | H | H | 2-F, 4-Cl |
| t-BuCCl(Me)CH$_2$ | OEt | O | H | H | 4-Cl |
| t-BuCCl(Me)CH$_2$ | Cl | O | H | Me | 4-I |
| t-BuCCl(Me)CH$_2$ | Cl | O | H | H | 4-Me |
| t-BuCCl(Me)CH$_2$ | Cl | O | H | H | 2,5-Me$_2$ |
| t-BuCCl(Me)CH$_2$ | Cl | O | H | H | 4-OCHF$_2$ |
| t-BuCCl(Me)CH$_2$ | Cl | S | H | H | 4-Cl |
| t-BuCCl(Me)CH$_2$ | Cl | S | H | H | 4-Bu-t |
| t-BuCCl(Me)CH$_2$ | Cl | S | H | H | 3-Me |
| t-BuCCl(Me)CH$_2$ | Cl | S | H | H | 4-SMe |
| t-BuCCl(Me)CH$_2$ | Cl | S | H | H | 4-I |
| t-BuCCl(Me)CH$_2$ | Cl | S | H | H | 4-SPr |
| t-BuCBr(Me)CH$_2$ | Cl | O | H | H | 4-Cl |
| t-BuCBr(Me)CH$_2$ | Cl | O | H | H | 4-Br |
| t-BuCBr(Me)CH$_2$ | Cl | O | H | H | 4-I |
| t-BuCBr(Me)CH$_2$ | Br | O | H | H | 4-Cl |
| t-BuCBr(Me)CH$_2$ | Br | O | H | H | 4-I |
| t-BuCBr(Me)CH$_2$ | I | O | H | H | 4-Cl |
| t-BuCBr(Me)CH$_2$ | I | O | H | H | 4-I |
| t-BuCBr(Me)CH$_2$ | Cl | O | H | H | 2,4-Cl$_2$ |
| t-BuCCl(Me)CH$_2$ | F | O | H | H | 4-Cl |
| t-BuCBr(Me)CH$_2$ | Me | O | H | H | 4-Cl |
| t-BuCBr(Me)CH$_2$ | OMe | O | H | H | 4-Cl |
| t-BuCBr(Me)CH$_2$ | OMe | O | H | H | 4-I |
| t-BuCBr(Me)CH$_2$ | SMe | O | H | H | 4-Cl |
| t-BuCBr(Me)CH$_2$ | SMe | O | H | H | 4-I |
| t-BuCBr(Me)CH$_2$ | Cl | O | H | H | 2,4-F$_2$ |
| t-BuCBr(Me)CH$_2$ | OBu | O | H | H | 4-Cl |
| t-BuCBr(Me)CH$_2$ | Cl | O | H | Et | 4-Cl |
| t-BuCBr(Me)CH$_2$ | Cl | O | H | H | 4-Bu-s |
| t-BuCBr(Me)CH$_2$ | Cl | O | H | H | 3,4-Cl$_2$ |
| t-BuCBr(Me)CH$_2$ | Cl | O | H | H | 4-OCF$_3$ |
| t-BuCBr(Me)CH$_2$ | Cl | S | H | H | 4-Cl |
| t-BuCBr(Me)CH$_2$ | Cl | S | H | H | 4-Bu-t |
| t-BuCBr(Me)CH$_2$ | Cl | S | H | H | 4-Me |
| t-BuCBr(Me)CH$_2$ | Cl | S | H | H | 4-COC$_7$H$_{15}$ |
| t-BuCBr(Me)CH$_2$ | Cl | S | H | H | 4-SPh |
| t-BuCHClC(Me)$_2$ | Cl | O | H | H | 4-Cl |
| t-BuCHClC(Me)$_2$ | Cl | O | H | H | 4-I |
| t-BuCHBrC(Me)$_2$ | Cl | O | H | H | 4-Cl |
| t-BuCHBrC(Me)$_2$ | Cl | O | H | H | 4-I |
| PrCHClCH$_2$ | Cl | O | H | H | 4-Cl |
| PrCHClCH$_2$ | Cl | O | H | H | 4-I |
| PrCHBrCH$_2$ | Cl | O | H | H | 4-Cl |
| PrCHBrCH$_2$ | Cl | O | H | H | 4-I |
| PrCHClCH(Me) | Cl | O | H | H | 4-Cl |
| PrCHClCH(Me) | Cl | O | H | H | 4-I |
| PrCHBrCH(Me) | Cl | O | H | H | 4-Cl |
| PrCHBrCH(Me) | Cl | O | H | H | 4-I |
| PrCHClCH(Et) | Cl | O | H | H | 4-Cl |
| PrCHClCH(Et) | Cl | O | H | H | 4-I |
| PrCHBrCH(Et) | Cl | O | H | H | 4-Cl |
| PrCHBrCH(Et) | Cl | O | H | H | 4-I |
| PrCHClCH(Pr) | Cl | O | H | H | 4-Cl |
| PrCHClCH(Pr) | Cl | O | H | H | 4-I |
| PrCHBrCH(Pr) | Cl | O | H | H | 4-Cl |
| PrCHBrCH(Pr) | Cl | O | H | H | 4-I |
| PrCCl(Me)CH$_2$ | Cl | O | H | H | 4-Cl |
| PrCCl(Me)CH$_2$ | Cl | O | H | H | 4-Br |
| PrCCl(Me)CH$_2$ | Cl | O | H | H | 4-I |
| PrCCl(Me)CH$_2$ | Cl | O | H | H | 2,4-Cl$_2$ |
| PrCCl(Me)CH$_2$ | Br | O | H | H | 4-Cl |
| PrCCl(Me)CH$_2$ | Br | O | H | H | 4-I |
| PrCCl(Me)CH$_2$ | I | O | H | H | 4-Cl |
| PrCCl(Me)CH$_2$ | I | O | H | H | 4-I |
| PrCCl(Me)CH$_2$ | F | O | H | H | 4-Cl |

TABLE 1-continued

In Compounds of the formula:

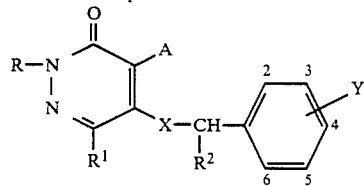

| R | A | X | R¹ | R² | Y |
|---|---|---|---|---|---|
| PrCCl(Me)CH$_2$ | Me | O | H | H | 4-Cl |
| PrCCl(Me)CH$_2$ | OMe | O | H | H | 4-Cl |
| PrCCl(Me)CH$_2$ | OMe | O | H | H | 4-I |
| PrCCl(Me)CH$_2$ | SMe | O | H | H | 4-Cl |
| PrCCl(Me)CH$_2$ | SMe | O | H | H | 4-I |
| PrCCl(Me)CH$_2$ | Cl | O | H | H | 2-F, 4-Cl |
| PrCCl(Me)CH$_2$ | Cl | O | H | H | 4-F |
| PrCCl(Me)CH$_2$ | Cl | O | H | H | 4-Br |
| PrCCl(Me)CH$_2$ | Cl | O | H | H | 4-CF$_3$ |
| PrCCl(Me)CH$_2$ | Cl | O | H | H | 4-Me |
| PrCCl(Me)CH$_2$ | Cl | O | H | H | 4-Ph |
| PrCCl(Me)CH$_2$ | Cl | O | H | H | 4-O(C$_6$H$_3$Cl-2, CF$_3$-4) |
| PrCCl(Me)CH$_2$ | Cl | O | H | H | 4-COC$_6$H$_4$Cl-4' |
| PrCCl(Me)CH$_2$ | Cl | O | H | H | 4-OCH$_2$C$_6$H$_4$Cl-4' |
| PrCCl(Me)CH$_2$ | Cl | O | H | H | 4-SMe |
| PrCCl(Me)CH$_2$ | Cl | S | H | H | 4-Cl |
| PrCCl(Me)CH$_2$ | Cl | S | H | H | 4-Bu-t |
| PrCCl(Me)CH$_2$ | Cl | S | H | H | 4-F |
| PrCCl(Me)CH$_2$ | Cl | S | H | H | 4-OCH$_2$C(Me)=CH$_2$ |
| PrCCl(Me)CH$_2$ | Cl | S | H | H | 4-CH$_2$-Q4 |
| PrCCl(Me)CH$_2$ | Cl | S | H | H | 4-C(Me)$_2$Et |
| PrCCl(Me)CH$_2$ | Cl | S | H | H | 4-CF$_3$ |
| BuCBr(Me)CH$_2$ | Cl | O | H | H | 4-Cl |
| BuCBr(Me)CH$_2$ | Cl | O | H | H | 4-Br |
| BuCBr(Me)CH$_2$ | Cl | O | H | H | 4-I |
| BuCBr(Me)CH$_2$ | Cl | O | H | H | 2,4-Cl$_2$ |
| BuCBr(Me)CH$_2$ | Br | O | H | H | 4-Cl |
| BuCBr(Me)CH$_2$ | Br | O | H | H | 4-I |
| BuCBr(Me)CH$_2$ | I | O | H | H | 4-Cl |
| BuCBr(Me)CH$_2$ | I | O | H | H | 4-I |
| BuCBr(Me)CH$_2$ | F | O | H | H | 4-Cl |
| BuCBr(Me)CH$_2$ | Me | O | H | H | 4-Cl |
| BuCBr(Me)CH$_2$ | OMe | O | H | H | 4-Cl |
| BuCBr(Me)CH$_2$ | OMe | O | H | H | 4-I |
| BuCBr(Me)CH$_2$ | SMe | O | H | H | 4-Cl |
| BuCBr(Me)CH$_2$ | SMe | O | H | H | 4-I |
| BuCBr(Me)CH$_2$ | SO$_2$Me | O | H | H | 4-Cl |
| BuCBr(Me)CH$_2$ | Cl | O | H | Me | 4-Cl |
| BuCBr(Me)CH$_2$ | Cl | O | Cl | H | 4-Cl |
| BuCBr(Me)CH$_2$ | Pr | O | H | H | 4-Cl |
| BuCBr(Me)CH$_2$ | SEt | O | H | H | 4-I |
| BuCBr(Me)CH$_2$ | Br | O | Cl | H | 4-Cl |
| BuCBr(Me)CH$_2$ | Cl | O | H | H | 3-Cl |
| BuCBr(Me)CH$_2$ | Cl | O | H | H | 2,3,4,5,6-F$_5$ |
| BuCBr(Me)CH$_2$ | Cl | O | H | H | 4-OHex |
| BuCBr(Me)CH$_2$ | Cl | O | H | H | 2,6-Cl$_2$, 4-F |
| BuCBr(Me)CH$_2$ | Cl | S | H | H | 4-Cl |
| BuCBr(Me)CH$_2$ | Cl | S | H | H | 4-Bu-t |
| BuCBr(Me)CH$_2$ | Cl | S | H | H | 4-O(CH$_2$)$_3$OMe |
| BuCBr(Me)CH$_2$ | Cl | S | H | H | 4-OCH$_2$C$_6$H$_4$CF$_3$-4' |
| BuCBr(Me)CH$_2$ | Cl | S | H | H | 4-Et |
| BuCBr(Me)CH$_2$ | Cl | S | H | H | 4-C(Me)$_2$CH$_2$OH |
| BuCBr(Me)CH$_2$ | Cl | S | H | H | 4-COC$_9$H$_{19}$ |
| BuCBr(Me)CH$_2$ | Bu | O | H | H | 4-Cl |
| BuCBr(Me)CH$_2$ | Cl | O | H | H | 4-OBu-s |
| BuCBr(Me)CH$_2$ | Cl | O | H | H | 2-Me, 4-Cl |
| BuCBr(Me)CH$_2$ | Cl | S | H | H | 4-Cl |
| BuCBr(Me)CH$_2$ | Cl | S | H | H | 4-Bu-t |
| BuCBr(Me)CH$_2$ | Cl | S | H | H | 4-Ph |
| BuCBr(Me)CH$_2$ | Cl | S | H | H | 4-C(Me)$_2$CH$_2$OCOMe |
| BuCBr(Me)CH$_2$ | Cl | S | H | H | 4-SBu |
| PrCH(Me)CHClCH$_2$ | Cl | O | H | H | 4-Cl |
| PrCH(Me)CHClCH$_2$ | Cl | O | H | H | 4-I |
| PrCH(Me)CHBrCH$_2$ | Cl | O | H | H | 4-Cl |
| PrCH(Me)CHBrCH$_2$ | Cl | O | H | H | 4-I |
| BuCHClCH$_2$ | Cl | O | H | H | 4-Cl |
| BuCHClCH$_2$ | Cl | O | H | H | 4-I |
| BuCHClCH$_2$ | Br | O | H | h | 4-Cl |
| BuCHClCH$_2$ | I | O | H | h | 4-Cl |
| BuCHBrCH$_2$ | Cl | O | H | H | 4-Cl |

TABLE 1-continued

In Compounds of the formula:

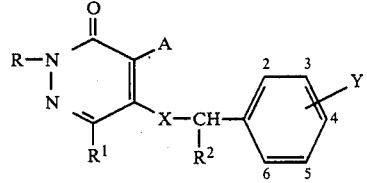

| R | A | X | R¹ | R² | Y |
|---|---|---|---|---|---|
| BuCHBrCH₂ | Cl | O | H | H | 4-I |
| BuCHBrCH₂ | Br | O | H | H | 4-Cl |
| BuCHBrCH₂ | I | O | H | H | 4-Cl |
| PenCHClCH₂ | Cl | O | H | H | 4-Cl |
| PenCHClCH₂ | Cl | O | H | H | 4-I |
| PenCHBrCH₂ | Cl | O | H | H | 4-Cl |
| PenCHBrCH₂ | Cl | O | H | H | 4-I |
| PenCHClCH(Me) | Cl | O | H | H | 4-Cl |
| PenCHClCH(Me) | Cl | O | H | H | 4-I |
| PenCHBrCH(Me) | Cl | O | H | H | 4-Cl |
| PenCHBrCH(Me) | Cl | O | H | H | 4-I |
| PenCCl(Me)CH₂ | Cl | O | H | H | 4-Cl |
| PenCCl(Me)CH₂ | Cl | O | H | H | 4-I |
| PenCCl(Me)CH₂ | I | O | H | H | 4-Cl |
| PenCBr(Me)CH₂ | Cl | O | H | H | 4-Cl |
| PenCBr(Me)CH₂ | Cl | O | H | H | 4-I |
| PenCBr(Me)CH₂ | I | O | H | H | 4-I |
| HexCHClCH₂ | Cl | O | H | H | 4-Cl |
| HexCHClCH₂ | Cl | O | H | H | 4-I |
| BuCCl(Me)CH₂ | Br | O | H | H | 4-I |
| BuCCl(Me)CH₂ | I | O | H | H | 4-Cl |
| BuCCl(Me)CH₂ | I | O | H | H | 4-I |
| BuCCl(Me)CH₂ | F | O | H | H | 4-Cl |
| BuCCl(Me)CH₂ | Me | O | H | H | 4-Cl |
| BuCCl(Me)CH₂ | OMe | O | H | H | 4-Cl |
| BuCCl(Me)CH₂ | OMe | O | H | H | 4-I |
| BuCCl(Me)CH₂ | SMe | O | H | H | 4-Cl |
| BuCCl(Me)CH₂ | SMe | O | H | H | 4-I |
| BuCCl(Me)CH₂ | SO₂Me | O | H | H | 4-Cl |
| BuCCl(Me)CH₂ | Cl | O | H | Me | 4-Cl |
| BuCCl(Me)CH₂ | Cl | O | Cl | H | 4-Cl |
| BuCCl(Me)CH₂ | Pr-i | O | H | H | 4-Cl |
| BuCCl(Me)CH₂ | SPr | O | H | H | 4-Cl |
| BuCCl(Me)CH₂ | Br | O | OMe | H | 4-Cl |
| BuCCl(Me)CH₂ | Cl | O | H | H | 4-Bu |
| BuCCl(Me)CH₂ | Cl | O | H | H | 4-F |
| BuCCl(Me)CH₂ | Cl | O | H | H | 2-OMe, 4-Cl |
| BuCCl(Me)CH₂ | Cl | S | H | H | 4-Cl |
| BuCCl(Me)CH₂ | Cl | S | H | H | 4-Bu-t |
| BuCCl(Me)CH₂ | Cl | S | H | H | 4-CF₃ |
| BuCCl(Me)CH₂ | Cl | S | H | H | 4-OCH₂C₆H₄Cl-' |
| BuCCl(Me)CH₂ | Cl | S | H | H | 4-C(Me)₂CH₂OMe |
| BuCCl(Me)CH₂ | Cl | S | H | H | 4-OCH₂CH=CHMe |
| BuCBr(Me)CH₂ | Cl | O | H | H | 4-Cl |
| BuCBr(Me)CH₂ | Cl | O | H | H | 4-Br |
| BuCBr(Me)CH₂ | Cl | O | H | H | 4-I |
| BuCBr(Me)CH₂ | Cl | O | H | H | 2,4-Cl₂ |
| BuCBr(Me)CH₂ | Br | O | H | H | 4-Cl |
| BuCBr(Me)CH₂ | Br | O | H | H | 4-I |
| BuCBr(Me)CH₂ | I | O | H | H | 4-Cl |
| BuCBr(Me)CH₂ | I | O | H | H | 4-I |
| BuCBr(Me)CH₂ | F | O | H | H | 4-Cl |
| BuCBr(Me)CH₂ | Me | O | H | H | 4-Cl |
| BuCBr(Me)CH₂ | OMe | O | H | H | 4-Cl |
| BuCBr(Me)CH₂ | SMe | O | H | H | 4-Cl |
| i-PrCBr(Me)CH₂ | Me | O | H | H | 4-Cl |
| i-PrCBr(Me)CH₂ | OMe | O | H | H | 4-Cl |
| i-PrCBr(Me)CH₂ | OMe | O | H | H | 4-I |
| i-PrCBr(Me)CH₂ | SMe | O | H | H | 4-Cl |
| i-PrCBr(Me)CH₂ | SMe | O | H | H | 4-I |
| i-PrCBr(Me)CH₂ | SO₂Me | O | H | H | 4-Cl |
| i-PrCBr(Me)CH₂ | F | O | H | H | 4-I |
| i-PrCBr(Me)CH₂ | SMe | O | H | H | 2,4-Cl₂ |
| i-PrCBr(Me)CH₂ | Cl | O | H | H | 4-OMe |
| i-PrCBr(Me)CH₂ | Cl | O | H | H | 4-C₆H₄Cl-4' |
| i-PrCBr(Me)CH₂ | Cl | O | H | H | 4-CN |
| i-PrCBr(Me)CH₂ | Cl | S | H | H | 4-Cl |
| i-PrCBr(Me)CH₂ | Cl | S | H | H | 4-Bu-t |
| i-PrCBr(Me)CH₂ | Cl | S | H | H | 4-CH₂Ph |
| i-PrCBr(Me)CH₂ | Cl | S | H | H | 4-C(Me)₂CN |

TABLE 1-continued

In Compounds of the formula:

| R | A | X | R¹ | R² | Y |
|---|---|---|----|----|---|
| i-BuCHClCH₂ | Cl | O | H | H | 4-Cl |
| i-BuCHClCH₂ | Cl | O | H | H | 4-I |
| i-BuCHBrCH₂ | Cl | O | H | H | 4-Cl |
| i-BuCHBrCH₂ | Cl | O | H | H | 4-I |
| s-BuCHClCH₂ | Cl | O | H | H | 4-Cl |
| s-BuCHClCH₂ | Cl | O | H | H | 4-I |
| s-BuCHBrCH₂ | Cl | O | H | H | 4-Cl |
| s-BuCHBrCH₂ | Cl | O | H | H | 4-I |
| t-BuCH₂CCl(Me)CH₂ | Cl | O | H | H | 4-Cl |
| t-BuCH₂CCl(Me)CH₂ | Cl | O | H | H | 4-I |
| t-BuCH₂CBr(Me)CH₂ | Cl | O | H | H | 4-Cl |
| t-BuCH₂CBr(Me)CH₂ | Cl | O | H | H | 4-I |
| BuCHClCH(Me) | Cl | O | H | H | 4-Cl |
| BuCHClCH(Me) | Cl | O | H | H | 4-I |
| BuCHBrCH(Me) | Cl | O | H | H | 4-Cl |
| BuCHBrCH(Me) | Cl | O | H | H | 4-I |
| BuCCl(Me)CH₂ | Cl | O | H | H | 4-Cl |
| BuCCl(Me)CH₂ | Cl | O | H | H | 4-Br |
| BuCCl(Me)CH₂ | Cl | O | H | H | 4-I |
| BuCCl(Me)CH₂ | Cl | O | H | H | 2,4-Cl₂ |
| BuCCl(Me)CH₂ | Br | O | H | H | 4-Cl |
| i-PrCCl(Me)CH₂ | Cl | O | H | H | 4-Cl |
| i-PrCCl(Me)CH₂ | Cl | O | H | H | 4-Br |
| i-PrCCl(Me)CH₂ | Cl | O | H | H | 4-I |
| i-PrCCl(Me)CH₂ | Cl | O | H | H | 2,4-Cl₂ |
| i-PrCCl(Me)CH₂ | Br | O | H | H | 4-Cl |
| i-PrCCl(Me)CH₂ | Br | O | H | H | 4-I |
| i-PrCCl(Me)CH₂ | I | O | H | H | 4-Cl |
| i-PrCCl(Me)CH₂ | I | O | H | H | 4-I |
| i-PrCCl(Me)CH₂ | F | O | H | H | 4-Cl |
| i-PrCCl(Me)CH₂ | Me | O | H | H | 4-Cl |
| i-PrCCl(Me)CH₂ | OMe | O | H | H | 4-Cl |
| i-PrCCl(Me)CH₂ | OMe | O | H | H | 4-I |
| i-PrCCl(Me)CH₂ | SMe | O | H | H | 4-Cl |
| i-PrCCl(Me)CH₂ | SMe | O | H | H | 4-I |
| i-PrCCl(Me)CH₂ | SO₂Me | O | H | H | 4-Cl |
| i-PrCCl(Me)CH₂ | Cl | O | H | Me | 4-Cl |
| i-PrCCl(Me)CH₂ | Cl | O | Cl | H | 4-Cl |
| i-PrCCl(Me)CH₂ | Cl | O | H | H | 2-Cl, 4-I |
| i-PrCCl(Me)CH₂ | Cl | O | H | H | 4-Ph |
| i-PrCCl(Me)CH₂ | Cl | O | H | H | 4-OCH₂CF₃ |
| i-PrCCl(Me)CH₂ | Cl | O | H | H | 2,6-Cl₂ |
| i-PrCCl(Me)CH₂ | Cl | S | H | H | 4-Cl |
| i-PrCCl(Me)CH₂ | Cl | S | H | H | 4-Bu-t |
| i-PrCCl(Me)CH₂ | Cl | S | H | H | 4-Et |
| i-PrCCl(Me)CH₂ | Cl | S | H | H | 4-COOEt |
| i-PrCCl(Me)CH₂ | Cl | S | H | H | 4-C₆H₄F-4' |
| i-PrCCl(Me)CH₂ | Cl | S | H | H | 4-COPh |
| i-PrCBr(Me)CH₂ | Cl | O | H | H | 4-Cl |
| i-PrCBr(Me)CH₂ | Cl | O | H | H | 4-Br |
| i-PrCBr(Me)CH₂ | Cl | O | H | H | 4-I |
| i-PrCBr(Me)CH₂ | Cl | O | H | H | 2,4-Cl₂ |
| i-PrCBr(Me)CH₂ | Br | O | H | H | 4-Cl |
| i-PrCBr(Me)CH₂ | Br | O | H | H | 4-I |
| i-PrCBr(Me)CH₂ | I | O | H | H | 4-Cl |
| i-PrCBr(Me)CH₂ | I | O | H | H | 4-I |
| i-PrCBr(Me)CH₂ | F | O | H | H | 4-Cl |
| HexCHBrCH₂ | Cl | O | H | H | 4-Cl |
| HexCHBrCH₂ | Cl | O | H | H | 4-I |
| i-BuCCl(Me)CH₂ | Cl | O | H | H | 4-Cl |
| i-BuCCl(Me)CH₂ | Cl | O | H | H | 4-Br |
| i-BuCCl(Me)CH₂ | Cl | O | H | H | 4-I |
| i-BuCCl(Me)CH₂ | Cl | O | H | H | 2,4-Cl₂ |
| i-BuCCl(Me)CH₂ | Br | O | H | H | 4-Cl |
| i-BuCCl(Me)CH₂ | I | O | H | H | 4-Cl |
| i-BuCCl(Me)CH₂ | I | O | H | H | 4-I |
| i-BuCCl(Me)CH₂ | Me | O | H | H | 4-Cl |
| i-BuCCl(Me)CH₂ | OMe | O | H | H | 4-Cl |
| i-BuCCl(Me)CH₂ | Sme | O | H | H | 4-Cl |
| i-BuCCl(Me)CH₂ | F | O | H | H | 4-Cl |

TABLE 1-continued

In Compounds of the formula:

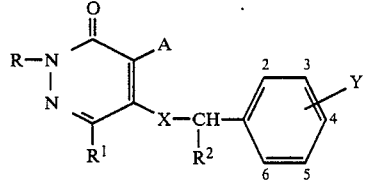

| R | A | X | R¹ | R² | Y |
|---|---|---|---|---|---|
| i-BuCCl(Me)CH₂ | Cl | O | H | H | 2-F,4-Cl |
| i-BuCCl(Me)CH₂ | Cl | O | H | H | 4-OCH₂CH(Me)—O-Q17 |
| i-BuCCl(Me)CH₂ | Cl | S | H | H | 4-Cl |
| i-BuCCl(Me)CH₂ | Cl | S | H | H | 4-Bu-t |
| i-BuCCl(Me)CH₂ | Cl | S | H | H | 4-(Q4) |
| i-BuCCl(Me)CH₂ | Cl | S | H | H | 4-OC(Me)₂CH₂OMe |
| i-BuCBr(Me)CH₂ | Cl | O | H | H | 4-Cl |
| i-BuCBr(Me)CH₂ | Cl | O | H | H | 4-Br |
| i-BuCBr(Me)CH₂ | Cl | O | H | H | 4-I |
| i-BuCBr(Me)CH₂ | Cl | O | H | H | 2,4-Cl₂ |
| i-BuCBr(Me)CH₂ | Br | O | H | H | 4-Cl |
| i-BuCBr(Me)CH₂ | I | O | H | H | 4-Cl |
| i-BuCBr(Me)CH₂ | Cl | S | H | H | 4-Cl |
| i-BuCBr(Me)CH₂ | Cl | S | H | H | 4-O(CH₂)₃C≡CCl |
| C₈H₁₇CHClCH₂ | Cl | O | H | H | 4-Cl |
| Me₂C(OMe)(CH₂)₃C(Me)=CHCHCl | Cl | O | H | H | 4-Cl |
| Me₂C(OMe)(CH₂)₃CCl(Me)CHClCH₂ | Cl | O | H | H | 4-Cl |
| C₁₄H₂₉CHClCH₂ | Cl | O | H | H | 4-Cl |
| Me₂C=CHCH₂CH₂CCl(Me)CHClCH₂ | Cl | O | H | H | 4-Cl |
| EtCH=C(Me)CH₂CH₂CHClC(Me)₂ | Cl | O | H | H | 4-Cl |
| HC≡C(CH₂)₁₀CHClCH₂ | Cl | O | H | H | 4-Cl |
| s-BuCCl(Me)CH₂ | Cl | O | H | H | 4-Cl |
| s-BuCCl(Me)CH₂ | Cl | O | H | H | 4-Br |
| s-BuCCl(Me)CH₂ | Cl | O | H | H | 4-I |
| s-BuCCl(Me)CH₂ | Cl | O | H | H | 2,4-Cl₂ |
| s-BuCCl(Me)CH₂ | Br | O | H | H | 4-Cl |
| s-BuCCl(Me)CH₂ | I | O | H | H | 4-Cl |
| s-BuCCl(Me)CH₂ | I | O | H | H | 4-I |
| s-BuCCl(Me)CH₂ | Me | O | H | H | 4-Cl |
| s-BuCCl(Me)CH₂ | OMe | O | H | H | 4-Cl |
| s-BuCCl(Me)CH₂ | SMe | O | H | H | 4-Cl |
| s-BuCCl(Me)CH₂ | F | O | H | H | 4-Cl |
| s-BuCCl(Me)CH₂ | Cl | O | H | H | 2-F, 4-Cl |
| s-BuCCl(Me)CH₂ | Cl | O | H | H | 4-O(CH₂)₃C≡CCl |
| s-BuCCl(Me)CH₂ | Cl | S | H | H | 4-Cl |
| s-BuCCl(Me)CH₂ | Cl | S | H | H | 4-Bu-t |
| s-BuCCl(Me)CH₂ | Cl | S | H | H | 4-Et |
| s-BuCCl(Me)CH₂ | Cl | S | H | H | 4-OCH₂CH(Me)—O-Q17 |
| s-BuCBr(Me)CH₂ | Cl | O | H | H | 4-Cl |
| s-BuCBr(Me)CH₂ | Cl | O | H | H | 4-Br |
| s-BuCBr(Me)CH₂ | Cl | O | H | H | 4-I |
| s-BuCBr(Me)CH₂ | Cl | O | H | H | 2,4-Cl₂ |
| s-BuCBr(Me)CH₂ | Br | O | H | H | 4-Cl |
| s-BuCBr(Me)CH₂ | I | O | H | H | 4-Cl |
| s-BuCBr(Me)CH₂ | Cl | O | H | H | 4-Bu-t |
| s-BuCBr(Me)CH₂ | Cl | S | H | H | 4-Cl |
| s-BuCBr(Me)CH₂ | Cl | S | H | H | 4-Bu-t |
| MeCH=CH(CH₂)₇CHClCH₂ | Cl | O | H | H | 4-Cl |
| (3,3-Me₂-Q21)CH₂CH₂C(Me)=CHCH₂CCl(Me)CH₂ | Cl | O | H | H | 4-Cl |
| Me₂C(OMe)(CH₂)₃CCl(Me)CH₂CH=CHCCl(Me)CH₂ | Cl | O | H | H | 4-Cl |
| CH₂=CH(CH₂)₁₂CHClCH₂ | Cl | O | H | H | 4-Cl |
| MeC≡C(CH₂)₃CHClCH₂ | Cl | O | H | H | 4-Cl |
| s-BuCBr(Me)CH₂ | Cl | S | H | H | 4-OC(Me)₂CH₂OEt |
| ClCH=CH | Cl | O | H | H | 4-Cl |
| ClCH=CH | Cl | O | H | H | 4-I |
| BrCH=CH | Cl | O | H | H | 4-Cl |
| BrCH=CH | Cl | O | H | H | 4-I |
| CH₂=C(Cl) | Cl | O | H | H | 4-Cl |
| CH₂=C(Cl) | Cl | O | H | H | 4-I |
| CH₂=C(Br) | Cl | O | H | H | 4-Cl |
| CH₂=C(Br) | Cl | O | H | H | 4-I |
| CH₂=C(CH₂Cl) | Cl | O | H | H | 4-Cl |
| CH₂=C(CH₂Cl) | Cl | O | H | H | 4-I |
| CH₂=C(CH₂Br) | Cl | O | H | H | 4-Cl |
| Me₂C=C(CH₂Cl) | Cl | O | H | H | 4-Cl |
| Me₂C=C(CH₂Cl) | Cl | O | H | H | 4-I |
| CH₂=C(Cl)CH₂ | Cl | O | H | H | 4-Cl |
| CH₂=C(Cl)CH₂ | Cl | O | H | H | 4-I |
| CH₂=C(Br)CH₂ | Cl | O | H | H | 4-Cl |
| Me₂C=C(Cl)CH₂ | Cl | O | H | H | 4-Cl |

TABLE 1-continued

In Compounds of the formula:

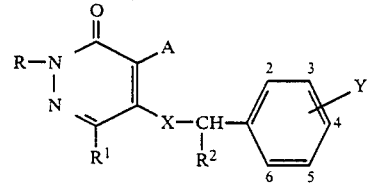

| R | A | X | $R^1$ | $R^2$ | Y |
|---|---|---|---|---|---|
| $Me_2C=C(Cl)CH_2$ | Cl | O | H | H | 4-I |
| $Me_2C=C(Br)CH_2$ | Cl | O | H | H | 4-Cl |
| $Me_2C=C(Br)CH_2$ | Cl | O | H | H | 4-I |
| $CH_2=CHCH(Me)CHClCH_2$ | Cl | O | H | H | 4-Cl |
| $CH_2=CHCH(Me)CHClCH_2$ | Cl | O | H | H | 4-I |
| $CH_2=CHCH(Me)CHBrCH_2$ | Cl | O | H | H | 4-Cl |
| $CH_2=CHCH(Me)CHBrCH_2$ | Cl | O | H | H | 4-I |
| $CH_2=CHCH_2CCl(Me)CH_2$ | Cl | O | H | H | 4-Cl |
| $CH_2=CHCH_2CCl(Me)CH_2$ | Cl | O | H | H | 4-I |
| $CH_2=CHCH_2CBr(Me)CH_2$ | Cl | O | H | H | 4-Cl |
| $CH_2=CHCH_2CBr(Me)CH_2$ | Cl | O | H | H | 4-I |
| $CH_2=C(Me)CH_2CHClCH_2$ | Cl | O | H | H | 4-Cl |
| $CH_2=C(Me)CH_2CHClCH_2$ | Cl | O | H | H | 4-I |
| $CH_2=C(Me)CH_2CHBrCH_2$ | Cl | O | H | H | 4-Cl |
| $CH_2=C(Me)CH_2CH_2CCl(Me)CH_2$ | Cl | O | H | H | 4-Cl |
| $CH_2=C(Me)CH_2CH_2CCl(Me)CH_2$ | Cl | O | H | H | 4-I |
| $CH_2=C(Me)CH_2CH_2CBr(Me)CH_2$ | Cl | O | H | H | 4-Cl |
| $CH_2=CHCH_2CH_2CHClCH_2$ | Cl | O | H | H | 4-Cl |
| $CH_2=CHCH_2CH_2CHClCH_2$ | Cl | O | H | H | 4-I |
| $CH_2=CHCH_2CH_2CHBrCH_2$ | Cl | O | H | H | 4-Cl |
| $CH_2=CHCH_2CH_2CCl(Me)CH_2$ | Cl | O | H | H | 4-Cl |
| $CH_2=CHCH_2CH_2CCl(Me)CH_2$ | Cl | O | H | H | 4-I |
| $CH_2=CHCH_2CH_2CBr(Me)CH_2$ | Cl | O | H | H | 4-Cl |
| $CH_2=C(Me)CH_2CH_2CHClCH_2$ | Cl | O | H | H | 4-Cl |
| $CH_2=C(Me)CH_2CH_2CHClCH_2$ | Cl | O | H | H | 4-I |
| $CH_2=C(Me)CH_2CH_2CHBrCH_2$ | Cl | O | H | H | 4-Cl |
| $CH_2=CHCH(Me)CH_2CHClCH_2$ | Cl | O | H | H | 4-Cl |
| $CH_2=CHCH(Me)CH_2CHClCH_2$ | Cl | O | H | H | 4-I |
| $CH_2=CHCH_2CH(Me)CHClCH_2$ | Cl | O | H | H | 4-Cl |
| $CH_2=CHCH_2CH(Me)CHClCH_2$ | Cl | O | H | H | 4-I |
| $CH_2=CHCH_2CH(Me)CHBrCH_2$ | Cl | O | H | H | 4-Cl |
| $CH_2=CHCH_2CH(Me)CHBrCH_2$ | Cl | O | H | H | 4-I |
| $MeCH=CHCH_2CHClCH_2$ | Cl | O | H | H | 4-Cl |
| $MeCH=CHCH_2CHClCH_2$ | Cl | O | H | H | 4-I |
| $MeCH=CHCH_2CHBrCH_2$ | Cl | O | H | H | 4-Cl |
| $MeCH=CHCH_2CHBrCH_2$ | Cl | O | H | H | 4-I |
| $CH_2=CH(CH_2)_3CHClCH_2$ | Cl | O | H | H | 4-Cl |
| $CH_2=CH(CH_2)_3CHClCH_2$ | Cl | O | H | H | 4-I |
| $CH_2=CH(CH_2)_3CHBrCH_2$ | Cl | O | H | H | 4-Cl |
| $CH_2=CH(CH_2)_3CHBrCH_2$ | Cl | O | H | H | 4-I |
| $CH_2=Ch(CH_2)_4CHClCH_2$ | Cl | O | H | H | 4-Cl |
| $CH_2=CH(CH_2)_2CHClCH_2$ | Cl | O | H | H | 4-I |
| $CH_2=CH(CH_2)_4CHClCH_2$ | Br | O | H | H | 4-Cl |
| $CH_2=CH(CH_2)_4CHClCH_2$ | I | O | H | H | 4-I |
| $Ch_2=CH(CH_2)_4CHBrCH_2$ | Cl | O | H | H | 4-Cl |
| $CH_2=CH(CH_2)_4CHBrCH_2$ | Cl | O | H | H | 4-I |
| $CH_2=C(Cl)CH_2$ | Cl | O | H | H | 4-Cl |
| $CH_2=C(Cl)CH_2$ | Cl | O | H | H | 4-I |
| $CH_2=C(Cl)CH_2$ | Br | O | H | H | 4-Cl |
| $CH_2=C(Cl)CH_2$ | I | O | H | H | 4-i |
| $Ch_2=C(CH_2Cl)CH_2$ | Cl | O | H | H | 4-Cl |
| $CH_2=C(CH_2Cl)CH_2$ | Cl | O | H | H | 4-I |
| $CH_2=C(CH_2Cl)CH_2$ | Br | O | H | H | 4-Cl |
| $Ch_2=C(CH_2Cl)CH_2$ | I | O | H | H | 4-I |
| $ClCH=CHCH_2$ | Cl | O | H | H | 4-Cl |
| $ClCH=CHCH_2$ | Cl | O | H | H | 4-I |
| $ClCH=CHCH_2$ | Br | O | H | H | 4-Cl |
| $ClCH=CHCH_2$ | I | O | H | H | 4-Cl |
| $BrCH=CHCH_2$ | Cl | O | H | H | 4-Cl |
| $BrCH=CHCH_2$ | Cl | O | H | H | 4-I |
| $ClCH=C(Cl)CH_2$ | Cl | O | H | H | 4-Cl |
| $ClCH=C(Cl)CH_2$ | Cl | O | H | H | 4-I |
| $ClCH=C(Cl)CH_2$ | Br | O | H | H | 4-Cl |
| $ClCH=C(Cl)CH_2$ | I | O | H | H | 4-Cl |
| $BrCH=C(Br)CH_2$ | Cl | O | H | H | 4-Cl |
| $BrCH=C(Br)CH_2$ | Cl | O | H | H | 4-I |
| $ClCH_2CH=CHCH_2$ | Cl | O | H | H | 4-Cl |
| $ClCH_2CH=CHCH_2$ | Cl | O | H | H | 4-I |
| $ClCH_2CH=CHCH_2$ | Br | O | H | H | 4-Cl |

TABLE 1-continued

In Compounds of the formula:

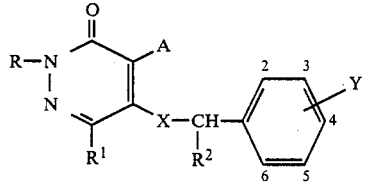

| R | A | X | R¹ | R² | Y |
|---|---|---|---|---|---|
| ClCH$_2$CH=CHCH$_2$ | I | O | H | H | 4-Cl |
| BrCN$_2$CN=CHCH$_2$ | Cl | O | H | H | 4-Cl |
| BrCN$_2$CH=CHCH$_2$ | Cl | O | H | H | 4-I |
| BrCH$_2$CH=CHCH$_2$ | Br | O | H | H | 4-Cl |
| BrCH$_2$CH=CHCH$_2$ | I | O | H | H | 4-Cl |
| MeC(Cl)=CHCH$_2$ | Cl | O | H | H | 4-Cl |
| MeC(Cl)=CHCH$_2$ | Cl | O | H | H | 4-I |
| MeC(Cl)=CHCH$_2$ | Br | O | H | H | 4-Cl |
| MeC(Cl)=CHCH$_2$ | I | O | H | H | 4-Cl |
| CH$_2$=CHCHClCH$_2$ | Cl | O | H | H | 4-Cl |
| CH$_2$=CHCHClCH$_2$ | Cl | O | H | H | 4-I |
| CH$_2$=CHCHClCH$_2$ | Br | O | H | H | 4-Cl |
| CH$_2$=CHCHClCH$_2$ | I | O | H | H | 4-Cl |
| ClCH$_2$C≡CCH$_2$ | Cl | O | H | H | 4-Cl |
| ClCH$_2$C≡CCH$_2$ | Cl | O | H | H | 4-I |
| ClC≡C | Cl | O | H | H | 4-Cl |
| ClC≡C | Cl | O | H | H | 4-I |
| BrC≡C | Cl | O | H | H | 4-I |
| ClC≡CCH$_2$ | Cl | O | H | H | methyl |
| ClC≡CCH$_2$ | Cl | O | H | H | 4-I |
| BrC≡CCH$_2$ | Cl | O | H | H | 4-Cl |
| BrC≡CCH$_2$ | Cl | O | H | H | 4-I |
| ClCH$_2$C≡C | Cl | O | H | H | 4-Cl |
| ClCH$_2$C≡C | Cl | O | H | H | 4-Cl |
| BrCH$_2$C≡C | Cl | O | H | H | 4-Cl |
| BrCH$_2$C≡C | Cl | O | H | H | 4-I |
| Q1-2,2-F$_2$ | Cl | O | H | H | 4-Cl |
| Q1-2,2-F$_2$ | Cl | O | H | H | 4-I |
| (Q1-2,2-Cl$_2$) | CH$_5$ | Cl | H | H | 4-Cl |
| (Q1-2,2-Cl$_2$)CH$_3$ | Cl | O | H | H | 4-I |
| (Q1-2,2-Br$_2$)CH$_2$ | Cl | O | O | H | H |
| (Q1-2,2-Br$_2$)CH$_2$ | Cl | O | H | H | 4-I |
| (Q1-2,2-F$_2$)CH$_2$ | Cl | O | H | H | 4-Cl |
| (Q1-2,2-F$_2$)CH$_2$ | C | O | H | H | 4-I |
| (Q1-2,2-F$_2$-3-Me)CH$_2$ | Cl | O | H | H | 4-Cl |
| (Q1-2,2-F$_2$-3-Me)CH$_2$ | Cl | O | H | H | 4-I |
| (Q1-2,2-Cl$_2$-3-Me)CH$_2$ | Cl | O | H | H | 4-Cl |
| (Q1-2,2-Cl$_2$-3-Me)CH$_2$ | Cl | O | H | H | 4-I |
| (Q1-2,2-F$_2$ 3,3-Me$_2$)CH$_2$ | Cl | O | H | H | 4-Cl |
| (Q1-2,2-F$_2$ 3,3-Me$_2$)CH$_2$ | Cl | O | H | H | 4-I |
| (Q1-2,2-Cl$_2$ 3,3-Me$_2$)CH$_2$ | Cl | O | H | H | 4-Cl |
| (Q1-2,2-Cl$_2$ 3,3-Me$_2$)CH$_2$ | Cl | O | H | H | 4-I |
| (Q1-2,2-Br$_2$ 3,3-Me$_2$)CH$_2$ | Cl | O | H | H | 4-Cl |
| (Q1-2,2-Br$_2$ 3,3-Me$_2$)CH$_2$ | Cl | O | H | H | 4-I |
| (Q1-2-Cl-3,3-Me$_2$)CH$_2$ | Cl | O | H | H | 4-Cl |
| (Q1-2-Cl-3,3-Me$_2$)CH$_2$ | Cl | O | H | H | 4-I |
| (Q1-2-cl-3-Me)CH$_2$ | Cl | O | H | H | 4-Cl |
| (Q1-2-Cl-3-Me)CH$_2$ | Cl | O | H | H | 4-I |
| (Q1-2,2-Cl$_2$-1-Me)CH(Me) | Cl | O | H | H | 4-Cl |
| (Q1-2,2-Cl$_2$-1-Me)CH(Me) | Cl | O | H | H | 4-I |
| (Q1-2,2-F$_2$-1-Me)CH$_2$ | Cl | O | H | H | 4-Cl |
| (Q1-2,2-F$_2$-1-Me)CH$_2$ | Cl | O | H | H | 4-I |
| (Q1-2,2-F$_2$-1-Cl)CH$_2$ | Cl | O | H | H | 4-Cl |
| (Q1-2,2-F$_2$-1-Cl)CH$_2$ | Cl | O | H | H | 4-I |
| (Q1-2,2-Cl$_2$l-Me)CH$_2$CH$_2$ | Cl | O | H | H | 4-Cl |
| (Q1-2,2-Cl$_2$-1-Mel) CH$_2$CH$_3$ | Cl | O | H | H | 4-I |
| (Q1-2,2-Cl$_2$3,3-Me$_2$)CH$_2$CH$_2$ | Cl | O | H | H | 4-Cl |
| (Q1-2,2-Cl$_2$3,3-Me$_2$)CH$_2$Ch$_2$ | Cl | O | H | H | 4-I |
| (Q1-2-Cl)CH$_2$CH$_2$ | Cl | O | H | H | 4-Cl |
| (Q1-2-Cl)CH$_2$Ch$_2$ | Cl | O | H | H | 4-I |
| (Q1-2,2-F$_2$)CH$_2$Ch$_2$ | Cl | O | H | H | 4-Cl |
| (Q1-2,2-F$_2$)CH$_2$CH$_2$ | Cl | O | H | H | 4-I |
| (Q1-2,2-F$_2$)CH$_2$Ch$_2$CH$_2$ | Cl | O | H | H | 4-Cl |
| (Q1-2,2-F$_2$)CH$_2$CH$_2$CH$_2$ | Cl | O | H | H | 4-I |
| (Q1-1-Cl)CH$_2$ | Cl | O | H | H | 4-Cl |
| (Q1-1-Cl)CH$_2$ | Cl | O | H | H | 4-I |
| (Q1-1-Cl)CH$_2$ | Br | O | H | H | 4-Cl |
| (Q1-1-Cl)CH$_2$ | I | O | H | H | 4-Cl |
| (Q1-1-Br)CH$_2$ | Cl | O | H | H | 4-Cl |
| (Q1-1-Br)CH$_2$ | Cl | O | H | H | 4-I |

TABLE 1-continued

In Compounds of the formula:

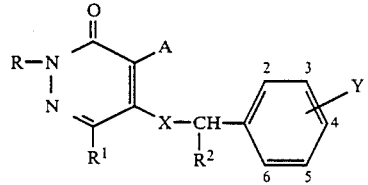

| R | A | X | R¹ | R² | Y |
|---|---|---|----|----|---|
| (Q1-1-Br)CH₂ | Br | O | H | H | 4-Cl |
| (Q1-1-Br)CH₂ | I | O | H | H | 4-Cl |
| (Q2-1-Cl)CH₂ | Cl | O | H | H | 4-Cl |
| (Q2-1-Cl)CH₂ | Cl | O | H | H | 4-I |
| (Q2-1-Cl)CH₂ | Br | O | H | H | 4-Cl |
| (Q2-1-Cl)CH₂ | I | O | H | H | 4-Cl |
| (Q2-1-Br)CH₂ | Cl | O | H | H | 4-Cl |
| (Q2-1-Br)CH₂ | Cl | O | H | H | 4-I |
| (Q2-1-Br)CH₂ | Br | O | H | H | 4-Cl |
| (Q2-1-Br)CH₂ | I | O | H | H | 4-Cl |
| (Q3-1-Cl)CH₂ | Cl | O | H | H | 4-Cl |
| (Q3-1-Cl)CH₂ | Cl | O | H | H | 4-I |
| (Q3-1-Cl)CH₂ | Br | O | H | H | 4-Cl |
| (Q3-1-Cl)CH₂ | I | O | H | H | 4-Cl |
| (Q3-1-Br)CH₂ | Cl | O | H | H | 4-Cl |
| (Q3-1-Br)CH₂ | Cl | O | H | H | 4-I |
| (Q3-1-Br)CH₂ | Br | O | H | H | 4-Cl |
| (Q3-1-Br)CH₂ | I | O | H | H | 4-Cl |
| Q3-2-Cl | Cl | O | H | H | 4-Cl |
| Q3-2-Cl | Cl | O | H | H | 2,4-Cl₂ |
| Q3-2-Cl | Cl | O | H | H | 4-I |
| Q3-2-Cl | Br | O | H | H | 4-Cl |
| Q3-2-Cl | I | O | H | H | 4-Cl |
| Q3-2-cl | Cl | S | H | H | 4-Cl |
| Q3-2-Cl | Cl | S | H | H | 4-Bu-t |
| Q3-2-Br | Cl | O | H | H | 4-Cl |
| Q3-2-Br | Cl | O | H | H | 2,4-Cl₂ |
| Q3-2-Br | Cl | O | H | H | 4-I |
| Q3-2-Br | Br | O | H | H | 4-Cl |
| Q3-2-Br | I | O | H | H | 4-Cl |
| Q3-2-Br | Cl | S | H | H | 4-Cl |
| Q3-2-Br | Cl | S | H | H | 4-Bu-t |
| Q3-CH(Cl)CH₂ | Cl | O | H | H | 4-Cl |
| Q3-CH(Cl)CH₂ | Cl | O | H | H | 4-I |
| Q3-CH(Br)CH₂ | Cl | O | H | H | 4-Cl |
| Q3-CH(Br)CH₂ | Cl | O | H | H | 4-I |
| Q3-1,2,3,3,4,4,5,5-F₈ | Cl | O | H | H | 4-Cl |
| Q3-1,2,3,3,4,4,5,5-F₈ | Cl | O | H | H | 4-I |
| Q3-1,2,3,3,4,4,5-F₇ | Cl | O | H | H | 4-Cl |
| Q3-1,2,3,3,4,4,5-F₇ | Cl | O | H | H | 4-I |
| Q4-CHClCH₂ | Cl | O | H | H | 4-Cl |
| Q4-CHClCH₂ | Cl | O | H | H | 4-I |
| Q4-CHBrCH₂ | Cl | O | H | H | 4-Cl |
| Q4-CHBrCH₂ | Cl | O | H | H | 4-I |
| (Q4-1-Cl)CH₂ | Cl | O | H | H | 4-Cl |
| (Q4-1-Cl)CH₂ | Cl | O | H | H | 4-I |
| (Q4-1-Cl)CH₂ | Br | O | H | H | 4-Cl |
| (Q4-1-Cl)CH₂ | I | O | H | H | 4-Cl |
| (Q4-1-Br)CH₂ | Cl | O | H | H | 4-Cl |
| (Q4-1-Br)CH₂ | Cl | O | H | H | 4-I |
| (Q4-1-Br)CH₂ | Br | O | H | H | 4-Cl |
| (Q4-1-Br)CH₂ | I | O | H | H | 4-Cl |
| Q4-1,2-Cl₂ | Cl | O | H | H | 4-Cl |
| Q4-1,2-Cl₂ | Cl | O | H | H | 4-I |
| Q4-1,2-C₂ | Br | O | H | H | 4-Cl |
| Q4-1,2-Cl₂ | I | O | H | H | 4-Cl |
| Q4-1,2-Br₂ | Cl | O | H | H | 4-Cl |
| Q4-1,2-Br₂ | Cl | O | H | H | 4-I |
| Q4-1,2-Br₂ | Br | O | H | H | 4-Cl |
| Q4-1,2-Br₂ | I | O | H | H | 4-Cl |
| Q4-2-Cl-2-Me | Cl | O | H | H | 4-Cl |
| Q4-2-Cl-2-Me | Cl | O | H | H | 4-I |
| Q4-2-Cl-2-Me | Br | O | H | H | 4-Cl |
| Q4-2-Cl-2-Me | I | O | H | H | 4-Cl |
| Q4-2-Br-2-Me | Cl | O | H | H | 4-Cl |
| Q4-2-Br-2-Me | Cl | O | H | H | 4-I |
| Q4-2-Br-2-Me | Br | O | H | H | 4-Cl |
| Q4-2-Br-2-Me | I | O | H | H | 4-Cl |
| Q4-2-Cl-1-Me | Cl | O | H | H | 4-Cl |
| Q4-2-Cl-1-Me | Cl | O | H | H | 4-I |

TABLE 1-continued

In Compounds of the formula:

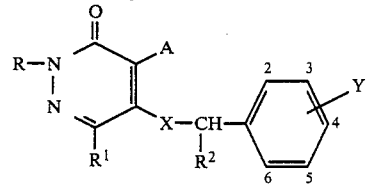

| R | A | X | R¹ | R² | Y |
|---|---|---|---|---|---|
| Q4-2-Cl-1-Me | Br | O | H | H | 4-Cl |
| Q4-2-Cl-1-Me | I | O | H | H | 4-Cl |
| Q4-2-Br-1-Me | Cl | O | H | H | 4-Cl |
| Q4-2-Br-1-Me | Cl | O | H | H | 4-I |
| Q4-2-Br-1-Me | Br | O | H | H | 4-Cl |
| Q4-2-Br-1-Me | I | O | H | H | 4-Cl |
| Q4-2,2-Cl₂ | Cl | O | H | H | 4-Cl |
| Q4-2,2-Cl₂ | Cl | O | H | H | 4-I |
| Q4-2,2-Cl₂ | Br | O | H | H | 4-Cl |
| Q4-2,2-Cl₂ | I | O | H | H | 4-Cl |
| Q4-2-Cl-2-Br | Cl | O | H | H | 4-Cl |
| Q4-2-Cl-2-Br | Cl | O | H | H | 4-I |
| Q4-2-Cl-2-Br | Br | O | H | H | 4-Cl |
| Q4-2-Cl-2-Br | I | O | H | H | 4-Cl |
| Q4-2-Cl-4-Me | Cl | O | H | H | 4-Cl |
| Q4-2-Cl-4-Me | Cl | O | H | H | 4-I |
| Q4-2-Cl-4-Me | Br | O | H | H | 4-Cl |
| Q4-2-Cl-4-Me | I | O | H | H | 4-Cl |
| Q4-2-Br-4-Me | Cl | O | H | H | 4-Cl |
| Q4-2-Br-4-Me | Cl | O | H | H | 4-I |
| Q4-2-Br-4-Me | Br | O | H | H | 4-Cl |
| Q4-2-Br-4-Me | I | O | H | H | 4-Cl |
| Q4-2-Cl-5-Me | Cl | O | H | H | 4-Cl |
| Q4-2-Cl-5-Me | Cl | O | H | H | 4-I |
| Q4-2-Cl-5-Me | Br | O | H | H | 4-Cl |
| Q4-2-Cl-5-Me | I | O | H | H | 4-Cl |
| Q4-2-Br-5-Me | Cl | O | H | H | 4-Cl |
| Q4-2-Br-5-Me | Cl | O | H | H | 4-I |
| Q4-2-Br-5-Me | Br | O | H | H | 4-Cl |
| Q4-2-Br-5-Me | I | O | H | H | 4-Cl |
| Q4-2-Cl | Cl | O | H | H | 4-Cl |
| Q4-2-Cl | Cl | O | H | H | 4-Br |
| Q4-2-Cl | Cl | O | H | H | 2,4-Cl₂ |
| Q4-2-Cl | Br | O | H | H | 4-Cl |
| Q4-2-Cl | Br | O | H | H | 4-I |
| Q4-2-Cl | I | O | H | H | 4-Cl |
| Q4-2-Cl | F | O | H | H | 4-Cl |
| Q4-2-Cl | Me | O | H | H | 4-Cl |
| Q4-2-Cl | OMe | O | H | H | 4-Cl |
| Q4-2-Cl | OMe | O | H | H | 4-I |
| Q4-2-Cl | SMe | O | H | H | 4-Cl |
| Q4-2-Cl | SMe | O | H | H | 4-I |
| Q4-2-Cl | SO₂Me | O | H | H | 4-Cl |
| Q4-2-Cl | Cl | O | H | Me | 4-Cl |
| Q4-2-Cl | Cl | O | Cl | H | 4-Cl |
| Q4-2-Cl | OMe | O | H | H | 4-Br |
| Q4-2-Cl | SO₂Et | O | H | H | 4-Cl |
| Q4-2-Cl | Cl | O | H | H | 2-Me |
| Q4-2-Cl | Cl | O | H | H | 4-OPr |
| Q4-2-Cl | Cl | O | H | H | 4-CF₃ |
| Q4-2-Cl | Cl | O | H | H | 2,4,5-Cl₃ |
| Q4-2-Cl | Cl | S | H | H | 4-Cl |
| Q4-2-Cl | Cl | S | H | H | 4-Bu-t |
| Q4-2-Cl | Cl | S | H | H | 4-C₆H₄Cl-4' |
| Q4-2-Cl | Cl | S | H | H | 4-OC₆H₄F-4' |
| Q4-2-Cl | Cl | S | H | H | 4-(Q4) |
| Q4-2-Cl | Cl | S | H | H | 4-SiMe₃ |
| Q4-2-Br | Cl | O | H | H | 4-Cl |
| Q4-2-Br | Cl | O | H | H | 4-Br |
| Q4-2-Br | Cl | O | H | H | 2,4-Cl₂ |
| Q4-2-Br | Br | O | H | H | 4-Cl |
| Q4-2-Br | Br | O | H | H | 4-I |
| Q4-2-Br | I | O | H | H | 4-Cl |
| Q4-2-Br | F | O | H | H | 4-Cl |
| Q4-2-Br | Me | O | H | H | 4-Cl |
| Q4-2-Br | OEt | O | H | H | 4-Cl |
| Q4-2-Br | SEt | O | H | H | 4-Cl |
| Q4-2-Br | SO₂Me | O | H | H | 4-Cl |
| Q4-2-Br | Cl | O | H | Et | 4-Cl |
| Q4-2-Br | Cl | O | Cl | H | 4-Cl |

TABLE 1-continued

In Compounds of the formula:

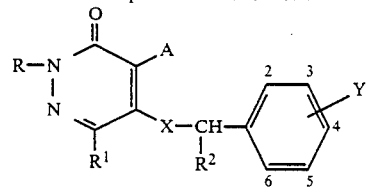

| R | A | X | R¹ | R² | Y |
|---|---|---|----|----|---|
| Q4-2-Br | Cl | O | H | H | 2-F,4-cl |
| Q4-2-Br | OPr | O | H | H | 4-Cl |
| Q4-2-Br | Cl | O | H | Bu | 4-I |
| Q4-2-Br | Cl | O | H | H | 4-Me |
| Q4-2-Br | Cl | O | H | H | 4-OCHF$_2$ |
| Q4-2-Br | Cl | S | H | H | 4-Cl |
| Q4-2-Br | Cl | S | H | H | 4-Bu-t |
| Q4-2-Br | Cl | S | H | H | 4-OC(Me)$_2$CH$_2$OPr |
| Q4-2-Br | Cl | S | H | H | 4-SMe |
| Q4-2-Br | Cl | S | H | H | 4-I |
| Q4-F$_{11}$ | Cl | O | H | H | 4-Cl |
| Q4-F$_{11}$ | Cl | O | H | H | 4-I |
| (Q4-F$_{11}$)CH$_2$ | Cl | O | H | H | 4-Cl |
| (Q4-F$_{11}$)CH$_2$ | cl | O | H | H | 4-I |
| (Q4-1,2,2,3,4,4,5,5,6,6-F$_{10}$-3-CFp$_3$)CH$_2$ | Cl | O | H | H | 4-Cl |
| (Q4-1,2,2,3,3,4,4,5,5,6,6-F$_{10}$-4-CF$_3$O)CH$_2$ | Cl | O | H | H | 4-Cl |
| Q5-2-Cl | Cl | O | H | H | 4-Cl |
| Q5-2-Cl | Cl | O | H | H | 2,4-Cl$_2$ |
| Q5-2-Cl | Cl | O | H | H | 4-I |
| Q5-2-Cl | Br | O | H | H | 4-Cl |
| Q5-2-Cl | I | O | H | H | 4-Cl |
| Q5-2-Cl | Cl | S | H | H | 4-Cl |
| Q5-2-Cl | Cl | S | H | H | 4-Bu-t |
| Q5-2-Cl | Cl | O | H | H | 4-Cl |
| Q5-2-Cl | Cl | O | H | H | 2,4-Cl$_2$ |
| Q5-2-Cl | Cl | O | H | H | 4-I |
| Q5-2-Cl | Br | O | H | H | 4-Cl |
| Q5-2-Cl | I | O | H | H | 4-Cl |
| Q5-2-Cl | Cl | S | H | H | 4-Cl |
| Q5-2-Cl | Cl | S | H | H | 4-Bu-t |
| FCH$_2$C(Me)$_2$ | Cl | O | H | H | 4-Cl |
| FCH$_2$C(Me)$_2$ | Cl | O | H | H | 4-I |
| Me$_2$CF | Cl | O | H | H | 4-Cl |
| Me$_2$CF | Cl | O | H | H | 4-I |
| (CF$_3$)$_2$CH | Cl | O | H | H | 4-Cl |
| (CF$_3$)$_2$CH | Cl | O | H | H | 4-I |
| (CF$_3$)$_2$CF | Cl | O | H | H | 4-Cl |
| (CF$_3$)$_2$CF | Cl | O | H | H | 4-I |
| CHF$_2$C(CF$_3$)F | Cl | O | H | H | 4-Cl |
| CHF$_2$C(CF$_3$)F | Cl | O | H | H | 4-I |
| (CHF$_2$)$_2$C(Me) | Cl | O | H | H | 4-Cl |
| (CHF$_2$)$_2$C(Me) | Cl | O | H | H | 4-I |
| MeCH(F)CH$_2$ | Cl | O | H | H | 4-Cl |
| MeCH(F)CH$_2$ | Cl | O | H | H | 4-I |
| CF$_3$CH$_2$CH$_2$ | Cl | O | H | H | 4-Cl |
| CF$_3$CH$_2$CH$_2$ | Cl | O | H | H | 4-I |
| CHF$_2$CF$_2$CH$_2$ | Cl | O | H | H | 4-Cl |
| CHF$_2$CF$_2$CH$_2$ | Cl | O | H | H | 4-I |
| CF$_3$CCl$_2$CH$_2$ | Cl | O | H | H | 4-Cl |
| CF$_3$CCl$_2$CH$_2$ | Cl | O | H | H | 4-I |
| CF$_3$CHFCF$_2$ | Cl | O | H | H | 4-Cl |
| CF$_3$CHFCF$_2$ | Cl | O | H | H | 4-I |
| CF$_3$CHFCF(CF$_3$) | Cl | O | H | H | 4-Cl |
| CF$_3$CHFCF(CF$_3$) | Cl | O | H | H | 4-I |
| CF$_3$CH=CH | Cl | O | H | H | 4-Cl |
| CF$_3$CH=CH | Cl | O | H | H | 4-I |
| CF$_3$CF=CF | Cl | O | H | H | 4-Cl |
| CF$_3$CF=CF | Cl | O | H | H | 4-I |
| CF$_3$CCl$_2$CCl(CF$_3$) | Cl | O | H | H | 4-Cl |
| CF$_3$CCl$_2$CCl(CF$_3$) | Cl | O | H | H | 4-I |
| CF$_3$CBrClCCl(CF$_3$) | Cl | O | H | H | 4-Cl |
| CF$_3$CF$_2$CF$_2$ | Cl | O | H | H | 4-Cl |
| CF$_3$CF$_2$CF$_2$ | Cl | O | H | H | 4-I |
| CF$_3$CHFCF$_2$ | Cl | O | H | H | 4-Cl |
| CF$_3$CHFCF$_2$ | Cl | O | H | H | 4-I |
| (CF$_3$)$_2$CFCH$_2$ | Cl | O | H | H | 4-Cl |
| (CF$_3$)$_2$CFCHFCF$_2$ | Cl | O | H | H | 4-Cl |
| (CF$_3$)$_2$CFCHFCF$_2$ | Cl | O | H | H | 4-I |
| CF$_2$=CFCH$_2$CH$_2$ | Cl | O | H | H | 4-Cl |
| CF$_2$=CFCH$_2$CH$_2$ | Cl | O | H | H | 4-I |

TABLE 1-continued

In Compounds of the formula:

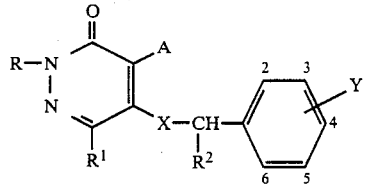

| R | A | X | $R^1$ | $R^2$ | Y |
|---|---|---|---|---|---|
| $C_3F_7CHClCH_2$ | Cl | O | H | H | 4-Cl |
| $C_3F_7CHClCH_2$ | Cl | O | H | H | 4-I |
| $C_3F_7CHBrCH_2$ | Cl | O | H | H | 4-Cl |
| $C_3F_7CHBrCH_2$ | Cl | O | H | H | 4-I |
| $H(CF_2)_4CH_2$ | Cl | O | H | H | 4-Cl |
| $H(CF_2)_4CH_2$ | Cl | O | H | H | 4-I |
| $H(CF_2)_6CH_2$ | Cl | O | H | H | 4-Cl |
| $H(CF_2)_6CH_2$ | Cl | O | H | H | 4-I |
| $F(CF_2)_3CF(CF_3)CH_2$ | Cl | O | H | H | 4-Cl |
| $F(CF_2)_3CF(CF_3)CH_2$ | Cl | O | H | H | 4-I |
| $F(CF_2)_5CHFCF_2$ | Cl | O | H | H | 4-Cl |
| $F(CF_2)_5CHFCF_2$ | Cl | O | H | H | 4-I |
| $F(CF_2)_8$ | Cl | O | H | H | 4-Cl |
| $F(CF_2)_8$ | Cl | O | H | H | 4-I |
| $CF_3CFClCF_2$ | Cl | O | H | H | 4-Cl |
| $CF_3CFClCF_2$ | Cl | O | H | H | 4-I |
| $CF_3CFBrCF_2$ | Cl | O | H | H | 4-Cl |
| $CF_3CF(OMe)CF_2$ | Cl | O | H | H | 4-Cl |
| $CF_3CF(OMe)CF_2$ | Cl | O | H | H | 4-I |
| Q6-3-Cl | Cl | O | H | H | 4-Cl |
| Q6-3-Cl | Cl | O | H | H | 4-I |
| Q6-3-Br | Cl | O | H | H | 4-Cl |
| Q6-3-Br | Cl | O | H | H | 4-I |
| (Q1-2,2-Me₂-3-COOEt)CHClC(Me)₂ | Cl | O | H | H | 4-Cl |
| (Q1-2,2-Me₂-3-COOEt)CHClC(Me)₂ | Cl | O | H | H | 4-I |
| (Q1-2,2-Me₂-3-COOEt)CHBrC(Me)₂ | Cl | O | H | H | 4-Cl |
| (Q1-2,2-Me-₂-3-COOEt)CH(CCl(Me)₂) | Cl | O | H | H | 4-Cl |
| (Q1-2,2-Me₂-3-COOEt)CH(CCl(Me)₂) | Cl | O | H | H | 4-I |
| Q3-1-Me-2-Cl | Cl | O | H | H | 4-Cl |
| Q3-1-Me-2-Cl | Cl | O | H | H | 4-I |
| Q3-1-Me-2-Br | Cl | O | H | H | 4-I |
| Q3-2-Me-1-Cl | Cl | O | H | H | 4-Cl |
| Q3-2-Me-1-Cl | Cl | O | H | H | 4-I |
| Q3-2-Me-1-Br | Cl | O | H | H | 4-Cl |
| Q4-1-Ph-2-Cl | Cl | O | H | H | 4-Cl |
| Q4-1-Ph-2-Cl | Cl | O | H | H | 4-I |
| Q4-1-Ph-2-Br | Cl | O | H | H | 4-Cl |
| Q4-2-Ph-1-Cl | Cl | O | H | H | 4-Cl |
| Q4-2-Ph-1-Cl | Cl | O | H | H | 4-I |
| Q4-2-Cl-3-CHMe(OMe) | Cl | O | H | H | 4-Cl |
| Q4-2-Cl-3-CHMe(OMe) | Cl | O | H | H | 4-I |
| Q4-2-Cl-6-CHMe(OMe) | Cl | O | H | H | 4-Cl |
| Q4-2-Cl-6-CHMe(OMe) | Cl | O | H | H | 4-I |
| Q4-2-Cl-3-CHMe(OCOMe) | Cl | O | H | H | 4-Cl |
| Q4-2-Cl-4-COMe | Cl | O | H | H | 4-Cl |
| Q4-2-Cl-4-COMe | Cl | O | H | H | 4-I |
| Q4-2-Cl-5-COMe | Cl | O | H | H | 4-I |
| Q7-2-Cl | Cl | O | H | H | 4-Cl |
| Q7-2-Cl | Cl | O | H | H | 4-I |
| Q7-2-Br | Cl | O | H | H | 4-Cl |
| Q7-2-Br | Cl | O | H | H | 4-I |
| Q8-1-Cl | Cl | O | H | H | 4-Cl |
| Q8-1-Cl | Cl | O | H | H | 4-I |
| Q8-1-Br | Cl | O | H | H | 4-I |
| Q8-3-Cl | Cl | O | H | H | 4-Cl |
| Q8-3-Cl | Cl | O | H | H | 4-I |
| Q8-3-Br | Cl | O | H | H | 4-Cl |
| Q7-1-Me-2-Cl | Cl | O | H | H | 4-Cl |
| Q7-1-Me-2-Cl | Cl | O | H | H | 4-I |
| Q7-1-Me-2-Cl | I | O | H | H | 4-Cl |
| Q8-1-Me-1-Cl | Cl | O | H | H | 4-Cl |
| Q8-1-Me-1-Cl | Cl | O | H | H | 4-I |
| Q8-1-Me-1-Cl | I | O | H | H | 4-Cl |
| Q10-4-Cl-4-OMe | Cl | O | H | H | 4-I |
| Q11-3-Cl-4-OMe | Cl | O | H | H | 4-Cl |
| Q9-3-Cl-6-COOMe | Cl | O | H | H | 4-Cl |
| Q10-2-Cl-6-COOMe | Cl | O | H | H | 4-Cl |
| Q9-3-Cl-6-CH₂OMe | Cl | O | H | H | 4-Cl |
| Q10-2-Cl-6-CH₂OEt | Cl | O | H | H | 4-Cl |
| Q9-3-Cl | Cl | O | H | H | 4-Cl |

TABLE 1-continued

In Compounds of the formula:

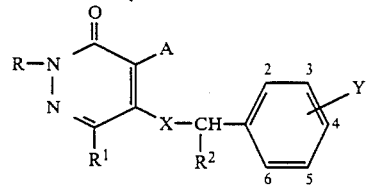

| R | A | X | R¹ | R² | Y |
|---|---|---|----|----|---|
| Q9-3-Cl | Cl | O | H | H | 4-I |
| Q9-3-Cl | Br | O | H | H | 4-Cl |
| Q9-3-Cl | I | O | H | H | 4-Cl |
| Q9-3-Cl | Cl | S | H | H | 4-Cl |
| Q9-3-Cl | Cl | S | H | H | 4-Bu-t |
| Q9-3-Br | Cl | O | H | H | 4-Cl |
| Q9-3-Br | Cl | O | H | H | 4-I |
| Q9-3-Br | Br | O | H | H | 4-Cl |
| Q9-3-Br | I | O | H | H | 4-Cl |
| Q9-3-Br | Cl | S | H | H | 4-Cl |
| Q9-3-Br | Cl | S | H | H | 4-Bu-t |
| Q10-2-Cl | Cl | O | H | H | 4-Cl |
| Q10-2-Cl | Cl | O | H | H | 4-I |
| Q10-2-Cl | Br | O | H | H | 4-Cl |
| Q10-2-Cl | I | O | H | H | 4-Cl |
| Q10-2-Cl | Cl | S | H | H | 4-Cl |
| Q10-2-Cl | Cl | S | H | H | 4-Bu-t |
| Q10-2-Br | Cl | O | H | H | 4-Cl |
| Q10-2-Br | Cl | O | H | H | 4-I |
| Q10-2-Br | Br | O | H | H | 4-Cl |
| Q10-2-Br | I | O | H | H | 4-Cl |
| Q10-2-Br | Cl | S | H | H | 4-Cl |
| Q10-2-Br | Cl | S | H | H | 4-Bu-t |
| Q9-3-Cl-6-OEt | Cl | O | H | H | 4-I |
| Q10-2-Cl-6-OEt | Cl | O | H | H | 4-Cl |
| Q10-2-Cl-6-OEt | Cl | O | H | H | 4-I |
| Q9-3-Cl-6-OMe | Cl | O | H | H | 4-Cl |
| Q10-2-Cl-6-OMe | Cl | O | H | H | 4-Cl |
| Q10-2-Cl-6-OMe | Cl | O | H | H | 4-I |
| Q12-2-Cl-1-Me | Cl | O | H | H | 4-Cl |
| Q12-2-Cl-1-Me | Cl | O | H | H | 4-I |
| Q13-1-Cl-1-Me | Cl | O | H | H | 4-Cl |
| Q13-1-Cl-1-Me | I | O | H | H | 4-I |
| Q12-2-Cl | Cl | O | H | H | 4-Cl |
| Q12-2-Cl | Cl | O | H | H | 4-I |
| Q12-2-Cl | Br | O | H | H | 4-Cl |
| Q12-2-Cl | I | O | H | H | 4-Cl |
| Q12-2-Cl | Cl | S | H | H | 4-Cl |
| Q12-2-Cl | Cl | S | H | H | 4-Bu-t |
| Q12-2-Br | Cl | O | H | H | 4-Cl |
| Q12-2-Br | Cl | O | H | H | 4-I |
| Q13-1-Cl | Cl | O | H | H | 4-Cl |
| Q13-1-Cl | Cl | O | H | H | 4-I |
| Q13-1-Cl | Br | O | H | H | 4-Cl |
| Q13-1-Cl | I | O | H | H | 4-Cl |
| Q13-1-Cl | Cl | S | H | H | 4-Cl |
| Q13-1-Cl | Cl | S | H | H | 4-Bu-t |
| Q13-1-Br | Cl | O | H | H | 4-Cl |
| Q13-1-Br | Cl | O | H | H | 4-I |
| Q14-1-Cl | Cl | O | H | H | 4-Cl |
| Q14-1-Cl | Cl | O | H | H | 4-I |
| Q14-1-Br | Cl | O | H | H | 4-Cl |
| Q14-1-Br | Cl | O | H | H | 4-I |
| Q15-1-Cl | Cl | O | H | H | 4-Cl |
| Q15-1-Cl | Cl | O | H | H | 4-I |
| Q15-1-Cl | Br | O | H | H | 4-Cl |
| Q15-1-Cl | I | O | H | H | 4-Cl |
| Q15-1-Cl | Cl | S | H | H | 4-Cl |
| Q15-1-Cl | Cl | S | H | H | 4-Bu-t |
| Q15-1-Br | Cl | O | H | H | 4-Cl |
| Q15-1-Br | Cl | O | H | H | 4-I |
| Q15-4-Cl | Cl | O | H | H | 4-Cl |
| Q15-4-Cl | Cl | O | H | H | 4-I |
| Q16-3-Cl | Cl | O | H | H | 4-Cl |
| Q16-3-Cl | Cl | O | H | H | 4-I |
| Q15-4-Cl-4-Me | Cl | O | H | H | 4-Cl |
| Q15-4-Cl-4-Me | Cl | O | H | H | 4-I |
| Q16-3-Cl-4-Me | Cl | O | H | H | 4-Cl |
| Q16-3-Cl-4-Me | Cl | O | H | H | 4-I |
| Q14-2-Cl-4-CHCl₂ | Cl | O | H | H | 4-Cl |

TABLE 1-continued

In Compounds of the formula:

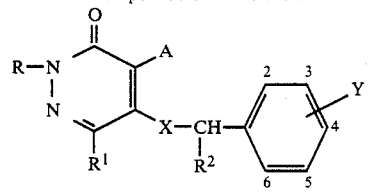

| R | A | X | R¹ | R² | Y |
|---|---|---|---|---|---|
| Q14-2-Cl-4-CHCl₂ | Cl | O | H | H | 4-I |
| Q15-1-Cl-4-CHCl₂ | Cl | O | H | H | 4-I |
| ClCH₂CHPh | Cl | O | H | H | 4-Cl |
| ClCH₂CHPh | Cl | O | H | H | 4-I |
| ClCH₂CHPh | Br | O | H | H | 4-Cl |
| ClCH₂CHPh | I | O | H | H | 4-Cl |
| PhCHClCH₂ | Cl | O | H | H | 4-Cl |
| PhCHClCH₂ | Cl | O | H | H | 4-I |
| BrCH₂CHPh | Cl | O | H | H | 4-Cl |
| PhCHBrCH₂ | Cl | O | H | H | 4-Cl |
| ClCH₂C(Me)Ph | Cl | O | H | H | 4-Cl |
| ClCH₂C(Me)Ph | Cl | O | H | H | 4-I |
| ClCH₂C(Me)Ph | Br | O | H | H | 4-Cl |
| ClCH₂C(Me)Ph | I | O | H | H | 4-Cl |
| PhCCl(Me)CH₂ | Cl | O | H | H | 4-Cl |
| PhCCl(Me)CH₂ | Cl | O | H | H | 4-I |
| PhCBr(Me)CH₂ | Cl | O | H | H | 4-Cl |
| PhCBr(Me)CH₂ | Cl | O | H | H | 4-I |
| MeCHClC(Me)Ph | Cl | O | H | H | 4-Cl |
| MeCHClC(Me)Ph | Cl | O | H | H | 4-I |
| MeCHClc(Et)Ph | Cl | O | H | H | 4-I |
| MeCHClCHPh | Cl | O | H | H | 4-Cl |
| MeCHClCHPh | Cl | O | H | H | 4-I |
| ClCH₂CH(Q-17) | Cl | O | H | H | 4-Cl |
| ClCH₂CH(Q-17) | Cl | O | H | H | 4-I |
| BrCH₂CH(Q-17) | Cl | O | H | H | 4-I |
| ClCH₂CH(Q-18) | Cl | O | H | H | 4-Cl |
| ClCH₂CH(Q-18) | Cl | O | H | H | 4-I |
| ClCH₂CH(Q-18) | Cl | O | H | H | 4-Cl |
| ClCH₂CH(Q-18) | Cl | O | H | H | 4-I |
| ClCH₂CH(Q-18) | Br | O | H | H | 4-Cl |
| ClCH₂CH(Q-18) | I | O | H | H | 4-Cl |
| ClCH₂CH(Q-18) | Cl | S | H | H | 4-Cl |
| ClCH₂CH(Q-18) | Cl | S | H | H | 4-Bu-t |
| BrCH₂CH(Q-18) | Cl | O | H | H | 4-Cl |
| BrCH₂CH(Q-18) | Cl | O | H | H | 4-I |
| Q19-5-Cl | Cl | O | H | H | 4-Cl |
| Q19-5-Cl | Cl | O | H | H | 4-I |
| Q19-5-Cl | Cl | O | H | H | 4-Cl |
| Q19-5-Cl | Cl | O | H | H | 4-I |
| Q19-5-Cl | Br | O | H | H | 4-Cl |
| Q19-5-Cl | I | O | H | H | 4-Cl |
| Q19-5-Cl | Cl | S | H | H | 4-Cl |
| Q19-5-Cl | Cl | S | H | H | 4-Bu-t |
| Q19-5-Br | Cl | O | H | H | 4-Cl |
| Q19-5-Br | Cl | O | H | H | 4-I |
| Q20-5-Cl | Cl | O | H | H | 4-Cl |
| Q20-5-Cl | Cl | O | H | H | 4-I |
| Q20-5-Cl | Cl | O | H | H | 4-Cl |
| Q20-5-Cl | Cl | O | H | H | 4-I |
| Q20-5-Cl | Br | O | H | H | 4-Cl |
| Q20-5-Cl | I | O | H | H | 4-Cl |
| Q20-5-Cl | Cl | S | H | H | 4-Cl |
| Q20-5-Cl | Cl | S | H | H | 4-Bu-t |
| Q20-5-Br | Cl | O | H | H | 4-Cl |
| Q20-5-Br | Cl | O | H | H | 4-I |
| EtOCH₂CHClCH₂ | Cl | O | H | H | 4-Cl |
| EtOCH₂CHClCH₂ | Cl | O | H | H | 4-I |
| EtOCH₂CHClCH₂ | Cl | O | H | H | 4-Cl |
| EtOCH₂CHClCH₂ | Cl | O | H | H | 4-I |
| EtOCH₂CHClCH₂ | Br | O | H | H | 4-Cl |
| EtOCH₂CHClCH₂ | I | O | H | H | 4-Cl |
| EtOCH₂CHClCH₂ | Cl | S | H | H | 4-Cl |
| EtOCH₂CHClCH₂ | Cl | S | H | H | 4-Bu-t |
| EtOCH₂CHBrCH₂ | Cl | O | H | H | 4-Cl |
| EtOCH₂CHBrCH₂ | Cl | O | H | H | 4-I |
| PrOCH₂CHClCH₂ | Cl | O | H | H | 4-Cl |
| PrOCH₂CHClCH₂ | Cl | O | H | H | 4-I |
| MeCCl(OMe)CH₂ | Cl | O | H | H | 4-Cl |
| MeCCl(OMe)CH₂ | Cl | O | H | H | 4-I |

TABLE 1-continued

In Compounds of the formula:

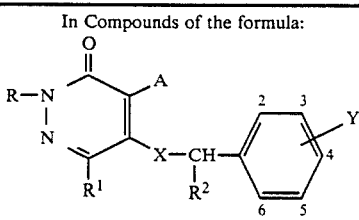

| R | A | X | R¹ | R² | Y |
|---|---|---|---|---|---|
| PrCCl(OMe)CH₂ | Cl | O | H | H | 4-Cl |
| PrCCl(OMe)CH₂ | Cl | O | H | H | 4-I |
| MeCCl(COOMe)CH₂ | Cl | O | H | H | 4-Cl |
| MeCCl(COOMe)CH₂ | Cl | O | H | H | 4-I |
| MeCCl(COOMe)CH₂ | Cl | O | H | H | 4-Cl |
| MeCCl(COOMe)CH₂ | Cl | O | H | H | 4-Cl |
| MeCCl(COOMe)CH₂ | Br | O | H | H | 4-Cl |
| MeCCl(COOMe)CH₂ | I | O | H | H | 4-Cl |
| MeCCl(COOMe)CH₂ | Cl | S | H | H | 4-Cl |
| MeCCl(COOMe)CH₂ | Cl | S | H | H | 4-Bu-t |
| MeCBr(COOMe)CH₂ | Cl | O | H | H | 4-Cl |
| MeCBr(COOMe)CH₂ | Cl | O | H | H | 4-I |
| MeCCl(COOEt)CH₂ | Cl | O | H | H | 4-Cl |
| MeCCl(COOEt)CH₂ | Cl | O | H | H | 4-I |
| MeCCl(COOEt)CH₂ | Cl | O | H | H | 4-Cl |
| MeCCl(COOEt)CH₂ | Cl | O | H | H | 4-I |
| MeCCl(COOEt)CH₂ | Br | O | H | H | 4-Cl |
| MeCCl(COOEt)CH₂ | I | O | H | H | 4-Cl |
| MeCCl(COOEt)CH₂ | Cl | S | H | H | 4-Cl |
| MeCCl(COOEt)CH₂ | Cl | S | H | H | 4-Bu-t |
| MeCBr(COOEt)CH₂ | Cl | O | H | H | 4-Cl |
| MeCBr(COOEt)CH₂ | Cl | O | H | H | 4-I |
| MeC(COOCH₂CH₂OEt)(Cl)CH₂ | Cl | O | H | H | 4-Cl |
| MeSCH₂CHClCH₂ | Cl | O | H | H | 4-Cl |
| MeSCH₂CHClCH₂ | Cl | O | H | H | 4-I |
| MeSCH₂CHClCH₂ | Cl | O | H | H | 4-I |
| MeCCl(SMe)CH₂ | Cl | O | H | H | 4-Cl |
| MeCCl(SMe)CH₂ | Cl | O | H | H | 4-I |
| PrCCl(SMe)CH₂ | Cl | O | H | H | 4-Cl |
| PrCCl(SMe)CH₂ | Cl | O | H | H | 4-I |
| PrCCl(CH₂OMe)CH₂ | Cl | O | H | H | 4-I |
| PrCCl(CH₂OMe)CH₂ | Cl | O | H | H | 4-Cl |
| PrCCl(CH₂OMe)CH₂ | Cl | O | H | H | 4-I |
| PrCCl(CH₂OMe)CH₂ | Cl | O | H | H | 4-Cl |
| MeCCl(CH₂CH₂OMe)CH₂ | Cl | O | H | H | 4-Cl |
| PrCCl(CH₂CH₂OMe)CH₂ | Cl | O | H | H | 4-Cl |
| PrCCl(CH₂CN)CH₂ | Cl | O | H | H | 4-Cl |
| PrCCl(CH₂CN)CH₂ | Cl | O | H | H | 4-I |
| PrCCl(CH₂COOMe)CH₂ | Cl | O | H | H | 4-I |
| PrCCl(CH₂COOMe)CH₂ | Cl | O | H | H | 4-Cl |
| NCCH₂CHClCH₂ | Cl | O | H | H | 4-Cl |
| NCCH₂CHClCH₂ | Cl | O | H | H | 4-I |
| NCCH₂CHClCH₂ | Cl | O | H | H | 4-Cl |
| NCCH₂CHClCH₂ | Cl | O | H | | 4-I |
| NCCH₂CHClCH₂ | Br | O | H | | 4-Cl |
| NCCH₂CHClCH₂ | I | O | H | H | 4-Cl |
| NCCH₂CHClCH₂ | Cl | S | H | H | 4-Cl |
| NCCH₂CHClCH₂ | Cl | S | H | H | 4-Bu-t |
| NCCH₂CHBrCH₂ | Cl | O | H | H | 4-Cl |
| NCCH₂CHBrCH₂ | Cl | O | H | H | 4-I |
| NCCH₂CCl(Me)CH₂ | Cl | O | H | H | 4-Cl |
| NCCH₂CCl(Me)CH₂ | Cl | O | H | H | 4-I |
| NCCH₂CCl(Me)CH₂ | Cl | O | H | H | 4-Cl |
| NCCH₂CCl(Me)CH₂ | Cl | O | H | H | 4-I |
| NCCH₂CCl(Me)CH₂ | Br | O | H | H | 4-Cl |
| NCCH₂CCl(Me)CH₂ | I | O | H | H | 4-Cl |
| NCCH₂CCl(Me)CH₂ | Cl | S | H | H | 4-Cl |
| NCCH₂CCl(Me)CH₂ | Cl | S | H | H | 4-Bu-t |
| NCCH₂Br(Me)CH₂ | Cl | O | H | H | 4-Cl |
| NCCH₂Br(Me)CH₂ | Cl | O | H | H | 4-I |
| PrCOOCCl(Me)CH₂ | Cl | O | H | H | 4-Cl |
| PrCOOCCl(Me)CH₂ | Cl | O | H | H | 4-I |
| MeCOOCH₂CHClCH₂ | Cl | O | H | H | 4-Cl |
| MeCOOCH₂CHClCH₂ | Cl | O | H | H | 4-I |
| MeCOOCH₂CHBrCH₂ | Cl | O | H | H | 4-Cl |
| EtCOOCH₂CHClCH₂ | Cl | O | H | H | 4-Cl |
| PrCOOCH₂CHClCH₂ | Cl | O | H | H | 4-I |
| MeCOOCH₂CCl(Me)CH₂ | Cl | O | H | H | 4-Cl |
| MeCOOCH₂CCl(Me)CH₂ | Cl | O | H | H | 4-I |
| MeCOOCH₂CCl(Me)CH₂ | I | O | H | H | 4-Cl |

TABLE 1-continued

In Compounds of the formula:

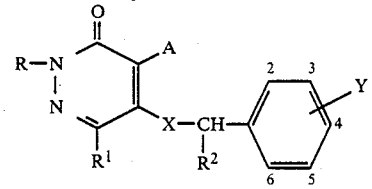

| R | A | X | R¹ | R² | Y |
|---|---|---|---|---|---|
| MeCOOCH₂CBr(Me)CH₂ | Cl | O | H | H | 4-Cl |
| EtCOOCH₂CCl(Me)CH₂ | Cl | O | H | H | 4-Cl |
| EtCOOCH₂CCl(Me)CH₂ | Cl | O | H | H | 4-I |
| MeCH(OMe)CH₂CHClCH₂ | Cl | O | H | H | 4-I |
| MeCH(OCOMe)CH₂CHClCH₂ | Cl | O | H | H | 4-Cl |
| PrCH(OMe)CH₂CHClCH₂ | Cl | O | H | H | 4-Cl |
| MeCH(OMe)CH₂CCl(Me)CH₂ | Cl | O | H | H | 4-Cl |
| MeCH(OMe)CH₂CCl(Me)CH₂ | Cl | O | H | H | 4-I |
| MeCH(OMe)CH₂CCl(Me)CH₂ | I | O | H | H | 4-Cl |
| MeCH(OMe)CH₂CBr(Me)CH₂ | Cl | O | H | H | 4-Cl |
| MeCH(OCOMe)CH₂CCl(Me)CH₂ | Cl | O | H | H | 4-Cl |
| EtCH(OMe)CH₂CCl(Me)CH₂ | Cl | O | H | H | 4-Cl |
| EtCH(OMe)CH₂CCl(Me)CH₂ | Cl | O | H | H | 4-I |
| EtCH(OCOMe)CH₂CCl(Me)CH₂ | Cl | O | H | H | 4-Cl |
| MeCH(OMe)CH(Me)CHClCH₂ | Cl | O | H | H | 4-Cl |
| EtCF(Me)CH(CN) | Cl | O | H | H | 4-Cl |
| EtCF(Me)CH(CN) | Cl | O | H | H | 4-I |
| CF₃C(CN)(Me) | Cl | O | H | H | 4-Cl |
| CF₃C(CN)(Me) | Cl | O | H | H | 4-I |
| MeOCH₂CCl(Me)CH₂ | Cl | O | H | H | 4-Cl |
| MeOCH₂CCl(Me)CH₂ | Cl | O | H | H | 4-I |
| MeOCH₂CCl(Me)CH₂ | Br | O | H | H | 4-Cl |
| MeOCH₂CCl(Me)CH₂ | I | O | H | H | 4-Cl |
| MeOCH₂CCl(Me)CH₂ | Cl | S | H | H | 4-Cl |
| MeOCH₂CCl(Me)CH₂ | Cl | S | H | H | 4-Bu-t |
| MeOCH₂CBr(Me)CH₂ | Cl | O | H | H | 4-Cl |
| MeOCH₂CBr(Me)CH₂ | Cl | O | H | H | 4-I |
| EtOCH₂CCl(Me)CH₂ | Cl | O | H | H | 4-Cl |
| EtOCH₂CCl(Me)CH₂ | Cl | O | H | H | 4-I |
| EtOCH₂CCl(Me)CH₂ | Br | O | H | H | 4-Cl |
| EtOCH₂CCl(Me)CH₂ | I | O | H | H | 4-Cl |
| EtOCH₂CCl(Me)CH₂ | Cl | S | H | H | 4-Cl |
| EtOCH₂CCl(Me)CH₂ | Cl | S | H | H | 4-Bu-t |
| EtOCH₂CBr(Me)CH₂ | Cl | O | H | H | 4-Cl |
| EtOCH₂CBr(Me)CH₂ | Cl | O | H | H | 4-I |
| PrOCH₂CCl(Me)CH₂ | Cl | O | H | H | 4-Cl |
| PrOCH₂CCl(Me)CH₂ | Cl | O | H | H | 4-I |
| MeSCH₂CCl(Me)CH₂ | Cl | O | H | H | 4-Cl |
| MeSCH₂CCl(Me)CH₂ | Cl | O | H | H | 4-I |
| MeSCH₂CCl(Me)CH₂ | Br | O | H | H | 4-Cl |
| MeSCH₂CCl(Me)CH₂ | I | O | H | H | 4-Cl |
| MeSCH₂CCl(Me)CH₂ | Cl | S | H | H | 4-Cl |
| MeSCH₂CCl(Me)CH₂ | Cl | S | H | H | 4-Bu-t |
| MeSCH₂CBr(Me)CH₂ | Cl | O | H | H | 4-Cl |
| MeSCH₂CBr(Me)CH₂ | Cl | O | H | H | 4-I |
| EtSCH₂CCl(Me)CH₂ | Cl | O | H | H | 4-Cl |
| EtSCH₂CCl(Me)CH₂ | Cl | O | H | H | 4-I |
| EtSCH₂CCl(Me)CH₂ | Br | O | H | H | 4-Cl |
| EtSCH₂CCl(Me)CH₂ | I | O | H | H | 4-Cl |
| EtSCH₂CCl(Me)CH₂ | Cl | S | H | H | 4-Cl |
| EtSCH₂CCl(Me)CH₂ | Cl | S | H | H | 4-Bu-t |
| EtSCH₂CBr(Me)CH₂ | Cl | O | H | H | 4-Cl |
| EtSCH₂CBr(Me)CH₂ | Cl | O | H | H | 4-I |
| PrSCH₂CCl(Me)CH₂ | Cl | O | H | H | 4-Cl |
| PrSCH₂CCl(Me)CH₂ | Cl | O | H | H | 4-I |
| MeCCl(CN)CH₂ | Cl | O | H | H | 4-Cl |
| MeCCl(CN)CH₂ | Cl | O | H | H | 4-I |
| MeCCl(CN)CH₂ | Br | O | H | H | 4-Cl |
| MeCCl(CN)CH₂ | I | O | H | H | 4-Cl |
| MeCCl(CN)CH₂ | Cl | S | H | H | 4-Cl |
| MeCCl(CN)CH₂ | Cl | S | H | H | 4-Bu-t |
| MeCBr(CN)CH₂ | Cl | O | H | H | 4-Cl |
| MeCBr(CN)CH₂ | Cl | O | H | H | 4-I |
| MeSO₂CCl(Me)CH₂ | Cl | O | H | H | 4-Cl |
| MeSO₂CCl(Me)CH₂ | Cl | O | H | H | 4-I |
| MeSO₂CBr(Me)CH₂ | Cl | O | H | H | 4-Cl |
| MeSO₂CCl(Pr)CH₂ | Cl | O | H | H | 4-Cl |
| BuSO₂CCl(Me)CH₂ | Cl | O | H | H | 4-Cl |
| Me₂NCCl(Me)CH₂ | Cl | O | H | H | 4-Cl |
| Me₂NCCl(Me)CH₂ | Cl | O | H | H | 4-I |

TABLE 1-continued

In Compounds of the formula:

| R | A | X | R¹ | R² | Y |
|---|---|---|----|----|---|
| Me₂NCCl(Et)CH₂ | Cl | O | H | H | 4-Cl |
| MeNHCCl(Pr)CH₂ | Cl | O | H | H | 4-Cl |
| EtOCONHCH₂CCl(Me)CH₂ | Cl | O | H | H | 4-Cl |
| MeOCONHCH₂CHClCH₂ | Cl | O | H | H | 4-Cl |
| MeNHCOOCHClCH₂ | Cl | O | H | H | 4-Cl |
| EtCH=NOCH₂CCl(Me)CH₂ | Cl | O | H | H | 4-Cl |
| EtCH=NOCH₂CHClCH₂ | Cl | O | H | H | 4-Cl |
| MeCH=NOCH₂CHBrCH₂ | Cl | O | H | H | 4-Cl |
| EtON=CHCH₂CCl(Me)CH₂ | Cl | O | H | H | 4-Cl |
| EtON=CHCHClCH₂ | Cl | O | H | H | 4-Cl |
| MeON=CHCHBrCH₂ | Cl | O | H | H | 4-Cl |
| Me₂CClCH₂ | Cl | O | H | H | 4-I |
| Me₂CClCH₂ | Cl | O | H | H | 4-OEt |
| Me₂CClCH₂ | Cl | O | H | H | 4-OPr-i |
| Me₂CClCH₂ | Cl | O | H | H | 4-OCF₃ |
| Me₂CClCH₂ | Cl | O | H | H | 4-OCHF₂ |
| Me₂CClCH₂ | Cl | O | H | H | 4-OCH₂CF₃ |
| Me₂CClCH₂ | Cl | O | H | H | 4-Et |
| Me₂CClCH₂ | Cl | O | H | H | 4-Pr-i |
| Me₂CClCH₂ | Me | O | H | H | 4-I |
| Me₂CClCH₂ | Br | O | H | H | 4-Cl |
| Me₂CClCH₂ | Br | O | H | H | 4-I |
| Me₂CClCH₂ | Cl | O | H | H | 4-CF₃ |
| Me₂CClCH₂ | OMe | O | H | H | 4-I |
| Me₂CBrCH₂ | Cl | O | H | H | 4-I |
| Me₂CBrCH₂ | Cl | O | H | H | 4-CF₃ |
| Me₂CBrCH₂ | Cl | O | H | H | 4-Et |
| Me₂CBrCH₂ | Cl | O | H | H | 4-OEt |
| Me₂CBrCH₂ | Cl | O | H | H | 4-OPr-i |
| Me₂CBrCH₂ | Cl | O | H | H | 4-OCF₃ |
| Me₂CBrCH₂ | Br | O | H | H | 4-I |
| Me₂CBrCH₂ | Br | O | H | H | 4-CF₃ |
| Me₂CBrCH₂ | Br | O | H | H | 4-Et |
| PrCCl(Me)CH₂ | Cl | O | H | H | 4-OEt |
| PrCCl(Me)CH₂ | Cl | O | H | H | 4-OPr-i |
| PrCCl(Me)CH₂ | Cl | O | H | H | 4-OPr |
| PrCCl(Me)CH₂ | Cl | O | H | H | 4-OCF₃ |
| PrCCl(Me)CH₂ | Cl | O | H | H | 4-CF₃ |
| PrCCl(Me)CH₂ | Cl | O | H | H | 4-Et |
| PrCCl(Me)CH₂ | Cl | O | H | H | 4-Pr-i |
| PrCCl(Me)CH₂ | Br | O | H | H | 4-Br |
| PrCCl(Me)CH₂ | Br | O | H | H | 4-CF₃ |
| PrCCl(Me)CH₂ | Br | O | H | H | 4-Et |
| PrCCl(Me)CH₂ | Br | O | H | H | 4-OEt |
| PrCBr(Me)CH₂ | Cl | O | H | H | 4-Br |
| MeCCl(CN)CH₂ | Cl | O | H | H | 4-Et |
| MeCCl(CN)CH₂ | Cl | O | H | H | 4-Pr-i |
| Me₂CClCH₂ | Cl | O | H | H | 4-I |
| Me₂CClCH₂ | Cl | O | H | H | 4-OEt |
| Me₂CClCH₂ | Cl | O | H | H | 4-OPr-i |
| Me₂CClCH₂ | Cl | O | H | H | 4-OCF₃ |
| Me₂CClCH₂ | Cl | O | H | H | 4-OCHF₂ |
| Me₂CClCH₂ | Cl | O | H | H | 4-OCH₂CF₃ |
| Me₂CClCH₂ | Cl | O | H | H | 4-Et |
| Me₂CClCH₂ | Cl | O | H | H | 4-Pr-i |
| Me₂CClCH₂ | Me | O | H | H | 4-I |
| Me₂CClCH₂ | Br | O | H | H | 4-Cl |
| Me₂CClCH₂ | Br | O | H | H | 4-I |
| Me₂CClCH₂ | Cl | O | H | H | 4-CF₃ |
| Me₂CClCH₂ | OMe | O | H | H | 4-I |
| Me₂CBrCH₂ | Cl | O | H | H | 4-I |
| Me₂CBrCH₂ | Cl | O | H | H | 4-CF₃ |
| Me₂CBrCH₂ | Cl | O | H | H | 4-Et |
| Me₂CBrCH₂ | Cl | O | H | H | 4-OEt |
| Me₂CBrCH₂ | Cl | O | H | H | 4-OPr-i |
| Me₂CBrCH₂ | Cl | O | H | H | 4-OCF₃ |
| Me₂CBrCH₂ | Br | O | H | H | 4-I |
| Me₂CBrCH₂ | Br | O | H | H | 4-CF₃ |
| Me₂CBrCH₂ | Br | O | H | H | 4-Et |
| PrCCl(Me)CH₂ | Cl | O | H | H | 4-OEt |

TABLE 1-continued

In Compounds of the formula:

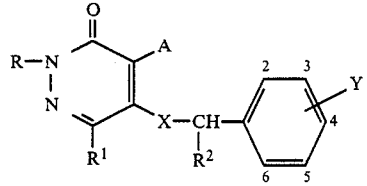

| R | A | X | R$^1$ | R$^2$ | Y |
|---|---|---|---|---|---|
| PrCCl(Me)CH$_2$ | Cl | O | H | H | 4-OPr-i |
| PrCCl(Me)CH$_2$ | Cl | O | H | H | 4-OPr |
| PrCCl(Me)CH$_2$ | Cl | O | H | H | 4-OCF$_3$ |
| PrCCl(Me)CH$_2$ | Cl | O | H | H | 4-CF$_3$ |
| PrCCl(Me)CH$_2$ | Cl | O | H | H | 4-Et |
| PrCCl(Me)CH$_2$ | Cl | O | H | H | 4-Pr-i |
| PrCCl(Me)CH$_2$ | Br | O | H | H | 4-Br |
| PrCCl(Me)CH$_2$ | Br | O | H | H | 4-CF$_3$ |
| PrCCl(Me)CH$_2$ | Br | O | H | H | 4-Et |
| PrCCl(Me)CH$_2$ | Br | O | H | H | 4-OEt |
| PrCBr(Me)CH$_2$ | Cl | O | H | H | 4-Br |
| PrCBr(Me)CH$_2$ | Cl | O | H | H | 4-Et |
| PrCBr(Me)CH$_2$ | Cl | O | H | H | 4-Pr-i |
| PrCBr(Me)CH$_2$ | Cl | O | H | H | 4-OEt |
| PrCBr(Me)CH$_2$ | Cl | O | H | H | 4-CF$_3$ |
| PrCBr(Me)CH$_2$ | Cl | O | H | H | 4-OCF$_3$ |
| PrCBr(Me)CH$_2$ | Cl | O | H | H | 4-Pr |
| PrCBr(Me)CH$_2$ | Br | O | H | H | 4-Br |
| PrCBr(Me)CH$_2$ | Br | O | H | H | 4-CF$_3$ |
| PrCBr(Me)CH$_2$ | Br | O | H | H | 4-OCF$_3$ |
| PrCBr(Me)CH$_2$ | Br | O | H | H | 4-Et |
| PrCBr(Me)CH$_2$ | Br | O | H | H | 4-Pr-i |
| PrCBr(Me)CH$_2$ | Br | O | H | H | 4-OEt |
| PrCBr(Me)CH$_2$ | Br | O | H | H | 4-OPr-i |
| Cl$_2$C=CH | Cl | O | H | H | 4-Cl |
| Cl$_2$C=CH | Cl | O | H | H | 4-Br |
| Cl$_2$C=CH | Cl | O | H | H | 4-I |
| Cl$_2$C=CH | Cl | O | H | H | 4-CF$_3$ |
| Cl$_2$C=CH | Cl | O | H | H | 4-Et |
| Cl$_2$C=CH | Cl | O | H | H | 4-OEt |
| Cl$_2$C=CH | Cl | O | H | H | 4-OPr-i |
| Cl$_2$C=CH | Cl | O | H | H | 4-Pr-i |
| Cl$_2$C=CH | Br | O | H | H | 4-I |
| Cl$_2$C=CH | Br | O | H | H | 4-Br |
| Cl$_2$C=CH | Br | O | H | H | 4-Et |
| Cl$_2$C=CH | Br | O | H | H | 4-CF$_3$ |
| Cl$_2$C=CH | Br | O | H | H | 4-OEt |
| Br$_2$C=CH | Cl | O | H | H | 4-I |
| Br$_2$C=CH | Cl | O | H | H | 4-OEt |
| Br$_2$C=CH | Cl | O | H | H | 4-Et |
| Br$_2$C=CH | Br | O | H | H | 4-I |
| Br$_2$C=CH | Br | O | H | H | 4-Br |
| Br$_2$C=CH | Br | O | H | H | 4-OEt |
| MeCCl=CH | Cl | O | H | H | 4-Cl |
| MeCCl=CH | Cl | O | H | H | 4-Br |
| MeCCl=CH | Cl | O | H | H | 4-I |
| MeCCl=CH | Cl | O | H | H | 4-CF$_3$ |
| MeCCl=CH | Cl | O | H | H | 4-OCF$_3$ |
| MeCCl=CH | Cl | O | H | H | 4-OCHF$_2$ |
| MeCCl=CH | Cl | O | H | H | 4-Et |
| MeCCl=CH | Cl | O | H | H | 4-Pr |
| MeCCl=CH | Cl | O | H | H | 4-Pr-i |
| MeCCl=CH | Cl | O | H | H | 4-OEt |
| MeCCl=CH | Cl | O | H | H | 4-OPr-i |
| MeCCl=CH | Br | O | H | H | 4-I |
| MeCCl=CH | Br | O | H | H | 4-Et |
| MeCCl=CH | Br | O | H | H | 4-CF$_3$ |
| MeCCl=CH | Br | O | H | H | 4-Cl |
| MeCBr=CH | Cl | O | H | H | 4-I |
| MeCBr=CH | Cl | O | H | H | 4-Et |
| MeCBr=CH | Cl | O | H | H | 4-CF$_3$ |
| MeCBr=CH | Br | O | H | H | 4-Br |
| MeCBr=CH | Br | O | H | H | 4-I |
| MeCBr=CH | Br | O | H | H | 4-Et |
| EtCCl=CH | Cl | O | H | H | 4-CF$_3$ |
| EtCCl=CH | Cl | O | H | H | 4-Br |
| EtCCl=CH | Cl | O | H | H | 4-I |
| EtCCl=CH | Cl | O | H | H | 4-Et |
| EtCCl=CH | Br | O | H | H | 4-I |
| PrCCl=CH | Cl | O | H | H | 4-I |

TABLE 1-continued

In Compounds of the formula:

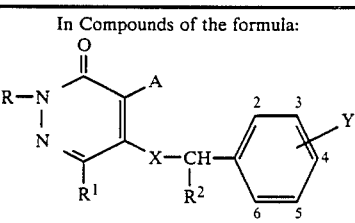

| R | A | X | R$^1$ | R$^2$ | Y |
|---|---|---|---|---|---|
| PrCCl=CH | Cl | O | H | H | 4-CF$_3$ |
| PrCCl=CH | Cl | O | H | H | 4-Et |
| PrCCl=CH | Cl | O | H | H | 4-Br |
| PrCCl=CH | Cl | O | H | H | 4-Cl |
| PrCCl=CH | Cl | O | H | H | 4-OCF$_3$ |
| PrCCl=CH | Br | O | H | H | 4-I |
| Me$_2$C=CH | Cl | O | H | H | 4-Cl |
| Me$_2$C=CH | Cl | O | H | H | 4-Br |
| Me$_2$C=CH | Cl | O | H | H | 4-I |
| Me$_2$C=CH | Cl | O | H | H | 4-Et |
| Me$_2$C=CH | Cl | O | H | H | 4-CF$_3$ |
| Me$_2$C=CH | Cl | O | H | H | 4-OEt |
| Me$_2$C=CH | Br | O | H | H | 4-I |
| Me$_2$C=CH | Br | O | H | H | 4-Et |
| MeC(Et)=CH | Cl | O | H | H | 4-Cl |
| MeC(Et)=CH | Cl | O | H | H | 4-I |
| MeC(Et)=CH | Cl | O | H | H | 4-CF$_3$ |
| MeC(Et)=CH | Cl | O | H | H | 4-Et |
| MeC(Et)=CH | Cl | O | H | H | 4-OEt |
| MeC(Et)=CH | Cl | O | H | H | 4-OCF$_3$ |
| MeC(Et)=CH | Cl | O | H | H | 4-Br |
| MeC(Et)=CH | Br | O | H | H | 4-I |
| MeC(Et)=CH | Br | O | H | H | 4-Et |
| MeC(Pr)=CH | Cl | O | H | H | 4-Cl |
| MeC(Pr)=CH | Cl | O | H | H | 4-Br |
| MeC(Pr)=CH | Cl | O | H | H | 4-I |
| MeC(Pr)=CH | Cl | O | H | H | 4-CF$_3$ |
| MeC(Pr)=CH | Cl | O | H | H | 4-Et |
| MeC(Pr)=CH | Cl | O | H | H | 4-OEt |
| MeC(Pr)=CH | Cl | O | H | H | 4-Pr-i |
| MeC(Pr)=CH | Br | O | H | H | 4-I |
| MeC(Pr)=CH | Br | O | H | H | 4-OPr-i |
| MeC(Pr-i)=CH | Cl | O | H | H | 4-I |
| MeC(Pr-i)=CH | Cl | O | H | H | 4-Et |
| MeC(Pr-i)=CH | Cl | O | H | H | 4-CF$_3$ |
| MeC(Pr-i)=CH | Cl | O | H | H | 4-OPr-i |
| MeC(Pr-i)=CH | Cl | O | H | H | 4-OEt |
| MeC(Pr-i)=CH | Cl | O | H | H | 4-OCF$_3$ |
| MeC(Pr-i)=CH | Br | O | H | H | 4-I |
| MeC(Bu)=CH | Cl | O | H | H | 4-I |
| MeC(Bu)=CH | Cl | O | H | H | 4-CF$_3$ |
| MeC(Bu)=CH | Cl | O | H | H | 4-Et |
| MeC(Bu)=CH | Cl | O | H | H | 4-OEt |
| MeC(Bu)=CH | Cl | O | H | H | 4-OCF$_3$ |
| MeC(Bu)=CH | Cl | O | H | H | 4-Pr-i |
| MeC(Bu)=CH | Br | O | H | H | 4-OPr-i |
| MeC(Pen)=CH | Cl | O | H | H | 4-Br |
| MeC(Pen)=CH | Cl | O | H | H | 4-I |
| MeC(Pen)=CH | Cl | O | H | H | 4-OEt |
| MeC(Pen)=CH | Cl | O | H | H | 4-Et |
| MeC(Hex)=CH | Cl | O | H | H | 4-I |
| MeC(Hex)=CH | Cl | O | H | H | 4-Br |
| MeC(Hex)=CH | Cl | O | H | H | 4-OPr-i |
| EtC(Et)=CH | Cl | O | H | H | 4-Br |
| EtC(Pr)=CH | Cl | O | H | H | 4-I |
| CF$_3$CCl=CH | Cl | O | H | H | 4-Cl |
| CF$_3$CCl=CH | Cl | O | H | H | 4-Br |
| CF$_3$CCl=CH | Cl | O | H | H | 4-I |
| CF$_3$CCl=CH | Cl | O | H | H | 4-Et |
| CF$_3$CCl=CH | Cl | O | H | H | 4-CF$_3$ |
| CF$_3$CCl=CH | Cl | O | H | H | 4-OPr-i |
| CF$_3$CCl=CH | Br | O | H | H | 4-I |
| CF$_3$CCl=CH | Br | O | H | H | 4-Et |
| CF$_3$CBr=CH | Cl | O | H | H | 4-I |
| CF$_3$CBr=CH | Cl | O | H | H | 4-Cl |
| CF$_3$CBr=CH | Cl | O | H | H | 4-Et |
| CF$_3$CBr=CH | Cl | O | H | H | 4-CF$_3$ |
| CF$_3$CBr=CH | Cl | O | H | H | 4-OPr-i |
| CF$_3$CBr=CH | Br | O | H | H | 4-I |
| CF$_3$CBr=CH | Br | O | H | H | 4-Br |

TABLE 1-continued

In Compounds of the formula:

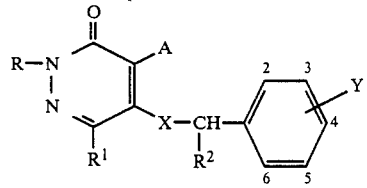

| R | A | X | R¹ | R² | Y |
|---|---|---|----|----|---|
| $CH_2=CH$ | Cl | O | H | H | 4-Cl |
| $CH_2=CH$ | Cl | O | H | H | 4-I |
| $CH_2=CH$ | Br | S | H | H | 4-$CF_3$ |
| $CH_2=CH$ | Br | O | H | H | 3,4-$Cl_2$ |
| $CH_2=CHCH_2$ | Cl | O | H | H | 4-I |
| $CH_2=CHCH_2$ | Cl | O | H | H | 4-Cl |
| $CH_2=CHCH_2$ | Br | O | H | H | 4-Br |
| $CH_2=CHCH_2$ | $CH_3$ | O | H | H | 4-Cl |
| $MeCH=CHCH_2$ | Cl | O | H | H | 4-$CF_3$ |
| $MeCH=CHCH_2$ | Cl | S | H | H | 4-I |
| $MeCH=CHCH_2$ | Br | O | H | H | 4-I |
| $CH_2=C(Me)CH_2$ | Cl | O | H | H | 4-Cl |
| $CH_2=C(Me)CH_2$ | Cl | O | H | H | 4-Br |
| $CH_2=C(Me)CH_2$ | Cl | O | H | H | 4-I |
| $CH_2=C(Me)CH_2$ | Cl | O | H | H | 4-Et |
| $CH_2=C(Me)CH_2$ | Cl | O | H | H | 4-Pr-i |
| $CH_2=C(Me)CH_2$ | Cl | O | H | H | 4-$CF_3$ |
| $CH_2=C(Me)CH_2$ | Cl | O | H | H | 4-OEt |
| $CH_2=C(Me)CH_2$ | Br | O | H | H | 4-$OCF_3$ |
| $CH_2=C(Me)CH_2$ | Br | O | H | H | 4-OPr-i |
| $CH_2=C(Me)CH_2$ | OMe | O | H | H | 4-Cl |
| $CH_2=C(Et)CH_2$ | Cl | O | H | H | 4-Cl |
| $CH_2=C(Et)CH_2$ | Cl | O | H | H | 4-I |
| $CH_2=C(Et)CH_2$ | Cl | O | H | H | 4-Br |
| $CH_2=C(Et)CH_2$ | Cl | O | H | H | 4-Et |
| $CH_2=C(Et)CH_2$ | Cl | O | H | H | 4-Pr |
| $CH_2=C(Et)CH_2$ | Br | O | H | H | 4-$CF_3$ |
| $CH_2=C(Et)CH_2$ | Br | O | H | H | 4-Et |
| $CH_2=C(Pr)CH_2$ | Cl | O | H | H | 4-I |
| $CH_2=C(Pr)CH_2$ | Cl | O | H | H | 4-Et |
| $CH_2=C(Pr)CH_2$ | Cl | O | H | H | 4-$CF_3$ |
| $CH_2=C(Pr)CH_2$ | Cl | O | H | H | 4-$OCF_3$ |
| $CH_2=C(Pr)CH_2$ | Br | O | H | H | 4-I |
| $CH_2=C(Bu)CH_2$ | Cl | O | H | H | 4-I |
| $CH_2=C(Bu)CH_2$ | Cl | O | H | H | 4-Cl |
| $CH_2=C(Bu)CH_2$ | Cl | O | H | H | 4-I |
| $CH_2=C(Bu)CH_2$ | Cl | O | H | H | 4-$CF_3$ |
| $CH_2=C(Bu)CH_2$ | Br | O | H | H | 4-Et |
| $MeCH=C(Me)CH_2$ | Cl | O | H | H | 4-I |
| $MeCH=C(Me)CH_2$ | Cl | O | H | H | 4-Et |
| $MeCH=C(Me)CH_2$ | Cl | O | H | H | 4-$CF_3$ |
| $MeCH=C(Me)CH_2$ | Cl | O | H | H | 4-$OCF_3$ |
| $MeCH=C(Me)CH_2$ | Br | O | H | H | 4-I |
| $MeCH=C(Me)CH_2$ | Br | O | H | H | 4-Et |
| $EtCH=C(Me)CH_2$ | Cl | O | H | H | 4-I |
| $EtCH=C(Me)CH_2$ | Cl | O | H | H | 4-Br |
| $EtCH=C(Me)CH_2$ | Cl | O | H | H | 4-Cl |
| $EtCH=C(Me)CH_2$ | Cl | O | H | H | 4-Et |
| $EtCH=C(Me)CH_2$ | Cl | O | H | H | 4-$CF_3$ |
| $EtCH=C(Me)CH_2$ | Br | O | H | H | 4-$CF_3$ |
| $PrCH=C(Me)CH_2$ | Cl | O | H | H | 4-Cl |
| $PrCH=C(Me)CH_2$ | Cl | O | H | H | 4-I |
| $PrCH=C(Me)CH_2$ | Br | O | H | H | 4-Et |
| $PrCH=C(Me)CH_2$ | Br | O | H | H | 4-$CF_3$ |
| $PrCH=C(Me)CH_2$ | Br | O | H | H | 4-Cl |
| $MeCH=C(Et)CH_2$ | Cl | O | H | H | 4-Br |
| $MeCH=C(Et)CH_2$ | Cl | O | H | H | 4-I |
| $MeCH=C(Et)CH_2$ | Cl | O | H | H | 4-Et |
| $MeCH=C(Et)CH_2$ | Cl | O | H | H | 4-$CF_3$ |
| $MeC=C(Me)CH_2$ | Cl | O | H | H | 4-Cl |
| $MeC=C(Me)CH_2$ | Cl | O | H | H | 4-I |
| $MeC=C(Me)CH_2$ | Cl | O | H | H | 4-Et |
| $MeC=C(Me)CH_2$ | Br | O | H | H | 4-OEt |
| $MeC=C(Et)CH_2$ | Cl | O | H | H | 4-$CF_3$ |
| $MeC=C(Et)CH_2$ | Cl | O | H | H | 4-I |
| $MeC=C(Et)CH_2$ | Br | O | H | H | 4-Br |
| $BuCH=C(Me)CH_2$ | Cl | O | H | H | 4-I |
| $BuCH=C(Me)CH_2$ | Cl | O | H | H | 4-$CF_3$ |
| $PenCH=C(Me)CH_2$ | Cl | O | H | H | 4-Et |
| $PenCH=C(Me)CH_2$ | Cl | O | H | H | 4-I |

TABLE 1-continued

In Compounds of the formula:

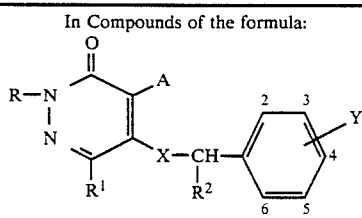

| R | A | X | R¹ | R² | Y |
|---|---|---|---|---|---|
| HexCH=C(Me)CH₂ | Cl | O | H | H | 4-I |
| HexCH=C(Me)CH₂ | Cl | O | H | H | 4-CF₃ |
| CH₂=CHC(Me)₂CH₂ | Cl | O | H | H | 4-Cl |
| CH₂=CHC(Me)₂CH₂ | Cl | O | H | H | 4-I |
| CH₂=CHC(Me)₂CH₂ | Cl | O | H | H | 4-Et |
| CH₂=CHC(Me)₂CH₂ | Cl | O | H | H | 4-CF₃ |
| MeCH=CHC(Me)₂CH₂ | Cl | O | H | H | 4-I |
| MeCH=CHC(Me)₂CH₂ | Cl | O | H | H | 4-Br |
| MeCH=CHC(Me)₂CH₂ | Cl | O | H | H | 4-Et |
| MeCH=CHC(Me)₂CH₂ | Br | O | H | H | 4-Et |
| HC≡CCH₂ | Cl | O | H | H | 4-Cl |
| HC≡CCH₂ | Br | O | H | H | 4-I |
| HC≡CCH₂ | Me | S | H | H | 4-CF₃ |
| CH₃C≡CCH₂ | Cl | O | H | H | 4-Cl |
| CH₃C≡CCH₂ | Br | S | H | H | 4-Br |
| HC≡CC(Me)₂CH₂ | Cl | O | H | H | 4-Cl |
| HC≡CC(Me)₂CH₂ | Cl | O | H | H | 4-I |
| HC≡CC(Me)₂CH₂ | Cl | O | H | H | 4-Et |
| HC≡CC(Me)₂CH₂ | Cl | O | H | H | 4-CF₃ |
| HC≡CC(Me)₂CH₂ | Br | O | H | H | 4-Cl |
| MeC≡CC(Me)₂CH₂ | Cl | O | H | H | 4-I |
| MeC≡CC(Me)₂CH₂ | Cl | O | H | H | 4-Et |
| MeC≡CC(Me)₂CH₂ | Cl | O | H | H | 4-CF₃ |
| MeC≡CC(Me)₂CH₂ | Br | O | H | H | 4-OCF₃ |
| CH₂=CHCH₂C(Me)₂CH₂ | Cl | O | H | H | 4-I |
| CH₂=CHCH₂C(Me)₂CH₂ | Cl | O | H | H | 4-Et |
| MeCH=CHCH₂C(Me)₂CH₂ | Cl | O | H | H | 4-CF₃ |
| HC≡CCH₂C(Me)₂CH₂ | Cl | O | H | H | 4-I |
| HC≡CCH₂C(Me)₂CH₂ | Cl | O | H | H | 4-Et |
| MeC≡CCH₂C(Me)₂CH₂ | Cl | O | H | H | 4-Cl |
| MeC≡CCH₂C(Me)₂CH₂ | Cl | O | H | H | 4-I |
| Me₂C(OMe)CH₂ | Cl | O | H | H | 4-Cl |
| Me₂C(OMe)CH₂ | Cl | O | H | H | 4-Br |
| Me₂C(OMe)CH₂ | Cl | O | H | H | 4-I |
| Me₂C(OMe)CH₂ | Cl | O | H | H | 4-CF₃ |
| Me₂C(OMe)CH₂ | Cl | O | H | H | 4-Et |
| Me₂C(OMe)CH₂ | Cl | O | H | H | 4-OEt |
| Me₂C(OMe)CH₂ | Br | O | H | H | 4-I |
| Me₂C(OEt)CH₂ | Cl | O | H | H | 4-I |
| Me₂C(OEt)CH₂ | Cl | O | H | H | 4-Et |
| Me₂C(OEt)CH₂ | Cl | O | H | H | 4-CF₃ |
| Me₂C(OEt)CH₂ | Cl | O | H | H | 4-OPr-i |
| Me₂C(OEt)CH₂ | Br | O | H | H | 4-I |
| Me₂C(OEt)CH₂ | Br | O | H | H | 4-Cl |
| Me₂C(OPr)CH₂ | Cl | O | H | H | 4-Cl |
| Me₂C(OPr)CH₂ | Cl | O | H | H | 4-Me |
| Me₂C(OPr)CH₂ | Cl | O | H | H | 4-Et |
| Me₂C(OPr)CH₂ | Cl | O | H | H | 4-CF₃ |
| Me₂C(OPr)CH₂ | Cl | O | H | H | 4-OCF₃ |
| Me₂C(OPr)CH₂ | Br | O | H | H | 4-I |
| Me₂C(OBu)CH₂ | Cl | O | H | H | 4-Cl |
| Me₂C(OBu)CH₂ | Cl | O | H | H | 4-Cl |
| Me₂C(OBu)CH₂ | Br | O | H | H | 4-I |
| Me₂C(OPen)CH₂ | Cl | O | H | H | 4-CF₃ |
| Me₂C(OPen)CH₂ | Cl | O | H | H | 4-OCF₃ |
| Me₂C(OHex)CH₂ | Cl | O | H | H | 4-Cl |
| Me₂C(OHex)CH₂ | Br | O | H | H | 4-Br |
| MeC(Et)(OMe)CH₂ | Cl | O | H | H | 4-Cl |
| MeC(Et)(OMe)CH₂ | Cl | O | H | H | 4-I |
| MeC(Pr)(OMe)CH₂ | Cl | O | H | H | 4-Cl |
| MeC(Pr)(OMe)CH₂ | Cl | O | H | H | 4-I |
| MeC(Pr)(OMe)CH₂ | Cl | O | H | H | 4-Et |
| MeC(Bu)(OMe)CH₂ | Cl | O | H | H | 4-Et |
| MeC(Bu)(OMe)CH₂ | Br | O | H | H | 4-I |
| MeC(Et)(OEt)CH₂ | Cl | O | H | H | 4-Cl |
| MeC(Et)(OEt)CH₂ | Cl | O | H | H | 4-I |
| MeC(Et)(OEt)CH₂ | Cl | O | H | H | 4-CF₃ |
| MeOCH₂C(Me)₂CH₂ | Cl | O | H | H | 4-I |
| MeOCH₂C(Me)₂CH₂ | Cl | O | H | H | 4-Cl |
| MeOCH₂C(Me)₂CH₂ | Cl | O | H | H | 4-Et |

TABLE 1-continued

In Compounds of the formula:

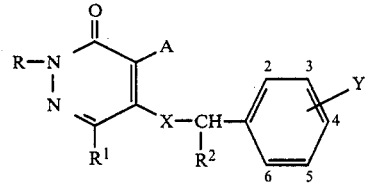

| R | A | X | R¹ | R² | Y |
|---|---|---|---|---|---|
| MeOCH₂C(Me)₂CH₂ | Cl | O | H | H | 4-CF₃ |
| MeOCH₂C(Me)₂CH₂ | Br | O | H | H | 4-I |
| EtOCH₂C(Me)₂CH₂ | Cl | O | H | H | 4-I |
| EtOCH₂C(Me)₂CH₂ | Cl | O | H | H | 4-Et |
| EtOCH₂C(Me)₂CH₂ | Cl | O | H | H | 4-CF₃ |
| EtOCH₂C(Me)₂CH₂ | Cl | O | H | H | 4-OCF₃ |
| EtOCH₂C(Me)₂CH₂ | Br | O | H | H | 4-I |
| PrOCH₂C(Me)₂CH₂ | Cl | O | H | H | 4-I |
| PrOCH₂C(Me)₂CH₂ | Cl | O | H | H | 4-Et |
| PrOCH₂C(Me)₂CH₂ | Cl | O | H | H | 4-OCF₃ |
| PrOCH₂C(Me)₂CH₂ | Cl | O | H | H | 4-OEt |
| MeOCH₂CH₂C(Me)₂CH₂ | Cl | O | H | H | 4-I |
| MeOCH₂CH₂C(Me)₂CH₂ | Cl | O | H | H | 4-Et |
| MeOCH₂CH₂C(Me)₂CH₂ | Cl | O | H | H | 4-Cl |
| MeOCH₂CH₂C(Me)₂CH₂ | Br | O | H | H | 4-Br |
| EtOCH₂CH₂C(Me)₂CH₂ | Cl | O | H | H | 4-I |
| EtOCH₂CH₂C(Me)₂CH₂ | Cl | O | H | H | 4-Et |
| EtOCH₂CH₂C(Me)₂CH₂ | Cl | O | H | H | 4-CF₃ |
| EtOCH₂CH₂C(Me)₂CH₂ | Cl | O | H | H | 4-OEt |
| MeO(CH₂)₃C(Me)₂CH₂ | Cl | O | H | H | 4-CF₃ |
| MeO(CH₂)₃C(Me)₂CH₂ | Cl | O | H | H | 4-I |
| EtO(CH₂)₃C(Me)₂CH₂ | Cl | O | H | H | 4-I |
| EtO(CH₂)₃C(Me)₂CH₂ | Cl | O | H | H | 4-Et |
| PrOCH₂CH₂C(Me)₂CH₂ | Cl | O | H | H | 4-Cl |
| PrOCH₂CH₂C(Me)₂CH₂ | Br | O | H | H | 4-I |

TABLE 2

In Compounds of the formula:

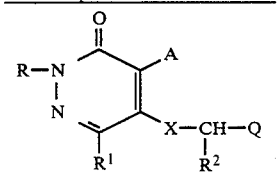

| R | A | X | R¹ | R² | Q |
|---|---|---|---|---|---|
| Cl₂CHC(Me)₂ | Cl | O | H | H | Q26-6-Cl |
| Cl₂CHC(Me)₂ | Cl | O | H | H | Q26-6-I |
| Cl₂CHC(Me)₂ | I | O | H | H | Q26-6-Cl |
| Cl₂CHC(Me)₂ | Cl | O | H | H | Q26-6-Br |
| Cl₂CHC(Me)₂ | Cl | O | H | H | Q26-6-OCH₂CF₃ |
| Cl₂CHC(Me)₂ | Cl | S | H | H | Q22 |
| Cl₂CHC(Me)₂ | Cl | S | H | H | Q22-5-Br |
| BrClCHC(Me)₂ | Cl | O | H | H | Q26-6-Cl |
| BrClCHC(Me)₂ | Cl | O | H | H | Q26-6-I |
| BrClCHC(Me)₂ | Cl | S | H | H | Q22-4-Br |
| Br₂CHC(Me)₂ | Cl | O | H | H | Q26-6-Cl |
| Br₂CHC(Me)₂ | Cl | O | H | H | Q26-6-I |
| Br₂CHC(Me)₂ | Cl | O | H | H | Q17-5-Cl |
| Br₂CHC(Me)₂ | Cl | O | H | H | Q17-5-Me |
| Br₂CHC(Me)₂ | Cl | O | H | H | Q26 |
| Br₂CHC(Me)₂ | Cl | S | H | H | Q22-5-Cl |
| Br₂CHC(Me)₂ | Cl | S | H | H | Q22-5-OPr |
| Cl₂CHCH(CH₂Cl) | Cl | O | H | H | Q26-6-Cl |
| Cl₂CHCH(CH₂Cl) | Cl | O | H | H | Q26-6-I |
| BrCH₂CBr(Me) | Cl | O | H | H | Q26-6-Cl |
| BrCH₂CBr(Me) | Cl | O | H | H | Q26-6-I |
| MeCCl₂CH₂ | Cl | O | H | H | Q26-6-Cl |
| MeCCl₂CH₂ | Cl | O | H | H | Q26-6-I |
| MeCCl₂CH₂ | I | O | H | H | Q26-6-Cl |
| MeCCl₂CH₂ | Cl | O | H | H | Q26-6-Br |
| MeCCl₂CH₂ | Cl | O | H | H | Q17-5-Cl |
| MeCCl₂CH₂ | Cl | O | H | H | Q26-6-CF₃ |
| MeCCl₂CH₂ | Cl | O | H | H | Q26-6-CN |
| MeCCl₂CH₂ | Cl | S | H | H | Q22-2,4-Me₂ |

TABLE 2-continued

In Compounds of the formula:

| R | A | X | R¹ | R² | Q |
|---|---|---|---|---|---|
| MeCCl₂CH₂ | Cl | S | H | H | Q22-2-OMe |
| MeCCl₂CH₂ | Cl | S | H | H | Q23 |
| MeCBrClCH₂ | Cl | O | H | H | Q26-6-Cl |
| MeCBrClCH₂ | Cl | O | H | H | Q26-6-I |
| MeCBr₂CH₂ | Cl | O | H | H | Q26-6-Cl |
| MeCBr₂CH₂ | Cl | O | H | H | Q26-6-Br |
| MeCBr₂CH₂ | Cl | O | H | H | Q26-6-F |
| MeCBr₂CH₂ | Cl | O | H | H | Q17-5-Me |
| MeCBr₂CH₂ | Cl | O | H | H | Q26-6-Me |
| MeCBr₂CH₂ | Cl | O | H | H | Q26-6-OPr |
| MeCBr₂CH₂ | Cl | S | H | H | Q23-5-Bu-t |
| MeCBr₂CH₂ | Cl | S | H | H | Q23-4-Me |
| ClCH₂CHClCHCl | Cl | O | H | H | Q26-6-Cl |
| ClCH₂CHClCHCl | Cl | O | H | H | Q26-6-I |
| BrCH₂CHBrCHBr | Cl | O | H | H | Q26-6-Cl |
| BrCH₂CHBrCHBr | Cl | O | H | H | Q26-6-I |
| ClCH₂CCl₂CH₂ | Cl | O | H | H | Q26-6-Cl |
| ClCH₂CCl₂CH₂ | Cl | O | H | H | Q26-6-I |
| ClCH₂CCl₂CH₂ | Br | O | H | H | Q26-6-Cl |
| ClCH₂CCl₂CH₂ | I | O | H | H | Q26-6-I |
| ClCH₂CCl₂CH₂ | Cl | O | H | H | Q26-6-Br |
| ClCH₂CCl₂CH₂ | Cl | O | H | H | Q17-5-Cl |
| ClCH₂CCl₂CH₂ | Cl | O | H | H | Q26-6-OEt |
| ClCH₂CCl₂CH₂ | Cl | O | H | H | Q26-6-SMe |
| ClCH₂CCl₂CH₂ | Cl | S | H | H | Q23-5-Me |
| ClCH₂CCl₂CH₂ | Cl | S | H | H | Q23-4-Cl |
| ClCH₂CBrClCH₂ | Cl | O | H | H | Q26-6-Cl |
| ClCH₂CBrClCH₂ | Cl | O | H | H | Q26-6-I |
| BrCH₂CBrClCH₂ | Cl | O | H | H | Q26-6-Cl |

TABLE 2-continued

In Compounds of the formula:

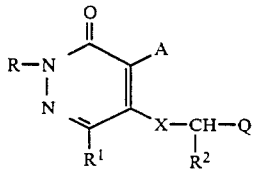

| R | A | X | R¹ | R² | Q |
|---|---|---|---|---|---|
| BrCH$_2$CBrClCH$_2$ | Cl | O | H | H | Q26-6-I |
| BrCH$_2$CBr$_2$CH$_2$ | Cl | O | H | H | Q26-6-Cl |
| BrCH$_2$CBr$_2$CH$_2$ | Cl | O | H | H | Q26-6-I |
| BrCH$_2$CBr$_2$CH$_2$ | Cl | O | H | H | Q26-6-Br |
| BrCH$_2$CBr$_2$CH$_2$ | Cl | O | H | H | Q17-5-Cl |
| BrCH$_2$CBr$_2$CH$_2$ | Cl | S | H | H | Q23-4-Br |
| BrCH$_2$CBr$_2$CH$_2$ | Cl | S | H | H | Q23-5-Cl |
| ClCH$_2$CHClCH$_2$ | Cl | O | H | H | Q26-6-Cl |
| ClCH$_2$CHClCH$_2$ | Cl | O | H | H | Q26-6-I |
| ClCH$_2$CHClCH$_2$ | Cl | O | H | H | Q26-6-F |
| ClCH$_2$CHClCH$_2$ | Cl | O | H | H | Q17-5-Me |
| ClCH$_2$CHClCH$_2$ | Cl | O | H | H | Q26-6-OMe |
| ClCH$_2$CHClCH$_2$ | Cl | O | H | H | Q26-5-Br |
| ClCH$_2$CHClCH$_2$ | Cl | S | H | H | Q23-5-Br |
| ClCH$_2$CHClCH$_2$ | Cl | S | H | H | Q23-4,5-Me$_2$ |
| ClCH$_2$CHBrCH$_2$ | Cl | O | H | H | Q26-6-Cl |
| ClCH$_2$CHBrCH$_2$ | Cl | O | H | H | Q26-6-I |
| BrCH$_2$CHClCH$_2$ | Cl | O | H | H | Q26-6-Cl |
| BrCH$_2$CHClCH$_2$ | Cl | O | H | H | Q26-6-I |
| BrCH$_2$CHBrCH$_2$ | Cl | O | H | H | Q26-6-Cl |
| BrCH$_2$CHBrCH$_2$ | Cl | O | H | H | Q26-6-I |
| BrCH$_2$CHBrCH$_2$ | I | O | H | H | Q26-6-Cl |
| BrCH$_2$CHBrCH$_2$ | Cl | O | H | H | Q26-6-Br |
| BrCH$_2$CHBrCH$_2$ | Cl | O | H | H | Q17-5-Cl |
| BrCH$_2$CHBrCH$_2$ | Cl | O | H | H | Q26-6-OPh |
| BrCH$_2$CHBrCH$_2$ | Cl | O | H | H | Q26-2-Cl |
| BrCH$_2$CHBrCH$_2$ | Cl | S | H | H | Q23-2-OMe |
| BrCH$_2$CHBrCH$_2$ | Cl | S | H | H | Q24 |
| ICH$_2$CHClCH$_2$ | Cl | O | H | H | Q26-6-Cl |
| ICH$_2$CHBrCH$_2$ | Cl | O | H | H | Q26-6-Cl |
| Me$_2$CClCHCl | Cl | O | H | H | Q26-6-Cl |
| Me$_2$CClCHCl | Cl | O | H | H | Q26-6-I |
| Me$_2$CClCHCl | Br | O | H | H | Q26-6-I |
| Me$_2$CClCHCl | Cl | O | H | H | Q17 |
| Me$_2$CClCHCl | Cl | S | H | H | Q24-5-Cl |
| Me$_2$CClCHBr | Cl | O | H | H | Q26-6-Cl |
| Me$_2$CClCHBr | Cl | O | H | H | Q26-6-I |
| Me$_2$CClCHBr | Cl | S | H | H | Q24-5-Me |
| Me$_2$CBrCHCl | Cl | O | H | H | Q26-6-Cl |
| Me$_2$CBrCHCl | Cl | O | H | H | Q17-5-Cl |
| Me$_2$CBrCHCl | Cl | O | H | H | Q17-5-Et |
| Me$_2$CBrCHBr | Cl | O | H | H | Q26-6-Cl |
| Me$_2$CBrCHBr | Cl | O | H | H | Q26-6-I |
| Me$_2$CBrCHBr | Cl | O | H | H | Q26-6-F |
| Me$_2$CBrCHBr | Br | O | H | H | Q17-5-Me |
| Me$_2$CBrCHBr | Cl | S | H | H | Q25 |
| (ClCH$_2$)$_2$CClCH$_2$ | Cl | O | H | H | Q26-6-Cl |
| (ClCH$_2$)$_2$CClCH$_2$ | Cl | O | H | H | Q26-6-I |
| (ClCH$_2$)$_2$CClCH$_2$ | Br | O | H | H | Q26-6-Cl |
| (ClCH$_2$)$_2$CClCH$_2$ | I | O | H | H | Q26-6-I |
| (ClCH$_2$)$_2$CClCH$_2$ | Cl | O | H | H | Q26-6-Br |
| (ClCH$_2$)$_2$CClCH$_2$ | Cl | O | H | H | Q17-5-Cl |
| (ClCH$_2$)$_2$CClCH$_2$ | Cl | O | H | H | Q17-6-Me |
| (ClCH$_2$)$_2$CClCH$_2$ | Cl | O | H | H | Q18-2,6-Cl$_2$ |
| (ClCH$_2$)$_2$CClCH$_2$ | Cl | S | H | H | Q25-2,4-Me$_2$ |
| (ClCH$_2$)$_2$CClCH$_2$ | Cl | S | H | H | Q27 |
| (ClCH$_2$)$_2$CBrCH$_2$ | Cl | O | H | H | Q26-6-Cl |
| (ClCH$_2$)$_2$CBrCH$_2$ | Cl | O | H | H | Q26-6-I |
| ClCH$_2$CBr(CH$_2$Br)CH$_2$ | Cl | O | H | H | Q26-6-Cl |
| ClCH$_2$CCl(Me)CH$_2$ | Cl | O | H | H | Q26-6-Cl |
| ClCH$_2$CCl(Me)CH$_2$ | Cl | O | H | H | Q26-6-I |
| ClCH$_2$CCl(Me)CH$_2$ | Br | O | H | H | Q26-6-Cl |
| ClCH$_2$CCl(Me)CH$_2$ | Br | O | H | H | Q26-6-I |
| ClCH$_2$CCl(Me)CH$_2$ | I | O | H | H | Q26-6-Cl |
| ClCH$_2$CCl(Me)CH$_2$ | I | O | H | H | Q26-6-I |
| ClCH$_2$CCl(Me)CH$_2$ | Cl | O | H | H | Q26-6-F |
| ClCH$_2$CCl(Me)CH$_2$ | Cl | O | H | H | Q17-5-Me |
| ClCH$_2$CCl(Me)CH$_2$ | Cl | O | H | H | Q18-2-Cl |
| ClCH$_2$CCl(Me)CH$_2$ | I | O | H | H | Q18-2-Cl-6-Me |
| ClCH$_2$CCl(Me)CH$_2$ | Cl | S | H | H | Q27-6-Me |
| ClCH$_2$CCl(Me)CH$_2$ | Cl | S | H | H | Q27-6-Cl |
| ClCH$_2$CCl(Me)CH$_2$ | Cl | S | H | H | Q26-6-Cl |
| ClCH$_2$CBr(Me)CH$_2$ | Cl | O | H | H | Q26-6-Cl |
| ClCH$_2$CBr(Me)CH$_2$ | Cl | O | H | H | Q26-6-I |
| ClCH$_2$CBr(Me)CH$_2$ | Cl | S | H | H | Q28 |
| ClCH$_2$CBr(Me)CH$_2$ | Cl | S | H | H | Q26-5-Cl |
| ClCH$_2$CHClCH(CH$_2$Cl) | Cl | O | H | H | Q26-6-Cl |
| ClCH$_2$CHClCH(CH$_2$Cl) | Cl | O | H | H | Q26-6-I |
| BrCH$_2$CHBrCH(CH$_2$Br) | Cl | O | H | H | Q26-6-Cl |
| MeCCl$_2$CH(CH$_2$Cl) | Cl | O | H | H | Q26-6-Cl |
| ClCH$_2$CHClC(Me)$_2$ | Cl | O | H | H | Q26-6-Cl |
| ClCH$_2$CHClCH(Me) | Cl | O | H | H | Q26-6-Cl |
| MeCHClCH(CH$_2$Cl) | Cl | O | H | H | Q26-6-Cl |
| ClCH$_2$CCl$_2$CHCl | Cl | O | H | H | Q26-6-Cl |
| ClCH$_2$CCl$_2$CHCl | Cl | O | H | H | Q26-6-I |
| ClCH$_2$CHClCCl(Me) | Cl | O | H | H | Q26-6-Cl |
| Cl$_2$CHCHClCH$_2$ | Cl | O | H | H | Q26-6-Cl |
| Cl$_2$CHCHClCH$_2$ | Cl | O | H | H | Q26-6-I |
| BrClCHCHBrCH$_2$ | Cl | O | H | H | Q26-6-I |
| Cl$_2$CHCCl$_2$CH$_2$ | Cl | O | H | H | Q26-6-Cl |
| Cl$_2$CHCCl$_2$CH$_2$ | Cl | O | H | H | Q26-6-I |
| Cl$_2$CHCCl$_2$CH$_2$ | Cl | O | H | H | Q26-6-Br |
| Cl$_2$CHCCl$_2$CH$_2$ | Cl | O | H | H | Q17-5-Cl |
| Cl$_2$CHCCl$_2$CH$_2$ | Cl | O | H | H | Q32 |
| Cl$_2$CHCCl$_2$CH$_2$ | Cl | S | H | H | Q28-4,6-Me$_2$ |
| Cl$_2$CHCCl$_2$CH$_2$ | Cl | S | H | H | Q29 |
| ClBrCHCClBrCH$_2$ | Cl | O | H | H | Q26-6-Cl |
| ClBrCHCClBrCH$_2$ | Cl | O | H | H | Q26-6-I |
| ClBrCHCClBrCH$_2$ | Br | O | H | H | Q32-2-Cl |
| ClBrCHCClBrCH$_2$ | Cl | S | H | H | Q30 |
| ClBrCHCClBrCH$_2$ | Cl | S | H | H | Q31 |
| ClCH$_2$CH$_2$CHClCH$_2$ | Cl | O | H | H | Q26-6-Cl |
| ClCH$_2$CH$_2$CHClCH$_2$ | Cl | O | H | H | Q26-6-I |
| MeCHClCHClCH$_2$ | Cl | O | H | H | Q26-6-Cl |
| MeCHClCHClCH$_2$ | Cl | O | H | H | Q26-6-I |
| Me$_2$CClCHClCH$_2$ | Cl | O | H | H | Q26-6-Cl |
| PrCCl(CH$_2$Cl)CH$_2$ | Cl | O | H | H | Q26-6-Cl |
| MeCCl$_2$CHClCH$_2$ | Cl | O | H | H | Q26-6-Cl |
| MeCCl$_2$CHClCH$_2$ | Cl | O | H | H | Q26-6-I |
| ClCH$_2$CH(Me) | Cl | O | H | H | Q26-6-Cl |
| ClCH$_2$CH(Me) | Cl | O | H | H | Q26-6-I |
| ClCH$_2$C(Me)$_2$ | Cl | O | H | H | Q26-6-Br |
| ClCH$_2$C(Me)$_2$ | Cl | O | H | H | Q17-5-Cl |
| Cl(CH$_2$)$_3$ | Cl | O | H | H | Q32-2-Me |
| Cl(CH$_2$)$_3$ | Cl | O | H | H | Q45 |
| Cl(CH$_2$)$_3$ | Cl | S | H | H | Q31 |
| Cl(CH$_2$)$_3$ | Cl | S | H | H | Q33 |
| Br(CH$_2$)$_3$ | Cl | O | H | H | Q26-6-Cl |
| Br(CH$_2$)$_3$ | Cl | O | H | H | Q26-6-I |
| Br(CH$_2$)$_3$ | Cl | S | H | H | Q30-2,6-Me$_2$ |
| Br(CH$_2$)$_3$ | Cl | S | H | H | Q31-5-Cl |
| I(CH$_2$)$_3$ | Cl | O | H | H | Q26-6-Cl |
| Me$_2$CClCH$_2$ | Cl | O | H | H | Q26-6-Cl |
| Me$_2$CClCH$_2$ | Br | O | H | H | Q26-6-Cl |
| Me$_2$CClCH$_2$ | I | O | H | H | Q26-6-I |
| Me$_2$CClCH$_2$ | Cl | O | H | H | Q26-6-F |
| Me$_2$CClCH$_2$ | I | O | H | H | Q17-5-Me |
| Me$_2$CClCH$_2$ | Cl | O | H | H | Q45-5-Me |
| Me$_2$CClCH$_2$ | Cl | O | H | H | Q50 |
| Me$_2$CClCH$_2$ | Cl | S | H | H | Q33-5-Cl |
| Me$_2$CClCH$_2$ | Cl | S | H | H | Q33-6-Cl |
| Me$_2$CBrCH$_2$ | Cl | O | H | H | Q26-6-Cl |
| Me$_2$CBrCH$_2$ | Cl | O | H | H | Q26-6-I |
| Me$_2$CBrCH$_2$ | Cl | O | H | H | Q26-6-Br |
| Me$_2$CBrCH$_2$ | I | O | H | H | Q17-5-Cl |
| Me$_2$CBrCH$_2$ | Cl | O | H | H | Q50-2-CF$_3$ |
| Me$_2$CBrCH$_2$ | Cl | O | H | H | Q50-2-Cl |
| Me$_2$CBrCH$_2$ | Cl | S | H | H | Q33-5-Me |

TABLE 2-continued

In Compounds of the formula:

[Structure: pyridazinone with R-N, N, R¹, A (=O and A substituent), and X-CH(R²)-Q side chain]

| R | A | X | R¹ | R² | Q |
|---|---|---|---|---|---|
| Me₂CBrCH₂ | Cl | S | H | H | Q33-6-OCF₃ |
| Cl(CH₂)₄ | Cl | O | H | H | Q26-6-Cl |
| Cl(CH₂)₄ | Cl | O | H | H | Q26-6-I |
| Br(CH₂)₄ | Cl | O | H | H | Q26-6-Cl |
| Br(CH₂)₄ | Cl | O | H | H | Q26-6-I |
| I(CH₂)₄ | Cl | O | H | H | Q26-6-Cl |
| I(CH₂)₄ | Cl | O | H | H | Q26-6-I |
| i-PrCCl(Me)CH₂ | Cl | O | H | H | Q26-6-Cl |
| i-PrCCl(Me)CH₂ | Cl | O | H | H | Q26-6-I |
| i-PrCCl(Me)CH₂ | Cl | O | H | H | Q26-6-F |
| i-PrCCl(Me)CH₂ | Cl | O | H | H | Q17-5-Me |
| i-PrCCl(Me)CH₂ | Cl | O | H | H | Q50-2-Me |
| i-PrCCl(Me)CH₂ | Cl | O | H | H | Q52-1-Me-5-Cl |
| i-PrCCl(Me)CH₂ | Cl | S | H | H | Q34 |
| i-PrCCl(Me)CH₂ | Cl | S | H | H | Q34-2-Me |
| i-PrCBr(Me)CH₂ | Cl | O | H | H | Q26-6-Cl |
| i-PrCBr(Me)CH₂ | Cl | O | H | H | Q26-6-I |
| i-PrCBr(Me)CH₂ | Cl | S | H | H | Q34-2-CF₃ |
| i-PrCBr(Me)CH₂ | Cl | S | H | H | Q35 |
| EtCCl(Me)CH₂ | Cl | O | H | H | Q26-6-Cl |
| EtCCl(Me)CH₂ | Cl | O | H | H | Q26-6-I |
| EtCCl(Me)CH₂ | I | O | H | H | Q26-6-Cl |
| EtCCl(Me)CH₂ | I | O | H | H | Q26-6-I |
| EtCCl(Me)CH₂ | Cl | O | H | H | Q26-6-F |
| EtCCl(Me)CH₂ | Cl | O | H | H | Q17-5-Me |
| EtCCl(Me)CH₂ | Cl | O | H | H | Q53-1-Me |
| EtCCl(Me)CH₂ | Cl | O | H | H | Q54 |
| EtCCl(Me)CH₂ | Cl | S | H | H | Q35-3-Me |
| EtCCl(Me)CH₂ | Cl | S | H | H | Q36 |
| EtCBr(Me)CH₂ | Cl | O | H | H | Q26-6-Cl |
| EtCBr(Me)CH₂ | Cl | O | H | H | Q26-6-I |
| EtCBr(Me)CH₂ | Cl | S | H | H | Q36-2-Et |
| EtCBr(Me)CH₂ | Cl | S | H | H | Q37-1-Me |
| Et₂CClCH₂ | Cl | O | H | H | Q26-6-Cl |
| Et₂CClCH₂ | Cl | O | H | H | Q26-6-I |
| Et₂CClCH₂ | I | O | H | H | Q26-6-Cl |
| Et₂CClCH₂ | Cl | O | H | H | Q26-6-Br |
| Et₂CClCH₂ | Cl | O | H | H | Q17-5-Cl |
| Et₂CClCH₂ | Cl | O | H | H | Q26-6-OCH₂CF₃ |
| Et₂CClCH₂ | Cl | O | H | H | Q18 |
| Et₂CClCH₂ | Cl | S | H | H | Q38-1-Me |
| Et₂CClCH₂ | Cl | S | H | H | Q39-1-Me |
| Et₂CBrCH₂ | Cl | O | H | H | Q26-6-Cl |
| Et₂CBrCH₂ | Cl | O | H | H | Q26-6-I |
| Et₂CBrCH₂ | Cl | S | H | H | Q40-1,3-Me₂ |
| Et₂CBrCH₂ | Cl | S | H | H | Q41-1-Me |
| t-BuCHClCH₂ | Cl | O | H | H | Q26-6-Cl |
| t-BuCCl(Me)CH₂ | Cl | O | H | H | Q26-6-Cl |
| t-BuCCl(Me)CH₂ | Cl | O | H | H | Q26-6-I |
| t-BuCCl(Me)CH₂ | Br | O | H | H | Q26-6-Cl |
| t-BuCCl(Me)CH₂ | I | O | H | H | Q26-6-Cl |
| t-BuCCl(Me)CH₂ | I | O | H | H | Q26-6-I |
| t-BuCCl(Me)CH₂ | Cl | O | H | H | Q26-6-Br |
| t-BuCCl(Me)CH₂ | Cl | O | H | H | Q17-5-Cl |
| t-BuCCl(Me)CH₂ | Cl | O | H | H | Q26 |
| t-BuCCl(Me)CH₂ | Cl | S | H | H | Q42 |
| t-BuCCl(Me)CH₂ | Cl | S | H | H | Q42-4-Me |
| t-BuCBr(Me)CH₂ | Cl | O | H | H | Q26-6-Cl |
| t-BuCBr(Me)CH₂ | Cl | O | H | H | Q26-6-I |
| t-BuCBr(Me)CH₂ | Cl | O | H | H | Q42-6-Me |
| t-BuCBr(Me)CH₂ | Cl | S | H | H | Q42-4-Cl |
| PrCCl(Me)CH₂ | Cl | O | H | H | Q26-6-Cl |
| PrCCl(Me)CH₂ | Cl | O | H | H | Q26-6-I |
| PrCCl(Me)CH₂ | I | O | H | H | Q26-6-Cl |
| PrCCl(Me)CH₂ | I | O | H | H | Q26-6-I |
| PrCCl(Me)CH₂ | Br | O | H | H | Q26-6-F |
| PrCCl(Me)CH₂ | I | O | H | H | Q17-5-Me |
| PrCCl(Me)CH₂ | Cl | O | H | H | Q26-6-CF₃ |
| PrCCl(Me)CH₂ | Cl | O | H | H | Q26-6-CN |
| PrCCl(Me)CH₂ | Cl | S | H | H | Q42-8-Me |
| PrCCl(Me)CH₂ | Cl | S | H | H | Q42-8-Cl |
| PrCBr(Me)CH₂ | Cl | O | H | H | Q26-6-Cl |
| PrCBr(Me)CH₂ | Cl | O | H | H | Q26-6-I |
| PrCBr(Me)CH₂ | Cl | S | H | H | Q43 |
| PrCBr(Me)CH₂ | Cl | S | H | H | Q43-2-Cl |
| i-PrCCl(Me)CH₂ | Cl | O | H | H | Q26-6-Cl |
| i-PrCCl(Me)CH₂ | Cl | O | H | H | Q26-6-I |
| i-PrCCl(Me)CH₂ | I | O | H | H | Q26-6-Cl |
| i-PrCCl(Me)CH₂ | Cl | O | H | H | Q26-6-Br |
| i-PrCCl(Me)CH₂ | F | O | H | H | Q17-5-Cl |
| i-PrCCl(Me)CH₂ | Br | O | H | H | Q26-6-Me |
| i-PrCCl(Me)CH₂ | I | O | H | H | Q26-6-OPr |
| i-PrCCl(Me)CH₂ | Cl | S | H | H | Q44 |
| i-PrCCl(Me)CH₂ | Cl | S | H | H | Q44-2-CF₃ |
| i-PrCBr(Me)CH₂ | Cl | O | H | H | Q26-6-Cl |
| i-PrCBr(Me)CH₂ | Cl | O | H | H | Q26-6-I |
| i-PrCBr(Me)CH₂ | Cl | S | H | H | Q45-5-Cl |
| i-PrCBr(Me)CH₂ | Cl | S | H | H | Q45-5,6-Me₂ |
| BuCCl(Me)CH₂ | Cl | O | H | H | Q26-6-Cl |
| BuCCl(Me)CH₂ | Cl | O | H | H | Q26-6-I |
| BuCCl(Me)CH₂ | I | O | H | H | Q26-6-I |
| BuCCl(Me)CH₂ | Cl | O | H | H | Q26-6-F |
| BuCCl(Me)CH₂ | Br | O | H | H | Q17-5-Me |
| BuCCl(Me)CH₂ | Cl | O | H | H | Q26-6-OEt |
| BuCCl(Me)CH₂ | Cl | S | H | H | Q45-6-Cl |
| BuCCl(Me)CH₂ | Cl | S | H | H | Q46 |
| BuCBr(Me)CH₂ | Cl | O | H | H | Q26-6-Cl |
| BuCBr(Me)CH₂ | Cl | S | H | H | Q46-3-Me |
| BuCBr(Me)CH₂ | Cl | S | H | H | Q46-6-Me |
| HexCHClCH₂ | Cl | O | H | H | Q26-6-Cl |
| HexCHClCH₂ | Cl | O | H | H | Q26-6-I |
| i-BuCCl(Me)CH₂ | Cl | O | H | H | Q26-6-Cl |
| i-BuCCl(Me)CH₂ | Cl | O | H | H | Q26-6-I |
| i-BuCCl(Me)CH₂ | Br | O | H | H | Q26-6-I |
| i-BuCCl(Me)CH₂ | I | O | H | H | Q26-6-I |
| i-BuCCl(Me)CH₂ | Cl | O | H | H | Q26-6-Br |
| i-BuCCl(Me)CH₂ | I | O | H | H | Q17-5-Cl |
| i-BuCCl(Me)CH₂ | Cl | O | H | H | Q26-6-OMe |
| i-BuCCl(Me)CH₂ | Cl | O | H | H | Q26-5-Br |
| i-BuCCl(Me)CH₂ | Cl | S | H | H | Q46-6-Cl |
| i-BuCCl(Me)CH₂ | Cl | S | H | H | Q47-7-Cl |
| i-BuCBr(Me)CH₂ | Cl | O | H | H | Q26-6-Cl |
| i-BuCBr(Me)CH₂ | Cl | S | H | H | Q46-6-F |
| i-BuCBr(Me)CH₂ | Cl | S | H | H | Q47 |
| s-BuCCl(Me)CH₂ | Cl | O | H | H | Q26-6-Cl |
| s-BuCCl(Me)CH₂ | Cl | O | H | H | Q26-6-I |
| s-BuCCl(Me)CH₂ | I | O | H | H | Q26-6-Cl |
| s-BuCCl(Me)CH₂ | I | O | H | H | Q26-6-I |
| s-BuCCl(Me)CH₂ | I | O | H | H | Q26-6-Br |
| s-BuCCl(Me)CH₂ | I | O | H | H | Q17-5-Cl |
| s-BuCCl(Me)CH₂ | I | O | H | H | Q26-6-OPh |
| s-BuCCl(Me)CH₂ | Me | O | H | H | Q26-2-Cl |
| s-BuCCl(Me)CH₂ | Cl | S | H | H | Q47-2,3-Me₂ |
| s-BuCCl(Me)CH₂ | Cl | S | H | H | Q48 |
| s-BuCBr(Me)CH₂ | Cl | O | H | H | Q26-6-Cl |
| s-BuCBr(Me)CH₂ | Cl | O | H | H | Q26-6-I |
| s-BuCBr(Me)CH₂ | Cl | S | H | H | Q48-5-Cl |
| s-BuCBr(Me)CH₂ | Cl | S | H | H | Q49-2,4-Me₂ |
| PenCCl(Me)CH₂ | Cl | O | H | H | Q26-6-Cl |
| PenCCl(Me)CH₂ | Cl | O | H | H | Q26-6-I |
| ClCH=CHCH₂ | Cl | O | H | H | Q26-6-Cl |
| ClCH=CHCH₂ | Cl | O | H | H | Q26-6-I |
| ClCH=C(Cl)CH₂ | Cl | O | H | H | Q26-6-Cl |
| ClCH=C(Cl)CH₂ | Cl | O | H | H | Q26-6-I |
| Q3-2-Cl | Cl | O | H | H | Q26-6-Cl |
| Q3-2-Cl | Cl | O | H | H | Q26-6-I |
| Q3-2-Cl | I | O | H | H | Q26-6-I |
| Q3-2-Cl | Cl | O | H | H | Q17-5-Cl |
| Q3-2-Cl | Cl | S | H | H | Q51-5-Me |

TABLE 2-continued

In Compounds of the formula:

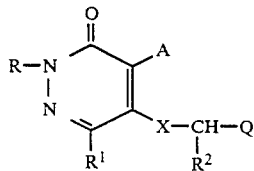

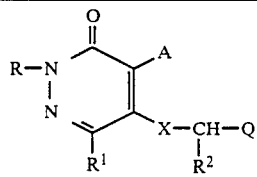

| R | A | X | R¹ | R² | Q |
|---|---|---|----|----|---|
| Q3-2-Cl | Cl | S | H | H | Q52-5-Me |
| Q3-2-Br | Cl | O | H | H | Q26-6-Cl |
| (Q4-1-Cl)CH₂ | Cl | O | H | H | Q26-6-Cl |
| (Q4-1-Cl)CH₂ | Cl | O | H | H | Q26-6-I |
| Q4-2-Cl | Cl | O | H | H | Q26-6-Cl |
| Q4-2-Cl | Cl | O | H | H | Q26-6-I |
| Q4-2-Cl | Br | O | H | H | Q26-6-Cl |
| Q4-2-Cl | I | O | H | H | Q26-6-I |
| Q4-2-Cl | Cl | O | H | H | Q26-6-F |
| Q4-2-Cl | Cl | O | H | H | Q17-5-Me |
| Q4-2-Cl | OMe | O | H | H | Q17 |
| Q4-2-Cl | SMe | O | H | H | Q17-5-Et |
| Q4-2-Cl | Cl | S | H | H | Q52-1,5-Me₂ |
| Q4-2-Cl | Cl | S | H | H | Q53 |
| Q4-2-Br | Cl | O | H | H | Q26-6-Cl |
| Q4-2-Br | Cl | O | H | H | Q26-6-I |
| Q4-2-Br | Cl | S | H | H | Q53-1-Ph |
| Q4-2-Br | Cl | S | H | H | Q53-1,3,4-Me₃ |
| Q5-2-Cl | Cl | O | H | H | Q26-6-Cl |
| Q5-2-Cl | Cl | O | H | H | Q26-6-I |
| Q5-2-Cl | Cl | S | H | H | Q54-1-Me-3-Bu-t |
| Q5-2-Br | Cl | O | H | H | Q26-6-Cl |
| Q10-2-Cl | Cl | O | H | H | Q26-6-Cl |
| Q10-2-Cl | Cl | O | H | H | Q26-6-I |
| Q10-2-Cl | Cl | S | H | H | Q26-6-Cl |
| Q10-2-Cl | Cl | S | H | H | Q26-6-I |
| Q10-2-Br | Cl | O | H | H | Q26-6-Cl |
| Q10-2-Br | Cl | S | H | H | Q17-5-Cl |
| MeCCl(OMe)CH₂ | Cl | O | H | H | Q26-6-Cl |
| MeCCl(OMe)CH₂ | Cl | O | H | H | Q26-6-I |
| PrCCl(OMe)CH₂ | Cl | O | H | H | Q26-6-Cl |
| MeCCl(COOMe)CH₂ | Cl | O | H | H | Q26-6-Cl |
| MeCCl(COOMe)CH₂ | Cl | O | H | H | Q26-6-I |
| MeCCl(SMe)CH₂ | Cl | O | H | H | Q26-6-Cl |
| MeCCl(SMe)CH₂ | Cl | O | H | H | Q26-6-I |
| PrCCl(SMe)CH₂ | Cl | O | H | H | Q26-6-Cl |
| PrCCl(CH₂OMe)CH₂ | Cl | O | H | H | Q26-6-Cl |
| PrCCl(CH₂SMe)CH₂ | Cl | O | H | H | Q26-6-Cl |
| MeCCl(CH₂CH₂OMe)CH₂ | Cl | O | H | H | Q26-6-Cl |
| PrCCl(CH₂CN)CH₂ | Cl | O | H | H | Q26-6-Cl |
| PrCCl(CH₂COOMe)CH₂ | Cl | O | H | H | Q26-6-Cl |
| NCCH₂CCl(Me)CH₂ | Cl | O | H | H | Q26-6-Cl |
| NCCH₂CCl(Me)CH₂ | Cl | O | H | H | Q26-6-I |
| MeCOOCH₂CCl(Me)CH₂ | Cl | O | H | H | Q26-6-Cl |
| MeCOOCH₂CCl(Me)CH₂ | Cl | O | H | H | Q26-6-I |
| EtCOOCH₂CCl(Me)CH₂ | Cl | O | H | H | Q26-6-Cl |
| MeOCH₂CCl(Me)CH₂ | Cl | O | H | H | Q26-6-Cl |
| MeOCH₂CCl(Me)CH₂ | Cl | O | H | H | Q26-6-I |
| EtOCH₂CCl(Me)CH₂ | Cl | O | H | H | Q26-6-Cl |
| PrOCH₂CCl(Me)CH₂ | Cl | O | H | H | Q26-6-Cl |
| MeSCH₂CCl(Me)CH₂ | Cl | O | H | H | Q26-6-Cl |
| MeSCH₂CCl(Me)CH₂ | Cl | O | H | H | Q26-6-I |
| EtSCH₂CCl(Me)CH₂ | Cl | O | H | H | Q26-6-Cl |
| PrSCH₂CCl(Me)CH₂ | Cl | O | H | H | Q26-6-Cl |
| MeCCl(CN)CH₂ | Cl | O | H | H | Q26-6-Cl |
| MeCCl(CN)CH₂ | Cl | O | H | H | Q26-6-I |
| MeSO₂CCl(Me)CH₂ | Cl | O | H | H | Q26-6-Cl |
| MeSO₂CCl(Me)CH₂ | Cl | O | H | H | Q26-6-I |
| Me₂NCCl(Me)CH₂ | Cl | O | H | H | Q26-6-Cl |
| Me₂NCCl(Me)CH₂ | Cl | O | H | H | Q26-6-I |
| Me₂CClCH₂ | Cl | O | H | H | Q26-6-Et |
| Me₂CClCH₂ | Cl | O | H | H | Q26-6-Br |
| Me₂CClCH₂ | Cl | O | H | H | Q26-6-CF₃ |
| Me₂CClCH₂ | Br | O | H | H | Q26-6-I |
| Me₂CClCH₂ | Cl | O | H | H | Q26-6-OEt |
| Me₂CClCH₂ | Cl | O | H | H | Q32-2-I |
| Me₂CClCH₂ | Cl | O | H | H | Q32-2-Cl |
| Me₂CClCH₂ | Cl | O | H | H | Q32-2-Et |
| Me₂CBrCH₂ | Cl | O | H | H | Q26-6-Et |
| Me₂CBrCH₂ | Cl | O | H | H | Q26-6-Br |
| Me₂CBrCH₂ | Cl | O | H | H | Q32-2-Cl |
| Me₂CBrCH₂ | Cl | O | H | H | Q32-2-Et |
| Me₂CBrCH₂ | Cl | O | H | H | Q32-2-OEt |
| Me₂CBrCH₂ | Br | O | H | H | Q26-6-I |
| Me₂CBrCH₂ | Br | O | H | H | Q26-6-Cl |
| PrCCl(Me)CH₂ | Cl | O | H | H | Q26-6-Et |
| PrCCl(Me)CH₂ | Cl | O | H | H | Q32-2-Et |
| PrCCl(Me)CH₂ | Cl | O | H | H | Q32-2-Cl |
| PrCCl(Me)CH₂ | Br | O | H | H | Q26-6-I |
| PrCCl(Me)CH₂ | Br | O | H | H | Q26-6-Cl |
| PrCCl(Me)CH₂ | Cl | O | H | H | Q17-5-CF₃ |
| PrCBr(Me)CH₂ | Br | O | H | H | Q26-6-Br |
| PrCBr(Me)CH₂ | Br | O | H | H | Q26-6-I |
| Cl₂C=CH | Cl | O | H | H | Q26-6-Cl |
| Cl₂C=CH | Cl | O | H | H | Q26-6-I |
| MeCCl=CH | Cl | O | H | H | Q26-6-I |
| MeCCl=CH | Cl | O | H | H | Q26-6-Et |
| EtCCl=CH | Cl | O | H | H | Q26-6-I |
| EtCCl=CH | Cl | O | H | H | Q26-6-Cl |
| EtCCl=CH | Cl | O | H | H | Q26-6-Br |
| PrCCl=CH | Cl | O | H | H | Q26-6-I |
| PrCCl=CH | Cl | O | H | H | Q26-6-Br |
| PrCCl=CH | Br | O | H | H | Q26-6-Br |
| Me₂C=CH | Cl | O | H | H | Q26-6-I |
| Me₂C=CH | Cl | O | H | H | Q26-6-Br |
| Me₂C=CH | Cl | O | H | H | Q26-6-Et |
| Me₂C=CH | Cl | O | H | H | Q26-6-Cl |
| MeC(Et)=CH | Cl | O | H | H | Q26-6-I |
| MeC(Et)=CH | Cl | O | H | H | Q26-6-Cl |
| MeC(Pr)=CH | Cl | O | H | H | Q26-6-Cl |
| MeC(Pr)=CH | Cl | O | H | H | Q26-6-I |
| MeC(Pr)=CH | Cl | O | H | H | Q26-6-Br |
| MeC(Bu)=CH | Cl | O | H | H | Q26-6-I |
| CF₃CCl=CH | Cl | O | H | H | Q26-6-Cl |
| CF₃CCl=CH | Cl | O | H | H | Q26-6-I |
| CF₃CBr=CH | Cl | O | H | H | Q26-6-I |
| CF₃CBr=CH | Cl | O | H | H | Q26-6-Br |
| CH₂=C(Me)CH₂ | Cl | O | H | H | Q26-6-Cl |
| CH₂=C(Me)CH₂ | Cl | O | H | H | Q26-6-I |
| CH₂=C(Me)CH₂ | Cl | O | H | H | Q26-6-Br |
| CH₂=C(Me)CH₂ | Br | O | H | H | Q26-6-I |
| CH₂=C(Et)CH₂ | Cl | O | H | H | Q26-6-I |
| CH₂=C(Et)CH₂ | Cl | O | H | H | Q26-6-Et |
| CH₂=C(Et)CH₂ | Cl | O | H | H | Q26-6-Br |
| CH₂=C(Pr)CH₂ | Cl | O | H | H | Q26-6-I |
| CH₂=C(Pr)CH₂ | Cl | O | H | H | Q26-6-Br |
| CH₂=C(Pr)CH₂ | Br | O | H | H | Q26-6-I |
| CH₂=C(Bu)CH₂ | Cl | O | H | H | Q26-6-I |
| CH₂=C(Bu)CH₂ | Cl | O | H | H | Q26-6-Br |
| MeCH=C(Me)CH₂ | Cl | O | H | H | Q26-6-I |
| MeCH=C(Me)CH₂ | Cl | O | H | H | Q26-6-Cl |
| MeCH=C(Me)CH₂ | Cl | O | H | H | Q26-6-Br |
| EtCH=C(Me)CH₂ | Cl | O | H | H | Q26-6-I |
| EtCH=C(Me)CH₂ | Cl | O | H | H | Q26-6-Br |
| EtCH=C(Me)CH₂ | Cl | O | H | H | Q26-6-Cl |
| EtCH=C(Me)CH₂ | Br | O | H | H | Q26-6-I |
| PrCH=C(Me)CH₂ | Cl | O | H | H | Q26-6-I |
| PrCH=C(Me)CH₂ | Cl | O | H | H | Q26-6-Br |
| MeCH=C(Et)CH₂ | Cl | O | H | H | Q26-6-I |
| MeCH=C(Et)CH₂ | Cl | O | H | H | Q26-6-Cl |
| MeCH=C(Et)CH₂ | Cl | O | H | H | Q32-2-Et |
| CH₂=CHC(Me)₂CH₂ | Cl | O | H | H | Q26-6-Cl |
| CH₂=CHC(Me)₂CH₂ | Cl | O | H | H | Q26-6-Br |
| MeCH=CHC(Me)₂CH₂ | Cl | O | H | H | Q26-6-I |
| MeCH=CHC(Me)₂CH₂ | Cl | O | H | H | Q26-6-Cl |
| HC≡CC(Me)₂CH₂ | Cl | O | H | H | Q26-6-I |
| HC≡CC(Me)₂CH₂ | Cl | O | H | H | Q26-6-Br |
| MeC≡CC(Me)₂CH₂ | Cl | O | H | H | Q26-6-I |
| MeC≡CC(Me)₂CH₂ | Cl | O | H | H | Q26-6-Cl |
| CH₂=CHCH₂C(Me)₂CH₂ | Cl | O | H | H | Q26-6-Br |

TABLE 2-continued

In Compounds of the formula:

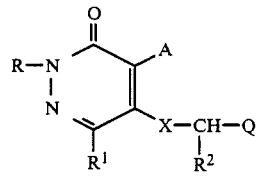

| R | A | X | R¹ | R² | Q |
|---|---|---|----|----|---|
| CH₂=CHCH₂C(Me)₂CH₂ | Cl | O | H | H | Q26-6-I |
| HC≡CCH₂C(Me)₂CH₂ | Cl | O | H | H | Q26-6-I |
| HC≡CCH₂C(Me)₂CH₂ | Cl | O | H | H | Q26-6-Cl |
| MeC≡CCH₂C(Me)₂CH₂ | Cl | O | H | H | Q26-6-Br |
| MeC≡CCH₂C(Me)₂CH₂ | Cl | O | H | H | Q26-6-I |
| Me₂C(OMe)CH₂ | Cl | O | H | H | Q26-6-Cl |
| Me₂C(OMe)CH₂ | Cl | O | H | H | Q26-6-Br |
| Me₂C(OMe)CH₂ | Cl | O | H | H | Q26-6-I |
| Me₂C(OEt)CH₂ | Cl | O | H | H | Q26-6-Cl |
| Me₂C(OEt)CH₂ | Cl | O | H | H | Q26-6-I |
| Me₂C(OPr)CH₂ | Cl | O | H | H | Q26-6-Br |
| Me₂C(OPr)CH₂ | Cl | O | H | H | Q26-6-I |
| MeC(Et)(OMe)CH₂ | Cl | O | H | H | Q26-6-Et |
| MeC(Et)(OMe)CH₂ | Cl | O | H | H | Q26-6-I |
| MeC(Pr)(OMe)CH₂ | Cl | O | H | H | Q26-6-I |
| MeC(Pr)(OMe)CH₂ | Cl | O | H | H | Q26-6-Br |
| MeOCH₂C(Me)₂CH₂ | Cl | O | H | H | Q26-6-Cl |

TABLE 2-continued

In Compounds of the formula:

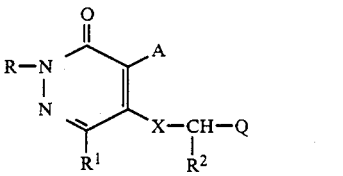

| R | A | X | R¹ | R² | Q |
|---|---|---|----|----|---|
| MeOCH₂C(Me)₂CH₂ | Cl | O | H | H | Q26-6-CF₃ |
| MeOCH₂C(Me)₂CH₂ | Cl | O | H | H | Q26-6-I |
| EtOCH₂C(Me)₂CH₂ | Cl | O | H | H | Q26-6-I |
| EtOCH₂C(Me)₂CH₂ | Cl | O | H | H | Q26-6-Br |
| EtOCH₂C(Me)₂CH₂ | Br | O | H | H | Q26-6-Cl |
| PrOCH₂C(Me)₂CH₂ | Cl | O | H | H | Q26-6-Cl |
| PrOCH₂C(Me)₂CH₂ | Cl | O | H | H | Q26-6-I |
| MeOCH₂CH₂C(Me)₂CH₂ | Cl | O | H | H | Q26-6-Br |
| MeOCH₂CH₂C(Me)₂CH₂ | Cl | O | H | H | Q26-6-Cl |
| MeOCH₂CH₂C(Me)₂CH₂ | Br | O | H | H | Q26-6-Cl |
| EtOCH₂CH₂C(Me)₂CH₂ | Cl | O | H | H | Q26-6-I |
| EtOCH₂CH₂C(Me)₂CH₂ | Cl | O | H | H | Q26-6-Br |
| EtOCH₂CH₂C(Me)₂CH₂ | Cl | O | H | H | Q26-6-Cl |
| MeO(CH₂)₃C(Me)₂CH₂ | Cl | O | H | H | Q26-6-Et |
| MeO(CH₂)₃C(Me)₂CH₂ | Cl | O | H | H | Q26-6-Cl |
| EtO(CH₂)₃C(Me)₂CH₂ | Cl | O | H | H | Q26-6-I |
| EtO(CH₂)₃C(Me)₂CH₂ | Cl | O | H | H | Q26-6-Cl |

TABLE 3

In compounds of the formula:

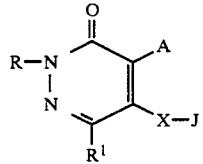

| R | A | X | R¹ | J |
|---|---|---|----|---|
| Me₂CClCH₂ | Cl | O | H | CH₂CH₂C₆H₄-3-Cl |
| Me₂CClCH₂ | Cl | O | H | CH₂CH₂C₆H₄-4-CF₃ |
| Me₂CClCH₂ | Cl | O | H | CH₂CH₂C₆H₄-4-Me |
| Me₂CClCH₂ | Cl | O | H | CH₂CH₂C₆H₄-4-OMe |
| Me₂CClCH₂ | Cl | O | H | CH₂CHMeC₆H₄-4-Me |
| Me₂CClCH₂ | Cl | O | H | CH₂CH₂CH₂C₆H₄-4-Me |
| Me₂CClCH₂ | Cl | O | H | CH₂CH₂OPh |
| Me₂CClCH₂ | Br | O | H | CH₂CH₂OPh |
| Me₂CClCH₂ | Cl | O | H | CH₂CHMeOPh |
| Me₂CClCH₂ | Cl | O | H | CH₂CH₂OC₆H₄-4-Cl |
| Me₂CClCH₂ | Cl | O | H | CH₂CH₂OC₆H₄-4-I |
| Me₂CClCH₂ | Cl | O | H | CH₂CH₂O-Q17 |
| Me₂CClCH₂ | Cl | O | H | CH₂CHMeO-Q17 |
| Me₂CClCH₂ | Cl | O | H | CH₂CH₂O-Q26 |
| Me₂CClCH₂ | Cl | O | H | CH₂CH₂O-Q28 |
| Me₂CClCH₂ | Cl | O | H | CH₂CH₂O-Q27 |
| Me₂CClCH₂ | Cl | O | H | CH₂CH₂O-Q24 |
| Me₂CClCH₂ | Cl | O | H | CH₂CH₂O-Q30 |
| Me₂CClCH₂ | Cl | O | H | CH₂CH₂O-Q48 |
| Me₂CClCH₂ | Cl | O | H | CH₂CH₂O-Q52 |
| Me₂CClCH₂ | Cl | O | H | CH₂CH₂O-Q23 |
| Me₂CClCH₂ | Cl | O | H | CH₂CH₂O-Q18 |
| Me₂CClCH₂ | Cl | O | H | CH₂CHMeO-Q28 |
| Me₂CClCH₂ | Cl | O | H | CH₂CHMeO-Q27 |
| Me₂CClCH₂ | Cl | O | H | CH₂CH₂O-Q17-5-Cl |
| Me₂CClCH₂ | Cl | S | H | CH₂CH₂O-Q17-5-Cl |
| Me₂CClCH₂ | Cl | O | H | CH₂CH₂O-Q38 |
| Me₂CClCH₂ | Cl | O | H | CH₂CH₂O-Q45 |
| Me₂CClCH₂ | Cl | O | H | CH₂CH₂O-Q54 |
| Me₂CClCH₂ | Cl | O | H | CH₂CH₂O-Q51 |
| Me₂CClCH₂ | Cl | O | H | CH₂CH₂O-Q49 |
| Me₂CClCH₂ | Cl | O | H | CH₂CH₂NH—Ph |
| Me₂CClCH₂ | Cl | O | H | CH₂CH₂N(Me)—Ph |
| Me₂CClCH₂ | Cl | O | H | CH₂CH₂S—Ph |
| Me₂CClCH₂ | Cl | O | H | CH₂CH₂NH-Q17 |
| Me₂CClCH₂ | Cl | O | H | CH(Me)CH₂O—Ph |
| Me₂CClCH₂ | Cl | O | H | (CH₂)₃CO₂Me |

TABLE 3-continued

In compounds of the formula:

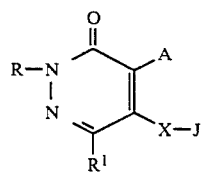

| R | A | X | R$^1$ | J |
|---|---|---|---|---|
| Me$_2$CClCH$_2$ | Cl | O | H | (CH$_2$)$_3$CO$_2$Et |
| Me$_2$CClCH$_2$ | Cl | O | H | CH$_2$CHMeCH$_2$CO$_2$Et |
| Me$_2$CClCH$_2$ | Cl | O | H | CH$_2$CH=CHCO$_2$Et |
| Me$_2$CClCH$_2$ | Cl | O | H | CH$_2$CMe=CHCO$_2$Et |
| Me$_2$CClCH$_2$ | Cl | O | H | CH$_2$CH$_2$OC(O)Et |
| Me$_2$CClCH$_2$ | Cl | O | H | CH$_2$CH$_2$OC(O)Pr |
| Me$_2$CClCH$_2$ | Cl | O | H | CH$_2$CH$_2$NHC(O)Pr |
| Me$_2$CClCH$_2$ | Cl | O | H | CH$_2$CH$_2$NHC(O)Bu—S |
| Me$_2$CClCH$_2$ | Cl | O | H | CH$_2$CH$_2$NHCO$_2$Et |
| Me$_2$CClCH$_2$ | Cl | O | H | (CH$_2$)$_3$C≡C—Cl |
| Me$_2$CClCH$_2$ | Cl | O | H | (CH$_2$)$_3$C≡C—Br |
| Me$_2$CClCH$_2$ | Cl | O | H | (CH$_2$)$_3$C≡C—I |
| Me$_2$CClCH$_2$ | Cl | O | H | (CH$_2$)$_3$C≡CCH$_2$OMe |
| Me$_2$CClCH$_2$ | Cl | O | H | CH$_2$CH=NOEt |
| Me$_2$CClCH$_2$ | Cl | O | H | CH$_2$CH=NOPr |
| Me$_2$CClCH$_2$ | Cl | O | H | CH$_2$CH=NOBu |
| Me$_2$CClCH$_2$ | Cl | O | H | CH$_2$CH=NOPr—i |
| Me$_2$CClCH$_2$ | Cl | O | H | CH$_2$CMe=NOPr |
| Me$_2$CClCH$_2$ | Cl | O | H | CH$_2$CH$_2$O—N=CHMe |
| Me$_2$CClCH$_2$ | Cl | O | H | CH$_2$CH$_2$O—N=CHEt |
| Me$_2$CBrCH$_2$ | Cl | O | H | CH$_2$CH$_2$OPh |
| Me$_2$CBrCH$_2$ | Cl | O | H | CH$_2$CH$_2$O-Q17 |
| Me$_2$CBrCH$_2$ | Cl | O | H | CH$_2$CH=NOPr |
| ClCH$_2$CCl(Me)CH$_2$ | Cl | O | H | CH$_2$CH$_2$OPh |
| ClCH$_2$CCl(Me)CH$_2$ | Cl | O | H | CH$_2$CH$_2$O-Q17 |
| ClCH$_2$CCl(Me)CH$_2$ | Cl | O | H | CH$_2$CH$_2$O-Q28 |
| ClCH$_2$CCl(Me)CH$_2$ | Cl | O | H | CH$_2$CHMePh |
| ClCH$_2$CCl(Me)CH$_2$ | Cl | O | H | CH$_2$CH$_2$O—N=CHMe |
| ClCH$_2$CCl(Me)CH$_2$ | Cl | O | H | CH$_2$CH=NOPr |
| ClCH$_2$CCl(Me)CH$_2$ | Br | O | H | CH$_2$CH=NOPr |
| ClCH$_2$CCl(Me)CH$_2$ | Me | O | H | CH$_2$CH$_2$O-Q17 |
| ClCH$_2$CCl(Me)CH$_2$ | Cl | S | H | CH$_2$CH$_2$OPh |
| ClCH$_2$CBr(Me)CH$_2$ | Cl | O | H | CH$_2$CH$_2$OPh |
| ClCH$_2$CBr(Me)CH$_2$ | Cl | O | H | CH$_2$CH$_2$O-Q17 |
| ClCH$_2$CBr(Me)CH$_2$ | Cl | O | H | CH$_2$CH=NOPr |
| EtCCl(Me)CH$_2$ | Cl | O | H | CH$_2$CH$_2$OPh |
| EtCCl(Me)CH$_2$ | Cl | O | H | CH$_2$CH$_2$O-Q17 |
| EtCCl(Me)CH$_2$ | Cl | O | H | CH$_2$CHMeOPh |
| EtCCl(Me)CH$_2$ | Cl | O | H | CH$_2$CH$_2$OC(O)Et |
| EtCCl(Me)CH$_2$ | Cl | O | H | CH$_2$CH$_2$ON=CHMe |
| EtCCl(Me)CH$_2$ | Cl | O | H | CH$_2$CH=NOPr |
| PrCCl(Me)CH$_2$ | Cl | O | H | CH$_2$CH$_2$OPh |
| PrCCl(Me)CH$_2$ | Cl | O | H | CH$_2$CH$_2$O-Q17 |
| PrCCl(Me)CH$_2$ | Cl | O | H | CH$_2$CH$_2$O-Q28 |
| PrCCl(Me)CH$_2$ | Cl | O | H | CH$_2$CH$_2$OC(O)Et |
| PrCCl(Me)CH$_2$ | Cl | O | H | CH$_2$CH=NOPr |
| PrCCl(Me)CH$_2$ | Cl | O | H | CH$_2$CH=NOEt |
| PrCCl(Me)CH$_2$ | Cl | O | H | CH$_2$CH(Me)CH$_2$CO$_2$Et |
| PrCCl(Me)CH$_2$ | Cl | O | H | CH$_2$CH$_2$ON=CHMe |
| PrCCl(Me)CH$_2$ | Cl | O | H | (CH$_2$)$_3$C≡C—Cl |
| PrCCl(Me)CH$_2$ | Cl | O | H | CH$_2$CH$_2$O-Q30 |
| PrCCl(Me)CH$_2$ | Cl | O | H | CH$_2$CH$_2$O-Q27 |
| PrCCl(Me)CH$_2$ | Cl | O | H | CH$_2$CH$_2$O-Q24 |
| PrCBr(Me)CH$_2$ | Cl | O | H | CH$_2$CH$_2$OPh |
| PrCBr(Me)CH$_2$ | Cl | O | H | CH$_2$CH$_2$O-Q17 |
| PrCBr(Me)CH$_2$ | Cl | O | H | CH$_2$CH=N—OPr |
| BuCCl(Me)CH$_2$ | Cl | O | H | CH$_2$CH=N—OPr |
| BuCCl(Me)CH$_2$ | Cl | O | H | CH$_2$CH$_2$OPh |
| MeOCH$_2$CCl(Me)CH$_2$ | Cl | O | H | CH$_2$CH$_2$OPh |
| MeOCH$_2$CCl(Me)CH$_2$ | Cl | O | H | CH$_2$CH=N—OPr |
| MeOCH$_2$CCl(Me)CH$_2$ | Cl | O | H | CH$_2$CH$_2$O-Q17 |
| EtOCH$_2$CCl(Me)CH$_2$ | Cl | O | H | CH$_2$CH$_2$OPh |
| EtOCH$_2$CCl(Me)CH$_2$ | Cl | O | H | CH$_2$CH=N—OPr |
| EtOCH$_2$CCl(Me)CH$_2$ | Cl | O | H | CH$_2$CH$_2$OC(O)Et |
| MeSCH$_2$CCl(Me)CH$_2$ | Cl | O | H | CH$_2$CH$_2$OPh |
| MeSCH$_2$CCl(Me)CH$_2$ | Cl | O | H | CH$_2$CH$_2$C≡CCH$_2$OMe |
| EtSCH$_2$CCl(Me)CH$_2$ | Cl | O | H | CH$_2$CH$_2$NHC(O)Pr |
| EtSCH$_2$CCl(Me)CH$_2$ | Cl | O | H | CH$_2$CH$_2$OPh |
| Q10-2-Cl | Cl | O | H | CH$_2$CH$_2$OPh |
| Q10-2-Cl | Cl | O | H | CH$_2$CH$_2$O-Q17 |

TABLE 3-continued

In compounds of the formula:

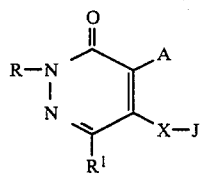

| R | A | X | R¹ | J |
|---|---|---|---|---|
| Q10-2-Cl | Cl | O | H | CH$_2$CH=NOPr |
| Q3-2-Cl | Cl | O | H | CH$_2$CH=NOPr |
| Q3-2-Cl | Cl | O | H | CH$_2$CH$_2$OPh |
| Q3-2-Cl | Cl | O | H | CH$_2$CH$_2$ON=CHMe |
| Q4-2-Cl | Cl | O | H | CH$_2$CH$_2$OPh |
| Q4-2-Cl | Cl | O | H | CH$_2$CH=NOPr |
| Q7-2-Cl | Cl | O | H | CH$_2$CHMeOPh |
| Q7-2-Cl | Cl | O | H | CH$_2$CH=NOPr |
| Q9-2-Cl | Cl | O | H | CH$_2$CH$_2$OPh |
| Q9-2-Cl | Cl | O | H | CH$_2$CH$_2$O-Q17 |
| Q9-2-Cl | Br | O | H | CH$_2$CH$_2$OPh |
| MeCCl(OMe) | Cl | O | H | CH$_2$CH$_2$OPh |
| MeCCl(OMe) | Cl | O | H | CH$_2$CH=NOPr |
| MeCCl(OMe) | Me | S | H | CH$_2$CHMeCH$_2$CO$_2$Et |
| MeCCl(OEt) | Cl | O | H | CH$_2$CH$_2$OPh |
| MeCCl(OEt) | Cl | O | H | CH$_2$CH$_2$OC(O)Pr-i |
| Cl$_2$C=CH | Cl | O | H | CH$_2$CH$_2$OPh |
| Cl$_2$C=CH | Cl | O | H | CH$_2$CH$_2$O-Q17 |
| Cl$_2$C=CH | Br | O | H | CH$_2$CH$_2$OPh |
| MeCCl=CH | Cl | O | H | CH$_2$CH$_2$OPh |
| MeCCl=CH | Cl | O | H | CH$_2$CH=NOPr |
| MeCCl=CH | Cl | S | H | CH$_2$CH$_2$ON=CHEt |
| EtCCl=CH | Cl | O | H | CH$_2$CH$_2$OPh |
| EtCCl=CH | Cl | O | H | CH$_2$CH$_2$O-Q17 |
| PrCCl=CH | Cl | O | H | CH$_2$CH$_2$OPh |
| PrCCl=CH | Cl | O | H | CH$_2$CH=NOPr |
| PrCCl=CH | Br | O | H | CH$_2$CH=NOPr |
| PrCCl=CH | Cl | O | H | CH$_2$CH$_2$O-Q17 |
| Me$_2$C=CH | Cl | O | H | CH$_2$CH$_2$O-Q17 |
| Me$_2$C=CH | Cl | O | H | CH$_2$CH$_2$O-Q17 |
| Me$_2$C=CH | Cl | O | H | CH$_2$CH=NOPr |
| Me$_2$C=CH | Cl | O | H | CH$_2$CH$_2$NHCO$_2$Et |
| Me$_2$C=CH | Cl | O | H | CH$_2$CH$_2$ON=CHMe |
| MeC(Et)=CH | Cl | O | H | CH$_2$CH$_2$OPh |
| MeC(Et)=CH | Cl | O | H | CH$_2$CH$_2$O-Q17 |
| MeC(Et)=CH | Cl | O | H | CH$_2$CH=NOPr |
| MeC(Pr)=CH | Cl | O | H | CH$_2$CH$_2$OPh |
| MeC(Pr)=CH | Cl | O | H | CH$_2$CH=NOPr |
| MeC(Pr)=CH | Br | O | H | CH$_2$CH$_2$O-Q17 |
| CF$_3$CCl=CH | Cl | O | H | CH$_2$CH$_2$OPh |
| CF$_3$CCl=CH | Cl | O | H | CH$_2$CH$_2$O-Q17 |
| CF$_3$CCl=CH | Cl | O | H | CH$_2$CH=NOPr |
| CH$_2$=C(Me)CH$_2$ | Cl | O | H | CH$_2$CH$_2$OPh |
| CH$_2$=C(Me)CH$_2$ | Br | O | H | CH$_2$CH$_2$CHMeC≡C—Br |
| CH$_2$=C(Me)CH$_2$ | I | O | H | CH$_2$CH$_2$O-Q17 |
| CH$_2$=C(Et)CH$_2$ | Cl | O | H | CH$_2$CH$_2$OPh |
| CH$_2$=C(Et)CH$_2$ | SO$_2$Me | O | H | CH$_2$CH$_2$NHC(O)Et |
| CH$_2$=C(Pr)CH$_2$ | Cl | O | H | CH$_2$CH$_2$OPh |
| CH$_2$=C(Pr)CH$_2$ | Cl | O | H | CH$_2$CH=NOPr |
| MeCH=C(Me)CH$_2$ | Cl | O | H | CH$_2$CH$_2$OPh |
| MeCH=C(Me)CH$_2$ | Cl | O | H | CH$_2$CH=NOPr |
| MeCH=C(Me)CH$_2$ | H | O | H | CH$_2$CH$_2$OPh |
| EtCH=C(Me)CH$_2$ | Cl | O | H | CH$_2$CH$_2$OPh |
| EtCH=C(Me)CH$_2$ | Cl | O | H | CH$_2$CH$_2$O-Q17 |
| EtCH=C(Me)CH$_2$ | Cl | O | H | CH$_2$CH=NOPr |
| PrCH=C(Me)CH$_2$ | Cl | O | H | CH$_2$CH$_2$OPh |
| PrCH=C(Me)CH$_2$ | Br | O | H | CH$_2$CH$_2$N(Et)-Q17 |
| CH$_2$=CHC(Me)$_2$CH$_2$ | Cl | O | H | CH$_2$CH$_2$OPh |
| CH$_2$=CHC(Me)$_2$CH$_2$ | Cl | O | H | CH$_2$CH$_2$O-Q17 |
| CH$_2$=CHC(Me)$_2$CH$_2$ | OMe | O | H | CH$_2$CHMeOPh |
| MeCH=CHC(Me)$_2$CH$_2$ | Cl | O | H | CH$_2$CHMeOPh |
| MeCH=CHC(Me)$_2$CH$_2$ | Cl | O | H | CH$_2$CH$_2$OPh |
| HC≡CC(Me)$_2$CH$_2$ | Cl | O | H | CH$_2$CH$_2$O-Q17 |
| HC≡CC(Me)$_2$CH$_2$ | Cl | O | H | CH$_2$CH$_2$OPh |
| HC≡CC(Me)$_2$CH$_2$ | OEt | O | H | (CH$_2$)$_3$C≡C—I |
| MeC≡CC(Me)$_2$CH$_2$ | Cl | O | H | CH$_2$CH$_2$OPh |
| MeC≡CC(Me)$_2$CH$_2$ | Cl | O | H | CH$_2$CHMeOPh |
| CH$_2$=CHCH$_2$C(Me)$_2$CH$_2$ | Cl | O | H | CH$_2$CH$_2$O-Q17 |
| CH$_2$=CHCH$_2$C(Me)$_2$CH$_2$ | Cl | O | H | CH$_2$CH=NOPr |
| HC≡CCH$_2$C(Me)$_2$CH$_2$ | Cl | O | H | CH$_2$CH$_2$OPh |

TABLE 3-continued

In compounds of the formula:

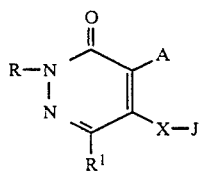

| R | A | X | R¹ | J |
|---|---|---|---|---|
| HC≡CCH₂C(Me)₂CH₂ | Cl | O | H | CH₂CH₂ON=CHMe |
| Me₂C(OMe)CH₂ | Cl | O | H | CH₂CH₂SPh |
| Me₂C(OMe)CH₂ | Cl | O | H | CH₂CH₂OPh |
| Me₂C(OMe)CH₂ | Cl | O | H | CH₂CH₂O-Q17 |
| Me₂C(OMe)CH₂ | Br | O | H | CH₂CH=NOPr |
| Me₂C(OEt)CH₂ | Cl | O | H | CH₂CH₂ON=CHMe |
| Me₂C(OEt)CH₂ | Cl | O | H | CH₂CH₂OPh |
| Me₂C(OEt)CH₂ | Cl | O | H | CH₂CHMeOPh |
| MeC(Et)(OMe)CH₂ | Cl | O | H | CH₂CH₂NHCO₂Bu |
| MeC(Et)(OMe)CH₂ | Cl | O | H | CH₂CH₂NHC(O)Et |
| MeC(Pr)(OMe)CH₂ | Cl | O | H | CH₂CH₂OPh |
| MeC(Pr)(OMe)CH₂ | Cl | O | H | CH₂CH₂CHEt—Ph |
| MeOCH₂C(Me)₂CH₂ | Cl | O | H | CH₂CH₂OPh |
| MeOCH₂C(Me)₂CH₂ | Cl | O | H | CH₂CHMeOPh |
| MeOCH₂C(Me)₂CH₂ | Cl | O | H | CH₂CH₂O-Q17 |
| MeOCH₂C(Me)₂CH₂ | Br | O | H | CH₂CH₂OPh |
| EtOCH₂C(Me)₂CH₂ | Cl | O | H | CH₂CH₂OPh |
| EtOCH₂C(Me)₂CH₂ | Cl | O | H | CH₂CH=NOPr |
| EtOCH₂C(Me)₂CH₂ | Cl | O | H | CH₂CH₂O-Q17 |
| EtOCH₂C(Me)₂CH₂ | Cl | S | H | CH₂CH₂NHPh |
| MeOCH₂CH₂C(Me)₂CH₂ | Cl | O | H | CH₂CH₂OPh |
| MeOCH₂CH₂C(Me)₂CH₂ | Cl | O | H | CH₂CH₂O-Q17 |
| MeOCH₂CH₂C(Me)₂CH₂ | Br | O | H | (CH₂)₃C≡C—Cl |
| MeOCH₂CH₂CCl(Me)CH₂ | Cl | O | H | CH₂CH₂OPh |
| MeOCH₂CH₂CCl(Me)CH₂ | Cl | O | H | CH₂CH₂O-Q17 |
| MeOCH₂CH₂CCl(Me)CH₂ | Cl | O | H | CH₂CH=NOPr |
| EtOCH₂CH₂C(Me)₂CH₂ | Cl | O | H | CH₂CH₂OPh |
| EtOCH₂CH₂C(Me)₂CH₂ | Cl | O | H | CH₂CH₂O-Q28 |
| MeO(CH₂)₃C(Me)₂CH₂ | Cl | O | H | CH₂CH=NOPr |
| MeO(CH₂)₃C(Me)₂CH₂ | Cl | O | H | CH₂CH₂OPh |

Q1 to Q56 in the Tables 1, 2 and 3 are groups represented by the folowing structural formula:

 Q1

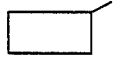 Q2

 Q3

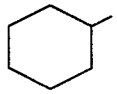 Q4

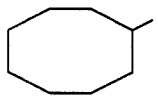 Q5

-continued

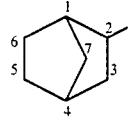 Q6

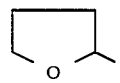 Q7

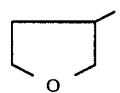 Q8

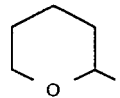 Q9

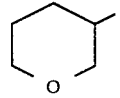 Q10

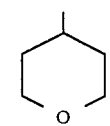 Q11

-continued
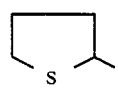 Q12
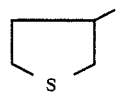 Q13
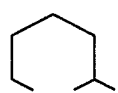 Q14
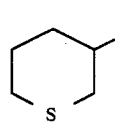 Q15
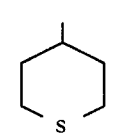 Q16
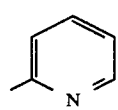 Q17
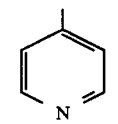 Q18
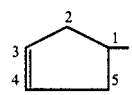 Q19
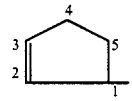 Q20
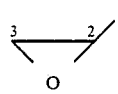 Q21
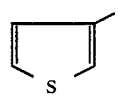 Q22
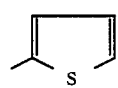 Q23
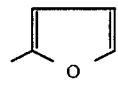 Q24
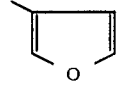 Q25
-continued
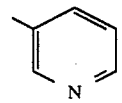 Q26
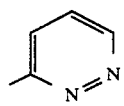 Q27
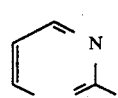 Q28
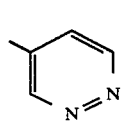 Q29
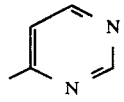 Q30
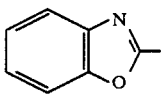 Q31
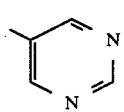 Q32
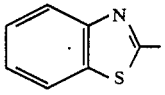 Q33
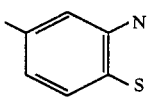 Q34
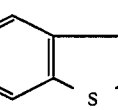 Q35
 Q36
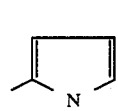 Q37
 Q38

The preparations of the compounds of the present invention are described in detail by way of the following examples which are not to restrict the invention.

PREPARATION EXAMPLE 1

Synthesis of 5-(4-t-butylbenzylthio)-4-chloro-2-[(2,2-dichloro-1,1-dimethyl)-ethyl]-3(2H)-pyridazinone (Compound No. 2)

In 10 ml of methanol were dissolved 0.73 g of 4,5-dichloro-2-[(2,2-dichloro-1,1-dimethyl)-ethyl]-3(2H)-pyridazinone and 0.45 g of 4-t-butylbenzyl-mercaptan. The resulting solution was suspended with 0.27 g of sodium carbonate and then stirred for 3 hours at room temperature. The solution was poured into ice water and then filtered off. The crystals thus obtained were recrystallized from benzene-hexane to give 0.8 g of the intended compound.

melting point (m.p.): 162°–163° C.

PREPARATION EXAMPLE 2

Synthesis of 4-bromo-5-(4-chloro-benzyloxyl)-2-[(2,3-dichloro-2-methyl)-propyl]-3(2H)-pyridazinone (Compound No. 12)

In 10 ml of N,N-dimethylformamide were dissolved 1.90 g of 4,5-dibromo-2-[(2,3-dichloro-2-methyl)-propyl]-3(2H)-pyridazinone and 0.71 g of 4-chlorobenzyl alcohol. The solution was suspended in 0.33 g of powdery potassium hydroxide. The reaction mixture was stirred for one night at room temperature. The resulting solution was poured into ice water and extracted with benzene. The extract was washed with saturated saline and then with water and freed of solvent by distillation under reduced pressure. The oil thus obtained was separated and purified by means of column chromatography (on silica gel, eluting with chloroform) to give 1.10 g of the intended compound.

m.p.: 112°–114° C.

PREPARATION EXAMPLE 3

Synthesis of 2-(3'-bromopropyl)-4-chloro-5-(4'-chlorobenzyloxy)-3(2H)-pyridazinone (Compound No. 19)

To a mixed solvent of 150 ml of water and 150 ml of ethanol was added 22.3 g of 4,5-dichloro-2-(3'-hydroxypropyl)-3(2H)-pyridazinone (0.1 mol) and 19.6 g of potassium hydroxide (0.35 mol) and then heated under reflux for about 10 hours. After reaction, ethanol was removed under reduced pressure and added with water to filter off the insoluble matters. The filtrate was converted into acidity by diluted hydrochloric acid and the crystals produced were filtered off. The crystals thus obtained were washed with water and dried to give 14.5 g of 4-chloro-5-hydroxy-2-(3'-hydroxypropyl)-3(2H)-pyridazinone.

To 150 ml of N,N-dimethylformamide were added 10.2 g of 4-chloro-5-hydroxy-2-(3'-hydroxypropyl)-3(2H)-pyridazinone (0.05 mol), 8.4 g of 4-chlorobenzyl chloride (0.052 mol) and 10.4 g of anhydrous potassium carbonate (0.075 mol) and heated for about 3 hours at 100° C. to 120° C. After reaction, the mixture solution was poured into water and extracted with ethyl acetate. The resulting solution was washed with water and then with aqueous solution of 5% sodium hydroxide and further with saturated saline. The solution was dried over anhydrous sodium sulfate and the solvent was distilled off under reduced pressure. The solid product thus obtained was washed with n-hexane and dried to obtain 12.3 g of 4-chloro-5-(4'-chlorobenzyloxy)-2-(3'-hydroxypropyl)-3(2H)-pyridazinone.

To 170 ml of chloroform were added 9.9 g of 4-chloro-5-(4'-chlorobenzyloxy)-2-(3'-hydroxypropyl)-3(2H)-pyridazinone (0.03 mol) and slowly added 9.4 g of thionyl bromide (0.045 mol) under stirring for about 2 hours at −5° to 5° C. After reaction, the resulting solution was added little by little with water and the chloroform layer was separated. The layer was washed with water and then with aqueous solution of 5% sodium hydrogen carbonate, and further washed with saturated saline and dried over anhydrous sodium sulfate and freed of solvent by distillation under reduced pressure. The solid product thus obtained was recrystallized from a mixed solvent of n-hexane-benzene to give 5.2 g of 2-(3'-bromopropyl)-4-chloro-5-(4'-chlorobenzyloxy)-3(2H)-pyridazinone.

m.p.: 83°–87° C.

PREPARATION EXAMPLE 4

Synthesis of 4-chloro-2-[(2-chloro-2-methyl)-pentyl]-5-(4-iodobenzyloxy)-3(2H)-pyridazinone (Compound No. 33)

The procedures in Preparation Example 2 were repeated by using 1.42 g of 4,5-dichloro-2-[(2-chloro-2-methyl)-pentyl]-3(2H)-pyridazinone and 1.17 g of 4-iodobenzyl alcohol to give 1.72 g of the intended compound.

m.p.: 114°–115° C.

PREPARATION EXAMPLE 5

Synthesis of 4-chloro-2-[(2,3-dichloro-2-methyl-prpyl]-5-[(2-iodo-5-pyridyl)-methoxy]-3(2H)-pyridazinone (Compound No. 202)

The procedures in Preparation Example 2 were repeated by using 1.45 g of 4,5-dichloro-2-[(2,3-dichloro-2-methyl)-propyl]-3(2H)-pyridazinone and 1.18 g of 2-iodo-5-pyridinemethanol to give 1.33 g of the intended compound.

m.p.: 117°–120° C.

PREPARATION EXAMPLE 6

Synthesis of 4-chloro-2-(2-chloro-2-methylpropyl)-5-(2-phenoxy-ethoxy)-3(2H)-pyridazinone (Compound No. 326)

In 10 ml of N,N-dimethylformamide were dissolved 1.85 g of 2-(2-chloro-2-methylpropyl)-4,5-dichloro-3(2H)-pyridazinone and 1.00 g of 2-phenoxy ethanol, and thereto was added 0.48 g of powdery potassium hydroxide. The mixture solution was stirred for one night at room temperature. Then, the procedures in Preparation Example 2 were repeated to give 1.9 g of the intended compound.

m.p.: 82°–83° C.

PREPARATION EXAMPLE 7

Synthesis of 5-(4-t-buthyl-α-methylbenzyloxy)-4-chloro-2-vinyl-3(2H)-pyridazinone (Compound No. 129)

In 60 ml of N,N-dimethylformamide were dissolved 2.7 g of 2-(2-bromoethyl)-4,5-dichloro-3(2H)-pyridazinone and 1.8 g of 4-t-buthyl-α-methyl-benzyl alcohol, and thereto were added 1.4 g of powdery potassium hydroxide. The solution was stirred for one night at room temperature. After reaction, the mixture solution was poured into water and extracted with benzene. The benzene layer was washed with water and dried over anhydrous sodium sulfate and freed of solvent by distillation under reduced pressure. The residual viscous liquid was separated by means of column chromatography (on silica gel, eluting with benzene-ethyl acetate) to give 2.2 g of the intended compound. (viscous liquid)

$^1$H-NMR (CDCl$_3$, δ, ppm)

1.37 (9H, s), 1.80 (3H, d, J=6 Hz), 4.95 (1H, d, J=9 Hz), 5.66 (1H, q, J=6 Hz), 5.67 (1H, d, J=15 Hz), 7.17–7.53 (4H, m), 7.68 (1H, d, d, J=9 Hz, 15 Hz), 7.78 (1H, s)

PREPARATION EXAMPLE 8

Synthesis of 4-chloro-2-(2-chloro-2-methylpentyl)-5-(4-ethylbenzyloxy)-3(2H)-pyridazinone (Compound No. 85)

In 20 ml of N,N-dimethylformamide were added 1.2 g of 2-(2-chloro-2-methylpentyl)-4,5-dichloro-3(2H)-pyridazinone and 0.64 g of 4-ethylbenzyl alcohol, and thereto was added 0.31 g of powdery potassium hydroxide under ice-cooling and stirred for one day at room temperature. Then, the procedures in Preparation Example 2 were repeated to give 600 mg of the intended compound.

m.p.: 81°–83° C.

PREPARATION EXAMPLE 9

Synthesis of 4-chloro-2-(2-chloro-2-methylpentyl)-5-(4-trifluoromethylbenzyloxy)-3(2H)-pyridazinone (Compound No. 56)

In 20 ml of N,N-dimethylformamide were dissolved 1.2 g of 2-(2-chloro-2-methylpentyl)-4,5-dichloro-3(2H)-pyridazinone and 0.78 g of 4-trifluoromethylbenzyl alcohol, and thereto were added 1.46 g of anhydrous potassium carbonate. The mixture solution was stirred for 8 hours at 50° C. Then, the procedures in Preparation Example 2 were repeated to give 1.0 g of the intended compound.

m.p.: 105°–106° C.

PREPARATION EXAMPLE 10

Synthesis of 4-chloro-2-(2-chloro-2-methylpropyl)-5-[(2-iodo-5-pyridyl)-methoxy]-3(2H)-pyridazinone and 4-chloro-5-[(2-iodo-5-pyridyl)-methoxy]-2-(2-methyl-1-propenyl)-3(2H)-pyridazinone (Compound Nos. 237 and 255)

In 10 ml of N,N-dimethylformamide were dissolved 1.4 g of 2-(2-chloro-2-methylpropyl)-4,5-dichloro-3(2H)-pyridazinone and 1.29 g of 2-iodo-5-pyridyl methanol, and thereto was added 0.33 g of powdery potassium hydroxide under ice-cooling. The mixture solution was stirred for one day at room temperature. Then, the procedures in Preparation Example 2 were repeated to give 0.74 g of 4-chloro-2-(2-chloro-2-methylpropyl)-5-[(2-iodo-5-pyridyl)methoxy]-3(2H)-pyridazinone (m.p.: 119°–123° C.) and 0.24 g of 4-chloro-5-[(2-iodo-5-pyridyl)-methoxy]-2-(2-methyl-1-propenyl)-3(2H)-pyridazinone (m.p.: 141°–142° C.).

PREPARATION EXAMPLE 11

Synthesis of 2-(2-chloro-2-methylpropyl)-5-(4-iodobenzyloxy)-4-methyl-3(2H)-pyridazinone (Compound No. 167)

In 5 ml of N,N-dimethylformamide were dissolved 0.33 g of 5-chloro-2-(2-chloro-2-methylpropyl)-4-methyl-3(2H)-pyridazinone and 0.33 g of 4-iodobenzyl alcohol, and thereto was added 0.1 g of powdery potassium hydroxide under ice-cooling. Then, the procedures in Preparation Example 2 were repeated to give 0.3 g of the intended compound.
m.p.: 121°–123° C.

PREPARATION EXAMPLE 12

Synthesis of 4,5-dichloro-2-(3-chloro-tetrahydro-2-pyranyl)-3(2H)-pyridazinone

In 20 ml of methylene chloride were dissolved 4 g of 2,4,5-trichloro-3(2H)-pyridazinone, and thereto dropwise added 2.5 g of 2,3-dihydro-pyran under ice-cooling. The solution was stirred for 30 minutes and the by-produced 4,5-dichloro-3(2H)-pyridazinone was filtered off. The filtrate was distilled off under reduced pressure. The oil thus obtained was separated by means of column chromatography (on silica gel, eluting with benzene) to give 1.5 g of trans-form as the first fraction (m.p.: 136°–137° C.) and 1.3 g of cis-form as the second fraction (m.p.: 109°–110° C.).

$^1$H-NMR (CDCl$_3$, δ, TMS)
Trans-form 1.50–2.20 (m, 4H), 3.50–4.60 (m, 3H), 5.86 (d, 1H, 10 Hz), 7.77 (s, 1H)
Cis-form 1.90–2.50 (m, 4H), 3.50–4.60 (m, 3H), 6.05 (d, 1H, 3 Hz), 7.83 (s, 1H)

PREPARATION EXAMPLE 13

Synthesis of 4,5-dichloro-2-(2,3-dichloro-2-propenyl)-3(2H)-pyridazinone

To a mixture of 10.8 g of 4,5-dichloro-3(2H)-pyridazinone and 9.5 g of anhydrous potassium carbonate were added 65 ml of N,N-dimethylformamide and stirred for 10 minutes at room temperature. Then, 10.0 g of 1,2,3-trichloro-1-propene (mixture of E-from and Z-form) were added to the mixture solution and were stirred for 6 hours at 40° C. The solution was poured into a large quantity of water and extracted with benzene, and freed of solvent by distillation under reduced pressure to give 6.0 g of the intended compound (mixture of E-form and Z-form). The compound thus obtained was separated into isomer (m.p.: 93.7°–94.6° C., 112.8°–114.8° C.) by means of column chromatography (on silica gel, eluting with benzene).

$^1$H-NMR (CDCl$_3$, δ, TMS)
Isomer 1 (m.p.: 93.7°–94.6° C.): 5.15 (s, 2H), 6.47 (s, 1H), 7.84 (s, 1H)
Isomer 2 (m.p.: 112.8°–114.8° C.). 5.00 (s, 2H), 6.70 (s, 1H), 7.84 (s, 1H)

PREPARATION EXAMPLE 14

Synthesis of 4,5-dichloro-2-(2-methyl-2-propenyl)-3(2H)-pyridazinone

To 50 ml of N,N-dimethylformamide were suspended 10 g of 4,5-dichloro-3(2H)-pyridazinone, 27 g of 3-chloro-2-methylpropene and 8.4 g of potassium carbonate. The mixtured solution was stirred for 5 hours at 40° C. Then, the procedures in Preparation Example 2 were repeated to give 4.9 g of the intended compound.
m.p.: 52°–54° C.

PREPARATION EXAMPLE 15

Synthesis of 2-(2-chloro-2-methyl-propyl)-4,5-dichloro-3(2H)-pyridazinone

In 100 ml of carbon tetrachloride were dissolved 5 g of 4,5-dichloro-2(2-methyl-2-propenyl)-3(2H)-pyridazinone and 0.1 g of trifluoromethyl ammonium chloride, and thereto were added 30 ml of concentrated hydrochloric acid. The mixture solution was stirred for 3 days at room temperature. The organic layer was separated and washed with water, and dried over anhydrous sodium sulfate and freed of solvent by distillation under reduced pressure to give 4.7 g of the intended compound.
m.p.: 61°–66° C.

Physical properties of compounds prepared according to any one of Preparation Examples 1 to 11 are shown in Tables 4, 5 and 6. In the Tables, Me represents methyl group, Et represents ethyl group, Pr represents propyl group, Bu represents butyl group, Pen represents pentyl group, Hex represents hexyl group, Ph represents unsubstituted phenyl group, t represents tertiary, s represents secondary, i represents iso and c represents cyclo.

The number of compounds listed in Tables 4, 5 and 6 will be referred to in the above Preparation Examples, and Formulation Examples and Test Examples later described.

TABLE 4

In Compounds of the formula:

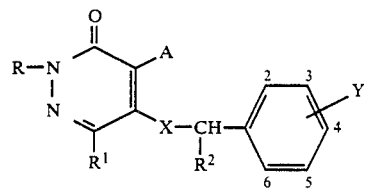

| No. | R | A | X | R$^1$ | R$^2$ | Y | m.p. (°C.) |
|---|---|---|---|---|---|---|---|
| 1 | Cl$_2$CHC(Me)$_2$ | Cl | O | H | H | 4-Cl | 108–109 |
| 2 | Cl$_2$CHC(Me)$_2$ | Cl | S | H | H | 4-Bu-t | 162–163 |
| 3 | ClCH$_2$CHClCH$_2$ | Cl | O | H | H | 4-Cl | 123–125 |
| 4 | ClCH$_2$CHClCH$_2$ | Cl | O | H | H | 2,4-Cl$_2$ | 96–98 |

TABLE 4-continued

In Compounds of the formula:

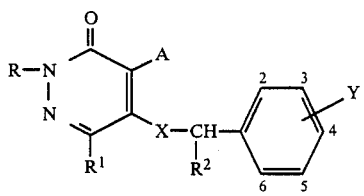

| No. | R | A | X | R$^1$ | R$^2$ | Y | m.p. (°C.) |
|---|---|---|---|---|---|---|---|
| 5 | ClCH$_2$CHClCH$_2$ | Cl | S | H | H | 4-Cl | 120–124 |
| 6 | ClCH$_2$CHClCH$_2$ | Cl | S | H | H | 4-Bu-t | 135–139 |
| 7 | Me$_2$CClCHCl | Cl | O | H | H | 4-Cl | 124–125 |
| 8 | Me$_2$CClCHCl | Cl | S | H | H | 4-Bu-t | 183–184 |
| 9 | ClCH$_2$CCl(Me)CH$_2$ | Cl | O | H | H | 4-Cl | 115–118 |
| 10 | ClCH$_2$CCl(Me)CH$_2$ | Cl | O | H | H | 4-I | 124–127 |
| 11 | ClCH$_2$CCl(Me)CH$_2$ | Cl | O | H | H | 2,4-Cl$_2$ | 111–117 |
| 12 | ClCH$_2$CCl(Me)CH$_2$ | Br | O | H | H | 4-Cl | 112–114 |
| 13 | ClCH$_2$CCl(Me)CH$_2$ | Br | O | H | H | 2,4-Cl$_2$ | 107–113 |
| 14 | ClCH$_2$CCl(Me)CH$_2$ | Cl | S | H | H | 4-Bu-t | 106–109 |
| 15 | ClCH$_2$CBr(Me)CH$_2$ | Cl | O | H | H | 4-Cl | 68–70 |
| 16 | ClCH$_2$CBr(Me)CH$_2$ | Cl | O | H | H | 2,4-Cl$_2$ | 130–133 |
| 17 | MeCHClCHClCH$_2$ | Cl | O | H | H | 4-Cl | 108–110 |
| 18 | MeCHClCHClCH$_2$ | Cl | O | H | H | 2,4-Cl$_2$ | 105–107 |
| 19 | Br(CH$_2$)$_3$ | Cl | O | H | H | 4-Cl | 83–87 |
| 20 | Br(CH$_2$)$_3$ | Cl | O | H | H | 4-I | 100–102 |
| 21 | Br(CH$_2$)$_3$ | Cl | S | H | H | 4-Bu-t | 130–132 |
| 22 | Br(CH$_2$)$_4$ | Cl | O | H | H | 4-Cl | 112–114 |
| 23 | Br(CH$_2$)$_4$ | Cl | O | H | H | 4-I | 101–104 |
| 24 | EtCCl(Me)CH$_2$ | Cl | O | H | H | 4-Cl | 118–120 |
| 25 | EtCCl(Me)CH$_2$ | Cl | O | H | H | 4-I | 122–124 |
| 26 | EtCCl(Me)CH$_2$ | Cl | O | H | H | 2,4-Cl$_2$ | 109–110 |
| 27 | Et$_2$CClCH$_2$ | Cl | O | H | H | 4-Cl | 100–101 |
| 28 | Et$_2$CClCH$_2$ | Cl | O | H | H | 4-I | 98–100 |
| 29 | Et$_2$CClCH$_2$ | Cl | S | H | H | 4-Cl | 75–78 |
| 30 | Et$_2$CClCH$_2$ | Cl | S | H | H | 4-Bu-t | 115–117 |
| 31 | t-BuCCl(Me)CH$_2$ | Cl | O | H | H | 4-I | 168–170 |
| 32 | PrCCl(Me)CH$_2$ | Cl | O | H | H | 4-Cl | 94–99 |
| 33 | PrCCl(Me)CH$_2$ | Cl | O | H | H | 4-I | 114–115 |
| 34 | PrCCl(Me)CH$_2$ | Cl | O | H | H | 2,4-Cl$_2$ | 114–116 |
| 35 | PrCCl(Me)CH$_2$ | Cl | S | H | H | 4-Bu-t | 110–111 |
| 36 | i-PrCCl(Me)CH$_2$ | Cl | O | H | H | 4-Cl | 123–125 |
| 37 | i-PrCCl(Me)CH$_2$ | Cl | O | H | H | 4-I | 124–126 |
| 38 | BuCCl(Me)CH$_2$ | Cl | O | H | H | 4-Cl | 90–92 |
| 39 | BuCCl(Me)CH$_2$ | Cl | O | H | H | 4-I | 78–79 |
| 40 | Q3-2-Cl | Cl | O | H | H | 4-Cl | 134–136 |
| 41 | Q3-2-Cl | Cl | O | H | H | 2,4-Cl$_2$ | 162–166 |
| 42 | Q3-2-Cl | Cl | S | H | H | 4-Bu-t | 143–144 |
| 43 | (Q4-1-Cl)CH$_2$ | Cl | O | H | H | 4-Cl | 113–115 |
| 44 | (Q4-1-Cl)CH$_2$ | Cl | O | H | H | 4-I | 155–156 |
| 45 | Q4-2-Cl (cis-form) | Cl | O | H | H | 4-Cl | 160–161 |
| 46 | Q4-2-Cl (cis-form) | Cl | O | H | H | 2,4-Cl$_2$ | 199–200 |
| 47 | Q4-2-Cl (cis-form) | Cl | S | H | H | 4-Cl | 142–144 |
| 48 | Q4-2-Cl (cis-form) | Cl | S | H | H | 4-Bu-t | 158–160 |
| 49 | Q5-2-Cl | Cl | O | H | H | 4-Cl | 120–121 |
| 50 | Q5-2-Cl | Cl | O | H | H | 2,4-Cl$_2$ | 140–141 |
| 51 | Q5-2-Cl | Cl | S | H | H | 4-Bu-t | 146–148 |
| 52 | Q9-3-Cl (trans-form) | Cl | O | H | H | 4-Cl | 168–170 |
| 53 | Q9-3-Cl (trans-form) | Cl | O | H | H | 4-Cl | 140–143 |
| 54 | PrCCl(Me)CH$_2$ | Cl | O | H | H | 2-F, 4-Cl | 84–86 |
| 55 | PrCCl(Me)CH$_2$ | Cl | O | H | H | 4-F | 100–101 |
| 56 | PrCCl(Me)CH$_2$ | Cl | O | H | H | 4-CF$_3$ | 105–106 |
| 57 | PrCCl(Me)CH$_2$ | Cl | O | H | H | 4-CO—(C$_6$H$_4$Cl-4) | 144–145 |
| 58 | PrCCl(Me)CH$_2$ | Cl | O | H | H | 4-SMe | 96–97 |
| 59 | PrCCl(Me)CH$_2$ | Cl | O | H | H | 4-OCH$_2$—(C$_6$H$_4$Cl-4) | 120–123 |
| 60 | ClCH=C(Cl)CH$_2$ | Cl | O | H | H | 4-Cl | 131–133 |
| 61 | ClCH=C(Cl)CH$_2$ | Cl | O | H | H | 4-I | 132–133 |
| 62 | PrCCl(Me)CH$_2$ | Cl | O | H | H | 4-Br | 112–113 |
| 63 | PrCCl(Me)CH$_2$ | Cl | O | H | H | 4-Me | 107–108 |
| 64 | PrCCl(Me)CH$_2$ | Cl | O | H | H | 4-Ph | 136–137 |
| 65 | PrCCl(Me)CH$_2$ | Cl | O | H | H | 4-O(C$_6$H$_3$Cl-2, CF$_3$-4) | 105–107 |
| 66 | PenCHClCH$_2$ | Cl | O | H | H | 4-I | 109–111 |
| 67 | HexCHClCH$_2$ | Cl | O | H | H | 4-Cl | 102–105 |
| 68 | HexCHClCH$_2$ | Cl | O | H | H | 4-I | 107–109 |
| 69 | ClCH$_2$CH(OEt) | Cl | O | H | H | 4-I | 121–122 |
| 70 | i-BuCCl(Me)CH$_2$ | Cl | O | H | H | 4-Cl | 102–103 |
| 71 | i-BuCCl(Me)CH$_2$ | Cl | O | H | H | 4-I | 111–113 |
| 72 | CH$_2$=C(Cl)CH$_2$ | Cl | O | H | H | 4-Cl | 86–88 |
| 73 | CH$_2$=C(Cl)CH$_2$ | Cl | O | H | H | 4-I | 133–134 |

TABLE 4-continued

In Compounds of the formula:

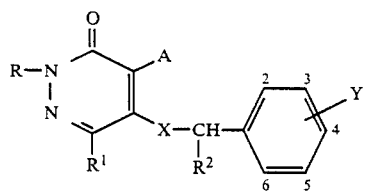

| No. | R | A | X | R$^1$ | R$^2$ | Y | m.p. (°C.) |
|---|---|---|---|---|---|---|---|
| 74 | ClCH=CHCH$_2$ | Cl | O | H | H | 4-I | 107–112 |
| 75 | MeOCH$_2$CCl(Me)CH$_2$ | Cl | O | H | H | 4-Cl | 99–101 |
| 76 | MeOCH$_2$CCl(Me)CH$_2$ | Cl | O | H | H | 4-I | 97–99 |
| 77 | Q9-3-Cl (trans-form) | Cl | O | H | H | 4-I | 159–162 |
| 78 | Q9-3-Cl (cis-form) | Cl | O | H | H | 4-I | 169–172 |
| 79 | PrCCl(Me)CH$_2$ | Cl | O | H | H | 3,4-Cl$_2$ | 102–104 |
| 80 | ClCH$_2$CH$_2$CCl(Me)CH$_2$ | Cl | O | H | H | 4-Cl | 100–101 |
| 81 | ClCH$_2$CH$_2$CCl(Me)CH$_2$ | Cl | O | H | H | 4-I | 99–104 |
| 82 | PrCCl(Me)CH$_2$ | Cl | O | H | H | 3-CF$_3$ | 93–94 |
| 83 | PrCCl(Me)CH$_2$ | Cl | O | H | H | 2-CF$_3$ | 108–110 |
| 84 | PrCCl(Me)CH$_2$ | Cl | O | H | H | 4-OMe | 82–83 |
| 85 | PrCCl(Me)CH$_2$ | Cl | O | H | H | 4-Et | 81–83 |
| 86 | PrCCl(Me)CH$_2$ | Cl | O | H | H | 3-O\\_CH$_2$_/4-O | 105–106 |
| 87 | PrCCl(Et)CH$_2$ | Cl | O | H | H | 4-I | 92–93 |
| 88 | EtCHClCCl(Me)CH$_2$ | Cl | O | H | H | 4-I | 129–131 |
| 89 | PenCCl(Me)CH$_2$ | Cl | O | H | H | 4-I | 100–102 |
| 90 | PenCCl(Me)CH$_2$ | Cl | O | H | H | 4-Cl | 88–90 |
| 91 | PenCCl(Me)CH$_2$ | Cl | O | H | H | 3-CF$_3$ | 43–45 |
| 92 | ClCH$_2$CH(OMe)CH$_2$ | Cl | O | H | H | 4-I | 108–109 |
| 93 | PrCCl(Me)CH$_2$ | Cl | O | H | H | 4-S(O)Me | 89–92 |
| 94 | PrCCl(Me)CH$_2$ | Cl | O | H | H | 4-SO$_2$Me | 142–144 |
| 95 | PrCCl(Me)CH$_2$ | Cl | O | H | H | 4-OPh | 99–100 |
| 96 | ClCH$_2$CCl(Me)CH$_2$ | Cl | O | H | H | 4-OPh | 116–121 |
| 97 | ClCH$_2$CCl(Me)CH$_2$ | Cl | O | H | H | 4-CF$_3$ | 107–109 |
| 98 | CH$_2$=C(CH$_2$Cl)CH$_2$ | Cl | O | H | H | 4-I | 96–98 |
| 99 | CH$_2$=C(CH$_2$Cl)CH$_2$ | Cl | S | H | H | 4-Bu-t | 125–127 |
| 100 | PrCCl(Me)CH$_2$ | Cl | O | H | H | 4-Pr | 68–69 |
| 101 | PrCCl(Me)CH$_2$ | Cl | O | H | H | 4-Pr-i | 101–102 |
| 102 | PrCCl(Me)CH$_2$ | Cl | O | H | H | 4-Bu | 68–70 |
| 103 | PrCCl(Me)CH$_2$ | Cl | O | H | H | 4-Bu-t | 116–117 |
| 104 | Me$_2$CClCH$_2$ | Cl | O | H | H | 4-I | 129–131 |
| 105 | (ClCH$_2$)$_2$CClCH$_2$ | Cl | O | H | H | 4-I | 111–112 |
| 106 | PrCCl(Me)CH$_2$ | Cl | O | H | H | 4-OEt | 73–74 |
| 107 | ClCH$_2$CH$_2$CCl(Me)CH$_2$ | Cl | O | H | H | 4-CF$_3$ | 94–95 |
| 108 | ClCH$_2$CH$_2$CCl(Me)CH$_2$ | Cl | O | H | H | 4-Et | 86–87 |
| 109 | EtOCH$_2$CCl(Me)CH$_2$ | Cl | O | H | H | 4-I | 105–106 |
| 110 | EtOCH$_2$CCl(Me)CH$_2$ | Cl | O | H | H | 4-CF$_3$ | 114–115 |
| 111 | EtOCH$_2$CCl(Me)CH$_2$ | Cl | O | H | H | 4-Et | 69–70 |
| 112 | MeOCH$_2$CH$_2$CCl(Me)CH$_2$ | Cl | O | H | H | 4-I | 63–64 |
| 113 | MeOCH$_2$CH$_2$CCl(Me)CH$_2$ | Cl | O | H | H | 4-CF$_3$ | 95–96 |
| 114 | MeOCH$_2$CH$_2$CCl(Me)CH$_2$ | Cl | O | H | H | 4-Et | 99–100 |
| 115 | Me$_2$CClCH$_2$ | Cl | O | H | H | 4-CF$_3$ | 119–121 |
| 116 | Me$_2$CClCH$_2$ | Cl | O | H | H | 4-Et | 122–125 |
| 117 | ClCH$_2$C(Me)(OMe)CH$_2$ | Cl | O | H | H | 4-I | 95–97 |
| 118 | Me$_2$CBrCH$_2$ | Cl | O | H | H | 4-I | 127–128 |
| 119 | Me$_2$CBrCH$_2$ | Cl | O | H | H | 4-Et | 128–129 |
| 120 | Me$_2$CBrCH$_2$ | Cl | O | H | H | 4-CF$_3$ | 127–129 |
| 121 | PrCCl(Me)CH$_2$ | Cl | O | H | H | 4-CN | 135–138 |
| 122 | ClCH$_2$CCl(Et)CH$_2$ | Cl | O | H | H | 4-I | 102–104 |
| 123 | ClCH$_2$CCl(Et)CH$_2$ | Cl | O | H | H | 4-CF$_3$ | 121–123 |
| 124 | ClCH$_2$CCl(Et)CH$_2$ | Cl | O | H | H | 4-Et | 76–78 |
| 125 | Cl(CH$_2$)$_3$CCl(Me)CH$_2$ | Cl | O | H | H | 4-I | 82–83 |
| 126 | Cl(CH$_2$)$_3$CCl(Me)CH$_2$ | Cl | O | H | H | 4-CF$_3$ | 82–83 |
| 127 | Q7-3-Cl | Cl | O | H | H | 4-I | 178–179 |
| 128 | CH$_2$=CH | Cl | O | H | H | 4-Me | 129–130 |
| 129 | CH$_2$=CH | Cl | O | H | Me | 4-Bu-t | oil |
| 130 | CH$_2$=CH | Cl | O | H | H | 3-F | 108–119 |
| 131 | CH$_2$=CH | Cl | O | H | H | 4-Cl | 151–153 |
| 132 | CH$_2$=CH | Cl | O | H | H | 4-CF$_3$ | 175–177 |
| 133 | CH$_2$=CH | Cl | O | H | H | 4-Ph | 189–191 |
| 134 | CH$_2$=CH | Cl | O | H | H | 4-OPr | 108–110 |
| 135 | CH$_2$=CH | Cl | O | H | H | 4-OCH$_2$—(C$_6$H$_4$F-4) | 125–129 |
| 136 | CH$_2$=CHCH$_2$ | Cl | S | H | H | 4-Bu-t | 131–134 |

TABLE 4-continued

In Compounds of the formula:

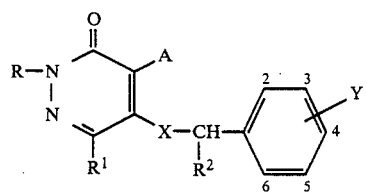

| No. | R | A | X | R¹ | R² | Y | m.p. (°C.) |
|---|---|---|---|---|---|---|---|
| 137 | CH$_2$=CHCH$_2$ | Cl | O | H | H | 4-Cl | 74–77 |
| 138 | CH$_2$=CHCH$_2$ | Cl | O | H | H | 4-Ph | 133–136 |
| 139 | CH$_2$=CHCH$_2$ | Cl | O | H | H | 4-CO—(C$_6$H$_4$Cl-4) | 133–136 |
| 140 | MeCH=CHCH$_2$ | Cl | O | H | H | 4-Me | 101–102 |
| 141 | MeCH=CHCH$_2$ | Cl | O | H | H | 4-Pr-i | 118–119 |
| 142 | MeCH=CHCH$_2$ | Cl | O | H | H | 4-Bu-t | 112–114 |
| 143 | MeCH=CHCH$_2$ | Cl | O | H | H | 4-F | 132–133 |
| 144 | MeCH=CHCH$_2$ | Cl | O | H | H | 4-Cl | 118–119 |
| 145 | MeCH=CHCH$_2$ | Cl | O | H | H | 3,4-Cl$_2$ | 143–144 |
| 146 | MeCH=CHCH$_2$ | Cl | O | H | H | 4-CO—(C$_6$H$_4$Cl-4) | 127–136 |
| 147 | HC≡CCH$_2$ | Cl | S | H | H | 4-Bu-t | 100–102 |
| 148 | HC≡CCH$_2$ | Cl | S | H | H | 4-Cl | 135–140 |
| 149 | HC≡CCH$_2$ | Cl | S | H | H | 4-Ph | 125–132 |
| 150 | CH$_2$=CH | Cl | S | H | H | 4-Bu-t | 115–116 |
| 151 | CH$_2$=C(Me)CH$_2$ | Cl | S | H | H | 4-Bu-t | 114–117 |
| 152 | CH$_2$=C(Me)CH$_2$ | Cl | O | H | H | 4-Cl | 113–115 |
| 153 | CH$_2$=C(Me)CH$_2$ | Cl | O | H | H | 4-I | 111–113 |
| 154 | MeOCH(Me)CH$_2$ | Cl | O | H | H | 4-Cl | 104–108 |
| 155 | Me$_2$C=CH | Cl | O | H | H | 4-I | 146–149 |
| 156 | Pr(Me)=CH | Me | O | H | H | 4-I | 106–108 |
| 157 | MeOC(Me)$_2$CH$_2$ | Cl | O | H | H | 4-I | 108–109 |
| 158 | MeOC(Me)$_2$CH$_2$ | Cl | O | H | H | 4-CF$_3$ | 91–92 |
| 159 | PrCCl(Me)CH$_2$ | Cl | O | H | H | 4-NO$_2$ | 121–122 |
| 160 | PrCCl(Me)CH$_2$ | Cl | O | H | H | 4-OCF$_3$ | 84–85 |
| 161 | PrCCl(Me)CH$_2$ | Cl | O | H | H | 4-CO$_2$Me | 98–99 |
| 162 | PrCCl(Me)CH$_2$ | Cl | O | H | H | 4-OPr-i | 112–113 |
| 163 | ClCH$_2$C(Me)$_2$CH$_2$ | Cl | O | H | H | 4-I | 103–109 |
| 164 | Me$_2$CClCH$_2$ | Cl | O | H | H | 4-OCF$_3$ | 79–81 |
| 165 | Me$_2$CClCH$_2$ | Cl | O | H | H | 4-CO$_2$Me | 157–158 |
| 166 | Me$_2$CClCH$_2$ | Cl | O | H | H | 4-OPr-i | 105–106 |
| 167 | Me$_2$CClCH$_2$ | Me | O | H | H | 4-I | 121–123 |
| 168 | EtCCl(Me)CH$_2$ | Cl | O | H | H | 4-OCF$_3$ | 74–75 |
| 169 | ClCH$_2$CCl(Me)CH$_2$ | Cl | O | H | H | 4-OCF$_3$ | 70–72 |
| 170 | ClCH$_2$CCl(Me)CH$_2$ | Cl | O | H | H | 4-CO$_2$Me | 172–174 |
| 171 | ClCH$_2$CCl(Me)CH$_2$ | Cl | O | H | H | 4-OEt | 103–104 |
| 172 | ClCH$_2$CCl(Me)CH$_2$ | Cl | O | H | H | 4-OPr-i | 94–95 |
| 173 | Cl(CH$_2$)$_3$CCl(Me)CH$_2$ | Cl | O | H | H | 4-Et | n$_D^{20}$ 1.5750 |
| 174 | ClCH=CHCH$_2$ (trans-form) | Cl | S | H | H | 4-Bu-t | 120–124 |
| 175 | ClCH=CHCH$_2$ (trans-form) | Cl | S | H | H | 4-Cl | 143–145 |
| 176 | PrCCl(Me)CH$_2$ | Cl | O | H | Me | 4-Cl | 55–62 |
| 177 | Pr(Me)C=CH (trans-form) | Cl | O | H | H | 4-I | 155–156 |
| 178 | Pr(Me)C=CH (cis-form) | Cl | O | H | H | 4-I | 128–129 |
| 179 | ClCH$_2$C(Me)=CH | Cl | O | H | H | 4-I | 128–129 |
| 180 | EtCH=C(Me)CH$_2$ | Cl | O | H | H | 4-I | 107–108 |

TABLE 5

In Compounds of the formula:

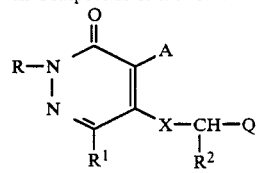

| No. | R | A | X | R¹ | R² | Q | m.p. (°C.) |
|---|---|---|---|---|---|---|---|
| 201 | ClCH$_2$CCl(Me)CH$_2$ | Cl | O | H | H | Q26-6-Cl | 117–119 |
| 202 | ClCH$_2$CCl(Me)CH$_2$ | Cl | O | H | H | Q26-6-I | 117–120 |
| 203 | ClCH$_2$CCl(Me)CH$_2$ | Br | O | H | H | Q26-6-Cl | 106–108 |
| 204 | ClCH$_2$CCl(Me)CH$_2$ | Br | O | H | H | Q26-6-I | 127–128 |
| 205 | Br(CH$_2$)$_3$ | Cl | O | H | H | Q26-6-Cl | 138–139 |

TABLE 5-continued

In Compounds of the formula:

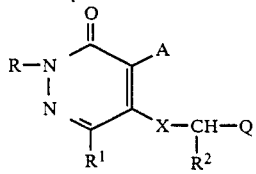

| No. | R | A | X | R¹ | R² | Q | m.p. (°C.) |
|---|---|---|---|---|---|---|---|
| 206 | EtCCl(Me)CH₂ | Cl | O | H | H | Q26-6-Cl | 124–126 |
| 207 | EtCCl(Me)CH₂ | Cl | O | H | H | Q26-6-I | 120–123 |
| 208 | Et₂CClCH₂ | Cl | O | H | H | Q26-6-Cl | 96–98 |
| 209 | Et₂CClCH₂ | Cl | O | H | H | Q26-6-I | 111–113 |
| 210 | t-BuCCl(Me)CH₂ | Cl | O | H | H | Q26-6-Cl | 177–178 |
| 211 | PrCCl(Me)CH₂ | Cl | O | H | H | Q26-6-Cl | 101–105 |
| 212 | PrCCl(Me)CH₂ | Cl | O | H | H | Q26-6-I | 96–97 |
| 213 | i-PrCCl(Me)CH₂ | Cl | O | H | H | Q26-6-Cl | 140–141 |
| 214 | BuCCl(Me)CH₂ | Cl | O | H | H | Q26-6-Cl | 90–92 |
| 215 | BuCCl(Me)CH₂ | Cl | O | H | H | Q26-6-I | 93–97 |
| 216 | (Q4—1—Cl)CH₂ | Cl | O | H | H | Q26-6-Cl | 128–130 |
| 217 | Q4—2—Cl (cis-form) | Cl | O | H | H | Q26-6-Cl | 187–188 |
| 218 | Q9—3—Cl (trans-form) | Cl | O | H | H | Q26-6-Cl | 147–149 |
| 219 | Q9—3—Cl (cis-form) | Cl | O | H | H | Q26-6-Cl | 189–192 |
| 220 | ClCH=C(Cl)CH₂ | Cl | O | H | H | Q26-6-Cl | 167–169(*) |
| 221 | ClCH=C(Cl)CH₂ | Cl | O | H | H | Q26-6-Cl | 103–105(**) |
| 222 | PenCHClCH₂ | Cl | O | H | H | Q26-6-Cl | 78–81 |
| 223 | HexCHClCH₂ | Cl | O | H | H | Q26-6-Cl | 90–92 |
| 224 | ClCH₂CH(OEt) | Cl | O | H | H | Q26-6-Cl | 116–117 |
| 225 | Br(CH₂)₄ | Cl | O | H | H | Q26-6-Cl | 115–116 |
| 226 | i-BuCCl(Me)CH₂ | Cl | O | H | H | Q26-6-Cl | 90–92 |
| 227 | CH₂=C(Cl)CH₂ | Cl | O | H | H | Q26-6-Cl | 111–113 |
| 228 | MeOCH₂CCl(Me)CH₂ | Cl | O | H | H | Q26-6-Cl | 97–99 |
| 229 | Q9-3-Cl (trans-form) | Cl | O | H | H | Q26-6-I | 157–158 |
| 230 | ClCH₂CH₂CCl(Me)CH₂ | Cl | O | H | H | Q26-6-Cl | 110–113 |
| 231 | PrCCl(Et)CH₂ | Cl | O | H | H | Q26-6-Cl | 89–91 |
| 232 | EtCHClCCl(Me)CH₂ | Cl | O | H | H | Q26-6-Cl | 130–131 |
| 233 | PenCCl(Me)CH₂ | Cl | O | H | H | Q26-6-Cl | 71–72 |
| 234 | ClCH₂CCl₂CH₂ | Cl | O | H | H | Q26-6-Cl | 141–143 |
| 235 | CH₂=C(CH₂Cl)CH₂ | Cl | O | H | H | Q26-6-Cl | 128–130 |
| 236 | Me₂CClCH₂ | Cl | O | H | H | Q26-6-Cl | 128–130 |
| 237 | Me₂CClCH₂ | Cl | O | H | H | Q26-6-I | 119–123 |
| 238 | (ClCH₂)₂CClCH₂ | Cl | O | H | H | Q26-6-Cl | 107–111 |
| 239 | ClCH₂CH₂CCl(Me)CH₂ | Cl | O | H | H | Q26-6-I | 78–80 |
| 240 | EtOCH₂CCl(Me)CH₂ | Cl | O | H | H | Q26-6-Cl | 96–98 |
| 241 | MeOCH₂CH₂CCl(Me)CH₂ | Cl | O | H | H | Q26-6-Cl | 87–90 |
| 242 | PrCCl(Me)CH₂ | Cl | O | H | H | Q55 | 81–83 |
| 243 | Me₂CBrCH₂ | Cl | O | H | H | Q26-6-Cl | 128–130 |
| 244 | Me₂CClCH₂ | Cl | O | H | H | Q26-6-Br | 142–143 |
| 245 | EtCCl(Me)CH₂ | Cl | O | H | H | Q26-6-Br | 126–128 |
| 246 | PrCCl(Me)CH₂ | Cl | O | H | H | Q26-6-Br | 113–115 |
| 247 | ClCH₂CCl(Me)CH₂ | Cl | O | H | H | Q26-6-Br | 129–130 |
| 248 | ClCH₂CCl(Et)CH₂ | Cl | O | H | H | Q26-6-Cl | 129–130 |
| 249 | Cl(CH₂)₃CCl(Me)CH₂ | Cl | O | H | H | Q26-6-Cl | 85–87 |
| 250 | Q7-3-Cl | Cl | O | H | H | Q26-6-Cl | 174–175 |
| 251 | Q7-3-Cl | Cl | O | H | H | Q26-6-I | 176–177 |
| 252 | MeCH=CHCH₂ | Cl | O | H | H | Q56 | 128–130 |
| 253 | MeCH=CHCH₂ | Cl | O | H | H | Q55 | 151–153 |
| 254 | CH₂=C(Me)CH₂ | Cl | O | H | H | Q26-6-Cl | 98–104 |
| 255 | (Me)₂C=CH | Cl | O | H | H | Q26-6-I | 141–142 |
| 256 | MeOC(Me)₂CH₂ | Cl | O | H | H | Q26-6-I | 120–121 |
| 257 | PrCCl(Me)CH₂ | Cl | O | H | H | Q26-6-OEt | 88–91 |
| 258 | PrCCl(Me)CH₂ | Cl | O | H | H | Q23-5-Me | 101–103 |
| 259 | PrCCl(Me)CH₂ | Cl | O | H | H | Q23-5-Br | 110–112 |
| 260 | PrCCl(Me)CH₂ | Cl | O | H | H | Q23-4-Br | 95–96 |
| 261 | PrCCl(Me)CH₂ | Cl | O | H | H | Q23-5-I | 106–108 |
| 262 | PrCCl(Me)CH₂ | Cl | O | H | H | Q26-6-OPr-i | 114–115 |
| 263 | ClCH₂C(Me)₂CH₂ | Cl | O | H | H | Q26-6-I | 131–132 |
| 264 | Me₂CClCH₂ | Cl | O | H | H | Q26-6-OEt | 108–110 |
| 265 | Me₂CClCH₂ | Me | O | H | H | Q26-6-I | 109–111 |
| 266 | ClCH₂CCl(Me)CH₂ | Cl | O | H | H | Q26-6-OEt | 89–90 |
| 267 | ClCH₂CCl(Me)CH₂ | Cl | O | H | H | Q23-5-Me | 99–101 |
| 268 | ClCH₂CCl(Me)CH₂ | Cl | O | H | H | Q23-5-Br | 89–91 |
| 269 | ClCH₂CCl(Me)CH₂ | Cl | O | H | H | Q23-4-Br | 120–122 |
| 270 | ClCH₂CCl(Me)CH₂ | Cl | O | H | H | Q23-5-I | 115–116 |
| 271 | Cl(CH₂)₃CCl(Me)CH₂ | Cl | O | H | H | Q26-6-I | 95–98 |
| 272 | PrCCl(Me)CH₂ | Cl | O | H | H | Q26-6-Et | 92–94 |

TABLE 5-continued

In Compounds of the formula:

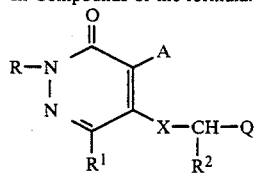

| No. | R | A | X | $R^1$ | $R^2$ | Q | m.p. (°C.) |
|---|---|---|---|---|---|---|---|
| 273 | Pr(Me)C=CH (trans -form) | Cl | O | H | H | Q26-6-I | 172–173 |
| 274 | ClCH$_2$C(Me)=CH | Cl | O | H | H | Q26-6-I | 136–137 |

(*) TLC (Silica gel: C$_6$H$_6$(10)—CH$_3$COOEt(1)) Rf value = 0.15
(**) TLC (Silica gel: C$_6$H$_6$(10)—CH$_3$COOEt(1)) Rf value = 0.22

TABLE 6

In Compounds of the formula:

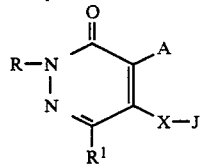

| No. | R | A | X | $R^1$ | J | m.p. (°C.) |
|---|---|---|---|---|---|---|
| 301 | ClCH$_2$CCl(Me)CH$_2$ | Cl | O | H | CH$_2$CH$_2$OC$_6$H$_4$-4-Cl | 106–107 |
| 302 | ClCH$_2$CCl(Me)CH$_2$ | Cl | O | H | CH$_2$CH(Me)O-Q17 | 69–70 |
| 303 | ClCH$_2$CCl(Me)CH$_2$ | Cl | O | H | CH$_2$CH$_2$OPh | 106–107 |
| 304 | ClCH$_2$CCl(Me)CH$_2$ | Cl | O | H | CH$_2$CH$_2$ON=CHMe | $n_d^{20}$ 1.3241 |
| 305 | PrCCl(Me)CH$_2$ | Cl | O | H | CH$_2$CH$_2$C$_6$H$_4$-4-Cl | 95–97 |
| 306 | PrCCl(Me)CH$_2$ | Cl | O | H | CH$_2$CH$_2$C$_6$H$_4$-3-Cl | 61–62 |
| 307 | PrCCl(Me)CH$_2$ | Cl | O | H | CH$_2$CH$_2$C$_6$H$_4$-3-Me | 49–51 |
| 308 | PrCCl(Me)CH$_2$ | Cl | O | H | CH$_2$CH$_2$C$_6$H$_4$-2-Me | 75–76 |
| 309 | PrCCl(Me)CH$_2$ | Cl | O | H | CH$_2$CH$_2$C$_6$H$_4$-4-F | 58–60 |
| 310 | PrCCl(Me)CH$_2$ | Cl | O | H | CH$_2$CH$_2$C$_6$H$_4$-4-CF$_3$ | 98–99 |
| 311 | PrCCl(Me)CH$_2$ | Cl | O | H | CH$_2$CH$_2$C$_6$H$_4$-3-CF$_3$ | 58–60 |
| 312 | PrCCl(Me)CH$_2$ | Cl | O | H | CH$_2$C(Me)$_2$O—(C$_6$H$_3$-2,5-Me$_2$) | 60–62 |
| 313 | PrCCl(Me)CH$_2$ | Cl | O | H | CH$_2$CMe=CH—(C$_6$H$_4$-4-Et) | 82–83 |
| 314 | PrCCl(Me)CH$_2$ | Cl | O | H | (CH$_2$)$_3$C≡C-Br | 53–56 |
| 315 | PrCCl(Me)CH$_2$ | Cl | O | H | CH$_2$CH$_2$C$_6$H$_4$-4-Me | $n_d^{20}$ 1.5641 |
| 316 | PrCCl(Me)CH$_2$ | Cl | O | H | CH$_2$CH$_2$C$_6$H$_3$-2,4-Cl$_2$ | 71–73 |
| 317 | PrCCl(Me)CH$_2$ | Cl | O | H | CH$_2$CHMeO—(C$_6$H$_3$-2,5-Me$_2$) | $n_d^{20}$ 1.5557 |
| 318 | PrCCl(Me)CH$_2$ | Cl | O | H | CH$_2$CH$_2$OPh | $n_d^{20}$ 1.5578 |
| 319 | PrCCl(Me)CH$_2$ | Cl | O | H | CH$_2$CH$_2$OC$_6$H$_4$-4-Me | 67–69 |
| 320 | PrCCl(Me)CH$_2$ | Cl | O | H | CH$_2$CH$_2$NHCO$_2$Et | 67–68 |
| 321 | PrCCl(Me)CH$_2$ | Cl | O | H | (CH$_2$)$_3$C≡CH | 59–61 |
| 322 | PrCCl(Me)CH$_2$ | Cl | O | H | CH$_2$CH$_2$ON=CHMe | $n_d^{20}$ 1.5314 |
| 323 | Me$_2$CClCH$_2$ | Cl | O | H | CH$_2$CH$_2$C$_6$H$_4$-4-CF$_3$ | 126–127 |
| 324 | Me$_2$CClCH$_2$ | Cl | O | H | (CH$_2$)$_3$C≡C—Br | $n_d^{20}$ 1.5670 |
| 325 | Me$_2$CClCH$_2$ | Cl | O | H | (CH$_2$)$_3$C≡CH | 42–44 |
| 326 | Me$_2$CClCH$_2$ | Cl | O | H | CH$_2$CH$_2$OPh | 82–83 |
| 327 | Me$_2$CClCH$_2$ | Cl | O | H | (CH$_2$)$_3$-Q17-5-Br | 109–110 |
| 328 | PrCCl(Me)CH$_2$ | Cl | O | H | (CH$_2$)$_3$Ph | 54–57 |
| 329 | PrCCl(Me)CH$_2$ | Cl | O | H | (CH$_2$)$_3$CO$_2$H | 93–95 |
| 330 | PrCCl(Me)CH$_2$ | Cl | O | H | CH$_2$C(Me)=NOPr | $n_d^{20}$ 1.3458 |
| 331 | PrCCl(Me)CH$_2$ | Cl | O | H | CH$_2$CH$_2$C≡CCH$_2$OMe | 45–47 |
| 332 | PrCCl(Me)CH$_2$ | Cl | O | H | (CH$_2$)$_3$CO$_2$Et | $n_d^{20}$ 1.5231 |
| 333 | ClCH$_2$CCl(Me)CH$_2$ | Cl | O | H | CH$_2$C(Me)=NOPr | 60–61 |
| 334 | Me$_2$CClCH$_2$ | Cl | O | H | CH$_2$CH$_2$C≡CCH$_2$OMe | $n_d^{20}$ 1.5453 |
| 335 | PrCCl(Me)CH$_2$ | Cl | O | H | CH$_2$C(Me)=CHCO$_2$Et | 88–90 |

The definition of Q in the Tables 4, 5 and 6 are the same as that of Q in the Tables 1, 2 and 3.

When the compounds according to the present invention are used for insecticidal, acaricidal and nematicidal compositions and compositions for expelling ticks parasitic on animals, they are generally mixed with suitable carriers, for instance, solid carriers such as clay, talc, bentonite or diatomaceous earth, or liquid carriers such as water, alcohols (e.g., methanol and ethanol), aromatic hydrocarbons (e.g., benzene, toluene and xylene), chlorinated hydrocarbons, ethers, ketones, esters (e.g., ethyl acetate) or acid amides (e.g., dimethylformamide). If desired, to these mixtures may be added emulsifier, dispersing agent, suspension agent, penetrating agent, spreader, stabilizer and the like to put them into practical use in the form of emulsifiable concentrate, oil solution, wettable powder, dust, granule, flowable or the like.

Moreover, the mixtures may be incorporated with other insecticides, various herbicides, fungicides, plant-growth regulating agents, synergists during formulation or application thereof, as necessary.

The amount of the compounds of the invention to be used as an active ingredient is suitably in the range of 0.005 to 50 kg per hectare although it varies depending upon the place and the seasons where the compounds are applied, manner of application, diseases and insect pests to be applied, cultivated crops to be protected and the like.

The following is formulatin proportion and kinds of various preparations of the present invention.

|  | Active ingredient | Carrier | Surface-active agent | Other component (adjuvant) |
|---|---|---|---|---|
| Emulsifiable concentrates | 1–25 | 52–95 | 3–20 | 0–20 |
| Oil solutions | 1–30 | 70–99 |  |  |
| Flowables | 1–70 | 10–90 | 1–20 | 0–10 |
| Wettable powders | 1–70 | 15–93 | 3–10 | 0–5 |
| Dusts | 0.01–30 | 67–99.5 |  | 0–3 |
| Granules | 0.01–30 | 67–99.5 |  | 0–8 |

The numeral values in the above table represent "percent by weight".

In use, emulsifiable concentrates, oil solutions, flowables and wettable powder are diluted with a predetermined amount of water and applied. Dusts and granules are directly applied without being diluted with water. The granules contain baits.

Each component of the above formulations is exemplified as follows.

Emulsifiable concentrates

Active ingredient: Present compound
Carrier: xylene, dimethylformamide, methylnaphthalene, cyclohexanone, dichlorobenzene, isophorone
Surface-active agent: Solpol 2680, Solpol 3005X, Solpol 3353
Other ingredients: piperonylbutoxide, benzotriazole

Oil solution

Active ingredient: Present compound
Carrier: xylene, methylcellosolve, kerosense

Flowables

Active ingredient: Present compound
Carrier: water
Surface-active agent: Lunox 1000C, Solpol 3353, Soprophor FL, Nippol, Agrisol S-710, sodium lignin sulfate
Other ingredients: Xanthan gum, formalin, ethylene glycol, propylene glycol

Wettable powders

Active ingredient: Present compound
Carrier: potassium carbonate, kaolinite, Zeeklite D, Zeeklite PFP, diatomaceous earth, talc
Surface-active ingredients: Solpol 5039, Lunox 1000C, calcium lignin sulfonate, sodium dodecyl benzenesulfonate, Solpol 5050, Solpol 005D, Solpol 5029-0
Other ingredient: Carplex #80

Dusts

Active ingredient: Present compound
Carrier: potassium carbonate, kaolinite, Zeeklite D, talc
Other ingredient: diisopropyl phosphate, Carplex #80

Granules (1)

Active ingredient: Present compound
carrier: potassium carbonate, kaolinite, bentonite, talc
Other ingredients: calcium lignin sulfonate, polyvinyl alcohol

Granules (2)

Active ingredient: Present compound
Carrier: wheat flour, wheat bran, corn grits, Zeeklite D
Other ingredients: paraffin, bean oil In the following, there are shown formulation examples of insecticidal, acaricidal and nematicidal compositions and compositions for ticks parasitic on animals, said compositions containing the compounds of the present invention as an active ingredient. These examples are only illustrative and not to restrict the present invention. In the following formulation examples, "part" means "part by weight".

Formulation Example 1: Emulsifiable concentrate

Present compound: 1 part
Xylene: 75 parts
N,N-dimethylformamide: 20 parts
Solpol 2680 (trade name: a mixture of a non-ionic surface-active agent and an anionic surface-active agent manufactured by Toho Chemical, Co., Ltd., Jap: 4 parts Formulation Example 2: Emulsifiable concentrate Present compound: 5 parts
Xylene: 70 parts
N,N-dimethylformamide: 20 parts
Solpol 2680: 5 parts Formulation Example 3: Emulsifiable concentrate Present compound: 10 parts
Xylene: 70 parts
N,N-dimethylformamide: 5 parts
Solpol 2680: 10 parts
Piperonyl butoxide: 5 parts Formulation Example 4: Emulsifiable concentrate Present compound: 20 parts
Xylene: 50 parts
N,N-dimethylformamide: 7 parts
Solpol 2680: 3 parts
Piperonyl butoxide: 20 parts Formulation Example 5: Emulsifiable concentrate Present compound: 25 parts
Xylene: 50 parts
N,N-dimethylformamide: 2 parts
Solpol 2680: 20 parts
Piperonyl butoxide: 3 parts In the above respective emulsifiable concentrates, each component of the respective emulsifiable concentrates are mixed intimately to form respective emulsifiable concentrates. Upon use, the emulsifiable concentrates are diluted with water up to one fiftieth to one twenty thousandth in concentration and applied at a rate of 0.005 to 50 kg of the active ingredient per hectare.

Formulation Example 6: Wettable powders

Present compound: 1 part
Zeeklite PFP (trade name, a mixture of kaolinite and sericite manufactured by Zeeklite Mining Industries, Co., Ltd.: 93 parts
Solpol 5039 (trade name, anionic surface-active agent manufactured by Toho Chemical, Co., Ltd., Japan): 4 parts
Carplex #80 (trade name, white carbon manufactured by Shionogi Seiyaku K.K., Japan): 2 parts

Formulation Example 7: Wettable powders

Present compound: 10 parts
Zeeklite PFP: 80 parts
Solpol 5039: 6 parts
Carplex #80: 4 parts

Formulation Example 8: Wettable powders

Present compound: 25 parts
Zeeklite PFP: 66 parts
Solpol 5039: 4 parts
Carplex #80: 2 parts
Calcium lignin sulfonate: 3 parts

Formulation Example 9: Wettable powder

Present compound: 50 parts
Zeeklite PFP: 47 parts
Solpol 5039: 2 parts
Carplex #80: 1 part

Formulation Example 10: Wettable powder

Present compound: 70 parts
Zeeklite PFP: 15 parts
Solpol 5039: 6 parts
Carplex #80: 4 parts
Calcium lignin sulfonate: 5 parts In the above respective wettable powders, each component of the respective wettable powders are intimately mixed and ground to form respective wettable powder. Upon use, the wettable powders are diluted with water up to one fiftieth to one twenty thousandth in concentration and applied at a rate of 0.005 to 50 kg of the active ingredient per hectare.

Formulation Example 11: Oil solutions

Present compound: 1 part
Methylcellosolve: 99 parts

Formulation Example 12: Oil solutions

Present compound: 20 parts
Methylcellosolve: 80 parts

Formulation Example 13: Oil solutions

Present compound: 30 parts
Methylcellosolve: 70 parts

In the above respective oil solutions, each component of the respective oil solutions are homogeneously mixed together to form the respective oil solutions. Upon use, the oil solutions are applied at a rate of 0.005 to 50 kg of the active ingredient per hectare.

Formulation Example 14: Dusts

Present compound: 0.01 part
Carplex #80 (trade name, white carbon manufactured by Shionogi Seiyaku K.K., Japan): 0.1 part
Clay: 99.5 parts
diisopropyl phosphate: 0.39 part

Formulation Example 15: Dusts

Present compound: 0.1 part
Carplex #80: 0.1 part
Clay: 99.5 parts
diisopropyl phosphate: 0.3 part

Formulation Example 16: Dusts

Present compound: 1 part
Clay: 99 parts

Formulation Example 17: Dusts

Present compound: 10 parts
Carplex #80: 0.2 part
Clay: 89 parts
diisopropyl phosphate: 0.8 part

Formulation Example 18: Dusts

Present compound: 30 parts
Carplex #80: 1 part
Clay: 67 parts
diisopropyl phosphate: 2 parts In the above respective dusts, components of the respective dusts are homogeneously mixed together to form the respective dusts. Upon use, the dusts are applied at a rate of 0.005 to 50 kg of the active ingredient per hectare.

Formulation Example 19: Granules (1)

Present compound: 0.01 part
Bentonite: 59.5 parts
Talc: 40 parts
Calcium lignin sulfonate: 0.49 part

Formulation Example 20: Granules (1)

Present compound: 0.5 part
Bentonite: 59.5 parts
Talc: 40 parts

Formulation Example 21: Granules (1)

Present compound: 1 part
Bentonite: 40 parts
Talc: 51 parts
Calcium lignin sulfonate: 8 parts

Formulation Example 22: Granules (1)

Present compound: 5 parts
Bentonite: 54 parts
Talc: 40 parts
calcium lignin sulfonate: 1 part

Formulation Example 23: Granules (1)

Present compound: 30 parts
Bentonite: 37 parts
Talc: 30 parts
calcium lignin sulfonate: 3 parts In the above respective granules (1), each components of the respective granules (1) are mixed intimately together and ground, incorporated with a small amount of water and mixed together with stirring. The resulting mixture is granulated by means of extrusion-granulator and dried to form granules. Upon use, the granule is applied to at a rate of 0.005 to 50 kg of the active ingredient per hectare.

Formulation Example 24: Granules (2)

Present compound: 0.01 part

Wheat flour: 49.5 parts
Wheat bran: 50 parts
Bean oil: 0.49 part

Formulation Example 25: Granules (2)

Present compound: 0.5 part
Wheat flour: 49.5 parts
Wheat bran: 50 parts

Formulation Example 26: Granules (2)

Present compound: 1 part
Wheat flour: 40 parts
Wheat bran: 51 parts
Bean oil: 4 parts
Paraffin: 4 parts Formulation Example 27: Granules (2)

Present compound: 5 parts
Wheat flour: 44 parts
Wheat bran: 50 parts
Bean oil: 1 part Formulation Example 28: Granules (2)

Present compound: 30 parts
Wheat flour: 27 parts
Wheat bran: 40 parts
Bean oil: 3 parts In the above respective granules (2), each components of the respective granules (2) are mixed intimately together to form respective bait. Upon use, the granule is applied at a rate of 0.005 to 50 kg of the active ingredient per hectare.

Formulation Example 29: Flowables

Present compound: 1 part
Solpol 3353 (trade name, non-ionic surface-active agent manufactured by Toho Chemicals, Co., Ltd., Japan): 0.9 part
Lunox 1000C (trade name, as anionic surface-active agent manufactured by Toho Chemicals, Co., Ltd., Japan): 0.1 part
1% aqueous solution of Xanthan gum (natural high-molecular compound): 8 parts
Water: 90 parts Formulation Example 30: Flowables Present compound: 15 parts
Solpol 3353: 15 parts
Lunox 1000C: 5 parts
Water: 65 parts Formulation Example 31: Flowables Present compound: 35 parts
Solpol 3353: 14 parts
Lunox 1000C: 1 part
1% aqueous solution of Xanthan gum 10 parts
Water: 45 parts Formulation Example 32: Flowables Present compound: 50 parts
Solpol 3353: 9 parts
Lunox 1000C: 1 part
1% aqueous solution of Xanthan gum: 10 parts
Water: 30 parts Formulation Example 33: Flowables Present compound: 70 parts
Solpol 3353: 9 parts
Lunox 1000C: 1 part
1% aqueous solution of Xanthan gum: 10 parts
Water: 10 parts In the above respective flowables, each component except the active ingredient (present compound) are uniformly mixed together to form a solution. The resulting mixture is added by the present compound thoroughly stirred and wet-ground by means of sand mill to form respective flowables. Upon use, the flowables are diluted up to one fiftieth to one twenty thousandth with water and applied at a rate of 0.005 to 50 kg of the active ingredient per hectare.

In the following, the effects of the present compounds as an insecticide are explained in detail by way of the test examples.

Test Example 1: Insecticidal test on Green rice leafhopper (*Nephotettix cincticeps*)

A 5% emulsifiable concentrate (or a 25% wettable powder) of a compound of the present invention was diluted with water containing a spreader to give a 500 ppm solution of the compound.

The stems and leaves of rice-plant in a 1/20000 are pot were sufficiently applied with the resulting solution and then airdried. Thereafter, 20 second instar nymphae of green rice leafhopper (*Nephotettix cincticeps*) which resist organic phosphorous insecticides and carbamate insecticides were released in the pot.

The rice-plant thus treated was covered with a cylindrical wire gauze and kept in a thermostatic chamber.

Thirty (30) days after, the number of the green rice leafhoppers parasitic on the rice-plant was counted and the mortality thereof was determined according to the following equation:

$$\text{Mortality (\%)} = \frac{\text{number of the insect killed}}{\text{number of insect released}} \times 100$$

The test was conducted twice for each compound. In the results, the following compounds exhibited high effects of 100% of mortality.

Compound Nos. 9, 10, 12, 15, 17, 19, 24, 25, 27, 28, 32, 33, 38, 39, 45, 49, 50, 52, 53, 75, 76, 77, 78, 80, 81, 85, 87, 92, 97, 104, 105, 107, 108, 109, 110, 111, 112, 113, 114, 115, 116, 117, 118, 120, 122, 124, 125, 126, 127, 155, 156, 201, 202, 203, 204, 206, 207, 208, 209, 211, 212, 218, 219, 226, 228, 229, 230, 231, 234, 236, 237, 238, 239, 240, 244, 245, 247, 250, 251, 314, 321, 324, 325

Test Example 2: Insecticidal test on Brown rice planthopper (*Nilaparvata lugens*)

The procedures in Test Example 1 were repeated by using second instar nymphae of brown rice planthopper (*Nilaparvata lugens*) instead of the second instar nymphae of green rice leafhoppers which resist organic phosphorous insecticides and carbamate insecticides. In the results, the following compounds exhibited high effects of 100% of mortality.

Compound Nos. 11, 25, 34, 48, 93, 201, 202, 203, 204, 205, 207, 208, 209, 211, 212, 214, 215, 219, 228, 229, 230, 231, 234, 236, 237, 238, 239, 240, 243, 244, 245, 246, 247, 249, 250, 251, 254, 255, 256, 257, 259, 263, 264, 265, 271, 302

Test Example 3: Insecticidal test on Red flour beetle (*Tribolium castaneum*)

In a transparent small test tube was placed 5% emulsifiable concentrate of a compound of the present invention (or a 25% wettable powder or a 20% oil solution thereof), and thereto was added acetone to give a 500 ppm acetone solution of the compound. Ten (10) cc of the acetone solution was added to 10 g of wheat flour placed in a laboratory dish of 9 cm in diameter. After stirring, acetone was distilled away from the mixture. Then, 10 adults each of male and female red flour beetle (*Tribolium castaneum*) were released in the dish. The dish containing the adults was kept in a thermostatic chamber.

Ninety (90) days after, evaluation was conducted by counting the number of the adults which came out.

The test was conducted twice of each compound.

As a result, no emerged adult was observed at all in the dish treated with any one of the following compounds.

Compound Nos. 9, 10, 12, 15, 19, 24, 25, 32, 33, 39, 70, 71, 75, 76, 77, 78, 79, 80, 81, 84, 85, 86, 87, 92, 93, 94, 95, 97, 100, 101, 102, 103, 104, 105, 106, 107, 108, 109, 110, 111, 112, 113, 114, 115, 116, 117, 118, 119, 120, 121, 122, 123, 124, 125, 126, 127, 155, 156, 159, 160, 161, 163, 164, 168, 169, 173, 201, 202, 203, 204, 206, 207, 208, 209, 211, 212, 226, 227, 228, 229, 230, 231, 232, 234, 235, 236, 237, 238, 239, 240, 241, 242, 243, 244, 245, 246, 247, 248, 249, 250, 251, 255, 257, 263, 264, 266, 271

Test Example 4: Insecticidal test on House mosquito (*Culex pipiens pallens*)

A 5% emulsifiable concentrate (or a 25% wettable powder or 20% oil solution) of a compound of the present invention was diluted with deionized water to give a 10 ppm solution of the compound.

Two hundred (200) ml of the solution was poured in a tall laboratory dish of 9 cm in diameter and 6 cm in height. Ten larvae of house mosquito (*Culex pipiens pallens*) were released in the dish. The dish containing the larvae was kept in a thermostatic chamber of 25° C.

Seven (7) days after, the number of the larvae killed was counted.

The test was conducted twice of each compound.

As the result, no emerged adult was observed at all in the dish treated with any one the following compounds.

Compound Nos. 1, 2, 3, 4, 5, 6, 9, 10, 12, 14, 15, 17, 18, 19, 24, 25, 27, 28, 30, 32, 33, 34, 35, 38, 39, 45, 49, 52, 53, 70, 71, 72, 73, 75, 76, 77, 78, 79, 80, 81, 82, 83, 84, 85, 86, 87, 88, 90, 92, 93, 94, 95, 96, 97, 98, 99, 100, 101, 102, 103, 104, 105, 107, 108, 109, 110, 111, 112, 113, 114, 115, 116, 117, 118, 119, 120, 122, 123, 124, 125, 126, 127, 155, 156, 158, 160, 163, 164, 168, 169, 173, 201, 202, 203, 204, 205, 206, 207, 208, 209, 211, 212, 215, 217, 218, 219, 224, 225, 226, 227, 228, 229, 230, 231, 232, 233, 234, 236, 237, 238, 239, 240, 241, 242, 244, 245, 246, 250, 251, 255, 257, 264, 266, 301

Test Example 5: Insecticidal test on Almond moth (*Cadra cautella*)

In a transparent small test tube was placed 5% emulsifiable concentrate of a compound of the present invention (or a 25% wettable powder or a 20% oil solution thereof), and thereto was added acetone to give a 500 ppm acetone solution of the compound. Ten (10) cc of the acetone solution was added to 10 g of rice bran placed in a laboratory dish of 9 cm in diameter. After stirring, acetone was distilled away from the mixture. Then, 10 larvae of almond moth (*Cadra cautella*) were released in the dish. The dish containing the larvae was kept in a thermostatic chamber.

Thirty (30) days after, evaluation was conducted by counting the number of the adults which came out.

The test was conducted twice of each compound.

As a result, no emerged adult was observed at all in the dish treated with any one of the following compounds.

Compound Nos. 9, 10, 11, 12, 15, 19, 24, 25, 27, 28, 32, 33, 34, 38, 39, 52, 53, 70, 71, 73, 74, 75, 76, 77, 78, 79, 80, 81, 84, 85, 86, 87, 89, 90, 92, 93, 94, 95, 97, 98, 100, 101, 102, 103, 104, 105, 106, 107, 108, 109, 110, 111, 112, 113, 114, 115, 116, 117, 118, 119, 120, 124, 125, 126, 127, 155, 156, 160, 162, 163, 164, 166, 167, 168, 169, 171, 172, 173, 201, 202, 203, 204, 206, 207, 208, 209, 211, 212, 214, 215, 217, 218, 219, 225, 226, 227, 228, 229, 230, 231, 232, 233, 234, 235, 236, 237, 238, 239, 240, 241, 242, 243, 244, 245, 246, 247, 249, 250, 251, 256, 257, 258, 259, 260, 261, 262, 263, 264, 265, 266, 268, 270, 271, 302, 314, 318, 319

Test Example 6: Insecticidal test on Green peach aphid (*Myzus persicae*)

A 5% emulsifiable concentrate (or a 25% wettable powder) of a compound of the present invention was diluted with water containing a spreader to give a 500 ppm solution of the compound.

Discs of leaves of cabbage (*Brassica oleracea*) were put in each laboratory dish of 3 cm in diameter in which a moistured paper was placed. In each laboratory dish was released 5 third instar nymphae of green peach aphid (*Myzus persicae*) and sprayed from a sprinkler.

The laboratory dishes were kept in a thermostatic chamber.

Seven (7) days after, the number of surviving green peach aphids was counted and the mortality thereof was determined according to the equation as described in Test Example 1. The test was conducted four times of each compound.

As a result, the following compounds exhibited high effects of 100% of mortality.

Compound Nos. 9, 10, 12, 15, 25, 27, 28, 32, 33, 34, 36, 37, 38, 39, 54, 55, 56, 58, 59, 61, 62, 64, 75, 76, 84, 85, 87, 93, 95, 96, 97, 100, 101, 102, 103, 104, 105, 107, 108, 110, 111, 115, 116, 118, 119, 120, 123, 124, 125, 126, 156, 159, 160, 161, 163, 164, 165, 167, 168, 169, 170, 173, 201, 202, 203, 204, 207, 208, 209, 211, 212, 215, 228, 231, 234, 244, 245, 246, 247, 250, 251, 255, 257, 259, 260, 261, 262, 264, 265, 266, 268, 270, 271, 301, 302, 303, 305, 306, 307, 310, 314, 318, 319, 320, 321

Test Example 7: Insecticidal test on Diamond back moth (*Plutella xylostella*)

A 5% emulsifiable concentrate (or a 25% wettable powder) of a compound of the present invention was diluted with water containing a spreader to give a 500 ppm solution of the compound.

Leaves of cabbage (*Brassica oleracea*) were dipped in the solution, air-dried and then put in a laboratory dish of 7 cm in diameter. Ten (10) third larvae of diamond back moth (*Plutella xylostella*) were released in each laboratory dish and kept in a thermostatic chamber.

Twenty (20) days after, the number of emerged adults was counted and the mortality thereof was determined according to the equation as described in Test Example 1. The test was conducted twice of each compound.

As a result, the follwoing compounds exhibited high effects of 100% of mortality.

Compound Nos. 9, 10, 11, 12, 15, 17, 19, 24, 25, 27, 28, 32, 33, 34, 38, 39, 80, 81, 85, 104, 105, 118, 119, 124, 125, 127, 155, 156, 201, 202, 203, 204, 206, 207, 211, 212, 214, 215, 230, 231, 234, 236, 237, 243, 244, 245, 246, 247, 249, 250, 251, 255, 256, 257, 263, 264, 265, 271

Test Example 8: Insecticidal test on Maize weevil (*Sitophilus oryzae*)

A 5% emulsifiable concentrate (or a 25% wettable powder) of a compound of the present invention was diluted with water containing a spreader to give a 500 ppm solution of the compound.

Ten (10) g of unmilled rice in a laboratory dish were dipped with the obtained solution and air-dried, and then maize weevil adults each 10 of male and female were released therein. The laboratory dishes were kept in a thermostatic chamber.

Ninety (90) days after, evaluation was conducted by counting the number of the adults which came out.

The test was conducted twice of each compound.

As a result, no emerged adult was observed at all in the dishes treated with any one of the following compounds.

Compound Nos. 24, 33, 62, 85, 100, 104, 106, 109, 115, 116, 118, 119, 120, 155, 160, 164, 165, 168, 203, 205, 206, 207, 211, 212, 228, 231, 237, 239, 240, 243, 244, 245, 246, 247, 249, 257, 264, 266

Test Example 9: Insecticidal test on German cockroach (*Blattella germanica*)

In a transparent small test tube was weighed and placed 5% emulsifiable concentrate of a compound of the present invention (or a 25% wettable powder or a 20% oil solution thereof), and thereto was added acetone to give a 500 ppm acetone solution of the compound. Ten (10) cc of the acetone solution was added to 10 g of powder feed for small animals placed in a laboratory dish of 9 cm in diameter. After stirring, acetone was distilled away from the mixture. This laboratory dish was placed in a large laboratory dish of 20 cm in diameter to prepare a bait. In this large laboratory dish were released 10 five instar nymphae of German cockroaches (*Blattella germanica*). The large laboratory dish was kept in a thermostatic chamber. In the large laboratory dish, a laboratory dish containing moistured sanitary cottom was placed so as to give a water to the nymphae.

Sixty (60) days after, evaluation was conducted by counting the number of the adults which came out.

The test was conducted twice of each compound.

As a result, no adult was observed at all in the dish treated with any one of the following compounds.

Compound Nos. 201, 202, 203, 204, 206, 207, 211, 212, 230, 236, 237, 239, 243, 244, 245, 246, 247, 250, 251, 257, 265, 266

What is claimed is:

1. A 3(2H)-pyridazinone compound of the formula

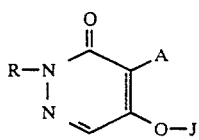

wherein,
R represents an alkyl group having 3 to 6 carbon atoms substituted by 1 to 3 halogen atoms;
A represents halogen atom;
J represents —CH₂—Q or

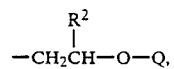

in which $R^2$ represents hydrogen atom or methyl group and Q represent

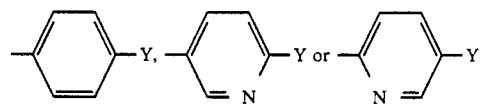

in which Y is selected from the group consisting of hydrogen atom, halogen atom, an alkyl group having 1 to 4 carbon atoms, an alkoxy group having 1 to 4 carbon atoms, a haloalkyl group having 1 to 4 carbon atoms and a haloalkoxy group having 1 to 4 carbon atoms.

2. A 3(2H)-pyridazinone compound as claimed in claim 1, wherein the compound has the following formula:

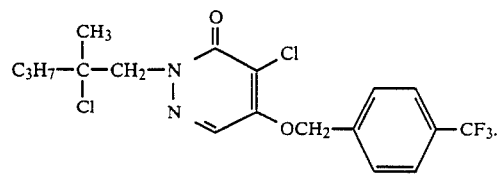

3. A 3(2H)-pyridazinone compound as claimed in claim 1, wherein the compound has the following formula:

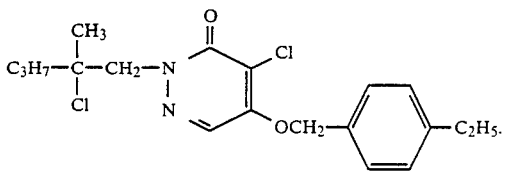

4. A 3(2H)-pyridazinone compound as claimed in claim 1, wherein the compound has the following formula:

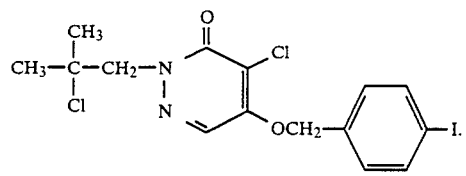

5. A 3(2H)-pyridazinone compound as claimed in claim 1, wherein the compound has the following formula:

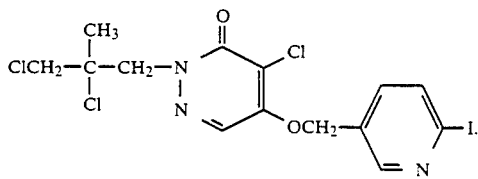

6. A 3(2H)-pyridazinone compound as claimed in claim 1, wherein the compound has the following formula:

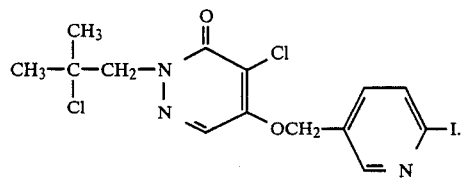

7. A 3(2H)-pyridazinone compound wherein the compound has the following formula:

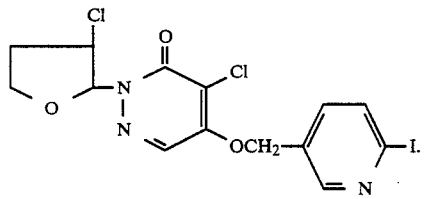

8. A 3(2H)-pyridazinone compound as claimed in claim 1, wherein the compound has the following formula:

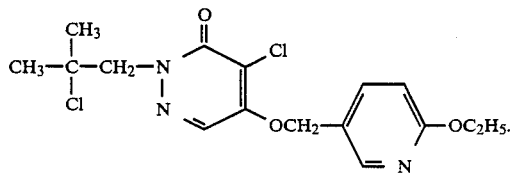

9. A 3(2H)-pyridazinone compound as claimed in claim 1, wherein the compound has the following formula:

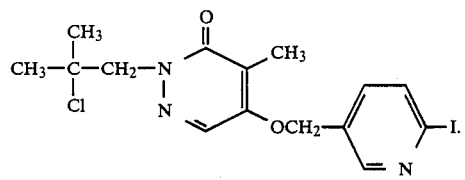

10. A 3(2H)-pyridazinone compound as claimed in claim 1, wherein the compound has the following formula:

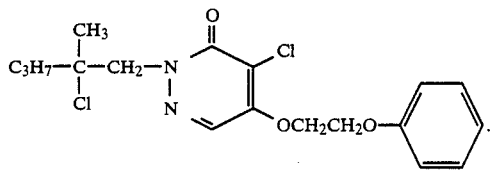

11. A 3(2H)-pyridazinone compound as claimed in claim 1, wherein the compound has the following formula:

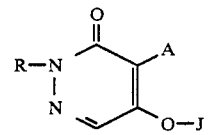

12. Insecticidal, acaricidal, nematicidal compositions and compositions for expelling ticks parasitic on animals, containing as an active ingredient a 3(2H)-pyridazinone compound of the formula:

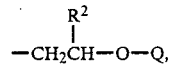

[I]

wherein,
R represents an alkyl group having 3 to 6 carbon atoms substituted by 1 to 3 halogen atoms;
A represents halogen atom;
J represents —CH$_2$—Q or $$-CH_2CH-O-Q,$$
$$\quad\quad\; |$$
$$\quad\quad R^2$$

in which R$^2$ represents hydrogen atom or methyl group and Q represent

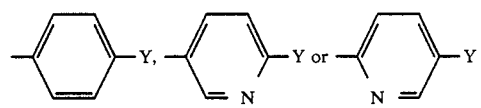

in which Y is selected from the group cosisting of hydrogen atom, halogen atom, an alkyl group having 1 to 4 carbon atoms, an alkoxy group having 1 to 4 carbon atoms, a haloalkyl group having 1 to 4 carbon atoms and a haloalkoxy group having 1 to 4 carbon atoms, and a carrier.

* * * * *

UNITED STATES PATENT AND TRADEMARK OFFICE
CERTIFICATE OF CORRECTION

PATENT NO.   :   4,945,091
DATED        :   July 31, 1990
INVENTOR(S)  :   Takahiro MAKABE ET AL.

It is certified that error appears in the above-identified patent and that said Letters Patent is hereby corrected as shown below:

On the Title Page:

Under Item [30], insert --Jun. 22, 1988  [JP]  Japan............63-154329

Signed and Sealed this

Twenty-second Day of December, 1992

Attest:

DOUGLAS B. COMER

Attesting Officer     Acting Commissioner of Patents and Trademarks